US009868781B2

(12) United States Patent
Xu et al.

(10) Patent No.: US 9,868,781 B2
(45) Date of Patent: Jan. 16, 2018

(54) ANTIBODIES FOR UBIQUITINATED PROTEINS

(75) Inventors: Guoqiang Xu, Elmhurst, NY (US); Samie R. Jaffrey, New York, NY (US)

(73) Assignee: Cornell University, Ithaca, NY (US)

( * ) Notice: Subject to any disclaimer, the term of this patent is extended or adjusted under 35 U.S.C. 154(b) by 1291 days.

(21) Appl. No.: 12/455,496

(22) Filed: Jun. 2, 2009

(65) Prior Publication Data

US 2009/0317409 A1 Dec. 24, 2009

Related U.S. Application Data

(60) Provisional application No. 61/058,084, filed on Jun. 2, 2008.

(51) Int. Cl.
G01N 33/53 (2006.01)
C07K 16/18 (2006.01)
C07K 16/44 (2006.01)
G01N 33/68 (2006.01)

(52) U.S. Cl.
CPC ............ *C07K 16/18* (2013.01); *C07K 16/44* (2013.01); *G01N 33/6803* (2013.01)

(58) Field of Classification Search
None
See application file for complete search history.

(56) References Cited

U.S. PATENT DOCUMENTS

| | | |
|---|---|---|
| 6,982,318 B1 | 1/2006 | Comb et al. |
| 2006/0148093 A1* | 7/2006 | Gygi et al. ............. 436/173 |

OTHER PUBLICATIONS

Mort et al. The use of cleavage site specific antibodies to delineate protein processing and breakdown pathways. Mol Pathol. Feb. 1999;52(1 ):11-8.*
Jung et al. Quantitative Mass Spectrometry of Histones H3.2 and H3.3 in Suz12-deficient Mouse Embryonic Stem Cells Reveals Distinct, Dynamic Post-translational Modifications at Lys-27 and Lys-36. May 1, 2010 Molecular & Cellular Proteomics, 9, 838-850.*
Tanaka et al. Efficient generation of antibodies to oncoproteins by using synthetic peptide antigens. PNAS, 1985 vol. 82 No. 10 3400-3404.*
Gram H, Phage display in proteolysis and signal transduction. Comb Chem High Throughput Screen. Feb. 1999;2(1):19-28.*
Vasilescu et al. Proteomic Analysis of Ubiquitinated Proteins from Human MCF-7 Breast Cancer Cells by Immunoaffinity Purification and Mass Spectrometry. Journal of Proteome Research 2005, 4, 2192-2200.*
Kim et al. Systematic and Quantitative Assessment of the Ubiquitin-Modified Proteome. Molecular Cell 44, 325-340, Oct. 21, 2011.*
Clementi et al. Antibodies Against Small Molecules. Ann Ist Super Sanita. 1991;27(1)139-43.*

Hershko, A. et al., "The Ubiquitin System" Annual Review Biochem (1998) pp. 425-479, vol. 6Hershko, A. et al., "The Ubiquitin System" Annual Review Biochem (1998) pp. 425-479, vol. 677.
Hicke, L., "Getting Down with Ubiquitin: Turning Off Cell-Surface Receptors, Transporters and Channels" Trends Cell Biol (1999) pp. 107-112, vol. 9.
Conaway, R.C. et al., "Emerging Roles of Ubiquitin in Transcription Regulation" Science (2002) pp. 1254-1258, vol. 296.
Ulrich, H.D., "Degradation or Maintenance: Actions of the Ubiquitin System on Eukaryotic Chromatin" Eukaryot Cell (2002) pp. 1-10, vol. 1.
Kirkpatrick, D.S., et al., "Weighing in on Ubiquitin: the Expanding Role of Mass-Spectrometry-Based Proteomics" Nat Cell Biol (2005) pp. 750-757, vol. 7.
Bonifacino, J.S. et al., "Ubiquitin and the Control of Protein Fate in the Secretory and Endocytic Pathways" Annu Rev Cell Dev Biol (1998) pp. 19-57, vol. 14.
Rechsteiner, M., "Ubiquitin-Mediated Pathways for Intracellular Proteolysis" Annu Rev Cell Biol (1987) pp. 1-30, vol. 3.
Nandi, D. et al., "The Ubiquitin-Proteasome System" Journal of Bioscience (2006) pp. 137-155, vol. 31.
Mukhopadhyay, D. et al., "Proteasome-Independent Functions of Ubiquitin in Endocytosis and Signaling" Science (2007) pp. 201-205, vol. 315.
Sun, L. et al., "The Novel Functions of Ubiquitination in Signaling" Current Opinion Cell Biol (2004) pp. 119-126, vol. 16.
Pickart, C.M., "Ubiquitin Enters the New Millennium" Mol Cell (2001) pp. 499-504, vol. 8.
Pickart, C.M., "Mechanisms Underlying Ubiquitination" Annu Rev Biochem (2001) pp. 503-533, vol. 70.
Xu, P., et al., "Dissecting the Ubiquitin Pathway by Mass Spectrometry" Biochim Biophys Acta (2006) pp. 1940-1947, vol. 1764.
Banerjee, A. et al., "Identification of a Ubiquitination-Target/Substrate-Interaction Domain of Cytochrome P-450 (CYP) 2E1" Drug Metab Dispos (2000) pp. 118-124, vol. 28.
Treier, M. et al., "Ubiquitin-Dependent c-Jun Degradation in vivo is Mediated by the Delta Domain" Cell (1004) pp. 787-798, vol. 78.
Baboshina, O.V. et al., "Novel Multiubiquitin Chain Linkages Catalyzed by the Conjugating Enzymes E2EPF and RAD6 are Recognized by 26 S Proteasome Subunit 5" J Biol Chem (1996) pp. 2823-2831, vol. 271.
Gregori, L. et al., "A Uniform Isopeptide-Linked Multiubiquitin Chain is Sufficient to Target Substrate for Degradation in Ubiquitin-Mediated Proteolysis" Journal of Biol Chem (1990) pp. 8354-8357, vol. 265.
Vasilescu, J. et al., "Proteomic Analysis of Ubiquitinated Proteins from Human MCF-7 Breast Cancer Cells by Immunoaffinity Purification and Mass Spectrometry" J Proteome Res (2005) pp. 2192-2200, vol. 4.
Vasilescu, J. et al., "The Proteomic Reactor Facilitates the Analysis of Affinity-Purified Proteins by Mass Spectrometry: Application for Identifying Ubiquitinated Proteins in Human Cells" J Proteome Res (2007) pp. 298-305, vol. 6.

(Continued)

*Primary Examiner* — Maher M Haddad
(74) *Attorney, Agent, or Firm* — Scully, Scott, Murphy & Presser, P.C.

(57) ABSTRACT

The invention relates to particular ubiquitination epitopes, antibodies that specifically recognize and bind to ubiquitinated proteins and peptides (particularly after the ubiquitin is removed by proteolytic cleavage) and to methods of using these epitopes and antibodies.

21 Claims, 41 Drawing Sheets

(56) References Cited

OTHER PUBLICATIONS

Peng, J. et al., "A Proteomics Approach to Understanding Protein Ubiquitination" Nat Biotechnol (2003) pp. 921-926, vol. 21.
Peng, J. et al., "Proteomic Analysis of Ubiquitin Conjugates in Yeast" Methods Enzymol (2005) pp. 367-381, vol. 399.
Jeon, H.B. et al., "A Proteomics Approach to Identify the Ubiquitinated Proteins in Mouse Heart" Biochem Biophys Res Commun (2007) pp. 731-736, vol. 357.
Kirkpatrick, D.S. et al., "Proteomic Identification of Ubiquitinated proteins From Human Cells Expressing His-Tagged Ubiquitin" Proteomics (2005) pp. 2104-2111, vol. 5.
Matsumoto, M. et al.. "Large-Scale Analysis of the Human Ubiquitin-Related Proteome" Proteomics (2005) pp. 4145-4151, vol. 5.
Denis, N. J. et al., "Tryptic Digestion of Ubiquitin Standards Reveals an Improved Strategy for Identifying Ubiquitinated Proteins by Mass Spectrometry" Proteomics (2007) pp. 868-874, vol. 7.
Chernorudskiy, A.L. et al., "UbiProt: a Database of Ubiquitylated Proteins" BMC Bioinformatics (2007) pp. 126, vol. 8.
McLachlin, D.T. et al., "Analysis of Phosphorylated Proteins and Peptides by Mass Spectrometry" Current Opinion Chem Biol (2001) pp. 591-602, vol. 5.
Ferguson, P.L. et al., "Proteome Analysis by Mass Spectrometry." Annu Rev Biophys Biomol Struct (2003) pp. 399-424, vol. 32.
Warren, M.R. et al., "Electrospray Ionization Tandem Mass Spectrometry of Model Peptides Reveals Diagnostic Fragment Ions for Protein Ubiquitination" Rapid Commun Mass Spectrom (2005) pp. 429-437, vol. 19.
Pedrioli, P.G. et al., "Automated Identification of SUMOylation Sites Using Mass Spectrometry and SUMmOn Pattern Recognition Software" Nat Methods (2006) pp. 533-539, vol. 3.
Denison, C. et al., "Proteomic Insights into Ubiquitin and Ubiquitin-like Proteins" Current Opinion Chem Biol (2005) pp. 69-75, vol. 9.
Wang, Q. et al., "Structure of S5a Bound to Monoubiquitin Provides a Model for Polyubiquitin Recognition" Journal of Mol Biol (2005) pp. 727-739, vol. 348.
Wang, H. et al., "Role of Histone H2A Ubiquitination in Polycomb Silencing" Nature (2004) pp. 873-878, vol. 431.
Nickel, B.E. et al., "Structure of Polyubiquitinated Histone H2A" Biochemistry (1989) pp. 964-968, vol. 28.
Gordon, D.M. et al., "Degradation of the kinesin Kip1p at Anaphase Onset is Mediated by the Anaphase-Promoting Complex and Cdc20p" Proc Natl Acad Sci USA (2001) pp. 12515-12520, vol. 98.
Lu, Z. et al., "Predicting Subcellular Localization of Proteins Using Machine-Learned Classifiers" Bioinformatics (2004) pp. 547-556, vol. 20.
Lu, C. et al., "Insulin-like peptide 6: Characterization of Secretory Status and Posttranslational Modifications" Endocrinology (2006) pp. 5611-5623, vol. 147.
Meerovitch, K. et al., "Preproparathyroid Hormone-Related Protein, a Secreted Peptide, is a Substrate for the Ubiquitin Proteolytic System" Journal of Biol Chem (1997) pp. 6706-6713, vol. 272.
Liao, W. et al., "Ubiquitin-Dependent and-Independent Proteasomal Degradation of apoB Associated with Endoplasmic Reticulum and Golgi Apparatus, Respectively, in HepG2 cells" Journal of Cell Biochem (2003) pp. 1019-1029, vol. 89.
Galan, J.M. et al., "'ER Degradation' of a Mutant Yeast Plasma Membrane Protein by the Ubiquitin-Proteasome Pathway" Faseb J (1998) pp. 315-323, vol. 12.
Plemper, R.K. et al., "Endoplasmic Reticulum Degradation—Reverse Protein Transport and its End in the Proteasome" Mol Biol Rep (1990) pp. 125-130, vol. 26.

Schwartz, D. et al., "An Iterative Statistical Approach to the Identification of Protein Phosphorylation Motifs From Large-Scale Data Sets" Nat Biotechnol (2005) pp. 1391-1398, vol. 23.
Ahmad, S. et al., "NETASA: Neural Network Based Prediction of Solvent Accessibility" Bioinformatics (2002) pp. 819-824, vol. 18.
Catic, A. et al., "Preferred in vivo Ubiquitination Sites" Bioinformatics (2004) pp. 3302-3307, vol. 20.
Jiang, Y.H. et al., "Human Disorders of Ubiquitination and Proteasomal Degradation" Current Opinion Pediatr (2004) pp. 419-426, vol. 16.
Nalepa, G. et al., "Drug Discovery in the Ubiquitin-Proteasome System" Nat Rev Drug Discov (2006) pp. 596-613, vol. 5.
Hao, G., et al., "SNOSID, a Proteomic Method for Identification of Cysteine S-nitrosylation Sites in Complex Protein Mixtures" Proc Natl Acad Sci USA (2006) pp. 1012-1017, vol. 103.
Benore-Parsons, M. et al., "Substrate Phosphorylation Can Inhibit Proteolysis by Trypsin-Like Enzymes." Arch Biochem Biophys (1989) pp. 274-280, vol. 272.
Schlosser, A. et al., "Analysis of Protein Phosphorylation by a Combination of Elastase Digestion and Neutral Loss Tandem Mass Spectrometry" Anal Chem (2001) pp. 170-176, vol. 73.
Molina, H. et al., "Global Proteomic Profiling of Phosphopeptides Using Electron Transfer Dissociation Tandem mass Spectrometry" Proc Natl Acad Sci USA (2007) pp. 2199-2204, vol. 104.
Thomas, P.D. et al., "PANTHER: a Library of Protein Families and Subfamilies Indexed by Function" Genome Res (2003) pp. 2129-2141, vol. 13.
Dennis, G., Jr. et al., "DAVID: Database for Annotation, Visualization, and Integrated Discovery" Genome Biol (2003) pp. P3, vol. 4.
Kabsch, W. et al., "Dictionary of Protein Secondary Structure: Pattern Recognition of Hydrogen-Bonded and Geometrical Features" Biopolymers (1983) pp. 2577-2637, vol. 22.
Jones, D.T., "Protein Secondary Structure Prediction Based on Position-Specific Scoring Matrices" Journal of Mol Biol (1999) pp. 195-202, vol. 292.
Linding, R. et al., "Protein Disorder Prediction: Implications for Structural Proteomics" Structure (2003) pp. 1453-1459, vol. 11.
Hubbard, S.J. et al., "Molecular Recognition-Conformational Analysis of Limited Proteolytic Sites and Serine Proteinase Protein Inhibitors" Journal of Mol Biol (1991) pp. 507-530, vol. 220.
Schneider, T.D. et al., "Sequence Logos—a New Way to Display Consensus Sequences" Nucleic Acids Research (1990) pp. 6097-6100, vol. 18.
Crooks, G.E. et al., "WebLogo: A Sequence Logo Generator" Genome Research (2004) pp. 1188-1190, vol. 14.
Hou, D. et al., "Activation-Dependent Ubiquitination of a T Cell Antigen Receptor Subunit on Multiple Intracellular Lysines" Journal of Biol Chem (1994) pp. 14244-14247, vol. 269, No. 19.
Layfield, R. et al., "Purification of Poly-Ubiquitinated Proteins by S5a-Affinity Chromatography" Proteomics (2001) pp. 773-777, vol. 1, No. 6.
Barderas R. et al., "Affinity Maturation of Antibodies Assisted by in silico Modeling" PNAS (Jul. 1, 2008) pp. 9029-9034, vol. 105, No. 26.
Pantazes, R.J. et al., "OptCDR: a General Computational Method for the Design of Antibody Complementarity Determining Regions for Targeted Epitope Binding" Protein Engineering, Design and Selection (2010) pp. 849-858, vol. 23, No. 11.
Dyson, M.R. et al., "Mapping Protein Interactions by Combining Antibody Affinity Maturation and Mass Spectrometry" Analytical Biochemistry (Oct. 1, 2011) pp. 25-35. vol. 417, No. 1.
Song, C.-X. et al., "Selective Chemical Labeling Reveals the Genome-Wide Distribution of 5-hydroxymethylcytosine" Nature Biotechnology (Jun. 3, 2011) pp. 68-72, vol. 29, No. 1.

* cited by examiner

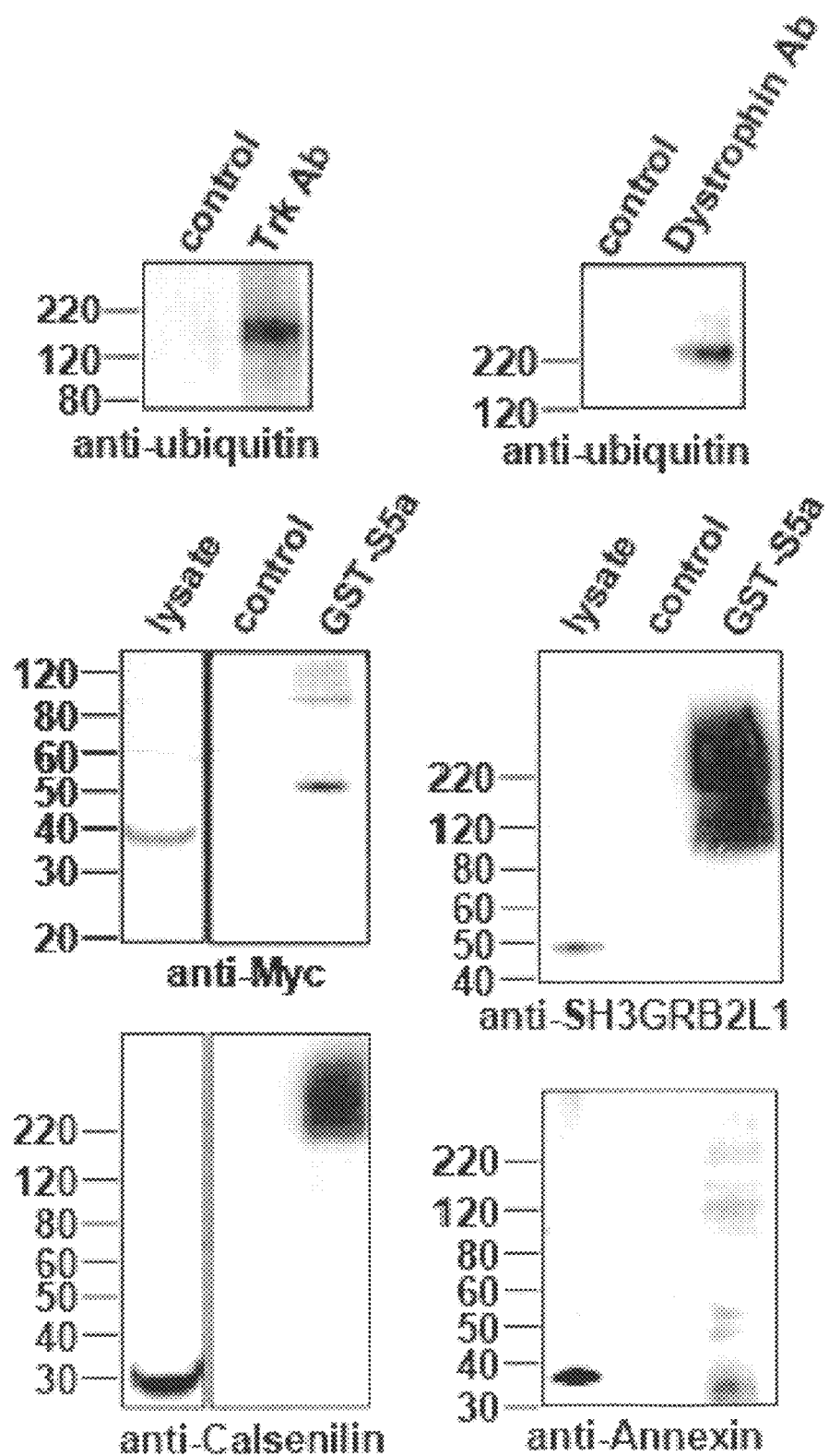

GG-insulin    100    10    4      2 ng mGG Ab

GG-insulin    17    1.7   0.68  0.34   pmol

GG-insulin  100   10    4    2    1  ng 17   1.7  0.68 0.34  0.17 pmol silver stain GG-beta lactoglubolin
0.1  0.01  µg

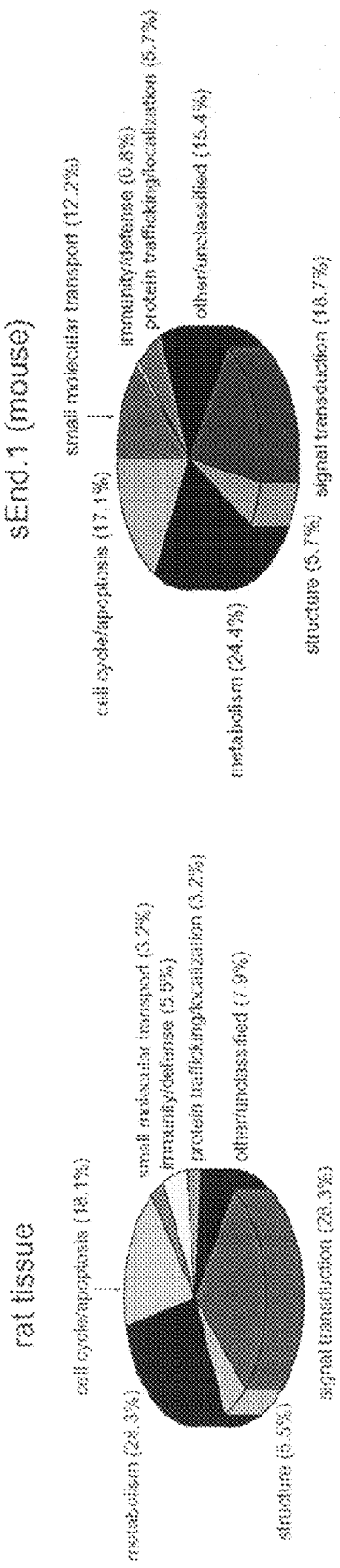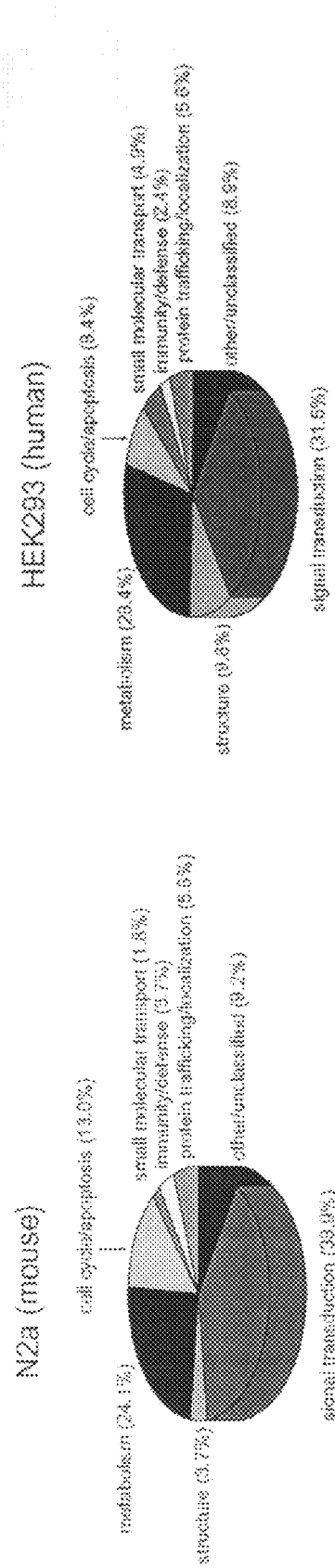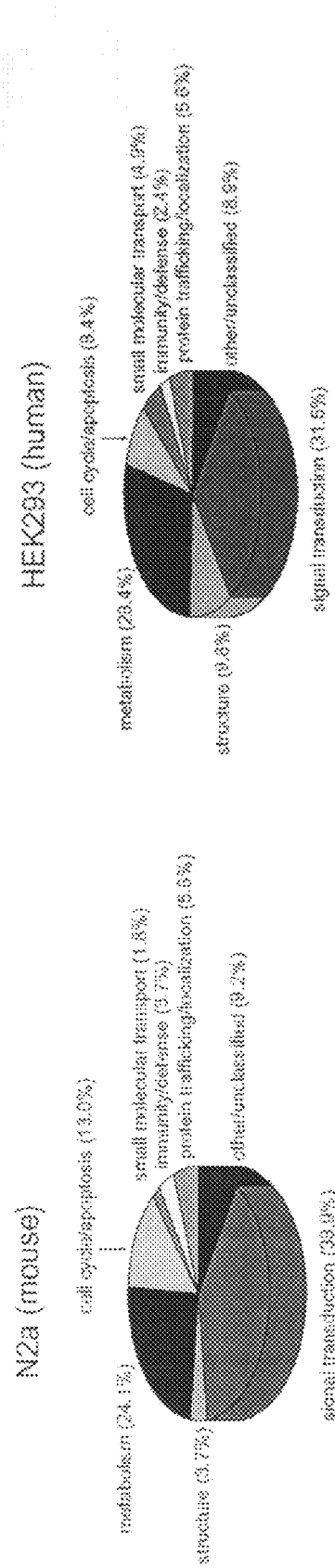
Fig. 21A Fig. 21B Fig. 21C Fig. 21D

| SEQ ID NO | Peptide Sequence Map | Ubiquitinated Lysines | z | Score | Accession | PROTEIN NAME | Fraction |
|---|---|---|---|---|---|---|---|
| 1 | (K)QNE/Q(A)K/E/MQQMV/K\|L\|EAE\|MDR(R) | K1162k | 3 | 13 | Q15147 | 1-PHOSPHATIDYLINOSITOL-4,5-BISPHOSPHATE PHOSPHODIESTERASE BETA 4 | HVW |
| 2 | (K)YHNGTkMVASA\|D\AY/K/\\\(PG\SRADFSEEYK(R) | K79k | 3 | 12 | P13233 | 2',3'-CYCLIC-NUCLEOTIDE 3'-PHOSPHODIESTERASE | BVM |
|  |  |  |  |  |  | 3-HYDROXYISOBUTYRATE DEHYDROGENASE, MITOCHONDRIAL |  |
| 3 | (K)TP/V/GF/\|GLGNM(GN/PMAkNL\|M\K(H) | K56k | 3 | 12 | P31937 | [PRECURSOR] | HLW |
| 4 | (K)QYKkAH\LGTVA/LkANV/P/FG\GASHA\K(G) | K37k | 3 | 12 | P62266 | 40S RIBOSOMAL PROTEIN S23 | HLW |
| 5 | (K)YAKYL/PH\SAGRI\YA/A/k(R) | K59k | 3 | 13 | P46782 | 40S RIBOSOMAL PROTEIN S5 | HLW |
| 6 | (K)MDEVY/K\/L/PNFLA/N\G\G(D)\GFQM\k(D) | K512k | 3 | 12 | P21589 | 5'-NUCLEOTIDASE [PRECURSOR] | HLW |
| 7 | (R)L/K\IVGL\|Q\VAVkA\|PGFGDNR(K) | K301k | 3 | 11 | *P63039 | 60 KDA HEAT SHOCK PROTEIN, MITOCHONDRIAL [PRECURSOR] | BVS |
| 8 | (K)NK/TGA\A\PIIDV\VRS/GYYK/V\LVGA\GK(L) | K114k | 3 | 11 | *P46776 | 60S RIBOSOMAL PROTEIN L27A | HLW |
| 9 | (R)DVYR/R\G\RI\V\F/ANAP\DSA/CV\GLR\K(K) | K696k | 3 | 11 | *P12382 | 6-PHOSPHOFRUCTOKINASE, LIVER TYPE | SLM |
| 10 | (K)ESQ/PEM/S/P/AL\HLMQNLD/TK\SKLR\PK(R) | K776k | 3 | 11 | *Q9Y4K1 | ABSENT IN MELANOMA 1 PROTEIN | HLW |
| 11 | (R)FGG/NkV/\)EKV\\\L\\ANNG\A\A\vKCM\R(S) | K119k K131k | 3 | 10 | *P11497 | ACETYL-COA CARBOXYLASE 1 | BVS |
| 12 | (R)K/L\G\\L/EQQ/H\QEQ/\QEH\k(L) | K202k K210k | 3 | 11 | Q6AY33 | ACROSIN-BINDING PROTEIN [PRECURSOR] | BVM |
| 13 | (R)K\K/ENEFSP\T\|NSTSQ/T/VS\SG\A\TNGAE\S\k(T) | K2641k | 3 | 10 | *P25054 | ADENOMATOUS POLYPOSIS COLI PROTEIN | HLW |
| 14 | (R)LQG/PKAG\|QM/E\NTNN/FH\/NL/YV\kR(H) | K284k | 3 | 12 | Q08462 | ADENYLATE CYCLASE, TYPE II | HLW |
| 15 | (K)K\L\G\L/V/F/DD\VG\VE/\INSRDV\k(V) | K397k | 3 | 12 | Q08163 | ADENYLYL CYCLASE-ASSOCIATED PROTEIN 1 | BVC |
| 16 | (R)VV\K\LE/NG/E\\ET\/A\|RFG\SG\PCK\T) | K123k | 3 | 12 | Q9HDC9 | ADIPOCYTE PLASMA MEMBRANE-ASSOCIATED PROTEIN | HLW |
| 17 | (R)LPL/N/QP/STQ\V/ANA\KGA\VTG\AK(D) | K116k | 3 | 10 | *Q99541 | ADIPOPHILIN | HLW |
| 18 | (R)EAQKQA\SI\EkV\SN\KG\K(R) | K759k | 3 | 12 | Q9UHB7 | AF4/FMR2 FAMILY MEMBER 4 | HLW |
| 19 | (K)LPV\L/VELS/P/DGSDS\RD/K\P\kLYR(L) | K401k | 3 | 12 | *P55196 | AFADIN | HLW |
| 20 | (R)Y/AEDKF/N\ETT\E/K\S\LL\K(M) | K407k | 3 | 13 | P43652 | AFAMIN [PRECURSOR] | HLW |
| 21 | (K)CV/YQSLYMGNEPTPTKSL\\S\k(I) | K173k | 3 | 12 | O75969 | A-KINASE ANCHOR PROTEIN 3 | HVW |
| 22 | (K)A/LNEEL/HL\QRIN\P\T\TV\KM(S) | K925k | 3 | 11 | Q99996 | A-KINASE ANCHOR PROTEIN 9 | HLW |
| 23 | (K)L\GTEKG\K\k\Nk(S) | K233k K235k | 3 | 13 | Q5XI97 | ALANYL-TRNA SYNTHETASE DOMAIN-CONTAINING PROTEIN 1 | LVN |
| 24 | (R)SN\E/S/L/KHN\\(QPAS\SK(W) | K76k | 3 | 12 | O35696 | ALPHA-2,8-SIALYLTRANSFERASE 8B | SLC |
| 25 | (K)QHLPSSGNGkSF/KA/GGEPSPACQ\P\VC\k\ALDP\R(G) | K228k | 3 | 11 | Q9D4H4 | ANGIOMOTIN-LIKE PROTEIN 1 | SLW |
| 26 | (R)SSDQDS/T/NKEA/EAAG\VK\P\|A\GVRPR(E) | K389k | 3 | 11 | Q92625 | ANKYRIN REPEAT AND SAM DOMAIN PROTEIN 1 | HLW |
| 27 | (K)A/EVV/NG/V/E/A\KYVT/VNNV\\N\V\\TK(I) | K279k | 3 | 14 | Q8IZ07 | ANKYRIN REPEAT DOMAIN PROTEIN 13 | HLW |
| 28 | (K)A/G/DLA/SLKV\KK\AFES/G\\PV\DM/K(D) | K521k | 3 | 13 | Q9NU02 | ANKYRIN REPEAT DOMAIN PROTEIN 5 | HLW |
| 29 | (K)K/GLDIPAKkP\PG\L\\DPPF\\kD\K(K) | K1651k | 3 | 11 | Q6UB99 | ANKYRIN REPEAT DOMAIN-CONTAINING PROTEIN 11 | HLW |
| 30 | (R)G/LAGY/SG/MGSD\T\HAVFC/VG/R\PK\A\RES\K(L) | K267k | 3 | 11 | Q8BXP5 | ANKYRIN REPEAT DOMAIN-CONTAINING PROTEIN 33 | SLW |
| 31 | (R)SGRS/A/L/H\HAVHSGH\\ETVNLL/NKGAS/LNVCDA\K\k(E) | K171k K172k | 3 | 11 | Q8BTI7 | ANKYRIN REPEAT DOMAIN-CONTAINING PROTEIN 52 | NLW |
| 32 | (R)IM/V/SR/S/EV/D\M/LK\\RSEFKR(K) | K308k | 3 | 13 | *P07355 | ANNEXIN A2 | HLW |
| 33 | (R)VSSQNL/V/A\/PV/YV\KH\NISF\KAENS\SCGR(F) | K2277k K283k | 3 | 11 | P53676 | AP-3 COMPLEX SUBUNIT MU-1 | BVM |
| 34 | (K)L\DV\\SMYR/ELLKD\L\S\K(E) | K2278k | 2 | 11 | *P04114 | APOLIPOPROTEIN B-100 [PRECURSOR] | HLW |
| 35 | (K)VQ/TDKG/TE\\VATV\N\L\V\LCTG//K\\WSSAYR\K(A) | K254k | 3 | 11 | Q9BRQ8 | APOPTOSIS-INDUCING FACTOR 2 | HVW |
| 36 | (K)QVGVN/PTS\DS\V\\V\GK\DQEVK(L) | K89k | 3 | 13 | Q722E3 | APRATAXIN | HLW |
| 37 | (R)LGPMA\L\\AFKLRG\\L/V\DR\k\R(S) | K230k | 3 | 11 | Q2KMM4 | ARACHIDONATE 12-LIPOXYGENASE, 12R TYPE | BVC |
| 38 | (K)SNN/I/F/L/HEGL\TV\KGDF\\GLA\TV\kTR(W) | K452k | 3 | 11 | P04627 | A-RAF PROTO-ONCOGENE SERINE/THREONINE-PROTEIN KINASE | NLW |
| 39 | (R)GG/N/E/KGPAA\\LRK/AGL\\VEK\\LK(E) | K26k K33k | 3 | 12 | P07824 | ARGINASE-1 | BVS |
| 40 | (K)G/K/D/KEVH/S\KR/G\DSGN\K(A) | K171k | 3 | 13 | Q9DBU6 | ARGININE/SERINE-RICH COILED COIL PROTEIN 1 | NLW |
| 41 | (K)G/K/D/KE/VHS\kR\G\DSG\M\K(A) | K163k | 3 | 11 | Q9DBU6 | ARGININE/SERINE-RICH COILED COIL PROTEIN 1 | NLW |
| 42 | (R)VVF/L/D/E\K\EA\ANAAN\\HSFEV\GL\P\E\K(Y) | K681k | 3 | 13 | Q2M3G0 | ATP-BINDING CASSETTE SUB-FAMILY B MEMBER 5 | HLW |
| 43 | (R)YD/SSLK/PV\/K\HVNAL\\\S\PGQK(I) | K1359k K1374k | 3 | 13 | *Q09429 | ATP-BINDING CASSETTE TRANSPORTER SUB-FAMILY C MEMBER 8 | LVC |

Fig. 22A

| | | | | | | |
|---|---|---|---|---|---|---|
| 44 | (K)GKTT/IKT/GYAS/V/LNK/VW/QMNPVDR(G) | K90k | 3 | 10 | | ATP-DEPENDENT RNA HELICASE DDX1 | SLW |
| 45 | (K)HGA/ITN/T/K/VQ\YRVSATDL\P\PE\LP\M(A) | K704k | 3 | 12 | *P41182 | B-CELL LYMPHOMA 6 PROTEIN | HLW |
| 46 | (K)V/FL/AECYNLCP\EQD\KILVAVVK/TLKD\ASDNARYK(D) | K565k | 3 | 9.9 | *P15209 | BDNF/NT-3 GROWTH FACTORS RECEPTOR [PRECURSOR] | NLW |
| 47 | (R)SVMQ/RYLEVDRG\EV\T\FLEVK(I) | K45k | 3 | 11 | P25098 | BETA-ADRENERGIC RECEPTOR KINASE 1 | HLW |
| 48 | (Q)NK\P/RS/P\VV/E/LSKVPLV\QRGSANGL(-) | KG67k | 3 | 10 | *P25098 | BETA-ADRENERGIC RECEPTOR KINASE 1 | HLW |
| 49 | (R)K/SNPGIW/E/NLEK(L) | K142k | 3 | 12 | Q96T60 | BIFUNCTIONAL POLYNUCLEOTIDE PHOSPHATASE/KINASE | HLW |
| 50 | (K)AMESAEQK/EQ\G\LS/RDVTTV\V\KLR\V\VSYS\k(K) | K2979k | 3 | 11 | *P51587 | BREAST CANCER TYPE 2 SUSCEPTIBILITY PROTEIN | HLW |
| 51 | (R)K/AD/TT/T/PTT/IDPIHEPP\SLPPEPK\TTTK(L) | K291k | 3 | 11 | O60885 | BROMODOMAIN-CONTAINING PROTEIN 4 | HLW |
| 52 | (K)MVE/L/KA\KVEQEFE\L\S\DK(L) | K4193k K4199k.3 | 3 | 11 | Q912U6 | BULLOUS PEMPHIGOID ANTIGEN 1, ISOFORMS 1/2/3/4 | SLM |
| 53 | (K)G/TQKP/YALKV\L\KKTV\DK\K(I) | K71k K79k | 3 | 11 | P13234 | CALCIUM/CALMODULIN-DEPENDENT PROTEIN KINASE TYPE IV | BVS |
| 54 | (K)S/QEG/KPKE\H\TEPK\ISL\PK(Q) | K68k | 3 | 12 | P20810 | CALPAIN INHIBITOR, CALPASTATIN | NLW |
| 55 | (K)I R/DK\EL\G\U/GRHE\MA\IV\K(Y) | K21k | 3 | 11 | O35350 | CALPAIN-1 CATALYTIC SUBUNIT | SLW |
| 56 | (R)KLGA/S/L/FTI/GF\AIY/E/VP\K\EM\HGN\K(Q) | K517k | 3 | 12 | P20807 | CALPAIN-3 | HLW |
| 57 | (K)WAFNLY/DI/NI\KDGYIT/K\IE/EIM\LAIMK(S) | K192k | 3 | 12 | Q9Y2W7 | CALSENILIN | HLW |
| 58 | (R)SLHAA/AVLL/I\V\IL/KE/QP/S\SV\PA\PV\NGSK(W) | K18k | 3 | 12 | O43570 | CARBONIC ANHYDRASE XII [PRECURSOR] | HLW |
| 59 | (R)VVQK/N/LVFV\VGL/SVQ/R/LA/D\PEVVLK(R) | K108k | 3 | 12 | *O95628 | CCR4-NOT TRANSCRIPTION COMPLEX SUBUNIT 4, E3 UBIQUITIN-PROTEIN LIGASE CNOT4 | HLW |
| 60 | (K)VFK/Q?/SK\PE\VN/KA\PFLEY\DQLKK(L) | K132k | 3 | 11 | *Q61490 | CD166 ANTIGEN [PRECURSOR] | NLW |
| 61 | (R)SVH\I L\K/EG\EQ\HVDD\VSSA\LKR(F) | K792k | 3 | 13 | Q96P48 | CENTAURIN DELTA 2 | HLW |
| 62 | (K)KA/AECKVD\S/IGSGRA\P\I/K\QGILL\K(R) | K370k | 3 | 12 | Q96P47 | CENTAURIN-GAMMA 3 | HLW |
| 63 | (K)SEK/TIQ\SDIQK\D\LDK\IS\K(D) | K1950k K1965K.3 | 3 | 12 | Q02224 | CENTROMERIC PROTEIN E | HVW |
| 64 | (K)QFSK\D/T/YSK/P\S\SG\ESDDH\CQ\R\EGEL\QK(E) | K2038k | 3 | 11 | O15078 | CENTROSOMAL PROTEIN CEP290 | HLW |
| 65 | (K)AG/V/S/AE/PTTRTY\D/LNKPPE/FSF\EK\AR(V, R)TY/DLN/KV/P/PEF/SF/EK\A\RVR(K) | | | | | | |
| 66 | (K)NTK/QQN/NAA/U/E\RGLYT\KY\ALK(K) | K146k | 3 | 12 | Q13237 | CGMP-DEPENDENT PROTEIN KINASE 2 | HVW |
| 67 | (R)ESN\TV\A\C\VDIFS/K/FSAY\KN*\K(Q) | K289k K302k | 3 | 12 | Q9NZA1 | CHLORIDE INTRACELLULAR CHANNEL PROTEIN 5 | HLW |
| 68 | (K)V/I/D/KGAGSG\G\AGQ\G\AGAL\A\R/PKVPS\R(N) | K130k | 3 | 11 | *Q8BXK9 | CHLORIDE INTRACELLULAR CHANNEL PROTEIN 5 | SLM |
| 69 | (K)E/L/QV/AND/KA\DMV\LKEVT/M\K(A) | K201k | 3 | 14 | O95503 | CHROMOBOX PROTEIN HOMOLOG 6 | HLW |
| 70 | (R)YS/PSHVRT\TQ/k\SY\HT\GK(K) | K3243k | 3 | 11 | Q8TE73 | CILIARY DYNEIN HEAVY CHAIN 5 | HLW |
| 71 | (R)RK/DKET\NS\E\GLV\NKTR(E) | K207k | 3 | 12 | P56748 | CLAUDIN-8 | HLW |
| | | K1291k K1303k | 3 | 12 | Q06194 | COAGULATION FACTOR VIII [PRECURSOR] | SLM |
| 72 | (K)E/IL/TKAM/RYF\SN\NE\EK\I\K(L) | K217k | 3 | 12 | Q8IWL3 | CO-CHAPERONE PROTEIN HSCB, MITOCHONDRIAL [PRECURSOR] | HLW |
| 73 | (K)DMERRQQQK\I\KM/OAEV\K(R) | K172k | 3 | 11 | Q9UL16 | COILED-COIL DOMAIN-CONTAINING PROTEIN 19 | HLW |
| 74 | (K)DW/A/N/CR/CSS\P\KG/SARNSLV\KA\K(R) | K231k | 3 | 12 | P38432 | COILIN | HLW |
| 75 | (R)G/P/P/GPAGK\PKGD\DGEA/GK\PGKAGER(G) | K194k | 3 | 12 | *P05539 | COLLAGEN ALPHA-1 (II) CHAIN [PRECURSOR] | LVN |
| 76 | (R)GHPGPPGP/P/GESQG\LPGAAGKEGTKGD\PG\PA\GLPGK(D) | K1051k | 3 | 12 | *Q9I03 | COLLAGEN ALPHA-1 (V) CHAIN [PRECURSOR] | BVN |
| 77 | (R)IE/G/N/Q/G/ARVGLVAVDKGVF\VLNKK\M\K(L) | K599k | 3 | 11 | P01026 | COMPLEMENT C3 [PRECURSOR] | BVS |
| 78 | (K)FW\I\G\L\QR/E\KG\K(C) | K100k | 2 | 12 | Q9ET61 | COMPLEMENT COMPONENT C1Q RECEPTOR [PRECURSOR] | BVS |
| 79 | (R)TSSQNINV/Q/V/L/NTNK\T/SAELLLP\V\K(E) | K957k | 3 | 11 | Q62682 | CONTACTIN-3 [PRECURSOR] | LVM |
| 80 | (R)ENKRIAIL\PD/G/S/L/RILNASKSD\FGK(Y) | K548k | 3 | 11 | O94779 | CONTACTIN-5 [PRECURSOR] | HLW |
| 81 | (K)F/PVDGKVLEG/N/TMA\DESLITGEA/M/PV\T\K\KPGSTVIAR(S) | | | | | | |
| 82 | (R)DAD/PIILS/LR/EAYRV/P\SK\QRDL(I) | K867k | 3 | 12 | P35670 | COPPER-TRANSPORTING ATPASE 2 | HLW |
| 83 | (R)KGIL\FRPF/THVK(I) | K405k | 3 | 13 | Q9BR76 | CORONIN-1B | HLW |
| 84 | (R)QGAFLVN/TV\AR/GGLVI\DE\K/ALA\QAL\K(E) | K283k | 2 | 10 | *P47941 | CRK-LIKE PROTEIN | NLW |
| 85 | (R)KRP/AT\D\DS\S/TVQ/N/V/R(A) | K280k | 3 | 10 | *Q13363 | C-TERMINAL BINDING PROTEIN 1 | HLW |
| 86 | (K)LPK7/L/QE/LRLH/D/NEITKLLK(K) | K165k | 3 | 11 | *P46527 | CYCLIN-DEPENDENT KINASE INHIBITOR 1B | HLW |
| | | K145k K159k | 3 | 10 | *Q01129 | DECORIN [PRECURSOR] | BVS |
| 87 | (K)TTKLHFE/A/LM\M\PVLVLD/V\N/D\DV\S\EEVTK(Q) | K262k | 3 | 11 | Q16854 | DEOXYGUANOSINE KINASE, MITOCHONDRIAL [PRECURSOR] | HLW |

Fig. 22B

| # | Sequence | ID | | | UniProt | Description | Code 1 | Code 2 |
|---|---|---|---|---|---|---|---|---|
| 88 | (K)GS/SQ]QP]NKV/TDK]M\k(M) | K411k | 2 | 11 | P49621 | DIACYLGLYCEROL KINASE BETA | BVS | |
| 89 | (K)M/S/Q/DSM/M\KL]KG/M\AAAGRSQGQHK(Q) | K90k | 3 | 10 | *O88797 | DISABLED HOMOLOG 2 | BVW | |
| 90 | (K)DKDF/AL/DVSANQP]VLVAVK\M]LRADAM\K(N) | K591k | 3 | 12 | Q16832 | DISCOIDIN DOMAIN-CONTAINING RECEPTOR 2 [PRECURSOR] | HVW | |
| 91 | (R)KL]D]SV]kRQ\KY\NK(E) | K175k K181k | 3 | 11 | *Q03468 | DNA EXCISION REPAIR PROTEIN ERCC-6 | HLW | |
| 92 | (K)TDK/L/]/GFSK]P\VRKKLSSQLGSLEK(F) | K732k K756k | 3 | 11 | Q9UHC1 | DNA MISMATCH REPAIR PROTEIN MLH3 | HLW | |
| 93 | (R)GKLQG]HDVDF]L]ITH/PKEGQEAGL]LP\R(V) | K339k | 3 | 12 | Q9NP87 | DNA POLYMERASE MU | HLW | |
| 94 | (K)LLKSVE/NL/G]V/SVVk]GT\EQY\QSK(L) | K65k | 3 | 11 | *P49643 | DNA PRIMASE LARGE SUBUNIT | HLW | |
| 95 | (R)RF/A/]GSQVS]E/H/S]I/KD\FT\k(Q) | K700k | 3 | 12 | *P33992 | DNA REPLICATION LICENSING FACTOR MCM5 | HLW | |
| 96 | (K)D/KKVAE]P]D\M\kK(k) | K194k | 3 | 13 | *Q9WUI0 | DNA TOPOISOMERASE 1 | BVC | |
| 97 | (R)REDPE/A/G/WLLYLKTGQM/YP\VAP\AM\NH\LDK(R) | K352k | 3 | 11 | Q62QJ5 | DNA2-LIKE HELICASE | SLW | |
| 98 | (K)GSRSQ\kEAF/PLAK]GE/V\D]TAP]Q\G\M\kD\LK(E) | K575k K593k | 3 | 13 | P48382 | DNA-BINDING PROTEIN RFX5 | HVW | |
| 99 | (K)DLL/LNTM/SQ/E\ER\AAYLSDP/RA\PPCEYK(D) | K3840k | 3 | 11 | *P78527 | DNA-DEPENDENT PROTEIN KINASE CATALYTIC SUBUNIT | HLW | |
| 100 | (K)SPS/N/CLVVGKVV/KGGTG]L]FE/LKQPL\R(-) | K1700k | 3 | 13 | O54889 | DNA-DIRECTED RNA POLYMERASE I LARGEST SUBUNIT | BVC | |
| 101 | (K)Y/KEAARLE]I]NVLEK\I\MEK(D) | K214k | 3 | 12 | P49760 | DUAL SPECIFICITY PROTEIN KINASE CLK2 | HLW | |
| 102 | (R)VLSFKTG/I]I]SLCKAH]LLE\D\K(Y) | K3200k | 3 | 15 | P11532 | DYSTROPHIN | HVW | |
| 103 | (K)M\SKE]A/TAG/KKS]KS]G\K(L) | K665k | 3 | 12 | Q9NV58 | E3 UBIQUITIN-PROTEIN LIGASE RNF19 | HVW | |
| 104 | (K)k/GVL/P\T\K[DIR/RMC\K(S) | K650k K663k | 2 | 11 | Q9D485 | EF-HAND DOMAIN-CONTAINING FAMILY MEMBER C2 | SLN | |
| 105 | (R)DCNS]P/LVL\GT\CKE\TFNLYYM\E]S\DDHGVK(F) | K133k | 3 | 11 | P29319 | EPHRIN TYPE-A RECEPTOR 3 [PRECURSOR] | NLW | |
| 106 | (K)S/KQDT/PA/LLP]P/KKPAPPR\VKP\PSGK(S) | K773k | 3 | 12 | *Q9UBC2 | EPIDERMAL GROWTH FACTOR RECEPTOR SUBSTRATE 15-LIKE 1 | HLW | |
| 107 | (K)N/D/P/FTSD/P/FTK\NPSLPS\K(L) | K694k | 3 | 11 | *Q9UBC2 | EPIDERMAL GROWTH FACTOR RECEPTOR SUBSTRATE 15-LIKE 1 | HLW | |
| 108 | | | | | | | | |
| 109 | (R)TGLSQ/L/HNAL/NDVKDV/Q\Q\SLAD/VSKDWRQ/SINTIES\LLK(D) | K107k | 3 | 11 | Q6KAR6 | EXOCYST COMPLEX COMPONENT 3 | SLW | |
| 110 | (K)NCF]]L\CATVT\TERP/V\QV\k\W\KV\K(K) | K51k | 3 | 11 | Q9NV70 | EXOCYST COMPLEX COMPONENT SEC3 | HLW, HVW | |
| 111 | (R)LQAEK]ALVEFTNSPDC]L]S]K(C) | K46k | 3 | 13 | Q9UIA9 | EXPORTIN 7 | HVW | |
| 112 | (K)SR/KKS/SE]GKK(G) | K539k | 3 | 10 | *Q04931 | FACT COMPLEX SUBUNIT SSRP1 | LVN | |
| 113 | (K)VK/S/]/WT\LDGGK/LV\HLQ\K(W) | K82k | 3 | 13 | P05413 | FATTY ACID-BINDING PROTEIN, HEART | HLW | |
| 114 | (R)LVWR\N/SV/R\GSL\K]S]L/SFFLkk(M) | K158k K159k | 3 | 11 | Q66H10 | F-BOX ONLY PROTEIN 39 | BVS | |
| 115 | (R)HLDLS/G/C\E\K\ITD/V\ALE\K\SR(A) | K395k | 3 | 12 | Q9UKA1 | F-BOX/LRR-REPEAT PROTEIN 5 | HLW | |
| 116 | (K)CK/VK/SL/LH\SPGDY/I\LL\SADK(Y) | K280k | 3 | 13 | Q9UKT8 | F-BOX/WD-REPEAT PROTEIN 2 | HLW | |
| 117 | (R)TPCT\V/SCN\V]P\V/VSGKE/CE\E\V\RK(G) | K247k | 3 | 10 | *P02675 | FIBRINOGEN BETA CHAIN [PRECURSOR] | HLW | |
| 118 | (R)LRS]PP\k/kGL]L]GS/PT\V\HK(V) | K397k K398k | 3 | 11 | *Q61851 | FIBROBLAST GROWTH FACTOR RECEPTOR 3 [PRECURSOR] | SVW | |
| 119 | (R)VTEAE\VPM/G/k]N\SHCVREVP\QEM\G/HT\VSV\K(Y) | K2150k | 3 | 11 | *O75369 | FILAMIN B | HLW | |
| 120 | (R)ML/E/Q]L]L]LAEKCH/RRTVYE\L\NE\N\E\K(H) | K173k | 3 | 12 | Q8K474 | FILAMIN-A-INTERACTING PROTEIN 1 | BVS | |
| 121 | (R)AW/A/RANS/LA\M\SGV/P\DD\IFK(L) | K92k | 3 | 12 | Q13045 | FLIGHTLESS-I PROTEIN HOMOLOG | HLW | |
| 122 | (R)TV/S/DN]SLS]N/SRGEGK\P\D\LL\K(F) | K308k | 3 | 12 | Q96RU3 | FORMIN-BINDING PROTEIN 1 | HLW | |
| 123 | (K)RTVSDNSLS]N/SRGEG\G/kP\D\LL\K(F) | K90k | 3 | 11 | P26323 | FRIEND LEUKEMIA INTEGRATION 1 TRANSCRIPTION FACTOR | SLC | |
| 124 | (K)CN/KLVGG]G/EANPM\V\NY\N/SYMDEK(N) | K542k | 3 | 12 | *P98174 | FYVE, RHOGEF AND PH DOMAIN-CONTAINING PROTEIN 1 | HLW | |
| 125 | (R)YE/L/]/LK]D/YLLK\LP/HG\S\PDS\K(D) | | | | | GAMMA-AMINOBUTYRIC-ACID RECEPTOR SUBUNIT ALPHA-1 [PRECURSOR] | | |
| 126 | (K)E/VK\P]E]TKP\P]E/P/k(K) | K409k | 3 | 11 | *P62813 | GENERAL TRANSCRIPTION FACTOR 3C POLYPEPTIDE 1 | LVC | |
| 127 | (K)KGSTDV]M/VARC]U/K\L]LLK(E) | K334k | 3 | 12 | Q8K284 | GLOMULIN | SVW | |
| 128 | (R)Kk/SLAM/\QLYINK]L]L]D]SQYGK(Y) | K382k K383k | 3 | 12 | Q92990 | GLUTAMATE RECEPTOR 1 [PRECURSOR] | HLW | |
| 129 | (R)L/E]I]/VSDGK\YG/A/R\DPDT\M(A) | K472k | 3 | 10 | *P23818 | GLUTAMATE RECEPTOR 2 [PRECURSOR] | SLW | |
| 130 | (R)N/A/V/NLAVLKL\NE\Q\G/L\LL\D\K\L\K(N) | K773k | 3 | 12 | *P42262 | GLYCOGEN DEBRANCHING ENZYME | HLW | |
| | (K)LFHVS]ED/PSD]LNEK/H\P\NLVHK(R) | K1358k | 3 | 12 | P35573 | GOLGIN SUBFAMILY B MEMBER 1 | HLW | |
| | (R)T/Q/L/N]D]S/L/k/EV/HQ\K(E) | K3039k | 3 | 15 | Q14789 | | HLW | |

| # | Site | Peptide | UniProt | Protein | Source |
|---|------|---------|---------|---------|--------|
| 131 | K165k | (K)SV/FAKH]G\L/EK/L/T\P\JGD\K(Y) | Q8TAA5 | GRPE PROTEIN HOMOLOG 2, MITOCHONDRIAL [PRECURSOR] | HLW |
| 132 | K237k K249k | (K)GEKE]EED/K]EDEE/K]P\K(l) | *P34058 | HEAT SHOCK PROTEIN HSP 90-BETA | BVC |
| 133 | K101k | (R)V\/V/S/E/GGR\P]K\VQV\EY\KGET\K(T) | *P54652 | HEAT SHOCK-RELATED 70 KDA PROTEIN 2 | HLW |
| 134 | K72k | (R)AHG/SK\VV\AA\V/GDAV\K\S]|AD/DV\GGALS\K(L) | P02008 | HEMOGLOBIN ZETA CHAIN | HLW |
| | | | | HERV-H_2Q24.3 PROVIRUS ANCESTRAL ENV POLYPROTEIN | |
| 135 | K219k | (R)SPTTNINE/T]l/GA\FQLH\T\DK\P\SI\NTD\K(L) | Q9N2K0 | [PRECURSOR] | HLW |
| 136 | K126k | (K)LFVGGLKGD/V/AEG\DL\EHFSQFGT/VE\kA\EHADK(Q) | Q13151 | HETEROGENEOUS NUCLEAR RIBONUCLEOPROTEIN A0 | HLW |
| 137 | K139k | (K)QTA]K/A\EGLG\DG\YR\L\V/JN\DG\k(L) | Q9BX68 | HISTIDINE TRIAD NUCLEOTIDE-BINDING PROTEIN 2 | HLW |
| 138 | K186k | (K)AP/k/SP\AK/AKT/VK\P]KAAKPK(T) | *P43274 | HISTONE H1.4 | SLW |
| 139 | K115k | (K)AL/VQND\T\L]LQ/V\KG/YG/ANG\SFK(L) | *Q92522 | HISTONE H1X | HLW |
| 140 | K120k | (K)L/GGV/T/l\AQG/GV/L/PNl\Q/A/V\L/PK\K(T) | *Q64522 | HISTONE H2A TYPE 2-B | NLW |
| 141 | K10k | (K)QT/AR\K]S]TG\G/K/A\P\R(K) | *Q6LED0 | HISTONE H3.1 | LVC, LVN |
| | | | | HISTONE-LYSINE N-METHYLTRANSFERASE, H3 LYSINE-79 | |
| 142 | K193k | (K)A/D/]l]P/A/k/YA/ETMDRE/FR\K\WMK(W) | *Q8TEK3 | SPECIFIC | HLW |
| | | | | HISTONE-LYSINE N-METHYLTRANSFERASE, H3 LYSINE-9 SPECIFIC | |
| 143 | K709k | (K)LRFH/P/k]Q/L\YF\SA\RQG/EL\QK(V) | Q9H9B1 | 5 | HLW |
| 144 | K237k | (R)MG/R/P\E\G\EGTPG/LT\A\K\K(L) | Q96ED9 | HOOK HOMOLOG 2 | HLW |
| | | | | HORMONALLY UP-REGULATED NEU TUMOR-ASSOCIATED | |
| 145 | K75k | (R)KLG/E/G/S]FV\/kVR(E) | *P57058 | KINASE | HLW |
| 146 | K2511k | (R)NK]PL\K]A\/L]D\TRFGRK(L) | *P42859 | HUNTINGTIN (HUNTINGTON DISEASE PROTEIN HOMOLOG) | SLC |
| 147 | K337k | (R)NG]QL\SR/\LS\L\kHG\EK(A) | Q92628 | HYPOTHETICAL PROTEIN KIAA0232 | HLW |
| 148 | K1699k | (K)FG/DRG/N/QLRKMLLQ\N\YLQ]N\R\k(S) | *P70227 | INOSITOL 1,4,5-TRISPHOSPHATE RECEPTOR TYPE 3 | NLW |
| 149 | K50k | (K)F/AADFK]TTA/M\V\V]Q\E\V\N\K(Q) | P49442 | INOSITOL POLYPHOSPHATE 1-PHOSPHATASE | SLW |
| 150 | K933k | (K)T/L]Tk]ED/I]lK(F) | P14735 | INSULIN-DEGRADING ENZYME | HLW |
| 151 | K162k | (K)GWPKT/HPG/GE/QkE/GTEV\ASLQ\l\RG\K(K) | P05019 | INSULIN-LIKE GROWTH FACTOR IB [PRECURSOR] | HLW |
| 152 | K52k K68k | (R)G/IDS/S/YRPS\QkDV/EPPK\S/STK\N\l\S\l\K(Q) | Q96CB8 | INTEGRATOR COMPLEX SUBUNIT 12 | HLW |
| | | | | INTERFERON-INDUCED PROTEIN WITH TETRATRICOPEPTIDE | |
| 153 | K391k | (R)kSENT/AIHH\YLEVA]L]KV\KDRS]PLLR(T) | Q13325 | REPEATS 5 | HVW |
| 154 | K45k | (R)RC/L/l/S/T/DM\VH\H]LEESF/QE/Ik\RA\l\QA\K(D) | Q9UHD0 | INTERLEUKIN-19 [PRECURSOR] | HLW |
| 155 | K608k | (K)EQLDA/L/EK]E]TVASk\LSEM/D\SFNNQLK(C) | Q9NZM3 | INTERSECTIN 2 | HLW |
| 156 | K700k | (K)Q/KRLQEEK\SQ\D]K(T) | Q920R6 | INTERSECTIN-2 | NLW |
| 157 | K209k | (K)IPVGSEEG\Y/R\SLFGQV/L/KD\I]]V\EK(I) | P27352 | INTRINSIC FACTOR [PRECURSOR] | HLW |
| | | | | ISOCITRATE DEHYDROGENASE [NADP], MITOCHONDRIAL | |
| 158 | K205k | (K)M/WK/S/P/NGT\RN\l/L/GGT\VFREPI\CK(N) | *P54071 | [PRECURSOR] | SLW |
| 159 | K334k | (R)E/V/RPSPSKAT/VKYT/ATVTKGAVTY\T\K\A\K(R) | Q92833 | JUMONJI PROTEIN | HLW |
| 160 | K415k | (K)S/E/LS/L/C/D/LAGSERCk\HQK(S) | P97329 | KINESIN FAMILY MEMBER 20A | SLW |
| 161 | K726k K742k | (K)KLL]HAMNK\kE]L]Q\RLQT\AQk(E) | Q9QXL2 | KINESIN FAMILY MEMBER 21A | SLN |
| 162 | K444k | (K)Q/LDDK\DDE/I]NQ]QSQ\k]NE\V(L) | Q12840 | KINESIN HEAVY CHAIN ISOFORM 5A | HVW |
| 163 | K143k | (R)NET/PSGDSQT]l/M\PSN/P/CL\MR(K) | Q8CON1 | KINESIN-LIKE PROTEIN KIF2B | SLC |
| 164 | K245k | (R)MGK/L/HL/VVD/LA\VSSE/RQA]KTG\ATGQ\R(L) | Q9Y496 | KINESIN-LIKE PROTEIN KIF3A | HLW |
| 165 | K277k | (R)KR/TFS/LQG\GG/GGGA\MGG\SGG\Q\GK(G) | P84550 | LADYBIRD HOMEOBOX COREPRESSOR 1 | HLW |
| 166 | K787k | (K)IM/GG/SGTE/VVL/E/KQKS]T]PK(S) | Q9ESV1 | LEUCINE ZIPPER PROTEIN 1 | BVC |
| 167 | K508k | (K)IPAK]lS]QMTNLQEL/HL\CHCPA\K(V) | Q7L1W4 | LEUCINE-RICH REPEAT-CONTAINING PROTEIN 5 [PRECURSOR] | HLW |
| 168 | K209k K214k | (K)NN/MNR/SNT\lQS\GPE]G5]L]VkSQ\SL\kSl\NPE\K(F) | Q498T9 | LEUCINE-RICH REPEAT-CONTAINING PROTEIN 8C | BVC |
| | | | | LIM DOMAIN AND ACTIN-BINDING PROTEIN 1, EPITHELIAL | |
| 169 | K250k | (R)KISE/N]SY\SLDD/L/EIGPG\QLS\S\STFDSEKNEV\SR(R) | Q9UHB6 | PROTEIN LOST IN NEOPLASM | HLW |
| 170 | K407k | (R)C/LEH\P\M\V]LVKF/lN\G/V\LYK/DK(R) | *P53667 | LIM DOMAIN KINASE 1 | HLW |
| 171 | K50k | (R)SGKY]L]A]TE]W\N\TVSK(L) | P61794 | LYSOPHOSPHATIDIC ACID RECEPTOR EDG-2 | LVC |
| 172 | K52k | (K)EAEA/FLEK\Y\G/Y/LNE\Q\VAPk\APTSTR(F) | Q9H239 | MATRIX METALLOPROTEINASE-28 [PRECURSOR] | HLW |

| # | Peptide | ID1 | ID2 | Accession | N | Protein | Tissue |
|---|---|---|---|---|---|---|---|
| 173 | (R)GRQ(T/V/D)(K/V/M)GIPK(E) | K812k | 3 | 10 | *Q14676 | MEDIATOR OF DNA DAMAGE CHECKPOINT PROTEIN 1 | HLW |
| 174 | (K)KVSFSSP/L||LGA|T|/Q(k)K(S) | K52k | 3 | 11 | O15480 | MELANOMA-ASSOCIATED ANTIGEN B3 | HLW |
| 175 | (K)K|I|PI/KR/TD||LKI\H/VVGDYR(D) | K77k | 3 | 14 | Q9CPR8 | MELANOMA-ASSOCIATED ANTIGEN G1 | SLN |
| 176 | (K)K)/PIK\R\TD||L(K\H/VVGDYR(D) | K87k | 3 | 11 | Q9CPR8 | MELANOMA-ASSOCIATED ANTIGEN G1 | SLN |
| 177 | (K)LQ/N/LQT/VR|L/VFK/|\Q/TQTPRKK(T) | K310k | 3 | 11 | Q8N9U0 | MEMBRANE TARGETING TANDEM C2 DOMAIN-CONTAINING PROTEIN 1 | HLW |
| 178 | (K)KGTELL/GV/DA/LGL·I\YD/PE\NR\L/LTPK(I) | K253k | 3 | 11 | *P25240 | MERLIN | HLW |
| 179 | (K)I/AQDLEMY\G|VNYF/T|I|R\NK(K) | K227k | 3 | 10 | *P46662 | MERLIN | SLC |
| 180 | (R)GSEG/K/PV,C|G|E/L/K/KEK(G) | K65k | 3 | 11 | *Q14833 | METABOTROPIC GLUTAMATE RECEPTOR 4 [PRECURSOR] | HLW |
| 181 | (R)VD/GDIILG\GL/VF|VHAK\GERGVA\P\CG\ELKKEK(G) | K57k | 3 | 12 | P70579 | METABOTROPIC GLUTAMATE RECEPTOR 8 [PRECURSOR] | BVM |
| 182 | (K)SS/CKENP/FN/RKPS\PAAS\PV\AT\K\K(A) | K631k | 3 | 10 | Q8N3F8 | MICAL-LIKE PROTEIN 1 | HLW |
| 183 | (K)VIVKKDK\PG|K\V\E|S|KPSVTEK(E) | K594k | 3 | 12 | *P15205 | MICROTUBULE-ASSOCIATED PROTEIN 1B | BVW |
| 184 | (K)Tk|P|E\EK)K(E) | K644k | 2 | 12 | *P15205 | MICROTUBULE-ASSOCIATED PROTEIN 1B | LVN |
| 185 | (K)SKPSA/ASPK/PGA\LK\ESSDKV/S/R\VA\SPkk(K) | K2282k K2283k | 3 | 10 | *P15205 | MICROTUBULE-ASSOCIATED PROTEIN 1B | BVC |
| 186 | (R)QW\|/GKH|RR|PR\TVSF\QAK(E) | K20k K32k | 3 | 12 | Q9CQF8 | MITOCHONDRIAL RIBOSOMAL PROTEIN 63 | NLW |
| 187 | (K)AD/PFSFK/A|RAK/SCG/EK\DSK(G) | K1010k K1015k | 3 | 10 | *O35099 | MITOGEN-ACTIVATED PROTEIN KINASE KINASE 5 | NLW, SLW |
| 188 | (K)KI||K/T/K/k|S|TW\EK(V) | K227k | 3 | 12 | O60669 | MONOCARBOXYLATE TRANSPORTER 2 | HVW |
| 189 | (K)RARA/D/PT/VESEEAF\k|S/RMEVK(V) | K116k | 2 | 11 | Q9R0Q4 | MORTALITY FACTOR 4-LIKE PROTEIN 2 | SLW |
| 190 | (R)A/k/LDSG\R\VLK|Q\SN\NRK(C) | K326k K341k | 3 | 11 | *P09416 | MYC PROTO-ONCOGENE PROTEIN | LVM |
| 191 | (R)GS/GK05/|HHP|A/RTAH/\YG|SLPQK(S) | K209k | 3 | 10 | *P02686 | MYELIN BASIC PROTEIN | HLW |
| 192 | (K)INKSE|S|V/VYADIR\K(D) | K258k | 3 | 12 | Q6AYT8 | MYELIN PROTEIN ZERO-LIKE PROTEIN 1 [PRECURSOR] | BVC, LVN |
| 193 | (K)E/FGGNADVK/KNL/VD/PF/V\NEVS\FA\GK(K) | K392k | 3 | 11 | Q9NZM1 | MYOFERLIN | HLW |
| 194 | (R)EAQNKP/FD|A/K/T/SVFVV/D|P|k\ESYVK(A) | K44k | 3 | 10 | *Q9Y623 | MYOSIN HEAVY CHAIN, SKELETAL MUSCLE, FETAL | HLW |
| 195 | (R)V/FDKE/G/NG/TVMGA\EH·H/V/LV|TLGEK(M) | K119k | 3 | 12 | P60660 | MYOSIN LIGHT POLYPEPTIDE 6 | HLW |
| 196 | (R)G/D/E/V/MV/ELAENGK(k)A) | K67k | 3 | 11 | *Q9JLT0 | MYOSIN-10 | LVN |
| 197 | (K)LK/K/L/EE\EQV/LEVDQMVCK(L) | K989k | 3 | 10 | *P35579 | MYOSIN-9 | HLW |
| 198 | (R)ETNKKQ|I|SKLTI/YO|A|R/PSV\NA\V\ANK(A) | K289k | 3 | 11 | Q13496 | MYOTUBULARIN | HLW |
| 199 | (K)Q/k/G/HY|L|A/GKV/I/GEFPG\VV/HCLD\FQK(M) | K4503k | 3 | 10 | *P20929 | NEBULIN | HLW |
| 200 | (K)GFI/E/L\RLDSLA/FLT\AK(R) | K4016k | 3 | 11 | Q80X84 | NEBULIN-RELATED-ANCHORING PROTEIN | NLW |
| 201 | (K)GFFE/L\RLDSLA/FLT\AK\AK(R) | K808k | 3 | 10 | *Q80X84 | NEBULIN-RELATED-ANCHORING PROTEIN | NLW |
| 202 | (K)GFFE/L\RLDSLA/FLT\AK\AK(R) | K810k | 3 | 11 | Q80X84 | NEBULIN-RELATED-ANCHORING PROTEIN | NLW |
| 203 | (K)KY/../LL/GVN|AEDS|PD|Q\SGIVADK(S) | K554k | 3 | 10 | O95631 | NETRIN-1 [PRECURSOR] | HLW |
| 204 | (R)LLQ/SAFSKN|ALSKQ\SPK|K\SP\SAK(L) | K677k K682k | 3 | 11 | P63239 | NEUROENDOCRINE CONVERTASE 1 [PRECURSOR] | SLW |
| 205 | (R)N/GVG/LEFNH/L|FGYGV\LD\AG/A\MV\KMA\k(D) | K454k | 3 | 14 | P16519 | NEUROENDOCRINE CONVERTASE 2 [PRECURSOR] | HLW |
| 206 | (K)E/EAk/SPGEAKS/PGEAK\SP/A\EA\KSPGNEAK(S) | K522k K528k | 3 | 11 | P19246 | NEUROFILAMENT TRIPLET H PROTEIN | SLW |
| 207 | (K)AST/DNSPSS\K/A\EDAPVAK\EEP\K(Q) | K162k | 3 | 13 | *P17677 | NEUROMODULIN | BVM, LVC, LVN |
| 208 | (K)DQTQKAAT|G\PFD/R/E\HLL\M\Y\LEK(E) | K58k | 3 | 12 | Q9NZR1 | NEURONAL TROPOMODULIN | HVW |
| 209 | (R)SN/SE/I/L/K/QFT/LRE|LRNK(R) | K683k | 3 | 11 | Q8R151 | NFX1-TYPE ZINC FINGER-CONTAINING PROTEIN 1 | SLN |
| 210 | (R)FG|S|KAHMERV/EEV|INK(E) | K391k | 3 | 10 | *P29475 | NITRIC-OXIDE SYNTHASE | HLW |
| 211 | (R)GGDVSD/SKQFVTYYPL|VE/D\KEEV\Q\RkR) | K338k | 3 | 11 | *Q00653 | NUCLEAR FACTOR NF-KAPPA-B P100 SUBUNIT | HLW |
| 212 | (K)Q/LLTGNT/DK/P/G\MIDRVL\NS\PL\LS\NK(T) | K677k | 3 | 13 | P48552 | NUCLEAR FACTOR RIP140 | HLW |
| 213 | (R)SGTSS/GAG/G|S|NTRGAPV\VPEL|GkPR(Q) | K1505k | 3 | 10 | *Q9WU42 | NUCLEAR RECEPTOR COREPRESSOR 2 | SLW |
| 214 | (R)C/KQLRR/A/A\L\GR\M/CLT\A\AK(R) | K1277k K1301k | 3 | 14 | Q99P77 | NUCLEOLAR GTP-BINDING PROTEIN 1 | BVM, LVC, LVN |
| 215 | (R)VGDLILAH/L||HkKCPYS/VP|FYPN\TFVK(E) | K526k K527k | 3 | 12 | Q53G57 | NUCLEOPORIN GLE1 | HVW |
| 216 | (K)QVKGSA/D|Y/A\SK(K) | K495k | 3 | 12 | *Q6P6T5 | OCCLUDIN | LVM |
| 217 | (K)QVKGSA/D|Y/A\SK(K) | K497k | 3 | 11 | *Q6P6T5 | OCCLUDIN | LVN |
| 218 | (R)I/V|SSIFKVPSS|Q|SI\HK(A) | K236k | 3 | 12 | P23272 | OLFACTORY RECEPTOR-LIKE PROTEIN 19 | LVC |
| 219 | (K)PY/VAK/L||ELFQN/GA/EV\P\PK\KCAR(V) | K61k K65k | 3 | 10 | *Q921N2 | ORIGIN RECOGNITION COMPLEX SUBUNIT 1 | SLW |
| 220 | (K)LFNYN/K\VLV\MNTGVE/A/GETACK\L\VARR(W) | K135k | 3 | 11 | P04182 | ORNITHINE AMINOTRANSFERASE, MITOCHONDRIAL [PRECURSOR] | BVC |
| 221 | (K)EMN/I|L|EL|SH/K\MMAV\K(K) | K1023k K1024k | 3 | 12 | Q9UPQ7 | PDZ DOMAIN-CONTAINING RING FINGER PROTEIN 3 | HLW |
| 222 | (R)GTD/SEHT\H/K/A\HI|L|V\PLEGT\SK\k(R) | K672k | 3 | 16 | Q96RV3 | PECANEX-LIKE PROTEIN 1 | HLW |

*Fig. 22E*

| # | Sequence | ID | | | Accession | Protein | Tissue |
|---|---|---|---|---|---|---|---|
| 223 | (R)K/S/V/R/PG\AS/Y/V\KR(Q) | K180k | | 3 | 11 | Q8NEY8 | PERIPHILIN 1 | HLW |
| 224 | (K)GATA/G/ASH\KGD/EVPP\IKK\INT\KAPGK(Q) | K198k | | 3 | 12 | O75167 | PHOSPHATASE AND ACTIN REGULATOR 2 | HLW |
| 225 | (R)EIDK/R/MNS\IK/P/DI\QLR\K(T) | K567k | | 3 | 11 | *Q63787 | PHOSPHATIDYLINOSITOL 3-KINASE REGULATORY SUBUNIT ALPHA | LVC, LVM |
| 226 | (K)K/QAAEYRE\DKRMN\S\IKPDL\I\QLR(K) | K551k | | 3 | 10 | *P27986 | PHOSPHATIDYLINOSITOL 3-KINASE REGULATORY SUBUNIT ALPHA | HLW |
| 227 | (R)L/E/Q\D/LLKQALDN\IR/EIDK\K(M) | K294k | | 3 | 10 | *Q63789 | PHOSPHATIDYLINOSITOL 3-KINASE REGULATORY SUBUNIT GAMMA | LVN |
| 228 | (R)EP/LRT/PL\KDV\L\KTHEL\CLVK(S) | K256k | | 3 | 11 | Q9ERS5 | PLECKSTRIN HOMOLOGY DOMAIN-CONTAINING FAMILY A MEMBER 2 | NLW, SLW |
| 229 | (K)I/K\PTSA/W/NL\AQ\KHV\K(L) | K667k | | 3 | 11 | *P54277 | PMS1 PROTEIN HOMOLOG 1 | HLW |
| 230 | (R)SFP/SEKR\VG/VL\S/SYPSDV\S/Y\R\GL\RG\SQDK(L) | K474k | | 3 | 11 | P54279 | PMS1 PROTEIN HOMOLOG 2 | NLW |
| 231 | (R)VDRMEH/S\I/GS\IVS/K\D/AVIV\IK\LE\IMERAK(L) | K874k | | 3 | 11 | *Q13563 | POLYCYSTIN-2 | HLW |
| 232 | (K)ID/KN\IE/D/R\KVK(D) | K555k | | 3 | 10 | *Q96RN5 | POSITIVE COFACTOR 2 GLUTAMINE/Q-RICH-ASSOCIATED PROTEIN | HLW |
| 233 | (K)GDPF/LAS/PTS\DREI\IA\P\K\VKE\R(T) | K364k | | 3 | 11 | *Q12809 | POTASSIUM VOLTAGE-GATED CHANNEL SUBFAMILY H MEMBER 2 | HLW |
| 234 | (K)LK\NN/N/V/F/VDKPAFP/EYK\V\AS\DAK(K) | K208k | | 3 | 11 | *Q96L42 | POTASSIUM VOLTAGE-GATED CHANNEL SUBFAMILY H MEMBER 8 | HLW |
| 235 | (R)DGALLIAG/S/EAP\KR\GSVLSK/PRT\GG\AG\A\GKPPK(R) | K56k | | 3 | 10 | *Q92351 | POTASSIUM VOLTAGE-GATED CHANNEL SUBFAMILY KQT MEMBER 2 | SLW |
| 236 | (K)CP/K/PS/AQ/EITN\ADSL\QLLEKE\VR\V\WF\CNR\R(Q) | K442k | | 3 | 10 | *P31361 | POU DOMAIN, CLASS 3, TRANSCRIPTION FACTOR 3 | NLW |
| 237 | (R)EYSVK\E/ILKLDSN/PS\KV\GVK(D) | K219k | | 3 | 11 | O75626 | PR DOMAIN ZINC FINGER PROTEIN 1 | HLW |
| 238 | (R)GVSSQ/E/T/A/G\GASA/HLVNF\KG\TDTVAGL\AL\IK\K(Y) | K216k | | 3 | 12 | P43490 | PRE-B CELL ENHANCING FACTOR [PRECURSOR] | HLW |
| 239 | (K)YVEAKDCLN/V\I\L/N\K\SM\E\GK(E) | K47k | | 3 | 13 | Q99471 | PREFOLDIN SUBUNIT 5 | HLW |
| 240 | (K)YVEAKDC/L\WVLN\N/K\SN\E\GK(E) | K55k | | 3 | 13 | Q99471 | PREFOLDIN SUBUNIT 5 | HLW |
| 241 | (K)QYYK/V\V\INSYPLAH/K\V\FLEEK(T) | K281k | | 3 | 11 | Q9UHI6 | PROBABLE ATP-DEPENDENT RNA HELICASE DDX20 | HLW |
| 242 | (R)WK\VAT/SK\EA\I\I\QLR(I) | K953k | | 3 | 11 | Q62780 | PROBABLE ATP-DEPENDENT RNA HELICASE DDX46 | LVN |
| 243 | (R)ANQS\I\V\PEDLVVM/AEQY/KL\N\QQK(R) | K610k | | 3 | 13 | Q86TM3 | PROBABLE ATP-DEPENDENT RNA HELICASE DDX53 | HLW |
| 244 | (R)G/G/D/G\NSI/GGVG\Q\K\VRLMK(E) | K89k | | 3 | 12 | O00469 | PROCOLLAGEN-LYSINE,2-OXOGLUTARATE 5-DIOXYGENASE 2 [PRECURSOR] | HLW |
| 245 | (R)SVP/AT/KGLLSPLMSRP\EIKV/GDQSGTGRGQK\VLP\K(G) | K184k K188k | | 3 | 12 | *Q00175 | PROGESTERONE RECEPTOR | SLM |
| 246 | (K)VT\VV/N\S/\KP/SVSVPT\E\GK(R) | K657k | | 3 | 14 | O95447 | PROTEIN C21ORF13 | HLW |
| 247 | (R)EMV/V\Q\IY/ISA/TSK\SIVGSK/VL\GGL\K\NSK(H) | K155k | | 3 | 13 | O70566 | PROTEIN DIAPHANOUS HOMOLOG 2 | SLW |
| 248 | (R)AVEKYSVK/P/EH\PN/LGSCN\P/S\L\YNT\FASK(Q) | K304k | | 3 | 12 | Q8BVV6 | PROTEIN KIAA0586 | HLW |
| 249 | (R)D/NM/S\VLVC\FS\NAPK\VS\DEAV\KK(D) | K300k | | 3 | 12 | O75688 | PROTEIN PHOSPHATASE 2C BETA ISOFORM, PROTEIN PHOSPHATASE 1B | HLW |
| 250 | (K)NEAA/F\L\SMTDSK\T\E\GK(F) | K319k | | 3 | 15 | P35247 | PULMONARY SURFACTANT-ASSOCIATED PROTEIN D [PRECURSOR] | HLW |
| 251 | (K)LKILM/D/KPE/MNV\V\L/K/NVK\P\DVQWVK(L) | K558k | | 3 | 12 | P55786 | PUROMYCIN-SENSITIVE AMINOPEPTIDASE | HLW |
| 252 | (R)K/ELN/K\ILE\GR\S\K(I) | K429k K433k | | 3 | 11 | P10515 | PYRUVATE DEHYDROGENASE COMPLEX E2 SUBUNIT | HLW |
| 253 | (R)DL/K\LEN/LM\L\DK\DGH/I/K(I) | K289k | | 3 | 10 | *P47196 | RAC-ALPHA SERINE/THREONINE-PROTEIN KINASE | BVS |
| 254 | (R)FVG/AEWVS\A\LDYLH/SG\RV\VRDLK(L) | K266k | | 3 | 10 | *Q63484 | RAC-GAMMA SERINE/THREONINE-PROTEIN KINASE | BVN |
| 255 | (R)DMK/S/N/N/IFLHEGLTV\K/\GDFGLA\TV\K\SR(W) | K483k | | 3 | 10 | *P11345 | RAF PROTO-ONCOGENE SERINE/THREONINE-PROTEIN KINASE | LVN |
| 256 | (R)LEGNTV\G/V/E\AARV\I\A\K\ALEK(K) | K71k | | 3 | 11 | P46060 | RAN GTPASE-ACTIVATING PROTEIN 1 | HLW |
| 257 | (R)EV/H/C\L\IG/M/KLSED\GTVT\GF\V\K(V) | K218k | | 3 | 11 | O35141 | RAS ASSOCIATION DOMAIN-CONTAINING FAMILY PROTEIN 5 | LVC |
| 258 | (R)IT/L\T/L/AK/V\QN\L/ANF\S\K(F) | K613k | | 3 | 12 | Q96PV0 | RAS GTPASE-ACTIVATING PROTEIN SYNGAP | HLW |
| 259 | (-)MA/K/S/AEVK\L\AIFGRAGVGK\S\AIVVR(F) | K8k | | 3 | 11 | Q8R367 | RAS-RELATED AND ESTROGEN-REGULATED GROWTH INHIBITOR | NLW, SLW |

Fig. 22H

| # | Sequence | ID | # | Accession | Description | Code |
|---|---|---|---|---|---|---|
| 260 | (R)(L/L)K/KKE/Q\NK/MNG/V\L\S(-) | K211k | 3 | Q5PQP2 | RECEPTOR-BINDING CANCER ANTIGEN EXPRESSED ON SISO CELLS | LVM, LVN |
| 261 | (K)ATH\PPPAS\PS/S/L\VK/VPSSA\T\GkR(Q) | K492k | 3 | O43566 | REGULATOR OF G-PROTEIN SIGNALING 14 | HLW |
| 262 | (K)EE/L\NN\RLK\DTQ\EQL/S\K\L\VK(D) | K996k | 3 | Q62868 | RHO-ASSOCIATED PROTEIN KINASE 2 | BVN |
| 263 | (R)EA/L\/G/D/K\APP\K\P\VP\(T) | K103k | 3 | Q5RJS9 | RIBOSOME PRODUCTION FACTOR 1 | LVN |
|   | (K)L/AK\QNT\NK\A\K\EW\I L\R(K), |   |   |   |   |   |
| 264 | (K)L/AK/QNT/NK\AK\EVN\L\R(K) | K198k K203k; K3 | 11 | Q9D657 | RIBOSOMERE CYCLING FACTOR, MITOCHONDRIAL [PRECURSOR] | SVW |
| 265 | (K)LDTP/ATSD\P/L/SDRGG/RkKR\K(R) | K786k | 3 | Q5XI59 | RING FINGER PROTEIN 10 | LVN |
| 266 | (R)RNH/C/F\Q\DFkEE\KP\QLENK(T) | K594k | 3 | Q8IYF1 | RNA POLYMERASE II TRANSCRIPTION FACTOR SIII SUBUNIT A2 | HLW |
| 267 | (R)Q\KCHS/P/PP/K\P\EPFPFGQS/G\Q\K\PALNGGKK(V) | K76k | 3 | Q63068 | RNA U SMALL NUCLEAR RNA EXPORT ADAPTER PROTEIN | BVM |
| 268 | (K)F/EAKLMPEVE\CFS\P\.\DL\FMVK(I) | K78k | 3 | Q6MXK5 | RNA/RNP COMPLEX-1-INTERACTING PHOSPHATASE | SLM |
| 269 | (K)VAS\SFDA/S/KAK\\P/S/Q/FSGK(I) | K322k | 3 | Q92545 | RW1 PROTEIN | HLW |
| 270 | (K)RLAV/F/S/Q\PIINK\V\KP\QLLK(T) | K3309k | 3 | Q92736 | RYANODINE RECEPTOR 2 | HLW |
| 271 | (R)K/AQ/A\AE\MKAA\NE\AE\GK(V) | K4324k | 3 | Q15413 | RYANODINE RECEPTOR 3 | HLW |
| 272 | (K)YL/KJ/E\T\NP\SLAQ\DTV\\\K(K) | K1715k | 3 | Q9NZJ4 | SACSIN | HLW |
| 273 | (R)K/GE\I\A\A\S/IAT\VHMR/P/YRKKS(-) | K283k | 3 | O75880 | SCO1 PROTEIN HOMOLOG, MITOCHONDRIAL [PRECURSOR] | HLW |
| 274 | (K)S/D/G\V/HK\RP/DJ/RK\SR(I) | K188k | 3 | Q9QX72 | SECIS-BINDING PROTEIN 2 | LVN |
| 275 | (K)RKD\T/KR\L\VLHMK(N) | K238k | 2 | Q5T4F7 | SECRETED FRIZZLED-RELATED PROTEIN 5 [PRECURSOR] | HLW |
| 276 | (K)DS/TKD/D/NS\NLGG/K/T\DE\A\K\GVK(T) | K400k | 3 | P47868 | SECRETOGRANIN-3 [PRECURSOR] | BVN, LVC |
| 277 | (K)DS/TKDD/NS\NL/G/G\KATD\EA\K\GVK(T) | K391k | 3 | P47868 | SECRETOGRANIN-3 [PRECURSOR] | LVN |
| 278 | (R)HGYTSS\L\LELP0\N\I\LNFV\K\K(H) | K395k | 3 | Q9C0C4 | SEMAPHORIN 4C [PRECURSOR] | HLW |
| 279 | (R)D/IkPDN\VLLD\VNG/H\VR\LAD\FGS\CLK(M) | K202k | 3 | Q7T50 | SERINE/THREONINE-PROTEIN KINASE MRCK BETA | NLW |
| 280 | (R)L/LS/AVA/KA\PD/R\(A) | K251k | 3 | *Q63433 | SERINE/THREONINE-PROTEIN KINASE N1 | LVN |
| 281 | (K)LDNT/V/VGQTWKP/ISNQSWD\Q\K(F) | K411k | 3 | *O08874 | SERINE/THREONINE-PROTEIN KINASE N2 | BVS |
| 282 | (K)E/KKP\KS\PSKD\AS/S\G/KENR(S) | K337k | 3 | Q61136 | SERINE/THREONINE-PROTEIN KINASE PRP4 HOMOLOG | SLW |
| 283 | (R)D/LKPE/N/J/L/D\CQGHVV/LT\DF\GLCK(E) | K242k | 3 | *Q9HBY8 | SERINE/THREONINE-PROTEIN KINASE SGK2 | HLW |
| 284 | (K)QNN\TA/K\LVK/VQ/LSKS\SEDE\EL\RK(L) | K122k | 3 | Q96QC0 | SERINE/THREONINE-PROTEIN PHOSPHATASE 1 REGULATORY SUBUNIT 10 | HLW |
|   |   |   |   |   | SERINE/THREONINE-PROTEIN PHOSPHATASE 1 REGULATORY |   |
| 285 | (K)EE/GK/SR\T\LP\E\P\L\T\EVK(A) | K165k | 3 | O55000 | SUBUNIT 10 | LVN |
| 286 | (K)A/OGK\KGS/AG/NTW\S\Q\L/S\NN\MK(D) | K212k | 3 | Q9Y6X0 | SET-BINDING PROTEIN | HLW |
| 287 | (K)S/FH/LS\PR\G\PPT\SEPP/V\V\PANKP\K(F) | K358k | 3 | P78314 | SH3 DOMAIN-BINDING PROTEIN 2 | HLW |
| 288 | (R)CKSE/G/TLID\LSE\GFSET\SF\ND\VVK(V) | K39k | 3 | Q9JJS5 | SH3 DOMAIN-BINDING PROTEIN 4 | LVW |
| 289 | (R)A/K/L/TML\N/TVS/K\RGQVAK(N) | K82k | 3 | O35964 | SH3-CONTAINING GRB2-LIKE PROTEIN 1, ENDOPHILIN-A2 | BVM |
| 290 | (R)AI/D/E/PNN/CK/G/\R\CE\K(Q) | K560k | 3 | Q9UL62 | SHORT TRANSIENT RECEPTOR POTENTIAL CHANNEL 5 | HLW |
| 291 | (K)EVCTALL\EA/DVNIK\L\VK\Q\L\LR(E) | K47k | 3 | Q6AY85 | SIGNAL RECOGNITION PARTICLE 54 KDA PROTEIN | BVS |
| 292 | (R)FNQ/AQEG/NIQMTV\M\L\D/KQK\ELD\SK(V) | K145k | 3 | *P42225 | SIGNAL TRANSDUCER AND ACTIVATOR OF TRANSCRIPTION 1 | SLW |
| 293 | (-)ME/NLQSKF\SLV/QGS/N\KKL\NG\M/ED\DGSPPV\K(K) | K7k K30k | 3 | *Q60665 | SKI-LIKE PROTEIN | SLW |
| 294 | (K)LS/S/GN/SKL/SS\SKFSN/PN\SSS\K(R) | K137k | 3 | O15444 | SMALL INDUCIBLE CYTOKINE A25 [PRECURSOR] | HLW |
| 295 | (K)D/L/TT/AEK\L\kR\ET\PWK(I) | K1014k | 3 | Q13621 | SOLUTE CARRIER FAMILY 12 MEMBER 1 | HVW |
| 296 | (R)KLL/SQL\VAR/k\VQDMM\NK(Q) | K51k | 3 | P16043 | SOMATOLIBERIN [PRECURSOR] | SLW |
| 297 | (K)SAK/\VVRR\P\R/TAK(M) | K160k | 3 | P30680 | SOMATOSTATIN RECEPTOR TYPE 2 | LVC, LVM, LVN |
| 298 | (R)L/K\GLA\LQRNQGR\FVGA\AEVQR(F) | K250k | 3 | *P16086 | SPECTRIN ALPHA CHAIN, BRAIN | BVC |
| 299 | (R)EVT/MK/K/G/D\V\LTLLS\S\NN\KDVVVK(V) | K1012k K1016k | 3 | *P02549 | SPECTRIN ALPHA CHAIN, ERYTHROCYTE | HLW |
| 300 | (K)YSHL\GKG/A/A/R\DAA\HMLQA/NK/T/MGC\VP\VANKR(D) | K177k | 3 | Q7TNE3 | SPERM-ASSOCIATED ANTIGEN 7 | SLW |
| 301 | (K)G/P/A/VP/PE/LD\KH/FL\CEA\C\GK(C) | K154k | 3 | Q9C0Q4 | SPROUTY HOMOLOG 4 | HLW |
| 302 | (K)KE/QA/L/QLAQ\\kMGFP/PNI\VE/SAAE\NMVK(L) | K225k K242k | 3 | Q9P2R7 | SUCCINYL-COA LIGASE [ADP-FORMING] BETA-CHAIN, MITOCHONDRIAL [PRECURSOR] | HLW |

| # | Sequence | Position | Col1 | Col2 | Accession | Protein | Code |
|---|---|---|---|---|---|---|---|
| 303 | (K)R/DF/G\SFE/K\F/K\EK(L) | K132k | 3 | 11 | *P09671 | SUPEROXIDE DISMUTASE [MN], MITOCHONDRIAL [PRECURSOR] | NLW, SLW |
| 304 | (K)R/DF/G\S/FE/K\F\K\EK(L) | K132k | 3 | 10 | *P07895 | SUPEROXIDE DISMUTASE [MN], MITOCHONDRIAL [PRECURSOR] | BVW, LVN |
| 305 | (R)KK/N/S/L\KDCVAGPVLGV\THFULTKTDNSVYL\k(L) | K90k K98k | 3 | 11 | C91YU8 | SUPPRESSOR OF SWI4 1 HOMOLOG | NLW |
| 306 | (K)LPV/K\VVQ\K\NDP\F\VVD\CGSD\K(L) | K1815k | 3 | 11 | O14497 | SWI-SNF COMPLEX PROTEIN P270 | HLW |
| 307 | (K)TK/QSE\N\L\K\QSIEK(Q) | K304k | 3 | 11 | Q15431 | SYNAPTONEMAL COMPLEX PROTEIN 1 | HLW |
| 308 | (K)M/G\k\KKT/L\V\V\kK | K643k K650k | 2 | 12 | Q9HCH5 | SYNAPTOTAGMIN-LIKE PROTEIN 2 | HLW |
| 309 | (K)ID/SI\ADHV\NS/A/AVNVEEGT\k/NLG\kAAkY\K(L) | K223k K226k | 3 | 12 | P56962 | SYNTAXIN-17 | HLW |
| 310 | (R)k/G/P/EDTAQLVAH/AV/LA\k\L\N\A\FK(A) | K193k K213k | 3 | 13 | Q64324 | SYNTAXIN-BINDING PROTEIN 2 | SLW |
| 311 | (K)S/AYS/ERL/k/F\NVA/J/k\I\NDRK(K) | K41k | 3 | 11 | Q9BXA7 | TESTIS-SPECIFIC SERINE/THREONINE-PROTEIN KINASE 1 | HLW |
| 312 | (K)KKPNPg/k\DK\RT/YEP\SSA\TP/VA\T\R(S) | K1909k | 3 | 11 | P53804 | TETRATRICOPEPTIDE REPEAT PROTEIN 3 | HLW |
| 313 | (K)EPHVEQ\TK\F\R\L\N\SE\GK(L) | K542k | 3 | 11 | Q8WY91 | THAP DOMAIN-CONTAINING PROTEIN 4 | HLW |
| 314 | (R)FKQ/E/G\VL/NSKV/G\M/DYR(S) | K636k | 3 | 11 | P52888 | THIMET OLIGOPEPTIDASE | HLW |
| 315 | (K)N/ALALF/VLPKE\GVQM/ELSVE\AA\MSSV\k(T) | K287k | 3 | 12 | P05543 | THYROXINE-BINDING GLOBULIN [PRECURSOR] | HLW |
| 316 | (K)QLEGA/C/YSG\KV\UWKV/T\DY\RV\K(R) | K409k | 3 | 12 | P70191 | TNF RECEPTOR-ASSOCIATED FACTOR 5 | SLW |
| 317 | (K)E/D/VSE/SVGA/SGQRP/VFGPVHk\Q\EQL\K(L) | K280k | 3 | 11 | Q9UPN9 | TRANSCRIPTION INTERMEDIARY FACTOR 1-GAMMA | HLW |
| 318 | (R)MITN/E/Q/DLKMFLLSKG/A/SkEVA\S\V\NS\R(Y) | K118k | 3 | 11 | Q99551 | TRANSCRIPTION TERMINATION FACTOR, MITOCHONDRIAL [PRECURSOR] | HLW |
| 319 | (K)QPGQDC/P/H\SCNLLCHPGP\CP\P\CPAFMTK(T) | K4331k | 3 | 10 | *Q12986 | TRANSCRIPTIONAL REPRESSOR NF-X1 | HLW |
| 320 | (R)S/K/W/HIPM\PSGK/G\YFN\F\GK(I) | K50k | 3 | 12 | Q8BXN9 | TRANSMEMBRANE PROTEIN 87A [PRECURSOR] | NLW, SLW |
| 321 | (R)K\QA\MWWRVP\S\DL\K(M) | K661k | 2 | 10 | *O94972 | TRIPARTITE MOTIF PROTEIN 37 | HVW |
| 322 | (R)ELNNKL\YP\THA/C/REYLK(N) | K183k | 3 | 11 | *P17752 | TRYPTOPHAN 5-HYDROXYLASE 1 | HLW |
| 323 | (-)M/A/KPT\SK\DS/G\L/kAE\K(F) | K12k | 3 | 12 | *Q61037 | TUBERIN | NLW |
| 324 | (R)GDV/VP\k\D\V\N\VA/A/A/k\T\K(R) | K326k K336k | 3 | 12 | Q6AY56 | TUBULIN ALPHA-8 CHAIN | BVS |
| 325 | (R)L-HEEWLL/R\E\E\K\A\QEEYFR\K(K) | K77k | 3 | 11 | Q64707 | U2 SMALL NUCLEAR RIBONUCLEOPROTEIN AUXILIARY FACTOR 35 KDA SUBUNIT-RELATED PROTEIN 1 | SLC |
| 326 | (R)GK/M/VSH/Q/CCKE\VU\D\YRSDR\R(E) | K327k | 3 | 12 | *Q93009 | UBIQUITIN CARBOXYL-TERMINAL HYDROLASE 7 | HLW |
| 327 | (R)SI\P/VLAkWQ/N/SYSIK(V) | K108k | 3 | 13 | Q15819 | UBIQUITIN-CONJUGATING ENZYME E2 VARIANT 2 | HLW |
| 328 | (K)FSL/QDPP\N\K\KPK(V) | K490k K492k | 3 | 11 | *O70199 | UDP-GLUCOSE 6-DEHYDROGENASE | BVC |
| 329 | (K)K/GKAES\CGHAT/V/S\SE/K\k\L\K(T) | K368k K369k | 3 | 12 | Q9NTX9 | UNCHARACTERIZED PROTEIN C20RF177 | HLW |
| 330 | (R)FQ/EIAEK\N\MEK/N\H\I\EK(S) | K695k K701k | 3 | 13 | Q6TFL3 | UNCHARACTERIZED PROTEIN C9ORF93 | HVW |
| 331 | (R)LLk\N\T\E/NM\KGFFGG\LLETK\LK(G) | K232k | 3 | 12 | Q8R0A7 | UNCHARACTERIZED PROTEIN KIAA0513 | SVW |
| 332 | (K)F/ALPY\IRD\VAKRV/K/AG\L\Q\K(A) | K242k | 3 | 12 | P70697 | UROPORPHYRINOGEN DECARBOXYLASE | SLM |
| 333 | (K)KMM\SNQYVP\VA\T\H\EEVK(M) | K863k | 3 | 11 | Q9BZF9 | UVEAL AUTOANTIGEN WITH COILED-COIL DOMAINS AND ANKYRIN REPEATS PROTEIN | HVW |
| 334 | (K)HEKELM/GL/K\S/N/I/A\ELKK(Q) | K826k K827k | 3 | 12 | Q8CGB3 | UVEAL AUTOANTIGEN WITH COILED-COIL DOMAINS AND ANKYRIN REPEATS PROTEIN | SLM, SLN |
| 335 | (K)EIHVNIEA\T/F\K/P\SS/EEYLH\I\T\E\PPSLS\PDT\K(L) | K2897k | 3 | 11 | P13611 | VERSICAN CORE PROTEIN [PRECURSOR] | HLW |
| 336 | (K)A/G/EA/ST\ET/K/KU/k\F\K\EV\K(N) | K250k | 3 | 13 | Q61048 | WW DOMAIN-BINDING PROTEIN 4 | SLC |
| 337 | (K)Y/GLLPSTS\NDFKYG\L\L\P\GA\YPNDF\k(Y) | K663k | 3 | 14 | Q9WTY8 | ZINC FINGER AND BTB DOMAIN-CONTAINING PROTEIN 10 | LVC |
| 338 | (K)HQRI\H\S\G/EK\PY\VCD\VCGK(A) | K737k | 3 | 12 | Q8WTR7 | ZINC FINGER PROTEIN 473 | HLW |
| 339 | (K)ED/QPG/HTk\DL\S/GPTKES/SK/GSPkM\PK(S) | K324k K327k | 3 | 11 | Q92610 | ZINC FINGER PROTEIN 592 | HLW |
| 340 | (K)VE/S/ELLCTRU/L\L\GG\GS/YKCM\K(Q) | K257k | 3 | 11 | *P70338 | ZINC FINGER PROTEIN GFI-1 | SLM |
| 341 | (R)SPGPDYSLR/L/ETVPAPGRAEGG/AV/SVA\GES\kMEPR(E) | K49k | 3 | 10 | *P70338 | ZINC FINGER PROTEIN GFI-1 | NLW |
| 342 | (K)KAE/NSIGKC\PTRTD/VAS\EK(A) | K22k | 3 | 12 | *Q61502 | ZINC FINGER PROTEIN GLI3 | SLC |
| 343 | (K)MD/L/NN/NS/LKT/KA/QV\PMVLT\AGP\k(W) | K141k K143k | 3 | 12 | Q8WW38 | ZINC FINGER PROTEIN ZFPM2 | HLW |

SEQUENCE LISTING

<160> NUMBER OF SEQ ID NOS: 350

<210> SEQ ID NO 1
<211> LENGTH: 22
<212> TYPE: PRT
<213> ORGANISM: Homo sapiens

<400> SEQUENCE: 1

Lys Gln Asn Glu Gln Ala Lys Glu Met Gln Gln Met Val Lys Leu Glu
 1               5                   10                  15

Ala Glu Met Asp Arg Arg
            20

<210> SEQ ID NO 2
<211> LENGTH: 30
<212> TYPE: PRT
<213> ORGANISM: Rattus norvegicus

<400> SEQUENCE: 2

Lys Tyr His Asn Gly Thr Lys Met Val Ser Ala Asp Ala Tyr Lys Ile
 1               5                   10                  15

Ile Pro Gly Ser Arg Ala Asp Phe Ser Glu Glu Tyr Lys Arg
            20                  25                  30

<210> SEQ ID NO 3
<211> LENGTH: 23
<212> TYPE: PRT
<213> ORGANISM: Homo sapiens

<400> SEQUENCE: 3

Lys Thr Pro Val Gly Phe Ile Gly Leu Gly Asn Met Gly Asn Pro Met
 1               5                   10                  15

Ala Lys Asn Leu Met Lys His
            20

<210> SEQ ID NO 4
<211> LENGTH: 25
<212> TYPE: PRT
<213> ORGANISM: Homo sapiens

<400> SEQUENCE: 4

Lys Gln Tyr Lys Lys Ala His Leu Gly Thr Ala Leu Lys Ala Asn Pro
 1               5                   10                  15

Phe Gly Gly Ala Ser His Ala Lys Gly
            20                  25

<210> SEQ ID NO 5
<211> LENGTH: 17
<212> TYPE: PRT
<213> ORGANISM: Homo sapiens

<400> SEQUENCE: 5

Lys Tyr Ala Lys Tyr Leu Pro His Ser Ala Gly Arg Tyr Ala Ala Lys
 1               5                   10                  15

Arg

<210> SEQ ID NO 6
<211> LENGTH: 26
<212> TYPE: PRT
<213> ORGANISM: Homo sapiens

<400> SEQUENCE: 6

```
Lys Met Asp Glu Val Tyr Lys Val Ile Leu Pro Asn Phe Leu Ala Asn
1               5                   10                  15
Gly Gly Asp Gly Phe Gln Met Ile Lys Asp
            20                  25

<210> SEQ ID NO 7
<211> LENGTH: 21
<212> TYPE: PRT
<213> ORGANISM: Rattus norvegicus

<400> SEQUENCE: 7

Arg Leu Lys Val Gly Leu Gln Val Val Ala Val Lys Ala Pro Gly Phe
1               5                   10                  15
Gly Asp Asn Arg Lys
            20

<210> SEQ ID NO 8
<211> LENGTH: 26
<212> TYPE: PRT
<213> ORGANISM: Homo sapiens

<400> SEQUENCE: 8

Lys Asn Lys Thr Gly Ala Ala Pro Ile Ile Asp Val Val Arg Ser Gly
1               5                   10                  15
Tyr Tyr Lys Val Leu Gly Lys Gly Lys Leu
            20                  25

<210> SEQ ID NO 9
<211> LENGTH: 25
<212> TYPE: PRT
<213> ORGANISM: Mus musculus

<400> SEQUENCE: 9

Arg Asp Val Tyr Arg Lys Gly Arg Val Phe Ala Asn Ala Pro Asp Ser
1               5                   10                  15
Ala Cys Val Ile Gly Leu Arg Lys Lys
            20                  25

<210> SEQ ID NO 10
<211> LENGTH: 27
<212> TYPE: PRT
<213> ORGANISM: Homo sapiens

<400> SEQUENCE: 10

Lys Glu Ser Gln Pro Glu Met Ser Pro Ala Leu His Leu Met Gln Asn
1               5                   10                  15
Leu Asp Thr Lys Ser Lys Leu Arg Pro Lys Arg
            20                  25

<210> SEQ ID NO 11
<211> LENGTH: 26
<212> TYPE: PRT
<213> ORGANISM: Rattus norvegicus

<400> SEQUENCE: 11

Arg Phe Gly Gly Asn Lys Val Ile Glu Lys Val Leu Ile Ala Asn Asn
1               5                   10                  15
Gly Ile Ala Ala Val Lys Cys Met Arg Ser
            20                  25

<210> SEQ ID NO 12
<211> LENGTH: 19
```

```
<212> TYPE: PRT
<213> ORGANISM: Rattus norvegicus

<400> SEQUENCE: 12

Arg Lys Leu Gly Leu Glu Gln Gln His Lys Gln Glu Gln Ile Gln Glu
1               5                   10                  15

His Lys Leu

<210> SEQ ID NO 13
<211> LENGTH: 30
<212> TYPE: PRT
<213> ORGANISM: Homo sapiens

<400> SEQUENCE: 13

Arg Lys Ile Lys Glu Asn Glu Phe Ser Pro Thr Asn Ser Thr Ser Gln
1               5                   10                  15

Thr Val Ser Ser Gly Ala Thr Asn Gly Ala Glu Ser Lys Thr
            20                  25                  30

<210> SEQ ID NO 14
<211> LENGTH: 24
<212> TYPE: PRT
<213> ORGANISM: Homo sapiens

<400> SEQUENCE: 14

Arg Leu Gln Gly Pro Lys Ala Gly Gln Met Glu Asn Thr Asn Asn Phe
1               5                   10                  15

His Asn Leu Tyr Val Lys Arg His
            20

<210> SEQ ID NO 15
<211> LENGTH: 24
<212> TYPE: PRT
<213> ORGANISM: Rattus norvegicus

<400> SEQUENCE: 15

Lys Lys Leu Gly Leu Val Phe Asp Asp Val Val Gly Ile Val Glu Ile
1               5                   10                  15

Ile Asn Ser Arg Asp Val Lys Val
            20

<210> SEQ ID NO 16
<211> LENGTH: 23
<212> TYPE: PRT
<213> ORGANISM: Homo sapiens

<400> SEQUENCE: 16

Arg Val Val Lys Leu Glu Asn Gly Glu Ile Glu Thr Ile Ala Arg Phe
1               5                   10                  15

Gly Ser Gly Pro Cys Lys Thr
            20

<210> SEQ ID NO 17
<211> LENGTH: 25
<212> TYPE: PRT
<213> ORGANISM: Homo sapiens

<400> SEQUENCE: 17

Arg Leu Pro Ile Leu Asn Gln Pro Ser Thr Gln Ile Val Ala Asn Ala
1               5                   10                  15

Lys Gly Ala Val Thr Gly Ala Lys Asp
            20                  25
```

<210> SEQ ID NO 18
<211> LENGTH: 17
<212> TYPE: PRT
<213> ORGANISM: Homo sapiens

<400> SEQUENCE: 18

Arg Glu Ala Gln Lys Gln Ala Ser Glu Lys Val Ser Asn Lys Gly Lys
1               5                   10                  15

Arg

<210> SEQ ID NO 19
<211> LENGTH: 24
<212> TYPE: PRT
<213> ORGANISM: Homo sapiens

<400> SEQUENCE: 19

Lys Leu Pro Tyr Leu Val Glu Leu Ser Pro Asp Gly Ser Asp Ser Arg
1               5                   10                  15

Asp Lys Pro Lys Leu Tyr Arg Leu
            20

<210> SEQ ID NO 20
<211> LENGTH: 17
<212> TYPE: PRT
<213> ORGANISM: Homo sapiens

<400> SEQUENCE: 20

Arg Tyr Ala Glu Asp Lys Phe Asn Glu Thr Thr Glu Lys Ser Leu Lys
1               5                   10                  15

Met

<210> SEQ ID NO 21
<211> LENGTH: 22
<212> TYPE: PRT
<213> ORGANISM: Homo sapiens

<400> SEQUENCE: 21

Lys Cys Val Tyr Gln Ser Leu Tyr Met Gly Asn Glu Pro Thr Pro Thr
1               5                   10                  15

Lys Ser Leu Ser Lys Ile
            20

<210> SEQ ID NO 22
<211> LENGTH: 21
<212> TYPE: PRT
<213> ORGANISM: Homo sapiens

<400> SEQUENCE: 22

Lys Ala Leu Asn Glu Glu Leu His Leu Gln Arg Ile Asn Pro Thr Thr
1               5                   10                  15

Val Lys Met Lys Ser
            20

<210> SEQ ID NO 23
<211> LENGTH: 12
<212> TYPE: PRT
<213> ORGANISM: Rattus norvegicus

<400> SEQUENCE: 23

Lys Ile Leu Gly Thr Glu Lys Gly Lys Asn Lys Ser
1               5                   10

```
<210> SEQ ID NO 24
<211> LENGTH: 17
<212> TYPE: PRT
<213> ORGANISM: Mus musculus

<400> SEQUENCE: 24

Arg Ser Asn Glu Ser Leu Lys His Asn Ile Gln Pro Ala Ser Ser Lys
 1               5                  10                  15

Trp

<210> SEQ ID NO 25
<211> LENGTH: 33
<212> TYPE: PRT
<213> ORGANISM: Mus musculus

<400> SEQUENCE: 25

Lys Gln His Leu Pro Ser Ser Gly Asn Gly Lys Ser Phe Lys Ala Gly
 1               5                  10                  15

Gly Glu Pro Ser Pro Ala Gln Pro Val Cys Lys Ala Leu Asp Pro Arg
            20                  25                  30

Gly

<210> SEQ ID NO 26
<211> LENGTH: 26
<212> TYPE: PRT
<213> ORGANISM: Homo sapiens

<400> SEQUENCE: 26

Arg Ser Ser Asp Gln Asp Ser Thr Asn Lys Glu Ala Glu Ala Ala Gly
 1               5                  10                  15

Val Lys Pro Ala Gly Val Arg Pro Arg Glu
            20                  25

<210> SEQ ID NO 27
<211> LENGTH: 24
<212> TYPE: PRT
<213> ORGANISM: Homo sapiens

<400> SEQUENCE: 27

Lys Ala Glu Val Val Asn Gly Tyr Glu Ala Lys Val Tyr Thr Val Asn
 1               5                  10                  15

Asn Val Asn Val Ile Thr Lys Ile
            20

<210> SEQ ID NO 28
<211> LENGTH: 22
<212> TYPE: PRT
<213> ORGANISM: Homo sapiens

<400> SEQUENCE: 28

Lys Ala Gly Asp Leu Ala Ser Leu Lys Lys Ala Phe Glu Ser Gly Ile
 1               5                  10                  15

Pro Val Asp Met Lys Asp
            20

<210> SEQ ID NO 29
<211> LENGTH: 22
<212> TYPE: PRT
<213> ORGANISM: Homo sapiens

<400> SEQUENCE: 29
```

-continued

Lys Lys Gly Leu Asp Ile Pro Ala Lys Pro Pro Gly Leu Asp Pro
1               5                   10                  15

Pro Phe Lys Asp Lys Lys
            20

<210> SEQ ID NO 30
<211> LENGTH: 29
<212> TYPE: PRT
<213> ORGANISM: Mus musculus

<400> SEQUENCE: 30

Arg Gly Leu Ala Gly Tyr Ser Gly Tyr Gly Ser Asp Thr His Ala Val
1               5                   10                  15

Phe Cys Val Gly Arg Pro Lys Ala Arg Glu Ser Lys Leu
            20                  25

<210> SEQ ID NO 31
<211> LENGTH: 35
<212> TYPE: PRT
<213> ORGANISM: Mus musculus

<400> SEQUENCE: 31

Arg Ser Gly Arg Ser Ala Leu His His Ala Val His Ser Gly His Leu
1               5                   10                  15

Glu Thr Val Asn Leu Leu Leu Asn Lys Gly Ala Ser Leu Asn Val Cys
            20                  25                  30

Asp Lys Glu
        35

<210> SEQ ID NO 32
<211> LENGTH: 21
<212> TYPE: PRT
<213> ORGANISM: Homo sapiens

<400> SEQUENCE: 32

Arg Ile Met Val Ser Arg Ser Glu Val Asp Met Leu Lys Ile Arg Ser
1               5                   10                  15

Glu Phe Lys Arg Lys
            20

<210> SEQ ID NO 33
<211> LENGTH: 29
<212> TYPE: PRT
<213> ORGANISM: Rattus norvegicus

<400> SEQUENCE: 33

Arg Val Ser Ser Gln Asn Leu Val Ala Ile Pro Val Tyr Val Lys His
1               5                   10                  15

Asn Ile Ser Phe Lys Glu Asn Ser Ser Cys Gly Arg Phe
            20                  25

<210> SEQ ID NO 34
<211> LENGTH: 19
<212> TYPE: PRT
<213> ORGANISM: Homo sapiens

<400> SEQUENCE: 34

Lys Leu Ile Asp Val Ile Ser Met Tyr Arg Glu Leu Leu Lys Asp Leu
1               5                   10                  15

Ser Lys Glu

```
<210> SEQ ID NO 35
<211> LENGTH: 31
<212> TYPE: PRT
<213> ORGANISM: Homo sapiens

<400> SEQUENCE: 35

Lys Val Gln Thr Asp Lys Gly Thr Glu Val Ala Thr Asn Leu Val Ile
 1               5                  10                  15

Leu Cys Thr Gly Ile Lys Ile Asn Ser Ser Ala Tyr Arg Lys Ala
            20                  25                  30

<210> SEQ ID NO 36
<211> LENGTH: 23
<212> TYPE: PRT
<213> ORGANISM: Homo sapiens

<400> SEQUENCE: 36

Lys Gln Val Gly Val Asn Pro Thr Ser Ile Asp Ser Val Val Ile Gly
 1               5                  10                  15

Lys Asp Gln Glu Val Lys Leu
            20

<210> SEQ ID NO 37
<211> LENGTH: 20
<212> TYPE: PRT
<213> ORGANISM: Rattus norvegicus

<400> SEQUENCE: 37

Arg Leu Gly Pro Met Ala Leu Ala Phe Lys Leu Arg Gly Leu Val Asp
 1               5                  10                  15

Arg Lys Arg Ser
            20

<210> SEQ ID NO 38
<211> LENGTH: 27
<212> TYPE: PRT
<213> ORGANISM: Mus musculus

<400> SEQUENCE: 38

Lys Ser Asn Asn Ile Phe Leu His Glu Gly Leu Thr Val Lys Ile Gly
 1               5                  10                  15

Asp Phe Gly Leu Ala Thr Val Lys Thr Arg Trp
            20                  25

<210> SEQ ID NO 39
<211> LENGTH: 22
<212> TYPE: PRT
<213> ORGANISM: Rattus norvegicus

<400> SEQUENCE: 39

Arg Gly Gly Val Glu Lys Gly Pro Ala Ala Leu Arg Lys Ala Gly Leu
 1               5                  10                  15

Val Glu Lys Leu Lys Glu
            20

<210> SEQ ID NO 40
<211> LENGTH: 20
<212> TYPE: PRT
<213> ORGANISM: Mus musculus

<400> SEQUENCE: 40

Lys Gly Lys Asp Lys Glu Val His Ser Ile Lys Arg Gly Asp Ser Gly
```

-continued

```
                1               5                  10                  15

Asn Ile Lys Ala
            20

<210> SEQ ID NO 41
<211> LENGTH: 20
<212> TYPE: PRT
<213> ORGANISM: Mus muculus

<400> SEQUENCE: 41

Lys Gly Lys Asp Lys Glu Val His Ser Ile Lys Arg Gly Asp Ser Gly
1               5                  10                  15

Asn Ile Lys Ala
            20

<210> SEQ ID NO 42
<211> LENGTH: 28
<212> TYPE: PRT
<213> ORGANISM: Homo sapiens

<400> SEQUENCE: 42

Arg Val Val Pro Leu Asp Glu Ile Lys Glu Ala Ala Asn Ala Ala Asn
1               5                  10                  15

Ile His Ser Phe Ile Glu Gly Leu Pro Glu Lys Tyr
            20                  25

<210> SEQ ID NO 43
<211> LENGTH: 23
<212> TYPE: PRT
<213> ORGANISM: Rattus norvegicus

<400> SEQUENCE: 43

Arg Tyr Asp Ser Ser Leu Lys Pro Val Leu Lys His Val Asn Ala Leu
1               5                  10                  15

Ile Ser Pro Gly Gln Lys Ile
            20

<210> SEQ ID NO 44
<211> LENGTH: 24
<212> TYPE: PRT
<213> ORGANISM: Mus musculus

<400> SEQUENCE: 44

Lys Gly Lys Thr Thr Ile Lys Thr Gly Ala Ser Val Leu Asn Lys Trp
1               5                  10                  15

Gln Met Asn Pro Tyr Asp Arg Gly
            20

<210> SEQ ID NO 45
<211> LENGTH: 26
<212> TYPE: PRT
<213> ORGANISM: Homo sapiens

<400> SEQUENCE: 45

Lys His Gly Ala Ile Thr Asn Thr Lys Val Gln Tyr Arg Val Ser Ala
1               5                  10                  15

Thr Asp Leu Pro Pro Glu Leu Pro Lys Ala
            20                  25

<210> SEQ ID NO 46
<211> LENGTH: 34
<212> TYPE: PRT
```

<213> ORGANISM: Mus musculus

<400> SEQUENCE: 46

Lys Val Phe Leu Ala Glu Cys Tyr Asn Leu Cys Pro Glu Gln Asp Lys
1               5                   10                  15

Ile Leu Val Ala Val Lys Thr Leu Lys Asp Ala Ser Asp Asn Ala Arg
            20                  25                  30

Lys Asp

<210> SEQ ID NO 47
<211> LENGTH: 19
<212> TYPE: PRT
<213> ORGANISM: Homo sapiens

<400> SEQUENCE: 47

Arg Ser Val Met Gln Lys Tyr Leu Glu Asp Arg Gly Glu Val Thr Phe
1               5                   10                  15

Glu Lys Ile

<210> SEQ ID NO 48
<211> LENGTH: 25
<212> TYPE: PRT
<213> ORGANISM: Homo sapiens

<400> SEQUENCE: 48

Lys Asn Lys Pro Arg Ser Pro Val Val Glu Leu Ser Lys Val Pro Leu
1               5                   10                  15

Val Gln Arg Gly Ser Ala Asn Gly Leu
            20                  25

<210> SEQ ID NO 49
<211> LENGTH: 13
<212> TYPE: PRT
<213> ORGANISM: Homo sapiens

<400> SEQUENCE: 49

Arg Lys Ser Asn Pro Gly Trp Glu Asn Leu Glu Lys Leu
1               5                   10

<210> SEQ ID NO 50
<211> LENGTH: 31
<212> TYPE: PRT
<213> ORGANISM: Homo sapiens

<400> SEQUENCE: 50

Lys Ala Met Glu Ser Ala Glu Gln Lys Glu Gln Gly Leu Ser Arg Asp
1               5                   10                  15

Val Thr Thr Val Trp Lys Leu Arg Ile Val Ser Tyr Ser Lys Lys
            20                  25                  30

<210> SEQ ID NO 51
<211> LENGTH: 29
<212> TYPE: PRT
<213> ORGANISM: Homo sapiens

<400> SEQUENCE: 51

Arg Lys Ala Asp Thr Thr Thr Pro Thr Thr Ile Asp Pro Ile His Glu
1               5                   10                  15

Pro Pro Ser Leu Pro Pro Glu Pro Lys Thr Thr Lys Leu
            20                  25

<210> SEQ ID NO 52
<211> LENGTH: 19
<212> TYPE: PRT
<213> ORGANISM: Mus musculus

<400> SEQUENCE: 52

Lys Met Val Glu Leu Lys Ala Lys Val Glu Gln Phe Glu Lys Leu Ser
1               5                   10                  15

Asp Lys Leu

<210> SEQ ID NO 53
<211> LENGTH: 20
<212> TYPE: PRT
<213> ORGANISM: Rattus norvegicus

<400> SEQUENCE: 53

Lys Gly Thr Gln Lys Pro Tyr Ala Leu Lys Val Leu Lys Lys Thr Val
1               5                   10                  15

Asp Lys Lys Ile
            20

<210> SEQ ID NO 54
<211> LENGTH: 19
<212> TYPE: PRT
<213> ORGANISM: Homo sapiens

<400> SEQUENCE: 54

Lys Ser Gln Glu Gly Lys Pro Lys Glu His Thr Glu Pro Lys Ser Leu
1               5                   10                  15

Pro Lys Gln

<210> SEQ ID NO 55
<211> LENGTH: 18
<212> TYPE: PRT
<213> ORGANISM: Mus musculus

<400> SEQUENCE: 55

Lys Lys Arg Asp Lys Glu Leu Gly Leu Gly Arg His Glu Asn Ala Ile
1               5                   10                  15

Lys Tyr

<210> SEQ ID NO 56
<211> LENGTH: 26
<212> TYPE: PRT
<213> ORGANISM: Homo sapiens

<400> SEQUENCE: 56

Arg Lys Leu Gly Ala Ser Leu Phe Thr Ile Gly Phe Ala Ile Tyr Glu
1               5                   10                  15

Val Pro Lys Glu Met His Gly Asn Lys Gln
            20                  25

<210> SEQ ID NO 57
<211> LENGTH: 26
<212> TYPE: PRT
<213> ORGANISM: Homo sapiens

<400> SEQUENCE: 57

Lys Trp Ala Phe Asn Leu Tyr Asp Ile Asn Lys Asp Gly Tyr Ile Thr
1               5                   10                  15

Lys Glu Glu Met Leu Ala Ile Met Lys Ser
            20                  25

-continued

<210> SEQ ID NO 58
<211> LENGTH: 29
<212> TYPE: PRT
<213> ORGANISM: Homo sapiens

<400> SEQUENCE: 58

Arg Ser Leu His Ala Ala Val Leu Leu Val Ile Leu Lys Glu
1               5                   10                  15

Gln Pro Ser Ser Pro Ala Pro Val Asn Gly Ser Lys Trp
            20                  25

<210> SEQ ID NO 59
<211> LENGTH: 25
<212> TYPE: PRT
<213> ORGANISM: Homo sapiens

<400> SEQUENCE: 59

Arg Val Val Gln Lys Asn Leu Val Phe Val Val Gly Leu Ser Gln Arg
1               5                   10                  15

Leu Ala Asp Pro Glu Val Leu Lys Arg
            20                  25

<210> SEQ ID NO 60
<211> LENGTH: 26
<212> TYPE: PRT
<213> ORGANISM: Mus musculus

<400> SEQUENCE: 60

Lys Val Phe Lys Gln Pro Ser Lys Pro Glu Ile Val Asn Lys Ala Pro
1               5                   10                  15

Phe Leu Glu Thr Asp Gln Leu Lys Leu
            20                  25

<210> SEQ ID NO 61
<211> LENGTH: 22
<212> TYPE: PRT
<213> ORGANISM: Homo sapiens

<400> SEQUENCE: 61

Arg Ser Val His Leu Lys Glu Gly Glu Gln His Val Asp Asp Val Ser
1               5                   10                  15

Ser Ala Leu Lys Arg Phe
            20

<210> SEQ ID NO 62
<211> LENGTH: 27
<212> TYPE: PRT
<213> ORGANISM: Homo sapiens

<400> SEQUENCE: 62

Lys Lys Ala Ala Glu Cys Lys Val Asp Ser Ile Gly Ser Gly Arg Ala
1               5                   10                  15

Ile Pro Ile Lys Gln Gly Ile Leu Leu Lys Arg
            20                  25

<210> SEQ ID NO 63
<211> LENGTH: 21
<212> TYPE: PRT
<213> ORGANISM: Homo sapiens

<400> SEQUENCE: 63

```
Lys Ile Ser Glu Lys Thr Ile Gln Ile Ser Asp Ile Gln Lys Asp Leu
1               5                   10                  15

Asp Lys Ser Lys Asp
            20
```

<210> SEQ ID NO 64
<211> LENGTH: 31
<212> TYPE: PRT
<213> ORGANISM: Homo sapiens

<400> SEQUENCE: 64

```
Lys Gln Phe Ser Lys Asp Thr Tyr Ser Lys Pro Ser Ile Ser Gly Ile
1               5                   10                  15

Glu Ser Asp Asp His Cys Gln Arg Glu Gln Glu Leu Gln Lys Glu
            20                  25                  30
```

<210> SEQ ID NO 65
<211> LENGTH: 28
<212> TYPE: PRT
<213> ORGANISM: Homo sapiens

<400> SEQUENCE: 65

```
Lys Ala Gly Val Ser Ala Glu Pro Thr Thr Arg Thr Tyr Asp Leu Asn
1               5                   10                  15

Lys Pro Pro Glu Phe Ser Phe Glu Lys Ala Arg Val
            20                  25
```

<210> SEQ ID NO 66
<211> LENGTH: 21
<212> TYPE: PRT
<213> ORGANISM: Homo sapiens

<400> SEQUENCE: 66

```
Lys Asn Thr Lys Gln Gln Asn Asn Ala Ala Leu Glu Arg Gly Leu Thr
1               5                   10                  15

Lys Ala Leu Lys Lys
            20
```

<210> SEQ ID NO 67
<211> LENGTH: 23
<212> TYPE: PRT
<213> ORGANISM: Mus musculus

<400> SEQUENCE: 67

```
Arg Glu Ser Asn Thr Ala Gly Ile Asp Ile Phe Ser Lys Phe Ser Ala
1               5                   10                  15

Tyr Ile Lys Asn Thr Lys Gln
            20
```

<210> SEQ ID NO 68
<211> LENGTH: 28
<212> TYPE: PRT
<213> ORGANISM: Homo sapiens

<400> SEQUENCE: 68

```
Lys Val Ile Asp Lys Gly Ala Gly Gly Gly Ala Gly Gln Gly Ala
1               5                   10                  15

Gly Ala Leu Ala Arg Pro Lys Val Pro Ser Arg Asn
            20                  25
```

<210> SEQ ID NO 69
<211> LENGTH: 21

```
<212> TYPE: PRT
<213> ORGANISM: Homo sapiens

<400> SEQUENCE: 69

Lys Glu Leu Gln Val Ala Asn Asp Lys Ala Asp Met Val Leu Lys Glu
1               5                   10                  15

Val Thr Met Lys Ala
            20

<210> SEQ ID NO 70
<211> LENGTH: 19
<212> TYPE: PRT
<213> ORGANISM: Homo sapiens

<400> SEQUENCE: 70

Arg Tyr Ser Ile Pro Ser His Arg Thr Thr Gln Lys Ser Tyr His Thr
1               5                   10                  15

Gly Lys Lys

<210> SEQ ID NO 71
<211> LENGTH: 18
<212> TYPE: PRT
<213> ORGANISM: Mus musculus

<400> SEQUENCE: 71

Arg Arg Lys Asp Lys Glu Thr Asn Ser Glu Gly Leu Val Asn Lys Thr
1               5                   10                  15

Arg Glu

<210> SEQ ID NO 72
<211> LENGTH: 19
<212> TYPE: PRT
<213> ORGANISM: Homo sapiens

<400> SEQUENCE: 72

Lys Glu Ile Leu Thr Lys Met Arg Tyr Phe Ser Asn Ile Glu Glu Lys
1               5                   10                  15

Ile Lys Leu

<210> SEQ ID NO 73
<211> LENGTH: 19
<212> TYPE: PRT
<213> ORGANISM: Homo sapiens

<400> SEQUENCE: 73

Lys Asp Met Glu Arg Arg Gln Gln Gln Lys Leu Lys Met Gln Ala Glu
1               5                   10                  15

Ile Lys Arg

<210> SEQ ID NO 74
<211> LENGTH: 24
<212> TYPE: PRT
<213> ORGANISM: Homo sapiens

<400> SEQUENCE: 74

Lys Asp Trp Ala Asn Gln Arg Cys Ser Ser Pro Lys Gly Ser Ala Arg
1               5                   10                  15

Asn Ser Leu Val Lys Ala Lys Arg
            20

<210> SEQ ID NO 75
```

-continued

```
<211> LENGTH: 26
<212> TYPE: PRT
<213> ORGANISM: Rattus norvegicus

<400> SEQUENCE: 75

Arg Gly Pro Pro Gly Pro Ala Gly Lys Pro Gly Asp Asp Gly Glu Ala
1               5                   10                  15

Gly Lys Pro Gly Lys Ala Gly Glu Arg Gly
            20                  25

<210> SEQ ID NO 76
<211> LENGTH: 37
<212> TYPE: PRT
<213> ORGANISM: Rattus norvegicus

<400> SEQUENCE: 76

Arg Gly His Pro Gly Pro Pro Gly Pro Pro Gly Glu Gln Gly Leu Pro
1               5                   10                  15

Gly Ala Ala Gly Lys Glu Gly Thr Lys Gly Asp Pro Gly Pro Ala Gly
            20                  25                  30

Leu Pro Gly Lys Asp
        35

<210> SEQ ID NO 77
<211> LENGTH: 28
<212> TYPE: PRT
<213> ORGANISM: Rattus norvegicus

<400> SEQUENCE: 77

Arg Ile Glu Gly Asn Gln Gly Ala Arg Val Gly Leu Val Ala Val Asp
1               5                   10                  15

Lys Gly Val Phe Val Leu Asn Lys Lys Asn Lys Leu
            20                  25

<210> SEQ ID NO 78
<211> LENGTH: 13
<212> TYPE: PRT
<213> ORGANISM: Rattus norvegicus

<400> SEQUENCE: 78

Lys Phe Trp Ile Gly Leu Gln Arg Glu Lys Gly Lys Cys
1               5                   10

<210> SEQ ID NO 79
<211> LENGTH: 26
<212> TYPE: PRT
<213> ORGANISM: Rattus norvegicus

<400> SEQUENCE: 79

Arg Thr Ser Ser Gln Asn Asn Val Gln Val Leu Asn Thr Asn Lys Thr
1               5                   10                  15

Ser Ala Glu Leu Leu Leu Pro Ile Lys Glu
            20                  25

<210> SEQ ID NO 80
<211> LENGTH: 27
<212> TYPE: PRT
<213> ORGANISM: Homo sapiens

<400> SEQUENCE: 80

Arg Glu Asn Lys Arg Ile Ala Ile Leu Pro Asp Gly Ser Leu Arg Ile
1               5                   10                  15
```

Leu Asn Ala Ser Lys Ser Asp Glu Gly Lys Tyr
                20                  25

<210> SEQ ID NO 81
<211> LENGTH: 39
<212> TYPE: PRT
<213> ORGANISM: Homo sapiens

<400> SEQUENCE: 81

Lys Phe Pro Val Asp Gly Lys Val Leu Glu Gly Asn Thr Met Ala Asp
1               5                   10                  15

Glu Ser Leu Ile Thr Gly Glu Ala Met Pro Val Thr Lys Lys Pro Gly
            20                  25                  30

Ser Thr Val Ile Ala Arg Ser
        35

<210> SEQ ID NO 82
<211> LENGTH: 24
<212> TYPE: PRT
<213> ORGANISM: Homo sapiens

<400> SEQUENCE: 82

Arg Asp Ala Asp Pro Ile Leu Ile Ser Leu Arg Glu Ala Tyr Val Pro
1               5                   10                  15

Ser Lys Gln Arg Asp Leu Lys Ile
            20

<210> SEQ ID NO 83
<211> LENGTH: 12
<212> TYPE: PRT
<213> ORGANISM: Mus musculus

<400> SEQUENCE: 83

Arg Lys Gly Leu Phe Pro Phe Thr His Val Lys Ile
1               5                   10

<210> SEQ ID NO 84
<211> LENGTH: 26
<212> TYPE: PRT
<213> ORGANISM: Homo sapiens

<400> SEQUENCE: 84

Arg Gln Gly Ala Phe Leu Val Asn Thr Ala Arg Gly Gly Leu Val Asp
1               5                   10                  15

Glu Lys Ala Leu Ala Gln Ala Leu Lys Glu
            20                  25

<210> SEQ ID NO 85
<211> LENGTH: 16
<212> TYPE: PRT
<213> ORGANISM: Homo sapiens

<400> SEQUENCE: 85

Arg Lys Arg Pro Ala Thr Asp Asp Ser Ser Thr Gln Asn Lys Arg Ala
1               5                   10                  15

<210> SEQ ID NO 86
<211> LENGTH: 21
<212> TYPE: PRT
<213> ORGANISM: Rattus norvegicus

<400> SEQUENCE: 86

Lys Leu Pro Lys Thr Leu Gln Glu Leu Arg Leu His Asp Asn Glu Ile

```
                1               5              10              15

Thr Lys Leu Lys Lys
            20

<210> SEQ ID NO 87
<211> LENGTH: 31
<212> TYPE: PRT
<213> ORGANISM: Homo sapiens

<400> SEQUENCE: 87

Lys Thr Thr Lys Leu His Phe Glu Ala Leu Met Asn Ile Pro Val Leu
 1               5                  10                  15

Val Leu Asp Val Asn Asp Asp Phe Ser Glu Glu Val Thr Lys Gln
            20                  25                  30

<210> SEQ ID NO 88
<211> LENGTH: 16
<212> TYPE: PRT
<213> ORGANISM: Rattus norvegicus

<400> SEQUENCE: 88

Lys Gly Ser Ser Gln Gln Pro Asn Lys Val Thr Asp Lys Asn Lys Met
 1               5                  10                  15

<210> SEQ ID NO 89
<211> LENGTH: 25
<212> TYPE: PRT
<213> ORGANISM: Rattus norvegicus

<400> SEQUENCE: 89

Lys Met Ser Gln Asp Ser Met Met Lys Leu Lys Gly Met Ala Ala Ala
 1               5                  10                  15

Gly Arg Ser Gln Gly Gln His Lys Gln
            20                  25

<210> SEQ ID NO 90
<211> LENGTH: 29
<212> TYPE: PRT
<213> ORGANISM: Homo sapiens

<400> SEQUENCE: 90

Lys Asp Lys Asp Phe Ala Leu Asp Val Ser Ala Asn Gln Pro Val Leu
 1               5                  10                  15

Val Ala Val Lys Met Leu Arg Ala Asp Ala Asn Lys Asn
            20                  25

<210> SEQ ID NO 91
<211> LENGTH: 14
<212> TYPE: PRT
<213> ORGANISM: Homo sapiens

<400> SEQUENCE: 91

Arg Lys Leu Asp Ser Val Lys Arg Gln Lys Tyr Asn Lys Glu
 1               5                  10

<210> SEQ ID NO 92
<211> LENGTH: 29
<212> TYPE: PRT
<213> ORGANISM: Homo sapiens

<400> SEQUENCE: 92

Lys Thr Asp Lys Leu Ile Gly Phe Ser Lys Pro Ile Val Arg Lys Lys
 1               5                  10                  15
```

Leu Ser Leu Ser Ser Gln Leu Gly Ser Leu Glu Lys Phe
            20                  25

<210> SEQ ID NO 93
<211> LENGTH: 28
<212> TYPE: PRT
<213> ORGANISM: Homo sapiens

<400> SEQUENCE: 93

Arg Gly Lys Leu Gln Gly His Asp Val Asp Phe Leu Ile Thr His Pro
 1               5                  10                  15

Lys Glu Gly Gln Glu Ala Gly Leu Leu Pro Arg Val
            20                  25

<210> SEQ ID NO 94
<211> LENGTH: 24
<212> TYPE: PRT
<213> ORGANISM: Homo sapiens

<400> SEQUENCE: 94

Lys Leu Leu Lys Ser Val Glu Asn Leu Gly Val Ser Tyr Val Lys Gly
 1               5                  10                  15

Thr Glu Gln Tyr Gln Ser Lys Leu
            20

<210> SEQ ID NO 95
<211> LENGTH: 21
<212> TYPE: PRT
<213> ORGANISM: Homo sapiens

<400> SEQUENCE: 95

Arg Arg Phe Ala Ile Gly Ser Gln Val Ser Glu His Ser Ile Ile Lys
 1               5                  10                  15

Asp Phe Thr Lys Gln
            20

<210> SEQ ID NO 96
<211> LENGTH: 13
<212> TYPE: PRT
<213> ORGANISM: Rattus norvegicus

<400> SEQUENCE: 96

Lys Asp Lys Lys Val Ala Glu Pro Asp Asn Lys Lys Lys
 1               5                  10

<210> SEQ ID NO 97
<211> LENGTH: 29
<212> TYPE: PRT
<213> ORGANISM: Mus musculus

<400> SEQUENCE: 97

Arg Arg Glu Asp Pro Glu Ala Gly Trp Leu Leu Tyr Leu Lys Thr Gly
 1               5                  10                  15

Gln Met Tyr Pro Val Pro Ala Asn His Leu Asp Lys Arg
            20                  25

<210> SEQ ID NO 98
<211> LENGTH: 29
<212> TYPE: PRT
<213> ORGANISM: Homo sapiens

<400> SEQUENCE: 98

```
Lys Gly Ser Arg Ser Gln Lys Glu Ala Phe Pro Leu Ala Lys Gly Glu
1               5                   10                  15

Val Asp Thr Ala Pro Gln Gly Asn Lys Asp Leu Lys Glu
            20                  25

<210> SEQ ID NO 99
<211> LENGTH: 29
<212> TYPE: PRT
<213> ORGANISM: Homo sapiens

<400> SEQUENCE: 99

Lys Asp Leu Leu Leu Asn Thr Met Ser Gln Glu Glu Lys Ala Ala Tyr
1               5                   10                  15

Leu Ser Asp Pro Arg Ala Pro Pro Cys Glu Tyr Lys Asp
            20                  25

<210> SEQ ID NO 100
<211> LENGTH: 27
<212> TYPE: PRT
<213> ORGANISM: Rattus norvegicus

<400> SEQUENCE: 100

Lys Ser Pro Ser Ala Cys Leu Val Val Gly Val Val Lys Gly Gly
1               5                   10                  15

Thr Gly Leu Phe Glu Leu Lys Gln Pro Leu Arg
            20                  25

<210> SEQ ID NO 101
<211> LENGTH: 20
<212> TYPE: PRT
<213> ORGANISM: Homo sapiens

<400> SEQUENCE: 101

Lys Tyr Lys Glu Ala Ala Arg Leu Glu Ile Asn Val Leu Glu Lys Ile
1               5                   10                  15

Asn Glu Lys Asp
            20

<210> SEQ ID NO 102
<211> LENGTH: 21
<212> TYPE: PRT
<213> ORGANISM: Homo sapiens

<400> SEQUENCE: 102

Arg Val Leu Ser Phe Lys Thr Gly Ile Ile Ser Leu Cys Lys Ala His
1               5                   10                  15

Leu Glu Asp Lys Tyr
            20

<210> SEQ ID NO 103
<211> LENGTH: 17
<212> TYPE: PRT
<213> ORGANISM: Homo sapiens

<400> SEQUENCE: 103

Lys Trp Ser Lys Glu Ala Thr Ala Gly Lys Lys Ser Lys Ser Gly Lys
1               5                   10                  15

Leu

<210> SEQ ID NO 104
<211> LENGTH: 16
<212> TYPE: PRT
```

<213> ORGANISM: Mus musculus

<400> SEQUENCE: 104

Lys Lys Gly Val Leu Pro Thr Lys Asp Ile Arg Arg Met Cys Lys Ser
1               5                   10                  15

<210> SEQ ID NO 105
<211> LENGTH: 31
<212> TYPE: PRT
<213> ORGANISM: Mus musculus

<400> SEQUENCE: 105

Arg Asp Cys Asn Ser Ile Pro Leu Val Leu Gly Thr Cys Lys Glu Thr
1               5                   10                  15

Phe Asn Leu Tyr Tyr Met Glu Ser Asp Asp His Gly Val Lys Phe
            20                  25                  30

<210> SEQ ID NO 106
<211> LENGTH: 26
<212> TYPE: PRT
<213> ORGANISM: Homo sapiens

<400> SEQUENCE: 106

Lys Ser Lys Gln Asp Thr Pro Ala Leu Pro Lys Lys Pro Ala Pro
1               5                   10                  15

Pro Arg Pro Lys Pro Pro Ser Gly Lys Ser
            20                  25

<210> SEQ ID NO 107
<211> LENGTH: 20
<212> TYPE: PRT
<213> ORGANISM: Homo sapiens

<400> SEQUENCE: 107

Lys Asn Asp Pro Phe Thr Ser Asp Pro Phe Thr Lys Asn Pro Ser Leu
1               5                   10                  15

Pro Ser Lys Leu
            20

<210> SEQ ID NO 108
<211> LENGTH: 40
<212> TYPE: PRT
<213> ORGANISM: Mus musculus

<400> SEQUENCE: 108

Arg Thr Gly Leu Ser Gln Leu His Asn Ala Leu Asn Asp Val Lys Asp
1               5                   10                  15

Ile Gln Gln Ser Leu Ala Asp Val Ser Lys Asp Trp Arg Gln Ser Ile
            20                  25                  30

Asn Thr Ile Glu Ser Leu Lys Asp
        35                  40

<210> SEQ ID NO 109
<211> LENGTH: 24
<212> TYPE: PRT
<213> ORGANISM: Homo sapiens

<400> SEQUENCE: 109

Lys Asn Cys Phe Leu Cys Ala Thr Val Thr Thr Glu Arg Pro Val Gln
1               5                   10                  15

Val Lys Val Val Lys Val Lys Lys
            20

<210> SEQ ID NO 110
<211> LENGTH: 21
<212> TYPE: PRT
<213> ORGANISM: Homo sapiens

<400> SEQUENCE: 110

Arg Leu Gln Ala Glu Lys Ala Leu Val Glu Phe Thr Asn Ser Pro Asp
 1               5                  10                  15

Cys Leu Ser Lys Cys
            20

<210> SEQ ID NO 111
<211> LENGTH: 12
<212> TYPE: PRT
<213> ORGANISM: Rattus norvegicus

<400> SEQUENCE: 111

Lys Ser Arg Lys Lys Ser Ser Glu Gly Lys Lys Gly
 1               5                  10

<210> SEQ ID NO 112
<211> LENGTH: 19
<212> TYPE: PRT
<213> ORGANISM: Homo sapiens

<400> SEQUENCE: 112

Lys Val Lys Ser Ile Val Thr Leu Asp Gly Gly Lys Leu Val His Leu
 1               5                  10                  15

Gln Lys Trp

<210> SEQ ID NO 113
<211> LENGTH: 23
<212> TYPE: PRT
<213> ORGANISM: Rattus norvegicus

<400> SEQUENCE: 113

Arg Leu Val Trp Arg Asn Ser Ile Arg Gly Ser Leu Ile Lys Ser Leu
 1               5                  10                  15

Ser Phe Phe Leu Lys Lys Met
            20

<210> SEQ ID NO 114
<211> LENGTH: 22
<212> TYPE: PRT
<213> ORGANISM: Homo sapiens

<400> SEQUENCE: 114

Arg His Leu Asp Leu Ser Gly Cys Glu Lys Ile Thr Asp Val Ala Leu
 1               5                  10                  15

Glu Lys Ile Ser Arg Ala
            20

<210> SEQ ID NO 115
<211> LENGTH: 22
<212> TYPE: PRT
<213> ORGANISM: Homo sapiens

<400> SEQUENCE: 115

Lys Cys Lys Val Lys Ser Leu Leu His Ser Pro Gly Asp Tyr Ile Leu
 1               5                  10                  15

Leu Ser Ala Asp Lys Tyr

20

<210> SEQ ID NO 116
<211> LENGTH: 25
<212> TYPE: PRT
<213> ORGANISM: Homo sapiens

<400> SEQUENCE: 116

Arg Thr Pro Cys Thr Val Ser Cys Asn Ile Pro Val Val Ser Gly Lys
1               5                   10                  15

Glu Cys Glu Glu Ile Ile Arg Lys Gly
            20                  25

<210> SEQ ID NO 117
<211> LENGTH: 18
<212> TYPE: PRT
<213> ORGANISM: Mus musculus

<400> SEQUENCE: 117

Arg Leu Arg Ser Pro Pro Lys Lys Gly Leu Gly Ser Pro Thr Val His
1               5                   10                  15

Lys Val

<210> SEQ ID NO 118
<211> LENGTH: 33
<212> TYPE: PRT
<213> ORGANISM: Homo sapiens

<400> SEQUENCE: 118

Arg Val Thr Glu Ala Glu Ile Val Pro Met Gly Lys Asn Ser His Cys
1               5                   10                  15

Val Arg Phe Val Pro Gln Glu Met Gly Val His Thr Val Ser Val Lys
            20                  25                  30

Tyr

<210> SEQ ID NO 119
<211> LENGTH: 25
<212> TYPE: PRT
<213> ORGANISM: Rattus norvegicus

<400> SEQUENCE: 119

Arg Met Leu Glu Gln Leu Leu Leu Ala Glu Lys Cys His Arg Arg Thr
1               5                   10                  15

Val Tyr Glu Leu Glu Asn Glu Lys His
            20                  25

<210> SEQ ID NO 120
<211> LENGTH: 22
<212> TYPE: PRT
<213> ORGANISM: Homo sapiens

<400> SEQUENCE: 120

Arg Ala Ile Val Ala Arg Ala Asn Ser Leu Lys Asn Ser Gly Val Pro
1               5                   10                  15

Asp Asp Ile Phe Lys Leu
            20

<210> SEQ ID NO 121
<211> LENGTH: 21
<212> TYPE: PRT
<213> ORGANISM: Homo sapiens

```
<400> SEQUENCE: 121

Arg Thr Val Ser Asp Asn Ser Leu Ser Asn Ser Arg Gly Glu Gly Lys
1               5                   10                  15

Pro Asp Leu Lys Phe
            20

<210> SEQ ID NO 122
<211> LENGTH: 24
<212> TYPE: PRT
<213> ORGANISM: Mus musculus

<400> SEQUENCE: 122

Lys Cys Asn Lys Leu Val Gly Gly Gly Glu Ala Asn Pro Met Asn Tyr
1               5                   10                  15

Asn Ser Tyr Met Asp Glu Lys Asn
            20

<210> SEQ ID NO 123
<211> LENGTH: 22
<212> TYPE: PRT
<213> ORGANISM: Homo sapiens

<400> SEQUENCE: 123

Arg Tyr Glu Leu Leu Leu Lys Asp Tyr Leu Leu Lys Leu Pro His Gly
1               5                   10                  15

Ser Pro Asp Ser Lys Asp
            20

<210> SEQ ID NO 124
<211> LENGTH: 14
<212> TYPE: PRT
<213> ORGANISM: Rattus norvegicus

<400> SEQUENCE: 124

Lys Glu Val Lys Pro Glu Thr Lys Pro Pro Glu Pro Lys Lys
1               5                   10

<210> SEQ ID NO 125
<211> LENGTH: 16
<212> TYPE: PRT
<213> ORGANISM: Mus musculus

<400> SEQUENCE: 125

Lys Lys Gly Thr Asp Val Met Val Arg Cys Leu Lys Leu Leu Lys Glu
1               5                   10                  15

<210> SEQ ID NO 126
<211> LENGTH: 21
<212> TYPE: PRT
<213> ORGANISM: Homo sapiens

<400> SEQUENCE: 126

Arg Lys Lys Ser Leu Ala Met Leu Gln Leu Tyr Ile Asn Lys Leu Asp
1               5                   10                  15

Ser Gln Gly Lys Tyr
            20

<210> SEQ ID NO 127
<211> LENGTH: 19
<212> TYPE: PRT
<213> ORGANISM: Mus musculus

<400> SEQUENCE: 127
```

-continued

Arg Leu Glu Ile Val Ser Asp Gly Lys Tyr Gly Ala Arg Asp Pro Asp
1               5                   10                  15

Thr Lys Ala

<210> SEQ ID NO 128
<211> LENGTH: 22
<212> TYPE: PRT
<213> ORGANISM: Homo sapiens

<400> SEQUENCE: 128

Arg Asn Ala Val Asn Leu Ala Val Leu Lys Leu Asn Glu Gln Gly Leu
1               5                   10                  15

Leu Asp Lys Leu Lys Asn
            20

<210> SEQ ID NO 129
<211> LENGTH: 23
<212> TYPE: PRT
<213> ORGANISM: Homo sapiens

<400> SEQUENCE: 129

Lys Leu Phe His Val Ser Glu Asp Pro Ser Leu Asn Glu Lys His
1               5                   10                  15

Pro Asn Leu Val His Lys Arg
            20

<210> SEQ ID NO 130
<211> LENGTH: 15
<212> TYPE: PRT
<213> ORGANISM: Homo sapiens

<400> SEQUENCE: 130

Arg Thr Gln Leu Asn Asp Ser Leu Lys Glu Ile His Gln Lys Glu
1               5                   10                  15

<210> SEQ ID NO 131
<211> LENGTH: 19
<212> TYPE: PRT
<213> ORGANISM: Homo sapiens

<400> SEQUENCE: 131

Lys Ser Val Phe Ala Lys His Gly Leu Glu Lys Leu Thr Pro Ile Gly
1               5                   10                  15

Asp Lys Tyr

<210> SEQ ID NO 132
<211> LENGTH: 17
<212> TYPE: PRT
<213> ORGANISM: Rattus norvegicus

<400> SEQUENCE: 132

Lys Gly Glu Lys Glu Glu Glu Asp Lys Glu Asp Glu Glu Lys Pro Lys
1               5                   10                  15

Ile

<210> SEQ ID NO 133
<211> LENGTH: 21
<212> TYPE: PRT
<213> ORGANISM: Homo sapiens

<400> SEQUENCE: 133

Arg Val Val Ser Glu Gly Gly Lys Pro Lys Val Gln Val Glu Tyr Lys
1               5                   10                  15

Gly Glu Thr Lys Thr
            20

<210> SEQ ID NO 134
<211> LENGTH: 28
<212> TYPE: PRT
<213> ORGANISM: Homo sapiens

<400> SEQUENCE: 134

Arg Ala His Gly Ser Lys Val Val Ala Val Gly Asp Ala Val Lys
1               5                   10                  15

Ser Ile Asp Asp Ile Gly Gly Ala Leu Ser Lys Leu
            20                  25

<210> SEQ ID NO 135
<211> LENGTH: 29
<212> TYPE: PRT
<213> ORGANISM: Homo sapiens

<400> SEQUENCE: 135

Arg Ser Pro Thr Thr Asn Ile Asn Glu Thr Ile Gly Ala Phe Gln Leu
1               5                   10                  15

His Ile Thr Asp Lys Pro Ser Ile Asn Thr Asp Lys Leu
            20                  25

<210> SEQ ID NO 136
<211> LENGTH: 36
<212> TYPE: PRT
<213> ORGANISM: Homo sapiens

<400> SEQUENCE: 136

Lys Leu Phe Val Gly Gly Leu Lys Gly Asp Val Ala Glu Gly Asp Leu
1               5                   10                  15

Ile Glu His Phe Ser Gln Phe Gly Thr Val Lys Ala Glu Ile Ile
            20                  25                  30

Ala Asp Lys Gln
        35

<210> SEQ ID NO 137
<211> LENGTH: 22
<212> TYPE: PRT
<213> ORGANISM: Homo sapiens

<400> SEQUENCE: 137

Lys Gln Thr Ala Lys Ala Glu Gly Leu Gly Asp Gly Tyr Arg Leu Val
1               5                   10                  15

Ile Asn Asp Gly Lys Leu
            20

<210> SEQ ID NO 138
<211> LENGTH: 21
<212> TYPE: PRT
<213> ORGANISM: Mus musculus

<400> SEQUENCE: 138

Lys Ala Pro Lys Ser Pro Ala Lys Ala Lys Thr Val Lys Pro Lys Ala
1               5                   10                  15

Ala Lys Pro Lys Thr
            20

```
<210> SEQ ID NO 139
<211> LENGTH: 23
<212> TYPE: PRT
<213> ORGANISM: Homo sapiens

<400> SEQUENCE: 139

Lys Ala Leu Val Gln Asn Asp Thr Leu Leu Gln Val Lys Gly Thr Gly
 1               5                  10                  15

Ala Asn Gly Ser Phe Lys Leu
            20

<210> SEQ ID NO 140
<211> LENGTH: 26
<212> TYPE: PRT
<213> ORGANISM: Mus musculus

<400> SEQUENCE: 140

Lys Leu Leu Gly Gly Val Thr Ile Ala Gln Gly Gly Val Leu Pro Asn
 1               5                  10                  15

Ile Gln Ala Val Leu Leu Pro Lys Lys Thr
            20                  25

<210> SEQ ID NO 141
<211> LENGTH: 15
<212> TYPE: PRT
<213> ORGANISM: Rattus norvegicus

<400> SEQUENCE: 141

Lys Gln Thr Ala Arg Lys Ser Thr Gly Gly Lys Ala Pro Arg Lys
 1               5                  10                  15

<210> SEQ ID NO 142
<211> LENGTH: 22
<212> TYPE: PRT
<213> ORGANISM: Homo sapiens

<400> SEQUENCE: 142

Lys Ala Asp Ile Pro Ala Lys Tyr Ala Glu Thr Met Asp Arg Glu Phe
 1               5                  10                  15

Arg Lys Trp Met Lys Trp
            20

<210> SEQ ID NO 143
<211> LENGTH: 21
<212> TYPE: PRT
<213> ORGANISM: Homo sapiens

<400> SEQUENCE: 143

Lys Leu Arg Phe His Pro Lys Gln Leu Tyr Phe Ser Ala Arg Gln Gly
 1               5                  10                  15

Glu Leu Gln Lys Val
            20

<210> SEQ ID NO 144
<211> LENGTH: 18
<212> TYPE: PRT
<213> ORGANISM: Homo sapiens

<400> SEQUENCE: 144

Arg Met Gly Arg Pro Glu Gly Glu Gly Thr Pro Gly Leu Thr Ala Lys
 1               5                  10                  15

Lys Leu
```

```
<210> SEQ ID NO 145
<211> LENGTH: 13
<212> TYPE: PRT
<213> ORGANISM: Homo sapiens

<400> SEQUENCE: 145

Arg Lys Leu Gly Glu Gly Ser Phe Ala Lys Val Arg Glu
1               5                   10

<210> SEQ ID NO 146
<211> LENGTH: 16
<212> TYPE: PRT
<213> ORGANISM: Mus musculus

<400> SEQUENCE: 146

Arg Asn Lys Pro Leu Lys Ala Leu Asp Thr Arg Phe Gly Arg Lys Leu
1               5                   10                  15

<210> SEQ ID NO 147
<211> LENGTH: 15
<212> TYPE: PRT
<213> ORGANISM: Homo sapiens

<400> SEQUENCE: 147

Arg Asn Gly Gln Ser Arg Leu Ser Leu Lys His Gly Glu Lys Ala
1               5                   10                  15

<210> SEQ ID NO 148
<211> LENGTH: 23
<212> TYPE: PRT
<213> ORGANISM: Mus musculus

<400> SEQUENCE: 148

Lys Phe Gly Asp Arg Gly Asn Gln Leu Arg Lys Met Leu Leu Gln Asn
1               5                   10                  15

Tyr Leu Gln Asn Arg Lys Ser
            20

<210> SEQ ID NO 149
<211> LENGTH: 21
<212> TYPE: PRT
<213> ORGANISM: Mus musculus

<400> SEQUENCE: 149

Lys Lys Phe Ala Ala Asp Phe Lys Thr Leu Ala Asp Val Leu Val Gln
1               5                   10                  15

Glu Val Ile Lys Gln
            20

<210> SEQ ID NO 150
<211> LENGTH: 11
<212> TYPE: PRT
<213> ORGANISM: Homo sapiens

<400> SEQUENCE: 150

Lys Thr Leu Thr Lys Glu Asp Ile Ile Lys Phe
1               5                   10

<210> SEQ ID NO 151
<211> LENGTH: 26
<212> TYPE: PRT
<213> ORGANISM: Homo sapiens
```

-continued

<400> SEQUENCE: 151

Lys Gly Trp Pro Lys Thr His Pro Gly Gly Glu Gln Lys Glu Gly Thr
1               5                   10                  15

Glu Ala Ser Leu Gln Ile Arg Gly Lys Lys
            20                  25

<210> SEQ ID NO 152
<211> LENGTH: 29
<212> TYPE: PRT
<213> ORGANISM: Homo sapiens

<400> SEQUENCE: 152

Arg Gly Ile Asp Ser Ser Tyr Arg Pro Ser Gln Lys Asp Val Glu Pro
1               5                   10                  15

Pro Lys Ile Ser Ser Thr Lys Asn Ile Ser Ile Lys Gln
            20                  25

<210> SEQ ID NO 153
<211> LENGTH: 25
<212> TYPE: PRT
<213> ORGANISM: Homo sapiens

<400> SEQUENCE: 153

Arg Lys Ser Glu Asn Thr Ala Ile His His Tyr Leu Glu Ala Leu Lys
1               5                   10                  15

Val Lys Asp Arg Ser Pro Leu Arg Thr
            20                  25

<210> SEQ ID NO 154
<211> LENGTH: 27
<212> TYPE: PRT
<213> ORGANISM: Homo sapiens

<400> SEQUENCE: 154

Arg Arg Cys Leu Ile Ser Thr Asp Met His His Ile Glu Glu Ser Phe
1               5                   10                  15

Gln Glu Ile Lys Arg Ala Ile Gln Ala Lys Asp
            20                  25

<210> SEQ ID NO 155
<211> LENGTH: 27
<212> TYPE: PRT
<213> ORGANISM: Homo sapiens

<400> SEQUENCE: 155

Lys Glu Gln Leu Asp Ala Leu Glu Lys Glu Thr Ala Ser Lys Leu Ser
1               5                   10                  15

Glu Met Asp Ser Phe Asn Asn Gln Leu Lys Cys
            20                  25

<210> SEQ ID NO 156
<211> LENGTH: 14
<212> TYPE: PRT
<213> ORGANISM: Mus musculus

<400> SEQUENCE: 156

Lys Gln Lys Arg Leu Gln Glu Glu Lys Ser Gln Asp Lys Thr
1               5                   10

<210> SEQ ID NO 157
<211> LENGTH: 25
<212> TYPE: PRT

<213> ORGANISM: Homo sapiens

<400> SEQUENCE: 157

Lys Ile Pro Val Gly Ser Glu Glu Gly Tyr Arg Ser Leu Phe Gly Gln
1               5                   10                  15

Val Leu Lys Asp Ile Val Glu Lys Ile
            20                  25

<210> SEQ ID NO 158
<211> LENGTH: 27
<212> TYPE: PRT
<213> ORGANISM: Mus musculus

<400> SEQUENCE: 158

Lys Met Trp Lys Ser Pro Asn Gly Thr Ile Arg Asn Ile Leu Gly Gly
1               5                   10                  15

Thr Val Phe Arg Glu Pro Ile Ile Cys Lys Asn
            20                  25

<210> SEQ ID NO 159
<211> LENGTH: 29
<212> TYPE: PRT
<213> ORGANISM: Homo sapiens

<400> SEQUENCE: 159

Arg Glu Val Arg Pro Ser Pro Ser Lys Thr Val Lys Tyr Thr Ala Thr
1               5                   10                  15

Val Thr Lys Gly Ala Val Thr Tyr Thr Lys Ala Lys Arg
            20                  25

<210> SEQ ID NO 160
<211> LENGTH: 21
<212> TYPE: PRT
<213> ORGANISM: Mus musculus

<400> SEQUENCE: 160

Lys Ile Ser Glu Leu Ser Leu Cys Asp Leu Ala Gly Ser Glu Arg Cys
1               5                   10                  15

Lys His Gln Lys Ser
            20

<210> SEQ ID NO 161
<211> LENGTH: 19
<212> TYPE: PRT
<213> ORGANISM: Mus musculus

<400> SEQUENCE: 161

Lys Lys Leu His Ala Met Asn Lys Glu Leu Gln Arg Leu Gln Thr Ala
1               5                   10                  15

Gln Lys Glu

<210> SEQ ID NO 162
<211> LENGTH: 20
<212> TYPE: PRT
<213> ORGANISM: Homo sapiens

<400> SEQUENCE: 162

Lys Gln Leu Asp Asp Lys Asp Asp Glu Ile Asn Gln Gln Ser Gln Leu
1               5                   10                  15

Ile Glu Lys Leu
            20

```
<210> SEQ ID NO 163
<211> LENGTH: 24
<212> TYPE: PRT
<213> ORGANISM: Mus musculus

<400> SEQUENCE: 163

Arg Asn Glu Thr Pro Ser Gly Asp Ser Gln Thr Leu Met Ile Pro Ser
 1               5                  10                  15

Asn Pro Cys Leu Met Lys Arg Lys
             20

<210> SEQ ID NO 164
<211> LENGTH: 26
<212> TYPE: PRT
<213> ORGANISM: Homo sapiens

<400> SEQUENCE: 164

Arg Met Gly Lys Leu His Leu Val Asp Leu Ala Gly Ser Glu Arg Gln
 1               5                  10                  15

Ala Lys Thr Gly Ala Thr Gly Gln Arg Leu
             20                  25

<210> SEQ ID NO 165
<211> LENGTH: 25
<212> TYPE: PRT
<213> ORGANISM: Homo sapiens

<400> SEQUENCE: 165

Arg Lys Arg Thr Phe Ser Leu Gln Gly Gly Gly Gly Gly Gly Ala Asn
 1               5                  10                  15

Gly Gly Ser Gly Gly Gln Gly Lys Gly
             20                  25

<210> SEQ ID NO 166
<211> LENGTH: 21
<212> TYPE: PRT
<213> ORGANISM: Rattus norvegicus

<400> SEQUENCE: 166

Lys Ile Met Gly Gly Ser Gly Thr Glu Val Val Leu Glu Lys Gln Lys
 1               5                  10                  15

Ser Thr Pro Lys Ser
             20

<210> SEQ ID NO 167
<211> LENGTH: 24
<212> TYPE: PRT
<213> ORGANISM: Homo sapiens

<400> SEQUENCE: 167

Lys Ile Pro Ala Lys Ile Ser Gln Met Thr Asn Leu Gln Glu Leu His
 1               5                  10                  15

Leu Cys His Cys Pro Ala Lys Val
             20

<210> SEQ ID NO 168
<211> LENGTH: 31
<212> TYPE: PRT
<213> ORGANISM: Rattus norvegicus

<400> SEQUENCE: 168

Lys Asn Asn Met Asn Arg Ser Asn Thr Ile Gln Ser Gly Pro Glu Gly
```

```
                1               5                  10                 15
Ser Leu Val Lys Ser Gln Ser Leu Lys Ser Ile Pro Glu Lys Phe
                20                 25                 30
```

<210> SEQ ID NO 169
<211> LENGTH: 34
<212> TYPE: PRT
<213> ORGANISM: Homo sapiens

<400> SEQUENCE: 169

```
Arg Lys Ile Ser Glu Asn Ser Tyr Ser Leu Asp Asp Leu Glu Ile Gly
 1               5                  10                 15
Pro Gly Gln Leu Ser Ser Ser Thr Phe Asp Ser Glu Lys Asn Glu Ser
                20                 25                 30
Arg Arg
```

<210> SEQ ID NO 170
<211> LENGTH: 20
<212> TYPE: PRT
<213> ORGANISM: Homo sapiens

<400> SEQUENCE: 170

```
Arg Cys Leu Glu His Pro Asn Val Leu Lys Phe Ile Gly Val Leu Tyr
 1               5                  10                 15
Lys Asp Lys Arg
                20
```

<210> SEQ ID NO 171
<211> LENGTH: 16
<212> TYPE: PRT
<213> ORGANISM: Rattus norvegicus

<400> SEQUENCE: 171

```
Arg Ser Gly Lys Tyr Leu Ala Thr Glu Trp Asn Thr Val Ser Lys Leu
 1               5                  10                 15
```

<210> SEQ ID NO 172
<211> LENGTH: 26
<212> TYPE: PRT
<213> ORGANISM: Homo sapiens

<400> SEQUENCE: 172

```
Lys Glu Ala Glu Ala Phe Leu Glu Lys Tyr Gly Tyr Leu Asn Glu Gln
 1               5                  10                 15
Val Pro Lys Ala Pro Thr Ser Thr Arg Phe
                20                 25
```

<210> SEQ ID NO 173
<211> LENGTH: 15
<212> TYPE: PRT
<213> ORGANISM: Homo sapiens

<400> SEQUENCE: 173

```
Arg Gly Arg Gln Thr Val Asp Lys Val Met Gly Ile Pro Lys Glu
 1               5                  10                 15
```

<210> SEQ ID NO 174
<211> LENGTH: 19
<212> TYPE: PRT
<213> ORGANISM: Homo sapiens

<400> SEQUENCE: 174

```
Lys Lys Val Ser Phe Ser Ser Pro Leu Ile Leu Gly Ala Thr Ile Gln
1               5                   10                  15
Lys Lys Ser

<210> SEQ ID NO 175
<211> LENGTH: 20
<212> TYPE: PRT
<213> ORGANISM: Mus musculus

<400> SEQUENCE: 175

Lys Lys Ile Pro Ile Lys Arg Thr Asp Ile Leu Lys His Val Val Gly
1               5                   10                  15

Asp Tyr Arg Asp
            20

<210> SEQ ID NO 176
<211> LENGTH: 20
<212> TYPE: PRT
<213> ORGANISM: Mus musculus

<400> SEQUENCE: 176

Lys Lys Ile Pro Ile Lys Arg Thr Asp Ile Leu Lys His Val Val Gly
1               5                   10                  15

Asp Tyr Arg Asp
            20

<210> SEQ ID NO 177
<211> LENGTH: 23
<212> TYPE: PRT
<213> ORGANISM: Homo sapiens

<400> SEQUENCE: 177

Lys Leu Gln Asn Leu Gln Thr Val Arg Leu Val Phe Lys Ile Gln Thr
1               5                   10                  15

Gln Thr Pro Arg Lys Lys Thr
            20

<210> SEQ ID NO 178
<211> LENGTH: 28
<212> TYPE: PRT
<213> ORGANISM: Homo sapiens

<400> SEQUENCE: 178

Lys Lys Gly Thr Glu Leu Leu Gly Val Asp Ala Leu Gly Leu His
1               5                   10                  15

Ile Tyr Asp Pro Glu Asn Arg Leu Thr Pro Lys Ile
            20                  25

<210> SEQ ID NO 179
<211> LENGTH: 20
<212> TYPE: PRT
<213> ORGANISM: Mus musculus

<400> SEQUENCE: 179

Lys Ile Ala Gln Asp Leu Glu Met Tyr Gly Val Asn Tyr Phe Thr Ile
1               5                   10                  15

Arg Asn Lys Lys
            20

<210> SEQ ID NO 180
<211> LENGTH: 16
<212> TYPE: PRT
```

-continued

```
<213> ORGANISM: Homo sapiens

<400> SEQUENCE: 180

Arg Gly Ser Glu Gly Lys Pro Cys Gly Glu Leu Lys Lys Glu Lys Gly
1               5                   10                  15

<210> SEQ ID NO 181
<211> LENGTH: 32
<212> TYPE: PRT
<213> ORGANISM: Rattus norvegicus

<400> SEQUENCE: 181

Arg Val Asp Gly Asp Ile Ile Leu Gly Gly Leu Phe Pro Val His Ala
1               5                   10                  15

Lys Gly Glu Arg Gly Val Pro Cys Gly Glu Leu Lys Lys Glu Lys Gly
                20                  25                  30

<210> SEQ ID NO 182
<211> LENGTH: 24
<212> TYPE: PRT
<213> ORGANISM: Homo sapiens

<400> SEQUENCE: 182

Lys Ser Ser Cys Lys Glu Asn Pro Phe Asn Arg Lys Pro Ser Pro Ala
1               5                   10                  15

Ala Ser Pro Ala Thr Lys Lys Ala
                20

<210> SEQ ID NO 183
<211> LENGTH: 22
<212> TYPE: PRT
<213> ORGANISM: Rattus norvegicus

<400> SEQUENCE: 183

Lys Val Ile Val Lys Lys Asp Lys Pro Gly Lys Val Glu Ser Lys Pro
1               5                   10                  15

Ser Val Thr Glu Lys Glu
                20

<210> SEQ ID NO 184
<211> LENGTH: 9
<212> TYPE: PRT
<213> ORGANISM: Rattus norvegicus

<400> SEQUENCE: 184

Lys Thr Lys Pro Glu Glu Lys Lys Glu
1               5

<210> SEQ ID NO 185
<211> LENGTH: 30
<212> TYPE: PRT
<213> ORGANISM: Rattus norvegicus

<400> SEQUENCE: 185

Lys Ser Lys Pro Ser Ala Ala Ser Pro Lys Pro Gly Ala Leu Lys Glu
1               5                   10                  15

Ser Ser Asp Lys Val Ser Arg Val Ala Ser Pro Lys Lys Lys
                20                  25                  30

<210> SEQ ID NO 186
<211> LENGTH: 19
<212> TYPE: PRT
<213> ORGANISM: Mus musculus
```

-continued

```
<400> SEQUENCE: 186

Arg Gln Trp Ile Gly Lys His Arg Arg Pro Arg Thr Val Ser Phe Gln
1               5                   10                  15

Ala Lys Glu

<210> SEQ ID NO 187
<211> LENGTH: 20
<212> TYPE: PRT
<213> ORGANISM: Mus musculus

<400> SEQUENCE: 187

Lys Ala Asp Pro Phe Ser Phe Lys Ala Arg Ala Lys Ser Cys Gly Glu
1               5                   10                  15

Asp Gly Lys Gly
            20

<210> SEQ ID NO 188
<211> LENGTH: 13
<212> TYPE: PRT
<213> ORGANISM: Homo sapiens

<400> SEQUENCE: 188

Lys Lys Ile Lys Thr Lys Lys Ser Thr Trp Glu Lys Val
1               5                   10

<210> SEQ ID NO 189
<211> LENGTH: 23
<212> TYPE: PRT
<213> ORGANISM: Mus musculus

<400> SEQUENCE: 189

Lys Arg Ala Arg Ala Asp Pro Thr Val Glu Ser Glu Glu Ala Phe Lys
1               5                   10                  15

Ser Arg Met Glu Val Lys Val
            20

<210> SEQ ID NO 190
<211> LENGTH: 19
<212> TYPE: PRT
<213> ORGANISM: Rattus norvegicus

<400> SEQUENCE: 190

Arg Ala Lys Leu Asp Ser Gly Arg Val Leu Lys Gln Ile Ser Asn Asn
1               5                   10                  15

Arg Lys Cys

<210> SEQ ID NO 191
<211> LENGTH: 23
<212> TYPE: PRT
<213> ORGANISM: Homo sapiens

<400> SEQUENCE: 191

Arg Gly Ser Gly Lys Asp Ser His His Pro Ala Arg Thr Ala His Tyr
1               5                   10                  15

Gly Ser Leu Pro Gln Lys Ser
            20

<210> SEQ ID NO 192
<211> LENGTH: 16
<212> TYPE: PRT
<213> ORGANISM: Rattus norvegicus
```

<400> SEQUENCE: 192

Lys Ile Asn Lys Ser Glu Ser Val Val Tyr Ala Asp Ile Arg Lys Asp
1               5                   10                  15

<210> SEQ ID NO 193
<211> LENGTH: 26
<212> TYPE: PRT
<213> ORGANISM: Homo sapiens

<400> SEQUENCE: 193

Lys Glu Ile Phe Gly Gly Asn Ala Asp Lys Lys Asn Leu Val Asp Pro
1               5                   10                  15

Phe Val Glu Val Ser Phe Ala Gly Lys Lys
            20                  25

<210> SEQ ID NO 194
<211> LENGTH: 27
<212> TYPE: PRT
<213> ORGANISM: Homo sapiens

<400> SEQUENCE: 194

Arg Ile Glu Ala Gln Asn Lys Pro Phe Asp Ala Lys Thr Ser Val Phe
1               5                   10                  15

Val Val Asp Pro Lys Glu Ser Tyr Val Lys Ala
            20                  25

<210> SEQ ID NO 195
<211> LENGTH: 27
<212> TYPE: PRT
<213> ORGANISM: Homo sapiens

<400> SEQUENCE: 195

Arg Val Phe Asp Lys Glu Gly Asn Gly Thr Val Met Gly Ala Glu Ile
1               5                   10                  15

Arg His Val Leu Val Thr Leu Gly Glu Lys Met
            20                  25

<210> SEQ ID NO 196
<211> LENGTH: 16
<212> TYPE: PRT
<213> ORGANISM: Rattus norvegicus

<400> SEQUENCE: 196

Arg Gly Asp Glu Val Met Val Glu Leu Ala Glu Asn Gly Lys Lys Ala
1               5                   10                  15

<210> SEQ ID NO 197
<211> LENGTH: 19
<212> TYPE: PRT
<213> ORGANISM: Homo sapiens

<400> SEQUENCE: 197

Lys Leu Lys Lys Leu Glu Glu Glu Gln Ile Ile Leu Glu Asp Gln Asn
1               5                   10                  15

Cys Lys Leu

<210> SEQ ID NO 198
<211> LENGTH: 26
<212> TYPE: PRT
<213> ORGANISM: Homo sapiens

<400> SEQUENCE: 198

```
Arg Glu Thr Asn Lys Gln Ile Ser Lys Leu Thr Ile Tyr Asp Ala Arg
1               5                   10                  15

Pro Ser Val Asn Ala Val Ala Asn Lys Ala
            20                  25

<210> SEQ ID NO 199
<211> LENGTH: 27
<212> TYPE: PRT
<213> ORGANISM: Homo sapiens

<400> SEQUENCE: 199

Lys Gln Lys Gly His Tyr Leu Ala Gly Lys Val Ile Gly Glu Phe Pro
1               5                   10                  15

Gly Val Val His Cys Leu Asp Phe Gln Lys Met
            20                  25

<210> SEQ ID NO 200
<211> LENGTH: 18
<212> TYPE: PRT
<213> ORGANISM: Homo sapiens

<400> SEQUENCE: 200

Lys Gln Lys Gly His Tyr Val Gly Thr Leu Thr Ala Arg Asp Asp Asn
1               5                   10                  15

Lys Ile

<210> SEQ ID NO 201
<211> LENGTH: 19
<212> TYPE: PRT
<213> ORGANISM: Mus musculus

<400> SEQUENCE: 201

Lys Gly Phe Glu Leu Arg Leu Asp Ser Leu Ala Phe Leu Thr Ala Lys
1               5                   10                  15

Ala Lys Arg

<210> SEQ ID NO 202
<211> LENGTH: 19
<212> TYPE: PRT
<213> ORGANISM: Mus musculus

<400> SEQUENCE: 202

Lys Gly Phe Glu Leu Arg Leu Asp Ser Leu Ala Phe Leu Thr Ala Lys
1               5                   10                  15

Ala Lys Arg

<210> SEQ ID NO 203
<211> LENGTH: 23
<212> TYPE: PRT
<213> ORGANISM: Homo sapiens

<400> SEQUENCE: 203

Lys Lys Tyr Leu Leu Leu Gly Asn Ala Glu Asp Ser Pro Asp Gln Ser
1               5                   10                  15

Gly Ile Val Ala Asp Lys Ser
            20

<210> SEQ ID NO 204
<211> LENGTH: 25
<212> TYPE: PRT
<213> ORGANISM: Mus musculus
```

-continued

<400> SEQUENCE: 204

Arg Leu Leu Gln Ser Ala Phe Ser Lys Asn Ala Leu Ser Lys Gln Ser
1               5                   10                  15

Pro Lys Lys Ser Pro Ser Ala Lys Leu
            20                  25

<210> SEQ ID NO 205
<211> LENGTH: 28
<212> TYPE: PRT
<213> ORGANISM: Homo sapiens

<400> SEQUENCE: 205

Arg Asn Gly Val Gly Leu Glu Phe Asn His Leu Phe Gly Tyr Gly Val
1               5                   10                  15

Leu Asp Ala Gly Ala Met Val Lys Met Ala Lys Asp
            20                  25

<210> SEQ ID NO 206
<211> LENGTH: 30
<212> TYPE: PRT
<213> ORGANISM: Mus musculus

<400> SEQUENCE: 206

Lys Glu Glu Ala Lys Ser Pro Gly Ala Lys Ser Pro Gly Glu Ala
1               5                   10                  15

Lys Ser Pro Ala Glu Ala Lys Ser Pro Gly Glu Ala Lys Ser
            20                  25                  30

<210> SEQ ID NO 207
<211> LENGTH: 23
<212> TYPE: PRT
<213> ORGANISM: Homo sapiens

<400> SEQUENCE: 207

Lys Ala Ser Thr Asp Asn Ser Pro Ser Lys Ala Glu Asp Ala Pro
1               5                   10                  15

Ala Lys Glu Glu Pro Lys Gln
            20

<210> SEQ ID NO 208
<211> LENGTH: 24
<212> TYPE: PRT
<213> ORGANISM: Homo sapiens

<400> SEQUENCE: 208

Lys Asp Gln Thr Gln Lys Ala Ala Thr Gly Pro Phe Asp Arg Glu His
1               5                   10                  15

Leu Leu Met Tyr Leu Glu Lys Glu
            20

<210> SEQ ID NO 209
<211> LENGTH: 19
<212> TYPE: PRT
<213> ORGANISM: Mus musculus

<400> SEQUENCE: 209

Arg Ser Asn Ser Glu Ile Leu Lys Gln Phe Thr Leu Arg Glu Leu Arg
1               5                   10                  15

Asn Lys Arg

```
<210> SEQ ID NO 210
<211> LENGTH: 17
<212> TYPE: PRT
<213> ORGANISM: Homo sapiens

<400> SEQUENCE: 210

Arg Phe Gly Ser Lys Ala His Met Glu Arg Leu Glu Glu Val Asn Lys
1               5                   10                  15

Glu

<210> SEQ ID NO 211
<211> LENGTH: 27
<212> TYPE: PRT
<213> ORGANISM: Homo sapiens

<400> SEQUENCE: 211

Arg Gly Gly Asp Val Ser Asp Ser Lys Gln Phe Thr Tyr Tyr Pro Leu
1               5                   10                  15

Val Glu Asp Lys Glu Glu Val Gln Arg Lys Arg
            20                  25

<210> SEQ ID NO 212
<211> LENGTH: 27
<212> TYPE: PRT
<213> ORGANISM: Homo sapiens

<400> SEQUENCE: 212

Lys Gln Leu Leu Thr Gly Asn Thr Asp Lys Pro Ile Gly Met Ile Asp
1               5                   10                  15

Arg Leu Asn Ser Pro Leu Leu Ser Asn Lys Thr
            20                  25

<210> SEQ ID NO 213
<211> LENGTH: 28
<212> TYPE: PRT
<213> ORGANISM: Mus musculus

<400> SEQUENCE: 213

Arg Ser Gly Thr Ser Ser Gly Ala Gly Gly Ser Ile Thr Arg Gly Ala
1               5                   10                  15

Pro Val Val Val Pro Glu Leu Gly Lys Pro Arg Gln
            20                  25

<210> SEQ ID NO 214
<211> LENGTH: 19
<212> TYPE: PRT
<213> ORGANISM: Rattus norvegicus

<400> SEQUENCE: 214

Arg Cys Lys Gln Leu Lys Arg Ala Ala Leu Gly Arg Met Cys Thr Ile
1               5                   10                  15

Ile Lys Arg

<210> SEQ ID NO 215
<211> LENGTH: 26
<212> TYPE: PRT
<213> ORGANISM: Homo sapiens

<400> SEQUENCE: 215

Arg Val Gly Asp Leu Ile Leu Ala His Leu His Lys Lys Cys Pro Tyr
1               5                   10                  15

Ser Val Pro Phe Tyr Pro Thr Phe Lys Glu
```

20                  25

<210> SEQ ID NO 216
<211> LENGTH: 13
<212> TYPE: PRT
<213> ORGANISM: Rattus norvegicus

<400> SEQUENCE: 216

Lys Gln Val Lys Gly Ser Ala Asp Tyr Lys Ser Lys Lys
1               5                   10

<210> SEQ ID NO 217
<211> LENGTH: 13
<212> TYPE: PRT
<213> ORGANISM: Rattus norvegicus

<400> SEQUENCE: 217

Lys Gln Val Lys Gly Ser Ala Asp Tyr Lys Ser Lys Lys
1               5                   10

<210> SEQ ID NO 218
<211> LENGTH: 18
<212> TYPE: PRT
<213> ORGANISM: Rattus norvegicus

<400> SEQUENCE: 218

Arg Ile Val Ser Ser Ile Phe Lys Val Pro Ser Ser Gln Ser Ile His
1               5                   10                  15

Lys Ala

<210> SEQ ID NO 219
<211> LENGTH: 26
<212> TYPE: PRT
<213> ORGANISM: Mus musculus

<400> SEQUENCE: 219

Lys Lys Pro Tyr Val Ala Lys Leu Ile Glu Leu Phe Gln Asn Gly Ala
1               5                   10                  15

Glu Val Pro Pro Lys Lys Cys Ala Arg Val
                20                  25

<210> SEQ ID NO 220
<211> LENGTH: 28
<212> TYPE: PRT
<213> ORGANISM: Rattus norvegicus

<400> SEQUENCE: 220

Lys Leu Phe Asn Tyr Asn Lys Val Leu Pro Met Asn Thr Gly Val Glu
1               5                   10                  15

Ala Gly Glu Thr Ala Cys Lys Leu Ala Arg Arg Trp
                20                  25

<210> SEQ ID NO 221
<211> LENGTH: 16
<212> TYPE: PRT
<213> ORGANISM: Homo sapiens

<400> SEQUENCE: 221

Lys Glu Met Asn Ile Leu Glu Leu Ser His Lys Lys Met Met Lys Lys
1               5                   10                  15

<210> SEQ ID NO 222
<211> LENGTH: 22

```
<212> TYPE: PRT
<213> ORGANISM: Homo sapiens

<400> SEQUENCE: 222

Arg Gly Thr Asp Ser Glu His Thr His Lys Ala His Leu Val Pro Glu
 1               5                  10                  15

Gly Thr Ser Lys Lys Arg
            20

<210> SEQ ID NO 223
<211> LENGTH: 13
<212> TYPE: PRT
<213> ORGANISM: Homo sapiens

<400> SEQUENCE: 223

Arg Lys Ser Val Arg Pro Gly Ala Ser Tyr Lys Arg Gln
 1               5                  10

<210> SEQ ID NO 224
<211> LENGTH: 27
<212> TYPE: PRT
<213> ORGANISM: Homo sapiens

<400> SEQUENCE: 224

Lys Gly Ala Thr Ala Gly Ala Ser His Lys Gly Asp Glu Val Pro Pro
 1               5                  10                  15

Ile Lys Lys Asn Thr Lys Ala Pro Gly Lys Gln
            20                  25

<210> SEQ ID NO 225
<211> LENGTH: 20
<212> TYPE: PRT
<213> ORGANISM: Rattus norvegicus

<400> SEQUENCE: 225

Arg Glu Ile Asp Lys Arg Met Asn Ser Ile Lys Pro Asp Leu Ile Gln
 1               5                  10                  15

Leu Arg Lys Thr
            20

<210> SEQ ID NO 226
<211> LENGTH: 26
<212> TYPE: PRT
<213> ORGANISM: Homo sapiens

<400> SEQUENCE: 226

Lys Lys Gln Ala Ala Glu Tyr Arg Glu Ile Asp Lys Arg Met Asn Ser
 1               5                  10                  15

Ile Lys Pro Asp Leu Ile Gln Leu Arg Lys
            20                  25

<210> SEQ ID NO 227
<211> LENGTH: 20
<212> TYPE: PRT
<213> ORGANISM: Rattus norvegicus

<400> SEQUENCE: 227

Arg Leu Glu Gln Asp Leu Lys Lys Gln Ala Leu Asp Asn Arg Glu Ile
 1               5                  10                  15

Asp Lys Lys Met
            20
```

```
<210> SEQ ID NO 228
<211> LENGTH: 22
<212> TYPE: PRT
<213> ORGANISM: Mus musculus

<400> SEQUENCE: 228

Arg Glu Pro Leu Arg Thr Ile Pro Leu Lys Asp Val Leu Lys Thr His
1               5                   10                  15

Glu Cys Leu Val Lys Ser
            20

<210> SEQ ID NO 229
<211> LENGTH: 16
<212> TYPE: PRT
<213> ORGANISM: Homo sapiens

<400> SEQUENCE: 229

Lys Ile Lys Pro Thr Ser Ala Trp Asn Leu Ala Gln Lys His Lys Leu
1               5                   10                  15

<210> SEQ ID NO 230
<211> LENGTH: 31
<212> TYPE: PRT
<213> ORGANISM: Mus musculus

<400> SEQUENCE: 230

Arg Ser Phe Pro Ser Glu Lys Arg Gly Val Leu Ser Ser Tyr Pro Ser
1               5                   10                  15

Asp Val Ile Ser Tyr Arg Gly Leu Arg Gly Ser Gln Asp Lys Leu
            20                  25                  30

<210> SEQ ID NO 231
<211> LENGTH: 31
<212> TYPE: PRT
<213> ORGANISM: Homo sapiens

<400> SEQUENCE: 231

Arg Val Asp Arg Met Glu His Ser Ile Gly Ser Ile Val Ser Lys Ile
1               5                   10                  15

Asp Ala Val Ile Val Lys Leu Glu Ile Met Glu Arg Ala Lys Leu
            20                  25                  30

<210> SEQ ID NO 232
<211> LENGTH: 11
<212> TYPE: PRT
<213> ORGANISM: Homo sapiens

<400> SEQUENCE: 232

Lys Ile Asp Lys Asn Glu Asp Arg Lys Lys Asp
1               5                   10

<210> SEQ ID NO 233
<211> LENGTH: 24
<212> TYPE: PRT
<213> ORGANISM: Homo sapiens

<400> SEQUENCE: 233

Lys Gly Asp Pro Phe Leu Ala Ser Pro Thr Ser Asp Arg Glu Ile Ile
1               5                   10                  15

Ala Pro Lys Ile Lys Glu Arg Thr
            20

<210> SEQ ID NO 234
```

```
<211> LENGTH: 25
<212> TYPE: PRT
<213> ORGANISM: Homo sapiens

<400> SEQUENCE: 234

Lys Leu Lys Ile Asn Asn Asn Val Phe Val Asp Lys Pro Ala Phe Pro
1               5                   10                  15

Glu Tyr Lys Val Ser Asp Ala Lys Lys
            20                  25

<210> SEQ ID NO 235
<211> LENGTH: 35
<212> TYPE: PRT
<213> ORGANISM: Mus musculus

<400> SEQUENCE: 235

Arg Asp Gly Ala Leu Leu Ile Ala Gly Ser Glu Ala Pro Lys Arg Gly
1               5                   10                  15

Ser Val Leu Ser Lys Pro Arg Thr Gly Ala Gly Ala Gly Lys Pro
            20                  25                  30

Pro Lys Arg
        35

<210> SEQ ID NO 236
<211> LENGTH: 33
<212> TYPE: PRT
<213> ORGANISM: Mus musculus

<400> SEQUENCE: 236

Lys Cys Pro Lys Pro Ser Ala Gln Glu Ile Thr Asn Leu Ala Asp Ser
1               5                   10                  15

Leu Gln Leu Glu Lys Glu Val Val Arg Val Trp Phe Cys Asn Arg Arg
            20                  25                  30

Gln

<210> SEQ ID NO 237
<211> LENGTH: 20
<212> TYPE: PRT
<213> ORGANISM: Homo sapiens

<400> SEQUENCE: 237

Arg Glu Tyr Ser Val Lys Glu Ile Leu Lys Leu Asp Ser Asn Pro Ser
1               5                   10                  15

Lys Gly Lys Asp
            20

<210> SEQ ID NO 238
<211> LENGTH: 35
<212> TYPE: PRT
<213> ORGANISM: Homo sapiens

<400> SEQUENCE: 238

Arg Gly Val Ser Ser Gln Glu Thr Ala Gly Ile Gly Ala Ser Ala His
1               5                   10                  15

Leu Val Asn Phe Lys Gly Thr Asp Thr Val Ala Gly Leu Ala Leu Ile
            20                  25                  30

Lys Lys Tyr
        35

<210> SEQ ID NO 239
<211> LENGTH: 20
```

```
<212> TYPE: PRT
<213> ORGANISM: Homo sapiens

<400> SEQUENCE: 239

Lys Tyr Val Glu Ala Lys Asp Cys Leu Asn Val Leu Asn Lys Ser Asn
1               5                   10                  15

Glu Gly Lys Glu
            20

<210> SEQ ID NO 240
<211> LENGTH: 20
<212> TYPE: PRT
<213> ORGANISM: Homo sapiens

<400> SEQUENCE: 240

Lys Tyr Val Glu Ala Lys Asp Cys Leu Asn Val Leu Asn Lys Ser Asn
1               5                   10                  15

Glu Gly Lys Glu
            20

<210> SEQ ID NO 241
<211> LENGTH: 21
<212> TYPE: PRT
<213> ORGANISM: Homo sapiens

<400> SEQUENCE: 241

Lys Gln Tyr Tyr Lys Val Val Asn Ser Tyr Pro Leu Ala His Lys Val
1               5                   10                  15

Phe Glu Glu Lys Thr
            20

<210> SEQ ID NO 242
<211> LENGTH: 13
<212> TYPE: PRT
<213> ORGANISM: Rattus norvegicus

<400> SEQUENCE: 242

Arg Trp Lys Val Thr Ser Lys Glu Ala Leu Gln Arg Ile
1               5                   10

<210> SEQ ID NO 243
<211> LENGTH: 24
<212> TYPE: PRT
<213> ORGANISM: Homo sapiens

<400> SEQUENCE: 243

Arg Ala Asn Gln Ser Val Pro Glu Asp Leu Val Val Met Ala Glu Gln
1               5                   10                  15

Tyr Lys Leu Asn Gln Gln Lys Arg
            20

<210> SEQ ID NO 244
<211> LENGTH: 20
<212> TYPE: PRT
<213> ORGANISM: Homo sapiens

<400> SEQUENCE: 244

Arg Gly Gly Asp Gly Ile Asn Ser Ile Gly Gly Gln Lys Val Arg
1               5                   10                  15

Leu Met Lys Glu
            20
```

```
<210> SEQ ID NO 245
<211> LENGTH: 37
<212> TYPE: PRT
<213> ORGANISM: Mus musculus

<400> SEQUENCE: 245

Arg Ser Val Pro Ala Thr Lys Gly Leu Leu Ser Pro Leu Met Ser Arg
 1               5                   10                  15

Pro Glu Ile Lys Val Gly Asp Gln Ser Gly Thr Gly Arg Gly Gln Lys
             20                  25                  30

Val Leu Pro Lys Gly
        35

<210> SEQ ID NO 246
<211> LENGTH: 18
<212> TYPE: PRT
<213> ORGANISM: Homo sapiens

<400> SEQUENCE: 246

Lys Val Thr Val Val Asn Ser Ile Lys Pro Ser Pro Thr Glu Gly
 1               5                   10                  15

Lys Arg

<210> SEQ ID NO 247
<211> LENGTH: 29
<212> TYPE: PRT
<213> ORGANISM: Mus musculus

<400> SEQUENCE: 247

Arg Glu Met Val Val Gln Tyr Ile Ser Ala Thr Ser Lys Ser Ile Val
 1               5                   10                  15

Gly Ser Lys Val Leu Gly Gly Leu Lys Asn Ser Lys His
             20                  25

<210> SEQ ID NO 248
<211> LENGTH: 30
<212> TYPE: PRT
<213> ORGANISM: Homo sapiens

<400> SEQUENCE: 248

Arg Ala Val Glu Lys Tyr Ser Val Lys Pro Glu His Pro Asn Leu Gly
 1               5                   10                  15

Ser Cys Asn Pro Ser Leu Tyr Asn Thr Phe Ala Ser Lys Gln
             20                  25                  30

<210> SEQ ID NO 249
<211> LENGTH: 25
<212> TYPE: PRT
<213> ORGANISM: Homo sapiens

<400> SEQUENCE: 249

Arg Asp Asn Met Ser Ile Val Leu Val Cys Phe Ser Asn Ala Pro Lys
 1               5                   10                  15

Val Ser Asp Glu Ala Val Lys Lys Asp
             20                  25

<210> SEQ ID NO 250
<211> LENGTH: 18
<212> TYPE: PRT
<213> ORGANISM: Homo sapiens

<400> SEQUENCE: 250
```

```
Lys Asn Glu Ala Ala Phe Leu Ser Met Thr Asp Ser Lys Thr Glu Gly
  1               5                  10                  15

Lys Phe

<210> SEQ ID NO 251
<211> LENGTH: 26
<212> TYPE: PRT
<213> ORGANISM: Homo sapiens

<400> SEQUENCE: 251

Lys Leu Lys Ile Leu Met Asp Lys Pro Glu Met Asn Val Val Leu Lys
  1               5                  10                  15

Asn Val Lys Pro Asp Gln Trp Val Lys Leu
             20                  25

<210> SEQ ID NO 252
<211> LENGTH: 14
<212> TYPE: PRT
<213> ORGANISM: Homo sapiens

<400> SEQUENCE: 252

Arg Lys Glu Leu Asn Lys Ile Leu Glu Gly Arg Ser Lys Ile
  1               5                  10

<210> SEQ ID NO 253
<211> LENGTH: 18
<212> TYPE: PRT
<213> ORGANISM: Rattus norvegicus

<400> SEQUENCE: 253

Arg Asp Leu Lys Leu Glu Asn Leu Met Leu Asp Lys Asp Gly His Ile
  1               5                  10                  15

Lys Ile

<210> SEQ ID NO 254
<211> LENGTH: 26
<212> TYPE: PRT
<213> ORGANISM: Rattus norvegicus

<400> SEQUENCE: 254

Arg Phe Tyr Gly Ala Glu Ile Val Ser Ala Leu Asp Tyr Leu His Ser
  1               5                  10                  15

Gly Lys Ile Val Tyr Arg Asp Leu Lys Leu
             20                  25

<210> SEQ ID NO 255
<211> LENGTH: 30
<212> TYPE: PRT
<213> ORGANISM: Rattus norvegicus

<400> SEQUENCE: 255

Arg Asp Met Lys Ser Asn Asn Ile Phe Leu His Glu Gly Leu Thr Val
  1               5                  10                  15

Lys Ile Gly Asp Phe Gly Leu Ala Thr Val Lys Ser Arg Trp
             20                  25                  30

<210> SEQ ID NO 256
<211> LENGTH: 22
<212> TYPE: PRT
<213> ORGANISM: Homo sapiens

<400> SEQUENCE: 256
```

-continued

Arg Leu Glu Gly Asn Thr Val Gly Val Glu Ala Ala Arg Val Ile Ala
1               5                   10                  15

Lys Ala Leu Glu Lys Lys
            20

<210> SEQ ID NO 257
<211> LENGTH: 22
<212> TYPE: PRT
<213> ORGANISM: Rattus norvegicus

<400> SEQUENCE: 257

Arg Glu Lys His Cys Leu Gly Met Lys Leu Ser Glu Asp Gly Thr Tyr
1               5                   10                  15

Thr Gly Phe Ile Lys Val
            20

<210> SEQ ID NO 258
<211> LENGTH: 19
<212> TYPE: PRT
<213> ORGANISM: Homo sapiens

<400> SEQUENCE: 258

Arg Thr Leu Thr Leu Ile Ala Lys Val Ile Gln Asn Leu Ala Asn Phe
1               5                   10                  15

Ser Lys Phe

<210> SEQ ID NO 259
<211> LENGTH: 26
<212> TYPE: PRT
<213> ORGANISM: Mus musculus

<400> SEQUENCE: 259

Met Ala Lys Ser Ala Glu Val Lys Leu Ala Ile Phe Gly Arg Ala Gly
1               5                   10                  15

Val Gly Lys Ser Ala Ile Val Val Arg Phe
            20                  25

<210> SEQ ID NO 260
<211> LENGTH: 15
<212> TYPE: PRT
<213> ORGANISM: Rattus norvegicus

<400> SEQUENCE: 260

Arg Leu Leu Lys Lys Glu Gln Asn Lys Met Gly Val Lys Leu Ser
1               5                   10                  15

<210> SEQ ID NO 261
<211> LENGTH: 25
<212> TYPE: PRT
<213> ORGANISM: Homo sapiens

<400> SEQUENCE: 261

Lys Ala Thr His Pro Pro Pro Ala Ser Pro Ser Ser Leu Val Lys Val
1               5                   10                  15

Pro Ser Ser Ala Thr Gly Lys Arg Gln
            20                  25

<210> SEQ ID NO 262
<211> LENGTH: 20
<212> TYPE: PRT
<213> ORGANISM: Rattus norvegicus

<400> SEQUENCE: 262

```
Lys Glu Glu Leu Asn Asn Lys Leu Lys Asp Thr Gln Glu Gln Leu Ser
 1               5                  10                  15

Lys Leu Lys Asp
            20
```

<210> SEQ ID NO 263
<211> LENGTH: 16
<212> TYPE: PRT
<213> ORGANISM: Rattus norvegicus

<400> SEQUENCE: 263

```
Arg Glu Ala Leu Gly Asp Lys Ala Pro Pro Lys Pro Val Pro Lys Thr
 1               5                  10                  15
```

<210> SEQ ID NO 264
<211> LENGTH: 16
<212> TYPE: PRT
<213> ORGANISM: Mus musculus

<400> SEQUENCE: 264

```
Lys Leu Ala Lys Gln Asn Thr Asn Lys Ala Lys Glu Asn Leu Arg Lys
 1               5                  10                  15
```

<210> SEQ ID NO 265
<211> LENGTH: 21
<212> TYPE: PRT
<213> ORGANISM: Rattus norvegicus

<400> SEQUENCE: 265

```
Lys Leu Asp Thr Pro Ala Thr Ser Asp Pro Leu Ser Asp Arg Gly Gly
 1               5                  10                  15

Arg Lys Arg Lys Arg
            20
```

<210> SEQ ID NO 266
<211> LENGTH: 19
<212> TYPE: PRT
<213> ORGANISM: Homo sapiens

<400> SEQUENCE: 266

```
Arg Arg Asn His Cys Phe Gln Asp Phe Lys Glu Glu Lys Pro Gln Glu
 1               5                  10                  15

Asn Lys Thr
```

<210> SEQ ID NO 267
<211> LENGTH: 31
<212> TYPE: PRT
<213> ORGANISM: Rattus norvegicus

<400> SEQUENCE: 267

```
Arg Gln Lys Cys His Ser Pro Pro Lys Pro Glu Pro Phe Pro Phe
 1               5                  10                  15

Gly Gln Ser Gly Gln Lys Pro Ala Leu Asn Gly Gly Lys Lys Val
            20                  25                  30
```

<210> SEQ ID NO 268
<211> LENGTH: 21
<212> TYPE: PRT
<213> ORGANISM: Mus musculus

<400> SEQUENCE: 268

```
Lys Phe Glu Ala Lys Leu Met Pro Glu Glu Cys Phe Ser Pro Leu Asp
```

```
                1               5                   10                  15
Leu Phe Asn Lys Ile
            20

<210> SEQ ID NO 269
<211> LENGTH: 22
<212> TYPE: PRT
<213> ORGANISM: Homo sapiens

<400> SEQUENCE: 269

Lys Val Ala Ser Ile Ser Phe Asp Ala Ser Lys Ala Lys Lys Pro Ser
1               5                   10                  15

Gln Phe Ser Gly Lys Ile
            20

<210> SEQ ID NO 270
<211> LENGTH: 21
<212> TYPE: PRT
<213> ORGANISM: Homo sapiens

<400> SEQUENCE: 270

Lys Arg Leu Ala Val Phe Ser Gln Pro Ile Ile Asn Lys Val Lys Pro
1               5                   10                  15

Gln Leu Leu Lys Thr
            20

<210> SEQ ID NO 271
<211> LENGTH: 18
<212> TYPE: PRT
<213> ORGANISM: Homo sapiens

<400> SEQUENCE: 271

Arg Lys Ala Gln Ala Ala Glu Met Lys Ala Ala Asn Glu Ala Glu Gly
1               5                   10                  15

Lys Val

<210> SEQ ID NO 272
<211> LENGTH: 21
<212> TYPE: PRT
<213> ORGANISM: Homo sapiens

<400> SEQUENCE: 272

Lys Tyr Leu Lys Ile Glu Glu Thr Asn Pro Ser Leu Ala Gln Asp Thr
1               5                   10                  15

Val Ile Ile Lys Lys
            20

<210> SEQ ID NO 273
<211> LENGTH: 20
<212> TYPE: PRT
<213> ORGANISM: Homo sapiens

<400> SEQUENCE: 273

Arg Lys Gly Glu Ile Ala Ala Ser Ile Ala Thr His Met Arg Pro Tyr
1               5                   10                  15

Arg Lys Lys Ser
            20

<210> SEQ ID NO 274
<211> LENGTH: 15
<212> TYPE: PRT
<213> ORGANISM: Rattus norvegicus
```

<400> SEQUENCE: 274

Lys Ser Asp Gly Tyr His Lys Arg Pro Asp Arg Lys Ser Arg Ile
1               5                   10                  15

<210> SEQ ID NO 275
<211> LENGTH: 14
<212> TYPE: PRT
<213> ORGANISM: Homo sapiens

<400> SEQUENCE: 275

Lys Arg Lys Asp Thr Lys Arg Leu Val Leu His Met Lys Asn
1               5                   10

<210> SEQ ID NO 276
<211> LENGTH: 22
<212> TYPE: PRT
<213> ORGANISM: Rattus norvegicus

<400> SEQUENCE: 276

Lys Asp Ser Thr Lys Asp Asp Asn Ser Asn Leu Gly Gly Lys Thr Asp
1               5                   10                  15

Glu Ala Lys Gly Lys Thr
            20

<210> SEQ ID NO 277
<211> LENGTH: 22
<212> TYPE: PRT
<213> ORGANISM: Rattus norvegicus

<400> SEQUENCE: 277

Lys Asp Ser Thr Lys Asp Asp Asn Ser Asn Leu Gly Gly Lys Thr Asp
1               5                   10                  15

Glu Ala Lys Gly Lys Thr
            20

<210> SEQ ID NO 278
<211> LENGTH: 21
<212> TYPE: PRT
<213> ORGANISM: Homo sapiens

<400> SEQUENCE: 278

Arg His Gly Tyr Thr Ser Ser Leu Glu Leu Pro Asp Asn Ile Leu Asn
1               5                   10                  15

Phe Val Lys Lys His
            20

<210> SEQ ID NO 279
<211> LENGTH: 27
<212> TYPE: PRT
<213> ORGANISM: Mus musculus

<400> SEQUENCE: 279

Arg Asp Ile Lys Pro Asp Asn Val Leu Leu Asp Val Asn Gly His Ile
1               5                   10                  15

Arg Leu Ala Asp Phe Gly Ser Cys Leu Lys Met
            20                  25

<210> SEQ ID NO 280
<211> LENGTH: 13
<212> TYPE: PRT
<213> ORGANISM: Rattus norvegicus

```
<400> SEQUENCE: 280

Arg Leu Leu Ser Ala Ala Lys Ala Pro Asp Arg Lys Ala
1               5                   10

<210> SEQ ID NO 281
<211> LENGTH: 24
<212> TYPE: PRT
<213> ORGANISM: Rattus norvegicus

<400> SEQUENCE: 281

Lys Leu Asp Asn Thr Val Val Gly Gln Thr Ile Trp Lys Pro Ile Ser
1               5                   10                  15

Asn Gln Ser Trp Asp Gln Lys Phe
            20

<210> SEQ ID NO 282
<211> LENGTH: 21
<212> TYPE: PRT
<213> ORGANISM: Mus musculus

<400> SEQUENCE: 282

Lys Glu Lys Lys Pro Ile Lys Ser Pro Ser Lys Asp Ala Ser Ser Gly
1               5                   10                  15

Lys Glu Asn Arg Ser
            20

<210> SEQ ID NO 283
<211> LENGTH: 26
<212> TYPE: PRT
<213> ORGANISM: Homo sapiens

<400> SEQUENCE: 283

Arg Asp Leu Lys Pro Glu Asn Ile Leu Leu Asp Cys Gln Gly His Val
1               5                   10                  15

Val Leu Thr Asp Phe Gly Leu Cys Lys Glu
            20                  25

<210> SEQ ID NO 284
<211> LENGTH: 24
<212> TYPE: PRT
<213> ORGANISM: Homo sapiens

<400> SEQUENCE: 284

Lys Gln Asn Asn Thr Ala Lys Leu Val Lys Gln Leu Ser Lys Ser Ser
1               5                   10                  15

Glu Asp Glu Glu Leu Arg Lys Leu
            20

<210> SEQ ID NO 285
<211> LENGTH: 20
<212> TYPE: PRT
<213> ORGANISM: Rattus norvegicus

<400> SEQUENCE: 285

Lys Glu Glu Gly Lys Ser Arg Thr Thr Leu Pro Glu Arg Pro Leu Thr
1               5                   10                  15

Glu Val Lys Ala
            20

<210> SEQ ID NO 286
<211> LENGTH: 22
<212> TYPE: PRT
```

<213> ORGANISM: Homo sapiens

<400> SEQUENCE: 286

Lys Ala Gln Gly Lys Gly Ser Ala Gly Asn Thr Trp Ser Gln Leu
1               5                   10                  15

Ser Asn Asn Asn Lys Asp
            20

<210> SEQ ID NO 287
<211> LENGTH: 25
<212> TYPE: PRT
<213> ORGANISM: Homo sapiens

<400> SEQUENCE: 287

Lys Ser Phe His Leu Ser Pro Arg Gly Pro Pro Thr Ser Glu Pro Pro
1               5                   10                  15

Pro Val Pro Ala Asn Lys Pro Lys Phe
            20                  25

<210> SEQ ID NO 288
<211> LENGTH: 25
<212> TYPE: PRT
<213> ORGANISM: Rattus norvegicus

<400> SEQUENCE: 288

Arg Cys Lys Ser Glu Gly Thr Leu Ile Asp Leu Ser Glu Gly Phe Ser
1               5                   10                  15

Glu Thr Ser Phe Asn Asp Val Lys Val
            20                  25

<210> SEQ ID NO 289
<211> LENGTH: 19
<212> TYPE: PRT
<213> ORGANISM: Rattus norvegicus

<400> SEQUENCE: 289

Arg Ala Lys Leu Thr Met Leu Asn Thr Val Ser Lys Ile Arg Gly Gln
1               5                   10                  15

Val Lys Asn

<210> SEQ ID NO 290
<211> LENGTH: 17
<212> TYPE: PRT
<213> ORGANISM: Homo sapiens

<400> SEQUENCE: 290

Arg Ala Ile Asp Glu Pro Asn Asn Cys Lys Gly Ile Arg Cys Glu Lys
1               5                   10                  15

Gln

<210> SEQ ID NO 291
<211> LENGTH: 21
<212> TYPE: PRT
<213> ORGANISM: Rattus norvegicus

<400> SEQUENCE: 291

Lys Glu Val Cys Thr Ala Leu Leu Glu Ala Asp Val Asn Ile Lys Val
1               5                   10                  15

Lys Gln Leu Arg Glu
            20

-continued

<210> SEQ ID NO 292
<211> LENGTH: 26
<212> TYPE: PRT
<213> ORGANISM: Mus musculus

<400> SEQUENCE: 292

Arg Phe Asn Gln Ala Gln Glu Gly Asn Ile Gln Asn Thr Val Met Leu
1               5                   10                  15

Asp Lys Gln Lys Glu Leu Asp Ser Lys Val
            20                  25

<210> SEQ ID NO 293
<211> LENGTH: 31
<212> TYPE: PRT
<213> ORGANISM: Mus musculus

<400> SEQUENCE: 293

Met Glu Asn Leu Gln Ser Lys Phe Ser Leu Val Gln Gly Ser Asn Lys
1               5                   10                  15

Lys Leu Asn Gly Met Glu Asp Asp Gly Ser Pro Pro Val Lys Lys
            20                  25                  30

<210> SEQ ID NO 294
<211> LENGTH: 23
<212> TYPE: PRT
<213> ORGANISM: Homo sapiens

<400> SEQUENCE: 294

Lys Leu Ser Ser Gly Asn Ser Lys Leu Ser Ser Ser Lys Phe Ser Asn
1               5                   10                  15

Pro Ile Ser Ser Ser Lys Arg
            20

<210> SEQ ID NO 295
<211> LENGTH: 17
<212> TYPE: PRT
<213> ORGANISM: Homo sapiens

<400> SEQUENCE: 295

Lys Asp Leu Thr Thr Ala Glu Lys Leu Lys Arg Glu Thr Pro Trp Lys
1               5                   10                  15

Ile

<210> SEQ ID NO 296
<211> LENGTH: 20
<212> TYPE: PRT
<213> ORGANISM: Mus musculus

<400> SEQUENCE: 296

Arg Lys Leu Leu Ser Gln Leu Tyr Ala Arg Lys Val Ile Gln Asp Ile
1               5                   10                  15

Met Asn Lys Gln
            20

<210> SEQ ID NO 297
<211> LENGTH: 13
<212> TYPE: PRT
<213> ORGANISM: Rattus norvegicus

<400> SEQUENCE: 297

Lys Ser Ala Lys Trp Arg Arg Pro Arg Thr Ala Lys Met
1               5                   10

```
<210> SEQ ID NO 298
<211> LENGTH: 22
<212> TYPE: PRT
<213> ORGANISM: Rattus norvegicus

<400> SEQUENCE: 298

Arg Leu Lys Gly Leu Ala Leu Gln Arg Gln Gly Lys Leu Phe Gly Ala
1               5                   10                  15

Ala Glu Val Gln Arg Phe
            20

<210> SEQ ID NO 299
<211> LENGTH: 24
<212> TYPE: PRT
<213> ORGANISM: Homo sapiens

<400> SEQUENCE: 299

Arg Glu Val Thr Met Lys Lys Gly Asp Val Leu Thr Leu Leu Ser Ser
1               5                   10                  15

Ile Asn Lys Asp Trp Trp Lys Val
            20

<210> SEQ ID NO 300
<211> LENGTH: 34
<212> TYPE: PRT
<213> ORGANISM: Mus musculus

<400> SEQUENCE: 300

Lys Tyr Ser His Leu Ile Gly Lys Gly Ala Ala Lys Asp Ala Ala His
1               5                   10                  15

Met Leu Gln Ala Asn Lys Thr Tyr Gly Cys Val Pro Val Ala Asn Lys
            20                  25                  30

Arg Asp

<210> SEQ ID NO 301
<211> LENGTH: 22
<212> TYPE: PRT
<213> ORGANISM: Homo sapiens

<400> SEQUENCE: 301

Lys Gly Pro Ala Val Pro Pro Glu Leu Asp Lys His Phe Leu Leu Cys
1               5                   10                  15

Glu Ala Cys Gly Lys Cys
            20

<210> SEQ ID NO 302
<211> LENGTH: 29
<212> TYPE: PRT
<213> ORGANISM: Homo sapiens

<400> SEQUENCE: 302

Lys Lys Glu Gln Ala Leu Gln Leu Ala Gln Lys Met Gly Phe Pro Pro
1               5                   10                  15

Asn Ile Val Glu Ser Ala Ala Glu Asn Met Val Lys Leu
            20                  25

<210> SEQ ID NO 303
<211> LENGTH: 14
<212> TYPE: PRT
<213> ORGANISM: Mus musculus

<400> SEQUENCE: 303
```

Lys Arg Asp Phe Gly Ser Phe Glu Lys Phe Lys Glu Lys Leu
1               5                   10

<210> SEQ ID NO 304
<211> LENGTH: 14
<212> TYPE: PRT
<213> ORGANISM: Rattus norvegicus

<400> SEQUENCE: 304

Lys Arg Asp Phe Gly Ser Phe Glu Lys Phe Lys Glu Lys Leu
1               5                   10

<210> SEQ ID NO 305
<211> LENGTH: 35
<212> TYPE: PRT
<213> ORGANISM: Mus musculus

<400> SEQUENCE: 305

Arg Lys Lys Asn Ser Leu Lys Asp Cys Val Ala Val Ala Gly Pro Leu
1               5                   10                  15

Gly Val Thr His Phe Leu Ile Leu Thr Lys Thr Asp Asn Ser Val Tyr
            20                  25                  30

Leu Lys Leu
        35

<210> SEQ ID NO 306
<211> LENGTH: 21
<212> TYPE: PRT
<213> ORGANISM: Homo sapiens

<400> SEQUENCE: 306

Lys Leu Pro Val Lys Ile Val Gln Lys Asn Asp Pro Phe Val Val Asp
1               5                   10                  15

Cys Ser Asp Lys Leu
            20

<210> SEQ ID NO 307
<211> LENGTH: 16
<212> TYPE: PRT
<213> ORGANISM: Homo sapiens

<400> SEQUENCE: 307

Lys Thr Lys Leu Gln Ser Glu Asn Leu Lys Gln Ser Ile Glu Lys Gln
1               5                   10                  15

<210> SEQ ID NO 308
<211> LENGTH: 12
<212> TYPE: PRT
<213> ORGANISM: Homo sapiens

<400> SEQUENCE: 308

Lys Met Gly Lys Lys Lys Thr Leu Val Val Lys Lys
1               5                   10

<210> SEQ ID NO 309
<211> LENGTH: 30
<212> TYPE: PRT
<213> ORGANISM: Homo sapiens

<400> SEQUENCE: 309

Lys Ile Asp Ser Ile Ala Asp His Val Asn Ser Ala Val Ala Asn Val
1               5                   10                  15

```
Glu Glu Gly Thr Lys Asn Leu Gly Ala Ala Lys Tyr Lys Leu
         20                  25                  30

<210> SEQ ID NO 310
<211> LENGTH: 23
<212> TYPE: PRT
<213> ORGANISM: Mus musculus

<400> SEQUENCE: 310

Arg Lys Gly Pro Glu Asp Thr Ala Gln Leu Ala His Ala Val Leu Ala
1               5                   10                  15

Lys Leu Asn Ala Phe Lys Ala
            20

<210> SEQ ID NO 311
<211> LENGTH: 21
<212> TYPE: PRT
<213> ORGANISM: Homo sapiens

<400> SEQUENCE: 311

Lys Ser Ala Tyr Ser Glu Arg Leu Lys Phe Asn Val Ala Ile Lys Ile
1               5                   10                  15

Ile Asp Arg Lys Lys
            20

<210> SEQ ID NO 312
<211> LENGTH: 24
<212> TYPE: PRT
<213> ORGANISM: Homo sapiens

<400> SEQUENCE: 312

Lys Lys Lys Pro Asn Pro Gly Lys Asp Lys Arg Thr Tyr Glu Pro Ser
1               5                   10                  15

Ser Ala Thr Pro Val Thr Arg Ser
            20

<210> SEQ ID NO 313
<211> LENGTH: 20
<212> TYPE: PRT
<213> ORGANISM: Homo sapiens

<400> SEQUENCE: 313

Lys Glu Pro His Val Glu Gln Ile Thr Arg Lys Phe Arg Leu Asn Ser
1               5                   10                  15

Glu Gly Lys Leu
            20

<210> SEQ ID NO 314
<211> LENGTH: 18
<212> TYPE: PRT
<213> ORGANISM: Homo sapiens

<400> SEQUENCE: 314

Arg Phe Lys Gln Glu Gly Val Leu Asn Ser Lys Val Gly Met Asp Tyr
1               5                   10                  15

Arg Ser

<210> SEQ ID NO 315
<211> LENGTH: 26
<212> TYPE: PRT
<213> ORGANISM: Homo sapiens

<400> SEQUENCE: 315
```

-continued

Lys Asn Ala Leu Ala Leu Phe Val Leu Pro Lys Glu Gly Gln Met Glu
1               5                   10                  15

Ser Val Glu Ala Ala Met Ser Ser Lys Thr
            20                  25

<210> SEQ ID NO 316
<211> LENGTH: 24
<212> TYPE: PRT
<213> ORGANISM: Mus musculus

<400> SEQUENCE: 316

Lys Gln Leu Glu Gly Ala Cys Tyr Ser Gly Lys Leu Ile Trp Lys Val
1               5                   10                  15

Thr Asp Tyr Arg Val Lys Lys Arg
            20

<210> SEQ ID NO 317
<211> LENGTH: 28
<212> TYPE: PRT
<213> ORGANISM: Homo sapiens

<400> SEQUENCE: 317

Lys Glu Asp Val Ser Glu Ser Val Gly Ala Ser Gly Gln Arg Pro Val
1               5                   10                  15

Phe Cys Pro Val His Lys Gln Glu Gln Leu Lys Leu
            20                  25

<210> SEQ ID NO 318
<211> LENGTH: 30
<212> TYPE: PRT
<213> ORGANISM: Homo sapiens

<400> SEQUENCE: 318

Arg Met Ile Thr Asn Glu Gln Asp Leu Lys Met Phe Leu Leu Ser Lys
1               5                   10                  15

Gly Ala Ser Lys Glu Val Ile Ala Ser Ile Ile Ser Arg Tyr
            20                  25                  30

<210> SEQ ID NO 319
<211> LENGTH: 31
<212> TYPE: PRT
<213> ORGANISM: Homo sapiens

<400> SEQUENCE: 319

Lys Lys Gln Pro Gly Gln Asp Cys Pro His Ser Cys Asn Leu Leu Cys
1               5                   10                  15

His Pro Gly Pro Cys Pro Pro Cys Pro Ala Phe Met Thr Lys Thr
            20                  25                  30

<210> SEQ ID NO 320
<211> LENGTH: 20
<212> TYPE: PRT
<213> ORGANISM: Mus musculus

<400> SEQUENCE: 320

Arg Ser Lys Trp His Ile Pro Met Pro Ser Gly Lys Gly Tyr Phe Asn
1               5                   10                  15

Phe Gly Lys Ile
            20

<210> SEQ ID NO 321

```
<211> LENGTH: 15
<212> TYPE: PRT
<213> ORGANISM: Homo sapiens

<400> SEQUENCE: 321

Arg Lys Gln Gln Ala Met Trp Arg Val Pro Ser Asp Leu Lys Met
1               5                   10                  15

<210> SEQ ID NO 322
<211> LENGTH: 18
<212> TYPE: PRT
<213> ORGANISM: Homo sapiens

<400> SEQUENCE: 322

Arg Glu Leu Asn Lys Leu Tyr Pro Thr His Ala Cys Arg Glu Tyr Leu
1               5                   10                  15

Lys Asn

<210> SEQ ID NO 323
<211> LENGTH: 15
<212> TYPE: PRT
<213> ORGANISM: Mus musculus

<400> SEQUENCE: 323

Met Ala Lys Pro Thr Ser Lys Asp Ser Gly Leu Lys Glu Lys Phe
1               5                   10                  15

<210> SEQ ID NO 324
<211> LENGTH: 20
<212> TYPE: PRT
<213> ORGANISM: Rattus norvegicus

<400> SEQUENCE: 324

Arg Gly Asp Val Val Pro Lys Asp Val Asn Val Ala Ile Ala Ala Ile
1               5                   10                  15

Lys Thr Lys Arg
            20

<210> SEQ ID NO 325
<211> LENGTH: 21
<212> TYPE: PRT
<213> ORGANISM: Mus musculus

<400> SEQUENCE: 325

Arg Leu His Glu Glu Trp Leu Leu Arg Glu Glu Lys Ala Gln Glu Glu
1               5                   10                  15

Phe Arg Ile Lys Lys
            20

<210> SEQ ID NO 326
<211> LENGTH: 21
<212> TYPE: PRT
<213> ORGANISM: Homo sapiens

<400> SEQUENCE: 326

Arg Gly Lys Met Val Ser Tyr Ile Gln Cys Lys Glu Val Asp Tyr Arg
1               5                   10                  15

Ser Asp Arg Arg Glu
            20

<210> SEQ ID NO 327
<211> LENGTH: 17
<212> TYPE: PRT
```

<213> ORGANISM: Homo sapiens

<400> SEQUENCE: 327

Arg Ser Ile Pro Val Leu Ala Lys Trp Gln Asn Ser Tyr Ser Ile Lys
1               5                   10                  15

Val

<210> SEQ ID NO 328
<211> LENGTH: 13
<212> TYPE: PRT
<213> ORGANISM: Rattus norvegicus

<400> SEQUENCE: 328

Lys Phe Ser Leu Gln Asp Pro Pro Asn Lys Pro Lys Val
1               5                   10

<210> SEQ ID NO 329
<211> LENGTH: 21
<212> TYPE: PRT
<213> ORGANISM: Homo sapiens

<400> SEQUENCE: 329

Lys Lys Gly Lys Ala Glu Ser Cys Gly His Ala Thr Val Ser Ser Glu
1               5                   10                  15

Lys Lys Leu Lys Thr
            20

<210> SEQ ID NO 330
<211> LENGTH: 19
<212> TYPE: PRT
<213> ORGANISM: Homo sapiens

<400> SEQUENCE: 330

Lys Phe Gln Glu Ile Ala Glu Lys Asn Met Glu Lys Leu Asn His Ile
1               5                   10                  15

Glu Lys Ser

<210> SEQ ID NO 331
<211> LENGTH: 22
<212> TYPE: PRT
<213> ORGANISM: Mus musculus

<400> SEQUENCE: 331

Arg Leu Leu Lys Asn Thr Glu Asn Met Lys Gly Phe Phe Gly Gly Leu
1               5                   10                  15

Glu Thr Lys Leu Lys Gly
            20

<210> SEQ ID NO 332
<211> LENGTH: 21
<212> TYPE: PRT
<213> ORGANISM: Mus musculus

<400> SEQUENCE: 332

Lys Phe Ala Leu Pro Tyr Ile Arg Asp Val Ala Lys Arg Val Lys Ala
1               5                   10                  15

Gly Leu Gln Lys Ala
            20

<210> SEQ ID NO 333
<211> LENGTH: 19
<212> TYPE: PRT

<213> ORGANISM: Homo sapiens

<400> SEQUENCE: 333

Lys Lys Met Met Ser Asn Gln Tyr Val Pro Val Lys Thr His Glu Glu
1               5                   10                  15

Val Lys Met

<210> SEQ ID NO 334
<211> LENGTH: 19
<212> TYPE: PRT
<213> ORGANISM: Mus musculus

<400> SEQUENCE: 334

Lys His Glu Lys Glu Leu Met Gly Leu Lys Ser Asn Ile Ala Glu Leu
1               5                   10                  15

Lys Lys Gln

<210> SEQ ID NO 335
<211> LENGTH: 33
<212> TYPE: PRT
<213> ORGANISM: Homo sapiens

<400> SEQUENCE: 335

Lys Glu Ile His Val Asn Ile Glu Ala Thr Phe Lys Pro Ser Ser Glu
1               5                   10                  15

Glu Tyr Leu His Ile Thr Glu Pro Pro Ser Leu Ser Pro Asp Thr Lys
            20                  25                  30

Leu

<210> SEQ ID NO 336
<211> LENGTH: 20
<212> TYPE: PRT
<213> ORGANISM: Mus musculus

<400> SEQUENCE: 336

Lys Ala Gly Glu Ala Ser Thr Glu Thr Lys Lys Leu Ile Ile Lys Phe
1               5                   10                  15

Lys Glu Lys Asn
            20

<210> SEQ ID NO 337
<211> LENGTH: 26
<212> TYPE: PRT
<213> ORGANISM: Rattus norvegicus

<400> SEQUENCE: 337

Lys Tyr Gly Leu Leu Pro Ser Thr Ser Asn Asp Phe Lys Tyr Gly Leu
1               5                   10                  15

Leu Pro Gly Ala Pro Asn Asp Phe Lys Tyr
            20                  25

<210> SEQ ID NO 338
<211> LENGTH: 20
<212> TYPE: PRT
<213> ORGANISM: Homo sapiens

<400> SEQUENCE: 338

Lys His Gln Arg Ile His Ser Gly Glu Lys Pro Tyr Val Cys Asp Tyr
1               5                   10                  15

Cys Gly Lys Ala
            20

<210> SEQ ID NO 339
<211> LENGTH: 27
<212> TYPE: PRT
<213> ORGANISM: Homo sapiens

<400> SEQUENCE: 339

Lys Glu Asp Gln Pro Gly His Thr Lys Asp Leu Ser Gly Pro Thr Lys
1               5                   10                  15

Glu Ser Ser Lys Gly Ser Pro Lys Met Pro Ser
            20                  25

<210> SEQ ID NO 340
<211> LENGTH: 23
<212> TYPE: PRT
<213> ORGANISM: Mus musculus

<400> SEQUENCE: 340

Lys Val Glu Ser Glu Leu Leu Cys Thr Arg Leu Leu Leu Gly Gly Gly
1               5                   10                  15

Ser Tyr Lys Cys Ile Lys Cys
            20

<210> SEQ ID NO 341
<211> LENGTH: 36
<212> TYPE: PRT
<213> ORGANISM: Mus musculus

<400> SEQUENCE: 341

Arg Ser Pro Gly Pro Asp Tyr Ser Leu Arg Leu Glu Thr Val Pro Ala
1               5                   10                  15

Pro Gly Arg Ala Glu Gly Gly Ala Val Ser Ala Gly Leu Ser Lys Met
            20                  25                  30

Glu Pro Arg Glu
        35

<210> SEQ ID NO 342
<211> LENGTH: 20
<212> TYPE: PRT
<213> ORGANISM: Mus musculus

<400> SEQUENCE: 342

Lys Lys Ala Glu Asn Ser Ile Gly Lys Cys Pro Thr Arg Thr Asp Val
1               5                   10                  15

Ser Glu Lys Ala
            20

<210> SEQ ID NO 343
<211> LENGTH: 25
<212> TYPE: PRT
<213> ORGANISM: Homo sapiens

<400> SEQUENCE: 343

Lys Met Asp Leu Asn Asn Asn Ser Leu Lys Thr Lys Ala Gln Val Pro
1               5                   10                  15

Met Val Leu Thr Ala Gly Pro Lys Trp
            20                  25

<210> SEQ ID NO 344
<211> LENGTH: 10
<212> TYPE: PRT
<213> ORGANISM: Artificial Sequence

```
<220> FEATURE:
<223> OTHER INFORMATION: A synthetic polypeptide

<400> SEQUENCE: 344

Ser Thr Leu His Leu Val Leu Arg Leu Arg
1               5                   10

<210> SEQ ID NO 345
<211> LENGTH: 20
<212> TYPE: PRT
<213> ORGANISM: Homo sapiens

<400> SEQUENCE: 345

Arg Thr Tyr Asp Leu Asn Lys Pro Pro Glu Phe Ser Phe Glu Lys Ala
1               5                   10                  15

Arg Val Arg Lys
            20

<210> SEQ ID NO 346
<211> LENGTH: 76
<212> TYPE: PRT
<213> ORGANISM: Homo sapiens

<400> SEQUENCE: 346

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 347
<211> LENGTH: 12
<212> TYPE: PRT
<213> ORGANISM: Homo sapiens

<400> SEQUENCE: 347

Ser Thr Leu His Leu Val Leu Arg Leu Arg Gly Gly
1               5                   10

<210> SEQ ID NO 348
<211> LENGTH: 4
<212> TYPE: PRT
<213> ORGANISM: Artificial Sequence
<220> FEATURE:
<223> OTHER INFORMATION: A synthetic polypeptide

<400> SEQUENCE: 348

Leu Arg Gly Gly
1

<210> SEQ ID NO 349
<211> LENGTH: 22
<212> TYPE: PRT
<213> ORGANISM: Homo sapiens

<400> SEQUENCE: 349

Lys Arg Thr Val Ser Asp Asn Ser Leu Ser Asn Ser Arg Gly Glu Gly
1               5                   10                  15
```

```
Lys Pro Asp Leu Lys Phe
                20

<210> SEQ ID NO 350
<211> LENGTH: 16
<212> TYPE: PRT
<213> ORGANISM: Mus musculus

<400> SEQUENCE: 350

Lys Leu Ala Lys Gln Asn Thr Asn Lys Ala Lys Glu Asn Leu Arg Lys
1               5                   10                  15
```

ANTIBODIES FOR UBIQUITINATED PROTEINS

This application claims benefit of the filing date of U.S. Provisional Ser. No. 61/058,084, filed Jun. 2, 2008, the contents of which are specifically incorporated herein by reference.

This invention was made with government support from the National Institute of Allergy and Infectious Diseases under grant number 5R21-AI068639, and from the National Cancer Institute under grant number 5T32CA062948-13. The U.S. government has certain rights in this invention.

BACKGROUND OF THE INVENTION

Ubiquitination has been shown to be a critical step in various cellular processes, including cell division, signal transduction, neurotransmission, and development (Bonifacino and Weissman 1998; Kirkpatrick, Denison et al. 2005), yet elucidation of the proteins targeted by ubiquitination has been difficult because of the technical challenge in recovering modified proteins. The alteration of ubiquitination pathways and patterns of ubiquitination induces many neurodegenerative diseases, such as Alzheimer's disease, Parkinson disease, Huntington disease, and cancers, such as breast cancer, ovarian cancer, as well as numerous other conditions (Jiang and Beaudet 2004). Similarly patterns of ubiquitination can serve as a marker for these diseases or provide insight into the mechanism of diseases or the effects of experimental treatments on cells. Although the mechanisms of these diseases are not the same, all of them significantly alter ubiquitination pathways in one way or another, for example, by mutation, overexpression, or impairment in the function of proteins that directly or indirectly regulate ubiquitination. Ubiquitination can have significant effects on cellular function by affecting protein localization, protein-protein interactions, and protein turnover.

Unfortunately, not many ubiquitination sites have currently been identified in mammalian cells. Therefore, information on how to manipulate ubiquitination and modulate some of the processes involving ubiquitination is lacking. Furthermore, methods to profile ubiquitination in cells and tissues are lacking, and would require tools that allow for the simple, sensitive, specific, and rapid detection of ubiquitination sites in biological samples.

SUMMARY OF THE INVENTION

This application describes polyclonal and monoclonal antibodies that have been generated that facilitate identification of ubiquitinated proteins in cells and tissues. These antibodies recognize a fragment of ubiquitin that is created after samples (comprising proteins that are ubiquitinated, either as pure proteins or in a mixture of proteins, such as a cell lysate) are treated with trypsin. The epitope that is recognized by the antibodies includes a diglycine moiety on the epsilon amines of lysines. After cleavage of an ubiquitinated protein, a peptide containing diglycine residues is present on lysine residues within the released peptides. Cleavage can be achieved using a variety of proteases (for example, trypsin or Arg-C can be used to generate a diglycyl moiety on formerly ubiquitinated proteins). The antibodies have been successfully used for immunopurification of ubiquitinated peptides obtained from mammalian cells and many ubiquitination sites have been identified by mass spectrometry of the immunoprecipitated peptides. Use of these antibodies to identify and isolate peptides containing the telltale residues of ubiquitinated lysines from a complex peptide mixture, has many applications. The peptides with these telltale residues can be separated from a complex mixture of peptides, where some peptides contain the these telltale residues and some do not, and analyzed to ascertain the sequences and origins of the ubiquitinated peptides. In addition, the specific sites of ubiquitination within the peptides and the proteins from which the peptides were derived, can be determined. For example, the antibodies described herein can be used to identify specific targets of ubiquitin ligases (there are over 500 in the human genome); to identify ubiquitination events that occur after a drug or other treatment; and to determine the proteins that are affected after a specific ubiquitin ligase inhibitor (e.g. nutlin) is applied to cells. Identification of ubiquitination sites will expand our understanding of the biological role of ubiquitination, will permit the discovery of substrates for specific protein ubiquitination ligases, and will enable the detection of substrates in ubiquitination-related diseases.

Therefore, one aspect of the invention is an isolated epitope comprising a diglycine (Gly-Gly) present on an epsilon amino group of a lysine in a protein. For example, the diglycine (Gly-Gly) present on the epsilon amino group of the lysine can include the following structure:

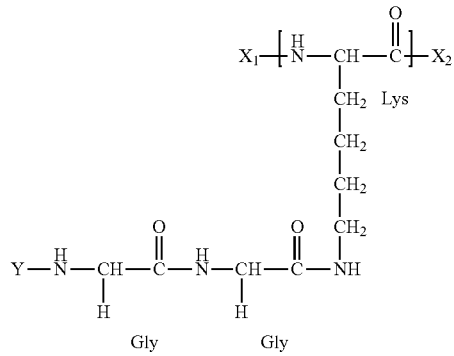

wherein: $X_1$ is hydrogen or a first peptide sequence;
$X_2$ is hydroxy or a second peptide sequence; and
Y is hydrogen or a ubiquitin peptide, wherein the Y ubiquitin peptide is not a full-length ubiquitin protein.
In some embodiments, the Y group can be Leu-Arg or STLHLVLRLR (SEQ ID NO:344). In other embodiments, the Y group can be hydrogen.

Another aspect of the invention is an antibody that specifically binds to a diglycine (Gly-Gly) epitope present on an epsilon amino group of a lysine in a protein. For example, the epitope can have the structure provided above, wherein: $X_1$ is hydrogen or a first peptide sequence; $X_2$ is hydroxy or a second peptide sequence; and Y is hydrogen or a ubiquitin peptide, wherein the Y ubiquitin peptide is not a full-length ubiquitin protein. Again, the Y group can be Leu-Arg or STLHLVLRLR (SEQ ID NO:344) in some embodiments and in other embodiments, the Y group can be hydrogen. The antibody can be a monoclonal or polyclonal antibody.

Another aspect of the invention is a method of detecting a ubiquitinated site in a test protein or a mixture of test proteins that comprises
(i) cleaving a test protein or a mixture of test proteins with a protease that cleaves ubiquitin to form a mixture of cleavage peptides;

(ii) contacting the cleavage peptides with an antibody that specifically binds to a diglycine (Gly-Gly) epitope present on an epsilon amino group of a lysine; and (iii) observing whether the antibody binds to a cleavage peptide, to thereby detect a ubiquitinated site in a test protein or a mixture of test proteins.

The diglycine (Gly-Gly) epitope present on an epsilon amino group of a lysine can have the structure shown above wherein: $X_1$ is hydrogen or a first peptide sequence; $X_2$ is hydroxy or a second peptide sequence; and Y is hydrogen or a ubiquitin peptide, wherein the Y ubiquitin peptide is not a full-length ubiquitin protein. In some embodiments, Y is Leu-Arg or STLHLVLRLR (SEQ ID NO:344). In other embodiments, Y is hydrogen. The protease that cleaves ubiquitin can also, in some instances, cleave the test protein or the mixture of test proteins.

In some embodiments, the protease that cleaves ubiquitin is a protease that cleaves on the C-terminal side of arginine or glutamic acid residues. For example, the protease that cleaves ubiquitin can be trypsin, Arg-C or Glu-C.

In some embodiments, step (i) is performed in the presence of $H_2{}^{18}O$. Thus, upon hydrolysis of peptide bonds by a protease, the C-terminal hydroxy group will be labeled with heavy oxygen ($^{18}O$), this allows determination of the amount or proportion of cleavage peptides labeled with $^{18}O$. Hence, different samples can be labeled in different ways, even during the proteolytical cleavage step.

In some embodiments, the method can also include sequencing the cleavage peptide to which the antibody binds to thereby determine the amino acid sequence of the cleavage peptide. For example, the sequencing can be performed by a method comprising mass spectrometry (e.g., LC-MS/MS).

In some embodiments, the method can also include identifying the ubiquitinated site in the cleavage peptide. The method can further include identifying the test protein from which the cleavage peptide was derived. In addition, the method can also include isolating the test protein.

The methods and antibodies described herein can be used to identify ubiquitination sites, patterns and profiles in a variety of samples. For example, the sample to be evaluated can be a body fluid, tissue sample, cell lysate, fractionated cellular material, cellular extract, cell culture supernatant, or cultured cells. Similarly, a variety of body fluids can be evaluated using the methods described herein. For example, the body fluid can be saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatitc fluid, tissue extract, or glandular secretion. In some embodiments, the sample is obtained from a mammal fed a diet containing an isotopically-labeled amino acid. In other embodiments, the sample is obtained from culture media containing an isotopically-labeled amino acid.

For example, when the sample is a selected cell or tissue type, the method can be adapted to include identifying substantially all prominently ubiquitinated proteins in the cell or tissue type to yield a ubiquitination profile of proteins from the cell or tissue type. In addition, the method can further include comparing the ubiquitination profile of proteins from the cell or tissue type with a ubiquitination profile of proteins from the cell or tissue type after treatment or exposure of the selected cells or tissues to a drug or test agent. The method can further include comparing the ubiquitination profile of proteins from the cell or tissue type with a ubiquitination profile of proteins from cells with a mutation (e.g., a deletion or insertion) or amplification of a gene encoding a ubiquitin ligase, a ubiquitin conjugating enzyme or a ubiquitin activating enzyme. For example, the mutation can substantially eliminate expression or function of an E3 ubiquitin ligase, an E2 ubiquitin conjugating enzyme or an E1 ubiquitin activating enzymes. The amplification of a gene encoding a ubiquitin ligase, a ubiquitin conjugating enzyme or a ubiquitin activating enzyme can lead to overexpression of the ubiquitin ligase, the ubiquitin conjugating enzyme or the ubiquitin activating enzyme.

Another aspect of the invention is a method of generating an antibody that comprises administering to a mammal an effective amount of an antigen comprising a diglycine (Gly-Gly) epitope linked to an epsilon amino group of a lysine, to generate and immune response against the epitope, to thereby generate an antibody that specifically binds to a diglycine (Gly-Gly) epitope present on an epsilon amino group of a lysine. The lysine to which the diglycine (Gly-Gly) epitope is linked can be part of a larger protein (e.g., a carrier protein, adjuvant molecule or other polymer).

Thus, the methods described herein can be used to identify the proteins that are ubiquitinated in specific types of cells. For example, cells derived from cancer, or cells and tissues obtained from patients with various diseases that may have altered ubiquitination as a cause or consequence of disease. In addition, the methods can be used to identify proteins that are ubiquitinated in cells that overexpress or have reduced levels of proteins that affect ubiquitination. Moreover, the methods can be used to measure ubiquitination in cells after treatment with a small molecule or a small interfering RNA that is predicted to affect ubiquitination. Assessment of the proteins that are ubiquitinated in these cells constitutes a "profile" of protein ubiquitination. Changes in this profile identify protein ubiquitination events that may be regulated by a specific disease, a protein of interest, or an experimental treatment of interest.

DESCRIPTION OF THE FIGURES

FIG. 1A schematically illustrates antigen synthesis. The ϵ-amine of lysines in histone was modified by Boc-Gly-Gly-NHS and then the Boc group was removed by TFA. The lysines in the final protein contain diglycine adducts on all lysine residues. FIG. 1B demonstrates the synthesis of diglycine-modified histone. To monitor the reaction of histone with Boc-Gly-Gly-NHS, the presence of amines, such as those in unmodified lysine, was detected by reacting proteins with the amine-modifying agent biotin-NHS, and subsequent western blotting with an anti-biotin antibody. Amines in histone were nearly completely lost after treatment with Boc-Gly-Gly-NHS, indicating near complete modification of all the lysines in histone. Removal of the Boc protecting group with TFA results in the formation of an amine at the N-terminus of the diglycine adduct. This step was essentially complete, as TFA-treated protein exhibited nearly complete recovery of amine reactivity. The position of three samples is slightly shifted due to the alteration of molecular weight and number of positive charges in the modified and unmodified samples. FIG. 1C shows the specificity of the purified antibody as evaluated by western blot of protein samples with proteins or lysates in which the lysines were either unmodified (A), or modified with Boc-Gly-Gly (B) or Gly-Gly-(C) adducts, respectively, from β-lactoglobulin, lysozyme, and rat brain lysate.

FIG. 2A-E illustrates that ubiquitinated proteins are readily identified by using the procedures and antibodies described herein. FIG. 2A shows a schematic diagram illustrating one strategy for identifying ubiquitinated proteins by immunoprecipitation of peptides with diglycine-modified lysines and tandem MS analysis. Note that "Ub (Arg-Gly-Gly)" is used to indicate that ubiquitin (with an Arg-Gly-Gly C-terminus) is attached to a ubiquitinated protein via an epsilon amine group of a lysine within the ubiquitinated protein. In this illustration, trypsin is used to cleave the ubiquitinated protein and sever the linkage between the arginine and the glycine near the C-terminus of the ubiquitin protein, thereby liberating a peptide with the diglycyl-lysine epitope, which can be used for immunopurification and detection of the ubiquitination site. FIG. 2B shows that the methods and antibodies described herein specifically identify ubiquitinated peptides from partially diglycine-modified BSA and lysozyme proteins. The diglycine-modified proteins were trypsinized and immunoprecipitated with control IgG from preimmune serum or with anti-diglycl lysine antibody. A total of six diglycine-modified peptides (i.d., Gly-Gly-modified peptides) were obtained from BSA and two from diglycine-modified lysozyme using the anti-diglycyl-lysine antibody, while no diglycine-modified peptides were recovered using IgG purified from preimmune serum. An MS/MS spectrum of one diglycine-modified peptide from each protein is presented. FIG. 2C shows representative spectra of trypsin-digested ubiquitinated peptides obtained from cultured cells and animal tissue. A peptide ion exhibiting loss of Gly-Gly from a lysine is indicated by a shadowed box in the lower panel. Peptide ions exhibiting a loss of Gly-Gly or Gly fragments were observed in 32.3% of the identified proteins. For this analysis, peaks reflecting a Gly-Gly or Gly loss of the appropriate m/z were counted only if they had an intensity of 10% of the most abundant fragment. FIG. 2D shows the number of ubiquitinated proteins and ubiquitination sites that were identified by LC-MS/MS. The number of proteins identified in experiments conducted by the inventors and reported in the literature is also shown. FIG. 2E verifies that the antibodies described herein specifically detect ubiquitinated proteins. Proteins from cell cultures and rat brain lysate were purified by GST-S5a pulldown and visualized by western blotting using an antibody directed against the indicated protein. For Trk neurotrophin receptor and dystrophin, proteins were immunoprecipitated and the immunoprecipitate was blotted with an anti-ubiquitin antibody. Agarose beads and protein A or protein G beads were used as a control for nonspecific pulldown and immunoprecipitation.

FIG. 3A-D illustrates bioinformatic analysis of ubiquitin remnant-modified lysines. FIG. 3A shows pie charts of biological processes and subcellular localization of ubiquitinated proteins analyzed by PANTHER and PENCE Proteome Analyst database, respectively. FIG. 3B illustrates a backbone amino acid sequence analysis of ubiquitinated peptides, showing that the antibodies described herein have no strong backbone sequence preference. A density plot of ratios of ubiquitinated lysines to all lysines was plotted by MATLAB. FIG. 3C shows the distribution of solvent accessible area (SAA) of all lysines and ubiquitinated lysines as a function of percentage of normalized SAA. The distribution of SAA of ubiquitinated lysines is slightly shifted to a large value. The two distributions are significantly different ($\chi^2$ analysis, p<0.01), which mainly resulted from the fraction above 75% SAA. The results were obtained from analysis of 24 PDB structures (25 ubiquitinated lysine and 1066 all lysine residues). FIG. 3D shows the distribution of secondary structures of all lysines and ubiquitinated lysines obtained from analysis of 24 PDB structures. **p-value<0.01; *p-value<0.05.

FIG. 5A shows a MS/MS spectrum of ubiquitinated peptides from the protein superoxide dismutase, which may play a role in amyotrophic lateral sclerosis (ALS) and other diseases. FIG. 5B shows a MS/MS spectrum of ubiquitinated peptides from the huntingtin protein involved in Huntington's disease. FIG. 5C shows a MS/MS spectrum of ubiquitinated peptides from the protein tuberin, which may play a role in Alzheimer's disease. FIG. 5D shows a MS/MS spectrum of ubiquitinated peptides from the protein Rho-associated protein kinase, which has a variety of effects upon cell adhesion, cell motility, vascular and smooth muscle contraction and cytokinesis.

FIG. 6A illustrated the normalized frequency of each of the 20 amino acids within a six amino acid span on either side of ubiquitinated lysines. Normalization was carried out against the frequency calculated for each amino acid using all lysines in all the proteins in the Swiss-Prot database. The ubiquitinated lysines are not counted and every amino acid in the protein in the Swiss-Prot database is counted no more than once. FIG. 6B shows sequence logo representations of extracted motifs for ubiquitinated peptides, obtained using the Motif-x (Schwartz & Gygi *Nat Biotechnol* 23, 1391-1398 (2005)) search algorithm with a significance of 0.000001. Sequence logos were automatically generated by Motif-x using Weblogo (Schneider et al. *Nucleic Acids Research* 18, 6097-6100 (1990); Crooks et al. *Genome Research* 14, 1188-1190 (2004)). In sequence logos, the height of each residue is proportional to the frequency in the subset of peptides (Schwartz & Gygi *Nat Biotechnol* 23, 1391-1398 (2005)). FIG. 6C illustrates a backbone amino acid sequence analysis of ubiquitinated peptides from yeast. A density plot was prepared as described in FIG. 3B except that proteins were used that were identified to be ubiquitinated in the yeast from a recent study. Peng et al., *Nat. Biotechnol.* 21, 921-926 (2003). Unlike in mammalian proteins, Asp, Glu, His, Pro are highly enriched (>2.3 times the expected value) at some positions.

FIG. 7A shows a solvent exposed ubiquitinated lysine for pulmonary surfactant-associated protein (PDB:1PW9). FIG. 7B shows a solvent buried ubiquitinated site for dystrophin (PDB:1EG3) The snapshots were prepared using PyMOL.

FIG. 10A and FIG. 10B show MALDI-TOF-MS spectra of the sample before and after monoclonal antibody purification, respectively.

FIGS. 11A and 11B are the MALDI-TOF-MS of a peptide containing two diglycine-modified lysines mixed with a BSA digest before and after anti-GG antibody purification, respectively. FIG. 11C is the MS/MS spectrum of the GG-modified peptide.

FIG. 14A shows a western blot (top) and the corresponding Coomassie stained gel (bottom) of electrophoretically separated angiotensin I and MARCKS polypeptides after reaction with Boc-diglycine-NHS, which will conjugate to primary amines on lysines and on the N-terminus of these proteins. Angiotensin I, which contains zero lysines (indicated as "K") while the MARCKS peptide has five lysines. Because angiotensin I does not contain any epsilon amines, there is only a single diglycine modification on the alpha-amine. This is readily detected by Coomassie staining (lower panel of FIG. 14A), where the modified protein exhibits a small upward mobility shift. However, this peptide exhibits no reactivity with the anti-diglycyl-lysine monoclonal antibodies ("mGGAb") used to probe the Western blot. In contrast, the MARCKS peptide, which contains five lysines, is reactive with the mGGAb after the MARCKS peptide was treated with Boc-diglycine-NHS and the diglycine epitope was introduced onto each of the five epsilon amines and one alpha-amine of the MARCKS peptide. FIG. 14A further illustrates the specificity of the anti-diglycyl antibodies (mGGAb) towards diglycyl-modified epsilon amines (but not N-terminal alpha-amines) using the peptide, Ac-MSH-NH$_2$, which contains no N-terminal alpha-amine (the alpha-amine is acetylated), and just one lysine. As shown for the MARCKS peptide in FIG. 14A, the conjugation of the diglycine to the Ac-MSH-NH$_2$ peptide is readily detected when (FIG. 14B). This is in contrast to Angiotensin I, where no diglycine epitopes are detected. The immunoreactivity of mGGAb for the Ac-MSH-NH$_2$ peptide therefore reflects binding of mGGAb to internal diglycyl-lysine, because the alpha-amine of the Ac-MSH-NH$_2$ peptide is acetylated.

FIG. 15A shows the MALDI-TOF-MS spectrum of a mixture of angiotensin I (one N-terminal GlyGly modification) and GlyGly-modified acetylated MSH peptide (one GlyGly-modified lysine). Both peptides are present in approximately equal amounts. FIG. 15B shows the MALDI-TOF-MS spectrum of angiotensin I/acetylated MSH peptides that bound to the polyclonal anti-diglycyl-lysine antibodies. The GlyGly-modified acetylated MSH peptide, with one internal lysine is present in substantially greater amounts, indicating that this peptide bound to the antibodies whereas the angiotensin I peptide with one N-terminal Gly-Gly did not. FIG. 15C shows the MALDI-TOF-MS spectrum of angiotensin I/acetylated MSH peptides that did not bind to the polyclonal anti-diglycyl-lysine antibodies. The angiotensin I peptide with one N-terminal Gly-Gly is present in greater amounts than the peptide with the internal Gly-Gly-lysine. These data illustrate that the anti-diglycyl-lysine antibodies can facilitate specific purification of peptides that have GlyGly-modified lysines.

FIG. 16A shows a dot blot spotted with a serial dilution of insulin (molecular weight ~5800 Da), which contains only one lysine in its heavy chain that was conjugated to the Gly-Gly moiety using procedures and reagents as described herein. The amount of insulin (in ng) and the corresponding molar quantity (in pmol) was as listed above and below, respectively, the dot blot. As shown, monoclonal antibody 49 binds effectively to amounts of the GlyGly-lysine-conjugated insulin as low as 2 nanograms (340 fmoles). FIG. 16B also shows a dot blot spotted with a serial dilution of insulin conjugated to the Gly-Gly moiety. The amount of insulin (in ng) and the corresponding molar quantity (in pmol) was as listed above and below, respectively, the dot blot. As shown, monoclonal antibody 49 binds effectively to amounts of the GlyGly-lysine-conjugated insulin as low as 1 nanogram (170 fmoles).

FIG. 17A shows a silver-stained gel of electrophoretically separated BSA from the flow-through from the Affi-gel (first three lanes) in the gel after the media was incubated with the immobilized diglycine-modified BSA. A blot to detect antibody was also performed and shown above the silver-stained gel. This blot shows that the antibody is depleted from the media by incubation with the immobilized diglycine-modified BSA. Acid elution (last four lanes of FIG. 17A), results in the elution of specific antibody bands, which can be seen in both the silver stain and Western blot at the top of FIG. 17A. FIG. 177B shows a Western dot blot of diglycine-modified lactoglobulin which was separated by SDS-PAGE and transferred to PVDF. The purified antibody readily recognizes 0.01 µg of this protein. Thus, the purified antibody has a high purity and can recognize GlyGly-modified proteins at least at nanogram level.

FIG. 21A-D shows that the types of biological processes in which various ubiquitinated proteins are involved varies depending upon the cell type. FIG. 21A shows the types of biological processes in which rat tissue ubiquitinated cells are involved. FIG. 21B shows the types of biological processes in which murine endothelioma (sEnd.1) ubiquitinated cells are involved. FIG. 21C shows the types of biological processes in which mouse neuroblastoma (N2a) ubiquitinated cells are involved. FIG. 21D shows the types of biological processes in which human embryo kidney (HEK293) ubiquitinated cells are involved.

FIG. 22A-H is a table listing LC-MS/MS identified diglycine-modified peptides with determined ubiquitination sites. The sequences of ubiquitinated peptides with SEQ ID NO:1-343, 345 and 349-350 are provided. The symbols, \, / and |, represent b-ions, y-ions, and both b-ions and y-ions, respectively. The location of the ubiquitinated lysine in the protein from which each peptide is derived is identified under the column "Ubiquitinated Lysines," using the notation "K" followed by the numerical position of the ubiquitinated lysine in the protein and a lower case "k" to indicate modification by diglycine on the indicated lysine. Proteins with isoforms previously reported to be ubiquitinated are indicated by a "*" in the accession ID column. The parentheses around N-terminal and C-terminal amino acids indicate that these amino acids are not actually present in the sequenced peptide but are present in the larger protein from which the peptide was derived. When a dash surrounded by parentheses is present (–), there is no preceding amino acid because the identified peptide is present at the end of the protein from it is derived. The charge of the peptide is listed under the column labeled "z." The three-letter code in "Fraction" column provides the following information: (1) the first letter indicates the origin of the sample, where H means HEK293, N means N2a, S means sEnd.1, B means rat brain, and L means rat liver; (2) the second letter indicates the treatment, L for LLnL and V for vehicle; (3) the third letter indicates the subcellular fraction, where W means whole lysate, C means cytosolic fraction, M means mitochondrial fraction, N means nuclear fraction, and S means synaptosomal fraction. Ubiquitin remnant-containing peptides that are derived from ubiquitin itself (i.e., polyubiquitin) have been excluded from this table.

DETAILED DESCRIPTION OF THE INVENTION

Figure 1A:
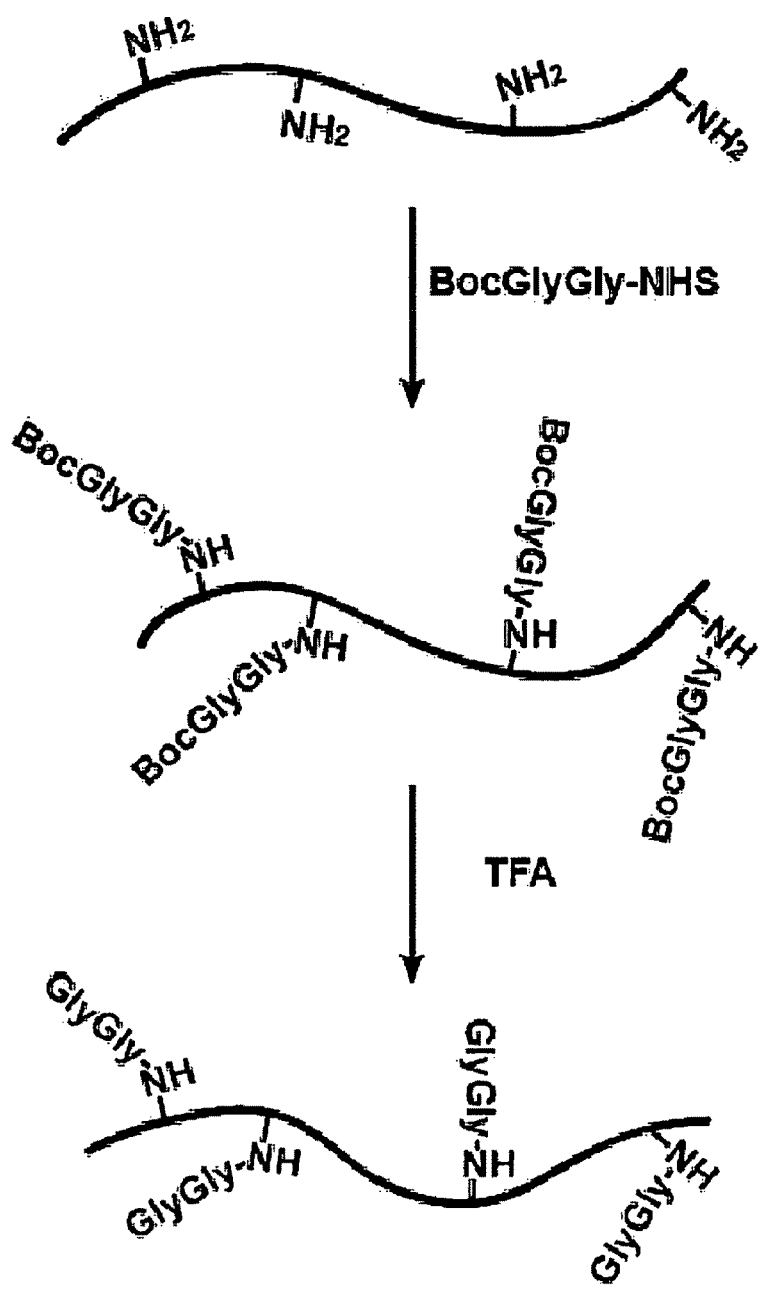
FIG. 1A-C illustrates how to make an antibody that selectively recognizes diglycine-modified lysines.

The invention relates to an antigen that includes a diglycine moiety on the epsilon (ε) amino group of lysine. This antigen can be used to generate antibodies that recognize ubiquitinated proteins. Antibodies directed against such diglycine-lysine-containing epitopes surprisingly recognize ubiquitination in a large variety of proteins, and are highly effective in binding to proteins and peptides that contain a diglycine adduct on lysines, thereby providing a reagent to efficiently isolate, enrich, and/or purify these peptides. These antibodies exhibit considerable selectivity, insofar as they exhibit negligible binding to peptides or proteins that lack diglycine adducts.

Antibodies are typically generated against large epitopes, to help insure that the antibody has the specificity and affinity that are needed for antibody binding. Also, antibodies are typically difficult to generate against epitopes that contain repeated amino acids (See Prediction of protein antigenic determinants from amino acid sequences, T P Hopp and K R Woods, Proc. Natl. Acad. Sci. U.S.A., 78: 3824-3828, 1981). However, as described herein the diglycyl-lysine antigen serves as an epitope that can result in the generation of antibodies with sufficient affinity to specifically bind diglycine-modified proteins in numerous applications, such as immunopurification, Western blotting, and dot blotting.

Ubiquitin is a small (76-amino acid) protein that is ubiquitously expressed in eukaryotes. Ubiquitination refers to the post-translational modification of a protein by the covalent attachment of one or more ubiquitin molecules to epsilon (ε) amine groups present on lysine residues in the protein to be ubiquitinated. The most prominent function of ubiquitin is labeling proteins for proteasomal degradation. Besides this function, ubiquitination also controls the stability, function, and intracellular localization of a wide variety of proteins, which complicates the isolation and identification of peptides containing this modification.

This application describes a method to identify ubiquitinated proteins and ubiquitin-modified lysine residues. In this approach, ubiquitinated proteins are proteolyzed to peptides containing a ubiquitin-derived diglycine adduct which are then affinity isolated and analyzed. Using this approach, the inventors have prepared ubiquitination profiles of specific cell types, and have identified more than 300 mammalian ubiquitinated proteins comprising nearly 400 diglycine-modified lysines. Analysis of these proteins provides insight into ubiquitination consensus sites, potential biological roles for ubiquitination and establishes that the antibodies described herein can be used to profile ubiquitination in biological samples.

Epitopes

An epitope that is useful for generating antibodies that specifically bind to protein targets of ubiquitination, includes the following structure, where the brackets indicate that the diglycine-lysine epitope can be present in a selected protein:

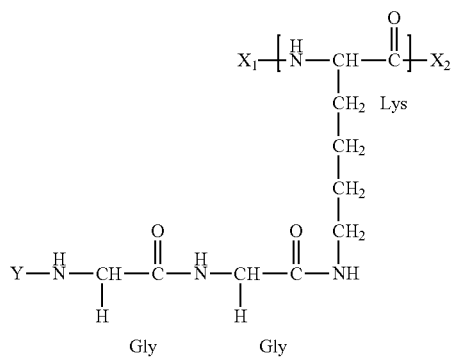

wherein $X_1$ is hydrogen or a first peptide sequence; $X_2$ is hydroxy or a second peptide sequence; and Y is hydrogen or a ubiquitin peptide, wherein the Y ubiquitin peptide is not a full-length ubiquitin protein. For example, Y can be Leu-Arg or STLHLVRLR (SEQ ID NO:344). The first and second peptide sequences can be peptide sequences from a selected protein of interest (e.g., a carrier). For example, the first peptide sequence can be a first carrier peptide sequence and/or the second peptide sequence can be a second carrier peptide sequence.

Such an epitope is present on ubiquitinated proteins because ubiquitination occurs by linkage of the C-terminal glycine of ubiquitin to ε-amine groups of lysines present in the protein target of ubiquitination. Thus, sequences for human ubiquitin typically contain Gly-Gly at the C-terminus, for example, as illustrated by the following sequence for human ubiquitin (SEQ ID NO:346):

```
 1 MQIFVKTLTG KTITLEVEPS DTIENVKAKI QDKEGIPPDQ
41 QRLIFAGKQL EDGRTLSDYN IQKESTLHLV LRLRGG
```

Thus the C-terminus of human ubiquitin typically includes Gly-Gly, and the sequence STLHLVLRLRGG (SEQ ID NO:347) is a longer C-terminal ubiquitin sequence. As described herein, an epitope that includes the Gly-Gly-lysine sequence, where the carboxylate group the Gly-Gly is linked to the ε-amine of a lysine, can be used to generate antibodies that specifically recognize ubiquitinated proteins and peptides.

However, antigenic epitopes useful for making such antibodies can have ubiquitin sequences in addition to the C-terminal Gly-Gly ubiquitin sequences. The length of the epitope amino acid Y sequence extending from the N-terminal glycine shown above can therefore vary. For example, in some embodiments, the epitope can include a Leu-Arg-Gly-Gly (SEQ ID NO:348) moiety that is linked through the C-terminal glycine to an ε-amine on a lysine in the same fashion as shown above. The Leu-Arg-Gly-Gly (SEQ ID NO:348) sequence is a longer portion of the C-terminal sequence of ubiquitin. Thus an epitope that includes SEQ ID NO:348 has additional ubiquitin sequences and these additional sequences will be present on ubiquitinated proteins naturally present in various samples that may be analyzed. While the methods described herein for identifying ubiquitination sites typically involve cleavage and removal of most of the ubiquitin sequences, the amount of ubiquitin sequences left on a ubiquitination site varies depending upon the protease selected for cleavage and removal of the ubiquitin. For example, it has been observed that after treatment with trypsin, which cleaves proteins on the C-terminal side of arginine and lysine, most ubiquitinated proteins are cleaved so that peptides with the ubiquitinated site have a diglycine linked to the ε-amine of lysine. However, about 20% of these ubiquitinated sites are partially cleaved, which leaves four C-terminal residues, Leu-Arg-Gly-Gly (SEQ ID NO:348), from ubiquitin linked to the ε-amine of a lysine residue. Therefore, another epitope of the invention includes Leu-Arg-Gly-Gly (SEQ ID NO:348) linked to the ε-amine group of lysine.

In other embodiments, the epitope is a STLHLVLRLRGG (SEQ ID NO:347) moiety, where the C-terminal glycine of this SEQ ID NO:347 peptide is linked to the ε-amine on a lysine. Such an epitope can be exposed and is readily detectable when ubiquitinated proteins are cleaved with Glu-C.

One reason to contemplate use of epitopes that include the SEQ ID NO:347 and/or SEQ ID NO:348 sequences is that the Gly-Gly-lysine epitope is very small, with just two glycines on the epsilon amine of lysine residues. Thus, in some cases the affinity and/or specificity of an anti-ubiquitinated site antibody can be improved by use of a longer antigen. The STLHLVLRLRGG (SEQ ID NO:347) moiety linked to the ε-amine on a lysine is formed as an epitope after Glu-C cleavage of ubiquitinated proteins, because the Glu-C protease is an enzyme that cleaves on the C-terminal side of glutamic acid. Thus, when a ubiquitin conjugate is cleaved with Glu-C, the remnant from ubiquitin on the ubiquitination sites, is STLHLVLRLRGG (SEQ ID NO:347).

The diglycine-lysine containing epitope(s) can be placed on one or more lysine residues in a selected protein. Such a protein can be carrier that facilitates generation of antibodies against the epitopes described herein. However, the epitopes described herein can also be placed on any selected protein of interest. In addition, the diglycine-lysine containing epitope(s) can be placed on the amino terminus of a selected protein and/or on any of the lysines present within the selected protein.

In some embodiments, the diglycine-lysine containing epitope is placed on one lysine, or two lysines, or three lysines, or four lysines, or five lysines, or six lysines, or seven lysines or eight lysines, or nine lysines, or ten lysines, or eleven lysines, or twelve lysines, thirteen lysines, or fourteen lysines, or fifteen lysines, or more than fifteen lysines.

Multiple copies of the diglycine-lysine containing epitopes can be placed on a selected protein by a method that involves reacting t-butyloxycarbonyl-peptide epitope-N-hydroxysuccinimide with the selected protein. For example, t-butyloxycarbonyl-Gly-Gly-N-hydroxysuccinimide can be reacted with the selected protein. Alternatively, the selected protein can be reacted with t-butyloxycarbonyl-Leu-Arg-Gly-Gly-N-hydroxysuccinimide or with t-butyloxycarbonyl-STLHLVLRLRGG-N-hydroxysuccinimide. Such a reaction can be carried out at room temperature using dimethyl sulfoxide (DMSO) as solvent. The reaction between the selected protein and t-butyloxycarbonyl-peptide epitope-N-hydroxysuccinimide can be repeated to facilitate complete reaction between the amino groups on the selected protein and the t-butyloxycarbonyl-peptide epitope-N-hydroxysuccinimide. The t-butyloxycarbonyl (Boc) group can be removed using trifluoroacetic acid (TFA) to yield a protein with one or more epitopes on the selected protein.

The protein selected for linkage to an epitope peptide can be any protein of interest to one of skill in the art. The selected protein can be from any species. For example, the selected protein can be a protein from any human or domesticated animal. Examples of species from which the selected protein can be obtained or derive include human, mouse, rat, rabbit, sheep, goat, horse, dog, cat, bird, plant, yeast, and other species.

The selected protein can have a function of interest or be obtained from a location of interest. For example, the protein can be an enzyme, a contractile protein, a structural protein, a hormonal protein, a storage protein, a transport protein, a secreted protein, a cell membrane protein, a cytoplasmic membrane, a nuclear protein, a protein involved in metabolism, a protein involved in cellular replication, a protein involved in chromosomal replication, a protein involved in transcription of DNA into RNA, as well as other types of proteins. In some embodiments, the protein selected for linkage to a diglycine-lysine epitope is a protein involved in a disease, disorder or condition. Further examples of proteins that can be selected for linkage to a diglycine-lysine epitope are available in various databases, for example, the Swiss-Prot database. FIG. 22 illustrates sequences of a variety of proteins that have, or can have, one or more diglycine-lysine epitopes.

Antibodies Directed Against the DiGlycine-Lysine Epitopes

Another aspect of the invention is an antibody that specifically binds to a diglycine-lysine epitope, or to a Leu-Arg-Gly-Gly-lysine (where the Leu-Arg-Gly-Gly (SEQ ID NO:348) peptide is linked to the ϵ-amine group of lysine), or to STLHLVLRLRGG-lysine (where the STLHLVLRLRGG (SEQ ID NO:347) peptide is linked to the ϵ-amine group of lysine). Thus, the antibody can specifically bind to an epitope that includes the following structure:

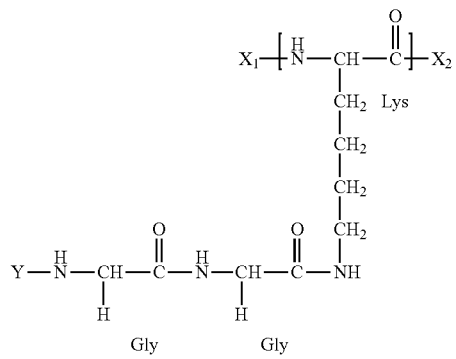

wherein $X_1$ is hydrogen or a first peptide sequence; $X_2$ is hydroxy or a second peptide sequence; and Y is hydrogen or a ubiquitin peptide, wherein the Y ubiquitin peptide is not a full-length ubiquitin protein. For example, Y can be Leu-Arg or STLHLVLRLR (SEQ ID NO:344). The first and second peptide sequences can be peptide sequences from a selected protein of interest (e.g., a carrier). For example, the first peptide sequence can be a first carrier peptide sequence and/or the second peptide sequence can be a second carrier peptide sequence.

The term "antibody," as used herein, refers to a full-length immunoglobulin molecule or an immunologically-active fragment of an immunoglobulin molecule such as the Fab or F(ab')$_2$ fragment generated by, for example, cleavage of the antibody with an enzyme such as pepsin or co-expression of an antibody light chain and an antibody heavy chain in bacteria, yeast, insect cell or mammalian cell. The antibody can also be an IgG, IgD, IgA, IgE or IgM antibody. In addition, the term "antibody" can include antibody fragments (e.g., CDR) linked or fused to other polypeptides. Moreover, the "antibody" as used herein means a single antibody or antibody type as well as a plurality of antibodies or types of antibodies.

As used herein, the term "binds specifically" or "specifically binds," in reference to an antibody/antigen interaction, means that the antibody binds with a particular antigen (e.g., the diglycine-lysine or other epitopes described herein) without substantially binding to other unrelated antigens. For example, the antibody has at least 50% or greater affinity, preferably about 75% or greater affinity, and more preferably, about 90% or greater affinity, to a particular polypeptide than to other unrelated polypeptides.

An antibody directed against the epitope(s) can be a polyclonal or monoclonal antibody. Polyclonal antibodies can be obtained by immunizing an animal (e.g., a mammal or bird) with a peptide or protein having one or more of the epitopes of the invention, and then isolating antibodies from the blood of the mammal using standard techniques including, for example, enzyme linked immunosorbent assay (ELISA) to determine antibody titer and protein A chromatography to obtain the antibody-containing IgG fraction.

A monoclonal antibody is a population of molecules having a common antigen binding site that binds specifically with a particular antigenic epitope. A monoclonal antibody can be obtained by selecting an antibody-producing cell from a mammal that has been immunized with one or more of the epitopes of the invention and fusing the antibody-producing cell, e.g. a B cell, with a myeloma to generate an antibody-producing hybridoma. A monoclonal antibody of the invention can also be obtained by screening a recombinant combinatorial library such as an antibody phage display library using, for example, a peptide or protein with one of the epitopes of the invention. See, for example, PHAGE DISPLAY—A LABORATORY MANUAL, Barbas, et al., eds. Cold Spring Harbor Laboratory Press, Cold Spring Harbor, N.Y., 2001; and Kontermann & Dübel, ANTIBODY ENGINEERING, Heidelberg: Springer-Verlag. Berlin, 2001. A monoclonal antibody of the invention can also be obtained by screening a recombinant combinatorial library such as a ribosome display library. See for example, Expert Review of Proteomics, 2: 421-430, 2005. Ribosome display: next-generation display technologies for production of antibodies in vitro. Mingyue He and Farid Khan.

An antibody of the invention can also be a murine, goat, sheep, rabbit, chimeric, humanized or fully human antibody. A murine, goat, rabbit, primate or sheep antibody is an antibody derived entirely from a murine, goat, rabbit, primate or sheep source, for example, an antibody derived from a murine, goat, rabbit, primate or sheep hybridoma generated from the fusion of a murine, goat, rabbit, primate or sheep myeloma cell and a murine, goat or sheep B-lymphocyte cell. A chimeric antibody is an antibody that has variable regions derived from a non-human source, e.g. murine, rabbit, goat or sheep or primate, and constant regions derived from a human source. A humanized antibody has antigen-binding regions, e.g. complementarity-determining regions, derived from a mouse source, and the remaining variable regions and constant regions derived from a human source. A fully human antibody is antibody from human cells or derived from transgenic mice carrying human antibody genes.

Methods to generate antibodies are well known in the art. For example, a polyclonal antibody of the invention can be prepared by immunizing a suitable animal with peptide or protein having one or more of the epitopes of the invention. The animal can be, for example, a rabbit, goat, sheep, rabbit, hamster, cow, chicken, monkey or mouse. At the appropriate time after immunization, antibody molecules can be isolated from the animal, e.g. from the blood or other fluid of the animal, and further purified using standard techniques that include, without limitation, precipitation using ammonium sulfate, gel filtration chromatography, ion exchange chromatography or affinity chromatography using protein A. In addition, an antibody-producing cell of the animal can be isolated and used to prepare a hybridoma cell that secretes a monoclonal antibody of the invention. Techniques for preparing monoclonal antibody-secreting hybridoma cells are known in the art. See, for example, Kohler and Milstein, Nature 256:495-97 (1975) and Kozbor et al. Immunol Today 4: 72 (1983). A monoclonal antibody of the invention can also be prepared using other methods known in the art, such as, for example, expression from a recombinant DNA molecule, or screening of a recombinant combinatorial immunoglobulin library using a mutant polypeptide of the invention.

Methods to generate chimeric and humanized monoclonal antibodies are also well known in the art and include, for example, methods involving recombinant DNA technology. A chimeric antibody can be produced by expression from a nucleic acid that encodes a non-human variable region and a human constant region of an antibody molecule. See, for example, Morrison et al., Proc. Nat. Acad. Sci. U.S.A. 86: 6851 (1984). A humanized antibody can be produced by expression from a nucleic acid that encodes non-human antigen-binding regions (complementarity-determining regions) and a human variable region (without antigen-binding regions) and human constant regions. See, for example, Jones et al., Nature 321:522-24 (1986); and Verhoeven et al., Science 239:1534-36 (1988). Completely human antibodies can be produced by immunizing engineered transgenic mice that express only human heavy and light chain genes. In this case, therapeutically useful monoclonal antibodies can then be obtained using conventional hybridoma technology. See, for example, Lonberg & Huszar, Int. Rev. Immunol. 13:65-93 (1995). Nucleic acids and techniques involved in design and production of antibodies are well known in the art. See, for example, Batra et al., Hybridoma 13:87-97 (1994); Berdoz et al., PCR Methods Appl. 4: 256-64 (1995); Boulianne et al. Nature 312: 643-46 (1984); Carson et al., Adv. Immunol. 38:274-311 (1986); Chiang et al., Biotechniques 7:360-66 (1989); Cole et al., Mol. Cell. Biochem. 62:109-20 (1984); Jones et al., Nature 321: 522-25 (1986); Larrick et al., Biochem Biophys. Res. Commun. 160:1250-56 (1989); Morrison, Annu. Rev. Immunol. 10:239-65 (1992); Morrison et al., Proc. Nat'l Acad. Sci. USA 81: 6851-55 (1984); Orlandi et al., Pro. Nat'l Acad. Sci. U.S.A. 86:3833-37 (1989); Sandhu, Crit. Rev. Biotechnol. 12:437-62 (1992); Gavilondo & Larrick, Biotechniques 29: 128-32 (2000); Huston & George, Hum. Antibodies. 10:127-42 (2001); Kipriyanov & Le Gall, Mol. Biotechnol. 26: 39-60 (2004).

Antibodies that react and bind to the epitopes described herein may also be isolated from phage antibody libraries using the techniques described in Clackson et al. Nature 352: 624-628 (1991), as well as in Marks et al., J. Mol. Biol. 222: 581-597 (1991) and U.S. patent application Ser. No. 10/939,309.

Another method for generating antibodies involves a Selected Lymphocyte Antibody Method (SLAM). The SLAM technology permits the generation, isolation and manipulation of monoclonal antibodies without the process of hybridoma generation. The methodology principally involves the growth of antibody forming cells, the physical selection of specifically selected antibody forming cells, the isolation of the genes encoding the antibody and the subsequent cloning and expression of those genes.

The antibodies can be mutated to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

The antibodies of the invention are isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or nonproteinaceous solutes. The term "isolated antibody" also includes antibodies within recombinant cells because at least one component of the antibody's natural environment will not be present. Ordinarily, however, isolated antibody will be prepared by at least one purification step.

If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: METHODS IN MOLECULAR BIOLOGY, Vol. 10, pages 79-104 (Humana Press (1992).

In some embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomassie blue or, preferably, silver stain.

The antibodies described herein include immunologically-active fragments of antibodies. Methods of making antibody fragments are also known in the art (see for example, Harlow and Lane, ANTIBODIES: A LABORATORY MANUAL, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Biotechnology* 11:1271-77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991). The antibodies described herein can be any CDR-containing polypeptides.

The antibodies that specifically bind to the diglycine-lysine epitope, and/or to the Leu-Arg-Gly-Gly-lysine epitope, and/or to the STLHLVLRLRGG-lysine epitope can be immobilized onto a solid support. Such immobilized antibodies can facilitate purification and analysis of peptides and proteins that have any of these epitopes. Examples of solid supports to which the antibodies can be immobilized include water miscible particles, such as agarose beads, sepharose beads, column chromatographic matrix materials, microtiter dish wells, and the like. Attachment can be through peptide/protein amine, sulfhydryl, carboxy, carboxylate and other reactive groups in the peptide/protein. For example, the peptides/proteins can be attached to an amine on the surface of the solid support under native condition. Such immobilized antibodies can, for example, be used for immune-purification of peptides generated from ubiquitinated proteins after cleavage with a protease (e.g., trypsin, Glu-C or Arg-C).

The antibodies that bind to the diglycine-lysine epitope, and/or to the Leu-Arg-Gly-Gly-lysine epitope, and/or to the STLHLVLRLRGG-lysine epitope can be linked to detectable labels. Alternatively, labeled secondary antibodies can be used to detect the antibodies that bind specifically to the diglycine-lysine epitope, and/or to the Leu-Arg-Gly-Gly-lysine epitope, and/or to the STLHLVLRLRGG-lysine epitope.

Any detectable label known in the art can be linked to the antibodies, including, for example, a radioactive label (e.g., $^3$H, $^{125}$I, $^{35}$S, $^{14}$C, $^{32}$P, $^{33}$P), an enzymatic label, such as horseradish peroxidase, alkaline peroxidase, glucose 6-phosphate dehydrogenase, etc., a chemiluminescent label, such as, acridinium derivatives, luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, INTRODUCTION TO IMMUNOCYTOCHEMISTRY, 2$^{nd}$ ed., Springer Verlag, N.Y. (1997) and in Haugland, HANDBOOK OF FLUORESCENT PROBES AND RESEARCH CHEMI (1996), which is a combined handbook and catalogue published by Molecular Probes, Inc., Eugene, Oreg., each of which is incorporated herein by reference. Additional detail can be found in Mattingly, P. G., and Adamczyk, M. (2002) *Chemiluminescent N-sulfonylacridinium-9-carboxamides and their application in clinical assays*, in LUMINESCENCE BIOTECHNOLOGY: INSTRUMENTS AND APPLICATIONS (Dyke, K. V., Ed.) pp 77-105, CRC Press, Boca Raton.

The detectable label can be bound to the antibody or secondary antibody either directly or through a coupling agent. An example of a coupling agent that can be used is EDAC (1-ethyl-3-(3-dimethylaminopropyl) carbodiimide, hydrochloride), which is commercially available from Sigma-Aldrich (St. Louis, Mo.). Other coupling agents that can be used are also available in the art as are methods for binding a detectable label to an antibody or nucleic acid. Additionally, many detectable labels can be purchased or synthesized that already contain end groups that facilitate the coupling of the detectable label to other proteins (e.g., antibodies) or nucleic acids, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

Detecting Ubiquitinated Proteins

Another aspect of the invention includes methods of detecting and/or identifying ubiquitinated proteins, including proteins that are the substrates of ubiquitin ligases. Previous strategies developed to identify targets of ubiquitination have largely relied upon educated guesses to identify proteins that are subject to ubiquitination. In most cases, proteins suspected to be ubiquitinated have been identified based on their instability or other properties typically associated with ubiquitination. These proteins are purified by immunoprecipitation and the presence of ubiquitin adducts is determined by anti-ubiquitin western blotting (Banerjee et al. *Drug Metab Dispos* 28, 118-124 (2000)). For example, the susceptibility of proteins to ubiquitination is usually measured by anti-ubiquitin western blot (Banerjee, Kocarek et al. 2000). Lysine mutation experiments have also been used to determine the location of lysine sites or local regions in a specific protein required for ubiquitination (Gregori, Poosch et al. 1990; Treier, Staszewski et al. 1994; Baboshina and Haas 1996). However, such mutation procedures are time consuming and can also stimulate the ubiquitination of nearby lysines after the mutation of the target lysines (Hou, Cenciarelli et al. 1994; Baboshina and Haas 1996). Thus, the lysines identified may be not the ubiquitination sites under physiological condition. These problems are solved by the methods of the invention. Moreover, despite the availability of these approaches, only 119 mammalian proteins have been identified as being ubiquitinated according to UbiProt database (Chemorudskiy et al. *BMC Bioinformatics* 8, 126 (2007)).

However, using the antibodies and methods described herein, the inventors have identified more than 300 mammalian ubiquitinated proteins comprising nearly 400 diglycine-modified lysines. Analysis of these proteins provides insight into ubiquitination consensus sites and identifies new potential biological roles for ubiquitination.

The methods for detecting ubiquitination utilize the fact that the C-terminus of ubiquitin is ligated to the ε-amine of lysines in ubiquitinated proteins. The three C-terminal residues of ubiquitin are Arg-Gly-Gly. Thus, the C-terminal glycine of ubiquitin is conjugated to a lysine in the target protein to form a ubiquitin conjugate. The methods of this invention employ a protease to cleave this conjugate, for example, after the Arg moiety to yield a Gly-Gly dipeptide remnant that is still conjugated to the lysine present in the target protein. Any protease that can cleave a peptidyl sequence on the C-terminal side of arginine or glutamic acid can be employed in the methods of the invention. Examples of proteases that cleave protein sequences on the C-terminal side of arginine include trypsin and Arg-C. An example of a protease that cleaves proteins on the C-terminal side of glutamic acid is the Glu-C protease.

Cleavage of a protein or mixture of proteins with such proteases yields a number of peptides, some of which contain the diglycine-lysine epitope, the Leu-Arg-Gly-Gly-lysine epitope, and/or to the STLHLVLRLRGG-lysine epitope, indicating that these peptides were conjugated to ubiquitin. Therefore, detection of any of these epitopes on a peptide after cleavage permits detection of the type and site of ubiquitination in a protein or mixture of proteins.

Accordingly, one aspect of the invention is a method of detecting ubiquitination in a protein, or mixture of proteins, that involves cleaving the protein, or mixture of proteins, with a protease that cleaves on the C-terminal side of arginine or glutamic acid to yield cleaved peptides, reacting the cleaved peptides with an antibody that specifically binds to a diglycine-lysine epitope, a Leu-Arg-Gly-Gly-lysine epitope, and/or to the STLHLVLRLRGG-lysine epitope, and observing which peptide(s) bind to the antibody. The method can further include identifying the peptide sequence and/or the protein from which the peptide was cleaved.

The peptide sequence, and/or the protein from which the peptide was cleaved, can be identified by available techniques. Such methods include mass spectrometry, Edman degradation, N-terminal amino acid analysis, C-terminal amino acid analysis and combinations thereof.

In some instances it may be easier to separate and/or purify the peptides prior to sequencing. Peptide/protein mixtures from ubiquitination studies can be complicated mixtures because each protein can have ten or more peptides after protease cleavage. Typically, only one or a few of these peptides are ubiquitinated. Moreover, when a mixture of tissues and/or cells are used as a sample, only a small portion of the proteins in such a sample is ubiquitinated while the rest is not ubiquitinated. Therefore, only a small percentage of peptides derived from complex mixture proteins in the sample are typically ubiquitinated. This can be a problem when using approaches that analyze and sequence peptides, such as mass spectrometry, because considerable instrument time may need to be devoted to sequencing peptides that do not have a diglycine modification. However, peptides and proteins with the diglycine-lysine epitope, the Leu-Arg-Gly-Gly-lysine epitope, and/or the STLHLVLRLRGG-lysine epitope can be separated from impurities (including any peptides or proteins that do not contain this epitope) using the antibodies that specifically bind to the diglycine-lysine epitope. Peptides that have the diglycine-lysine epitope, the Leu-Arg-Gly-Gly-lysine epitope, and/or the STLHLVLRLRGG-lysine epitope can also be separated by available peptide purification procedures including, for example, by using ion-exchange chromatography, hydrophobic interaction chromatography, gel filtration chromatography, high pressure liquid chromatography, gel electrophoresis and any other procedure available to one of ordinary skill in the art.

One method for determining the sequence of peptides involves mass spectrometry (MS), for example, MALDI, MALDI-TOF-MS, LC-MS, LC-MS/MS, as well as MS that uses other separation techniques, such as capillary electrophoresis. In some embodiments, liquid chromatography/mass spectrometry can be used, which involves passing the peptides that contain the diglycine-lysine epitope, the Leu-Arg-Gly-Gly-lysine epitope, and/or the STLHLVLRLRGG-lysine epitope through a high pressure liquid chromatography column. At the end of this column, the solution is sprayed into the mass spectrometer out of a narrow nozzle charged to a high positive potential. The collision energy applied to the droplets causes the peptides to fragment at different locations in the peptide so that different "peaks" of the ions can be detected, where the distance between peaks is proportional to the ratio of mass to charge on the fragment. The mass spectrum is analyzed by computer and often compared against a database of previously sequenced proteins in order to determine the sequences of the fragments. This process is then repeated as necessary. For example, if a complex mixture of peptides is present, the peptides can be separated, or if a peptide of interest is very long, the peptide can be partially cleaved (e.g. with a protease) to generate overlapping peptide fragments. These purified and/or partially cleaved peptides can then be analyzed by liquid chromatography/mass spectrometry as described above. Use of a computer can facilitate analysis of the mass spectrometry results (e.g., mass information, or tandem mass spectrometry fragmentation data) so that the sequences can readily be determined of the peptides and/or protein that contain the diglycine-lysine epitope, the Leu-Arg-Gly-Gly-lysine epitope, and/or the STLHLVLRLRGG-lysine epitope.

Peptides fragment in a reasonably well-documented manner when using mass spectrometry (P. Roepstorrf, J. Fohlmann, *Biomed. Mass Spectrom.*, 1984, 11, 601; R. S. Johnson, K. Biemann, *Biomed. Environ. Mass Spectrom.*, 1989, 18, 945). The protonated molecules fragment along the peptide backbone and also show some side-chain fragmentation with certain instruments (Four-Sector Tandem Mass Spectrometry of Peptides, A. E. Ashcroft, P. J. Derrick in "Mass Spectrometry of Peptides" ed. D. M. Desiderio, CRC Press, Florida, 1990). In general, there are three different types of bonds that can fragment along the amino acid backbone: the NH—CH, CH—CO, and CO—NH bonds. Each bond breakage gives rise to two species, one neutral and the other one charged. Only the charged species is monitored by the mass spectrometer. The charge can stay on either of the two fragments depending on the chemistry and relative proton affinity of the two species. Hence there are six possible fragment ions for each amino acid residue, where three ions can form having the charge retained on the N-terminal fragment, and three ions can form having the charge retained on the C-terminal fragment. The most common cleavage sites are at the CO—NH bonds, which give rise to the b ions and/or the y ions. The mass difference between two adjacent b ions, or y ions, is indicative of a particular amino acid residue. Thus, mass spectrometers have been found to be extremely useful peptide sequencing.

Another procedure for determining the sequence of peptides involves partial hydrolysis of epitope-containing peptides to generate a series of overlapping peptide fragments. These fragments can be separated and analyzed by N-terminal amino acid analysis, C-terminal amino acid analysis, Edman degradation and analysis procedures and any other available procedures.

Another aspect of the invention involves obtaining quantitative information on the abundance of diglycine-modified peptides, which will allow those of skill in the art to make inferences about the abundance of the ubiquitinated protein in a sample. One method for obtaining quantitative information involves the use of a SILAC (Stable isotope labeling with amino acids in cell culture) technique in which differences in peptide abundance between two or more samples can be determined. In this approach, at least one sample is prepared by growing the sample in the presence of specific amino acids that contain a label (e.g., a stable heavy isotope). These labeled amino acids can, for example, be one or more of the following amino acids: lysine, leucine, arginine, histidine, etc. This procedure can be performed by adding the labeled amino acids to the culture media for tissue culture cells or cultured tissue, or providing the amino acids to an animal in the diet. The cells incorporate the modified amino acid. When the sample is harvested and digested, the peptides that are derived from the sample that was prepared in the presence of the labeled amino acid will have a higher mobility than control samples, which are cultured in media without these added amino acids. Typically each cell population is different, for example, they may express a different gene or small interfering RNA, or may the different cell populations have significant genomic differences, such as cancer cells versus normal cells. The two cell populations may differ by an experimental treatment, such as treatment with a hormone, drug, small interfering RNA, or a protein. By comparing these samples simultaneously, the relative differences in abundance of diglycine-modified peptides in the sample can be determined. Further information on these procedures is available in Ong et al., Molecular & Cell Proteomics 1: 376-86 (2002); Ong et al., Journal of Proteome Research 2: 173-81 (2003); Ong & Mann, Nature Protocols 1: 2650-60 (2006); Ong & Mann, Methods in Molecular Biology 359: 37-52 (2007).

Another aspect of this invention is to measure the abundance of diglycine-containing peptides by labeling peptides with heavy water ($H_2^{18}O$). In this technique, peptides are obtained from a sample, and then treated with trypsin, but potentially other proteases as well, and $H_2^{18}$ to label the carboxyl terminus with $^{18}O$. This can impart a 2 or 4 Da mass difference on these peptides, compared to a control sample with is either untreated or labeled with "light" water $H_2^{16}O$. The labeling with $H_2^{18}O$ often is performed after peptides are obtained by protease digestion, however, peptides can be labeled during the protease digestion step by including $H_2^{18}O$ during this step. Further information on this procedure is described in Heller et al. Journal of the American Society for Mass Spectrometry. 14:704-718 (2003); Yao, et al. Anal Chem. 73:2836-2842 (2001).

Another aspect of this invention involves determining the abundance of diglycine-containing peptides using techniques that are commonly used in quantitative proteomics (see for example: Mass spectrometry based targeted protein quantification: methods and applications. Pan S, Aebersold R, Chen R, Rush J, Goodlett D R, McIntosh M W, Zhang J, Brentnall T A. J Proteome Res. 2009 February; 8(2):787-97.)

Another aspect of this invention involves use of the antibodies described herein to purify proteins that are modified on lysines with ubiquitin or proteins other than ubiquitin, but that result in a diglycine epitope after protease treatment. For example, such diglycine epitope-tagged proteins can result when ubiquitin or ubiquitin-like protein is expressed in cells, where the ubiquitin and/or the ubiquitin-like protein will become covalently linked to other proteins. Thus, a ubiquitin-like protein could be expressed in cells, e.g. one which already has a carboxyl terminus sequence that would result in a diglycine-adduct on target lysines after digestion. This ubiquitin-like protein could be engineered to contain the desired diglycine adduct, or it may occur naturally in the amino acid sequence. Proteins that are modified with these ubiquitin-like proteins may be isolated or enriched via the epitope tag, for example, after digestion with a protease as described herein. The digested proteins would then be recognized and bound by the anti-diglycyl-lysine antibody.

Once the sequence of an ubiquitin epitope-containing peptide is known, the protein from which that peptide was derived can be identified because the complete sequence of the human genome and the proteins encoded therein is known. Thus, protein databases can be searched to ascertain what proteins have the sequence of the ubiquitin epitope-containing peptide. The identities of the ubiquitin epitope-containing peptides and the proteins from which they are derived can therefore be determined using these and other types of peptide/protein separation and sequencing methods combined with bioinformatics analysis and/or proteomic sequence searches.

Moreover, the antibodies that bind to the diglycine-lysine epitope, and/or to the Leu-Arg-Gly-Gly-lysine epitope, and/or to the STLHLVLRLRGG-lysine epitope can be used in any immunopurification, immunoassay or other procedure for detecting and evaluating ubiquitinated proteins and/or peptides. For example, the antibodies can be used for detection, purification and/or quantification of ubiquitinated proteins and/or peptides using methods known to one of ordinary skill in the art such as histochemical staining, Western Blot analysis, dot blot analysis, immunoprecipitation, enzyme-linked immunosorbent assays (ELISA) and the like. Measurement of the ubiquitinated proteins and/or peptides can include measurements of fragments of the protein or peptide, wherein the fragments arise from enzymatic or chemical hydrolysis of the protein or peptide.

For example, a ubiquitinated protein can be detected by forming a complex between the ubiquitinated protein or peptide (or an proteolytic digest of such a ubiquitinated protein or peptide) and a labeled antibody that binds to the diglycine-lysine epitope, and/or to the Leu-Arg-Gly-Gly-lysine epitope, and/or to the STLHLVLRLRGG-lysine epitope. After formation of the labeled complex, the amount of label in the complex can be detected or quantified using techniques known in the art. For example, if an enzymatic label is used, the labeled complex is reacted with a substrate for the label that gives a detectable and/or quantifiable reaction such as the development of color. If the label is a radioactive label, the label is detected and/or quantified using a scintillation counter. If the label is a fluorescent label, the label is detected and/or quantified by stimulating the label with a light of one color (which is known as the "excitation wavelength") and detecting another color (which is known as the "emission wavelength") that is emitted by the label in response to the stimulation. If the label is a chemiluminescent label, the label is detected and/or quantified by detecting the light emitted either visually or by using luminometers, x-ray film, high speed photographic film, a CCD (charged coupled device) camera, etc. For solution phase assays, once the amount of the label in the complex has been detected and/or quantified, the concentration of ubiquitinated protein or peptide in the test sample is determined, for example, by use of a standard curve that has been generated using serial dilutions of the ubiquitinated protein or peptide of known concentration.

Immunoassays can be used to detect ubiquitinated proteins and/or peptides that employ any of the polyclonal or monoclonal antibodies that bind to any of the epitopes described herein. In some embodiments, the immunoassay involves immunohistochemistry, radioimmunoassays, competitive binding assays, sandwich assays, or immunoprecipitation assays. Antibodies that bind to the diglycine-lysine epitope, and/or to the Leu-Arg-Gly-Gly-lysine epitope, and/or to the STLHLVLRLRGG-lysine epitope can be combined or attached to a detectable label as described herein. The choice of label used will vary depending upon the application and can be made by one skilled in the art.

Radioimmunoassays typically use radioactivity in the measurement of complexes between antibodies ubiquitinated proteins and/or peptides. Hence, in such a method, the antibody is radio-labeled. The antibody is reacted with unlabeled ubiquitinated proteins or peptides. The radio-labeled complex can be separated from unbound material, for example, by precipitation and/or centrifugation. The amount of complex is then quantified either by measuring the radiation directly or by observing the effect that the radiolabel has on a fluorescent molecule, such as depheny-loxazole (DPO). The latter approach requires less radioactivity and is more sensitive. This approach, termed scintillation, measures the fluorescent transmission of a dye solution that has been excited by a radiolabel, such as $^3$H or $^{32}$P. The extent of binding is determined by measuring the intensity of the fluorescence released from the fluorescent particles. This method, termed scintillation proximity assay (SPA), has the advantage of being able to measure antibody complexes formed in situ without the need for washing off unbound radioactive antibody.

Competitive binding assays rely on the ability of a labeled competitor to compete with the test sample analyte for binding with a limited amount of antibody. The labeled competitor may be a ubiquitinated polypeptide, peptide, fragment, variant or derivative thereof. The amount of test sample is inversely proportional to the amount of competitor that becomes bound to the antibodies. To facilitate determination of the amount of competitor that becomes bound, the antibodies employed are generally made insoluble either before or after the competition. This is done so that the competitor and analyte that are bound to the antibodies may be conveniently separated from the competitor and analyte that remain unbound.

Sandwich assays involve the use of two antibodies, each capable of binding to a different immunogenic portion, or epitope, of the product to be detected. In a sandwich assay, the test sample analyte is bound by a first antibody which is immobilized on a solid support, and thereafter a second antibody binds to the analyte, thus forming an insoluble three part complex (David & Greene, U.S. Pat. No. 4,376,110). The second antibody may itself by labeled with a detectable moiety (direct sandwich assays) or may be measured using a third antibody that binds the second bonding entity and is labeled with a detectable moiety (indirect sandwich assay). For example, one type of sandwich assay is an ELISA assay, in which case the detectable moiety is an enzyme.

Typically, sandwich assays include "forward" assays in which the antibody bound to the solid phase is first contacted with the sample being tested to extract the ubiquitinated proteins or peptides from the sample by formation of a binary solid phase complex between the immobilized antibody and the ubiquitinated proteins or peptides. After a suitable incubation period, the solid support is washed to remove unbound fluid sample, including any unreacted ubiquitinated proteins or peptides, if any. The solid support is then contacted with the solution containing an unknown quantity of labeled antibody (which functions as a label or reporter molecule). After a second incubation period to permit the labeled antibody to react with the complex between the immobilized antibody and the ubiquitinated proteins or peptides, the solid support is washed a second time to remove the unreacted labeled antibody.

Other types of sandwich assays that may be used include the so-called "simultaneous" and "reverse" assays. A simultaneous assay involves a single incubation step wherein the labeled and unlabeled antibodies are, at the same time, both exposed to the sample being tested. The unlabeled antibody is immobilized onto a solid support, while the labeled antibody is free in solution with the test sample. After the incubation is completed, the solid support is washed to remove unreacted sample and uncomplexed labeled antibody. The presence of labeled antibody associated with the solid support is then determined as it would be in a conventional "forward" sandwich assay.

In a "reverse" assay, stepwise addition is utilized, first of a solution of labeled antibody to a test sample, followed by incubation, and then later by addition of an unlabeled antibody bound to a solid support. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Hence, the antibodies described herein can be used in a variety of immunoassays, immuno-detection and immuno-purification procedures.

Other Uses of the Antibodies and Methods

Specifically Enrich Peptides Derived from Ubiquitinated Proteins and Significantly Increase Efficiency for High-Throughput Identification of Ubiquitination Sites.

By using the antibodies described herein in conjunction with immunopurification procedures and subsequent analysis of the peptides isolated with LC-MS/MS, about 400 ubiquitination sites in over 300 proteins from mammalian cells and tissues have successfully been identified under physiological conditions. Most of the ubiquitination sites have not previously been identified.

Identification of Substrates for Specific Ubiquitin Ligase and Identification of Potential Targets for Ubiquitination-Related Diseases.

In human ubiquitination pathways, there are about five hundred ubiquitin ligases (E3) interacting with substrates and ubiquitin conjugating enzymes (E2), which carry ubiquitin from ubiquitin activating enzymes (E1). The E3s are highly diverse and have different crystal structures, such as HECT, RING or ubiquitin interacting complex, during the transfer of ubiquitin molecule from E2 to substrates. The diversity of the E3 ligases indicates that these ligases may recognize various substrates. However, up to now, only limited substrates have been identified for specific E1, E2 and E3 ligases due to the difficult technical challenges of substrate identification. However, the antibodies described herein can facilitate these analyses so that the specific substrates for specific E1, E2 or E3 ligases can be identified.

Diagnostics of Ubiquitination-Related Diseases.

Many diseases, such as Alzheimer's disease, Parkinson's disease, breast cancer, etc, are correlated with the alteration of ubiquitination pathways, for example, deficiency of ubiquitin enzymes, accumulation of ubiquitinated proteins, etc. Currently, these diseases are diagnosed through clinical abnormality, usually at a late and incurable stage. Using the methods described herein these diseases may be diagnosed at an early stage, permitting early treatment options for the patient.

The common feature of these diseases is the alteration of ubiquitinated proteins in human cells. Using the antibodies described herein and optionally other pre-purification techniques, such as GST-S5A or an anti-ubiquitin antibody, one of skill in the art may quantify the relative abundance of the ubiquitinated proteins from patient sample or normal sample and then to identify ubiquitination-related diseases at early stage.

The experiments described herein have identified many disease-related ubiquitinated proteins, such as Huntingtin, Dystrophin, Apolipoprotein B-100, Superoxide dismutase, Tuberin, Rho-associated protein kinase 2, Neurexin-1-alpha precursor, etc., in normal cells. These studies demonstrated that the antibodies described herein can be used to identify ubiquitination-related diseases.

Drug Screening for Ubiquitination-Related Diseases.

In order to treat ubiquitination-related diseases, it is desirable to find drugs that reverse the abnormal ubiquitination pathways toward normal. In the drug screening stage, the use of the antibodies described herein and subsequent mass spectrometry analysis can identify the change of the ubiquitination level in the presence of different drugs in abnormal cells, thereby identifying possible drug candidates for treatment of ubiquitination-related diseases. Similarly, certain diseases, whether they involve abnormalities in ubiquitination or not, may benefit from increased or decreased ubiquitination of a specific protein that may affect the manifestation of a specific condition, biological state, or disease. In this case, in the drug screening stage, the use of the antibodies described herein and subsequent mass spectrometry analysis can identify the change of the ubiquitination level in the presence of different drugs in normal or abnormal cells, thereby identifying proteins that are affected by a specific drug or other treatment, and thereby suggesting potential uses for a drug or other treatment.

The following non-limiting Examples illustrate certain aspects of the invention.

Example 1: Materials and Methods

The Example illustrates some of the materials and methods used in developing the subject matter of the claims.

Antigen Design and Antibody Purification.

Lysine-rich histone (10 mg, sample A) from calf thymus (type III-S, Sigma) was dissolved in 100 mM NaHCO$_3$ buffer (10 ml) at pH 10. 50 mM t-butyloxycarbonyl-Gly-Gly-N-hydroxysuccinimide (500 µl, Boc-Gly-Gly-NHS; Derrien D., et al., Glycoconj J. 1989, 6, 241-55) in DMSO was added to histone solution and the reaction was carried out at room temperature for 1 h by shaking on a plate rotator. This step was repeated three additional times and sample B was obtained. For deprotection of the Boc group, neat trifluoroacetic acid (6 ml, TFA, Sigma) was added and the solution was shaken for 2 h at room temperature. The reaction was neutralized and stopped by adding 10 M NaOH dropwise on ice (sample C). All of sample C and part of sample A and sample B were dialyzed four times against 20 mM acetic acid followed by lyophilization. The degree of the reaction was accessed by anti-biotin (Sigma) western blot after samples A, B, and C were reacted with 5 mM biotin-NHS (Sigma) for 10 min. The absence of biotin incorporation as measured by the absence of a signal by Western blotting, indicates that all the amines in the protein were reacted with the Boc-Gly-Gly-NHS. The same protocol was used to prepare Boc-Gly-Gly- and Gly-Gly-modified β-lactoglobulin, hen egg white lysozyme, bovine serum albumin, and rat brain lysate for antibody evaluation, all of which were prepared and tested for their ability to incorporate Gly-Gly and serve as antigens.

These Gly-Gly-protein antigens were used for antibody production in rabbits (Invitrogen). Bleeds were collected at five, eight, ten weeks. The antibody was purified by Melon gel IgG purification kit (Pierce) according to the manufacturer's protocol and evaluated using β-lactoglobulin, hen egg white lysozyme, and rat brain lysate. The 10-week antibody was used in all experiments due to the high specificity and higher titer.

Cell Culture and Subcellular Fractionation.

Human embryo kidney (HEK293), mouse neuroblastoma (N2a) and murine endothelioma (sEnd.1) cells were cultured in Dulbecco's modified Eagle's medium (DMEM, Invitrogen) with 4.5 g/l glucose for HEK293 and N2a cells and 1 g/l glucose for sEnd.1 cells, respectively, supplemented with 10% fetal bovine serum, 100 units/ml penicillin G, and 100 µg/ml streptomycin at 37° C. When the confluence reached ~60% after three days, cells were treated with the proteasome inhibitor 50 µM N-acetyl-Leu-Leu-norleucinal (LLnL, Calbiochem) in DMSO and incubated for 24 h prior to harvest.

Cells were cultured in five or twenty 10-cm-diameter Petri dishes for the samples without and with further subcellular fractionation, respectively. The cells were briefly washed with phosphate buffered saline (PBS) buffer and centrifuged at 1000 g for 10 min at 4° C. The cell pellet was dissolved in lysis buffer containing 150 mM NaCl, 50 mM tris-HCl, 250 mM glucose, 50 µM LLnL, 5 mM iodoacetamide, 1 mM phenylmethylsulfonyl fluoride (PMSF) at pH 7.4.

For animal tissues, rat brain and rat liver (~2 g) were briefly washed with lysis buffer and cut into small pieces. Lysis buffer (five volumes) was added to the tissue. The samples were homogenized in a Dounce homogenizer with 10-15 strokes. Rat tissues were filtered through four layers cheese cloth to remove cell debris. The homogenate was centrifuged at 1000 g at 4° C. to obtain the crude nuclear fraction. The supernatant was further centrifuged at 100,000 g for 90 min. The pellet was regarded as crude mitochondrial fraction and the supernatant as cytosolic fraction. In order to obtain crude synaptosomal fraction from rat brain, the resulting supernatant after removing nuclear fraction was further centrifuged at 10,000 g for 15 min and the pellet was collected. All the pellets were washed twice with 10 ml lysis buffer and centrifuged again at the corresponding speeds and the pellets were dissolved in 2 ml (for rat tissues) or 0.5 ml (for cell cultures) freshly prepared lysis buffer with 6 M urea at pH 8. The cytosolic fraction was concentrated using Amicon Ultra centrifugal filter tubes (5 kDa molecular weight cutoff, Millipore) and the pH was adjusted to 8. For the samples without fractionation, lysis buffer with 6 M urea (pH 8) was directly added.

Sample Preparation and Purification.

All the samples were sonicated for 10 s on ice and adjusted to 20 mM dithiothreitol for 1 h at 25° C. Iodoacetamide (Sigma) was added to a final concentration of 80 mM and incubated at 25° C. for 30 min in the dark and then desalted (Zeba desalting spin columns, Pierce) with buffer exchange to 20 mM ammonia bicarbonate. The desalted samples were digested with TPCK-treated trypsin (Sigma) at 37° C. for 24 h. The digestion was quenched by addition of a final concentration of 1 mM PMSF (in ethanol) twice, each for 30 min at room temperature.

Affinity resin was prepared by coupling the antibody to NHS-activated agarose (Sigma) in 0.1 M sodium bicarbonate buffer with 0.5 M NaCl for 24 h. The resin was washed with 0.1 M tris buffer. Peptide-containing samples were diluted to 5 ml (with PBS) followed by incubation with antibody resin for 2 h at 4° C. Then the sepharose beads were washed with 5 ml PBS, 5 ml 0.5 M NaCl in PBS, 5 ml distilled water (twice each) followed by elution by eight times of 400 µl 0.1% formic acid in 50% acetonitrile in distilled water. The eluted samples were filtered through a 0.2 µm spin column (Pall Life Sciences) and concentrated to 50 µl for nano LC-MS/MS analysis.

LC-MS/MS Analysis.

The samples were analyzed by nano LC-MS/MS to obtain peptide sequence information using the similar settings as described in the literature (Hao et al., *Proc Natl Acad Sci USA* 103, 1012-1017 (2006). The nano LC-MS/MS was performed with an 1100 series LC coupled to an XCT plus ion trap mass spectrometer. The purified samples were injected onto a 0.3×5 mm Zorbax 300SB-C18 sample-enrichment column at a flow rate of 3 µl/min 100% solvent A. Peptides were resolved on a 0.075×150 mm Zorbax 300SB-C18 analytical column at a flow rate of 0.35 µl/min with a gradient of 5-45% solvent B for 40 min. Solvent A was 0.1% formic acid (Fluka) and 3% acetonitrile (Fisher) in MS/MS grade water (Fisher) and solvent B consisted of 0.1% formic acid and 90% acetonitrile. The LC column eluate was introduced into the ion trap mass spectrometer via electrospray using a 15 µm diameter silica emitter needle. Mass spectra were acquired in positive-ion mode with automated data-dependent MS/MS on the four most intense ions from precursor MS scans and every selected precursor peak was analyzed no more than twice within 1 min.

Database Search of MS/MS Data for Peptide and Protein Identification.

Analysis of MS/MS spectra for peptide and protein identification was performed by protein database searching with Spectrum Mill software (Rev A.03.02, Agilent) against Swiss-Prot database released in February 2007. Raw MS/MS spectra were first extracted to MS/MS spectra that could be assigned to at least four y- or b-series ions and searched against the Swiss-Prot database. During the extraction step, scans with the same precursor ±1.4 m/z were merged within a time frame of ±15 s, charges up to a maximum of 5 were assigned to the precursor ion, and the $^{12}C$ peak was determined by the Data Extractor. Key search parameters were a minimum matched peak intensity of 50%, a precursor mass tolerance of ±2.5 Da, and a product mass tolerance of ±0.7 Da. The fixed modification was iodoacetamide for cysteines for all the samples. A variable modification of diglycine was set for lysine residues and the maximal modification number was set as two. The false positive rate was estimated by searching the MS/MS spectra against a random protein database with same number of amino acids for each entry as the original database for several groups of extracted MS/MS spectra. The threshold used for peptide identification was a score of >10 and an SPI % (the percentage of assigned spectrum intensity of total spectrum intensity) of >60%, which gave a 5% rate of false positive. In the peptide list, only the highest scoring member of each peptide group is shown and only peptides with a charge state of 2 and 3 are reported. Finally, all MS/MS spectra were manually validated and the spectra with low quality fragmentations were removed. The peptides with a score between 10 and 11 are included only when the ubiquitination of the corresponding proteins has been reported previously.

Search parameters were adjusted so that four trypsin missed cleavages were allowed. This increased tolerance is based on our finding that ubiquitination increased the number of missed cleavages. The ubiquitin-remnant containing peptides had an average length of 20.7 amino acids. This is higher than the average size of tryptic peptides identified by ion trap mass spectrometry and can be explained by a high number of trypsin missed-cleavages. On average, 1.5 missed cleavages per peptide were found without counting the modified lysines. As a control, the number of missed-cleavage sites for a rat brain lysate with only cysteines blocked with iodoacetamide showed that tryptic peptides have an average length of 15.6 amino acids and 0.32 missed-cleavages under similar experimental conditions. Thus, the number of missed cleavages is nearly five times higher for ubiquitinated peptides. Moreover, the inventors observed that 35% of the ubiquitinated peptides have basic amino acids (Arg or Lys) within 2 amino acids from the ubiquitination site, which hampers the efficiency of trypsin digestion (see also, Benore-Parsons et al. *Arch Biochem Biophys* 272, 274-280 (1989); Schlosser et al. *Anal Chem* 73, 170-176 (2001)) while under control conditions, only 12% of peptides exhibit similarly close to Arg or Lys residues. Unlike an analysis of tryptic phosphopeptides (Molina et al. *Proc Natl Acad Sci USA* 104, 2199-2204 (2007)), no significant difference was observed in the frequency of acidic amino acids within two amino acids between diglycine-modified lysines and lysines from control samples. Our results indicate that ubiquitination hinders trypsin digestion, most likely because of the large size of ubiquitin chain or the remaining residues after trypsin digestion of ubiquitin, the presence of basic amino acids in proximity to the ubiquitination sites, and the branching topology of the ubiquitination sites. A similar phenomenon has also been found for phosphopeptides (Molina et al. *Proc Natl Acad Sci USA* 104, 2199-2204 (2007)). For this reason, a higher number of missed-cleavage sites have been allowed during the database search although higher charge states are filtered out.

Biochemical Validation of Ubiquitination.

Some identified ubiquitinated proteins were verified by western blotting pulldowns obtained with glutathione agarose immobilized GST-S5a. Note that S5a is a subunit of the 26S proteasome and has strong affinity for polyubiquitin chains (Wang et al., *J Mol Biol* 348, 727-739 (2005)). The expression vector, pGEX4T2-S5a, was transformed and grown in BL21(DE3) *E. coli* and protein expression was induced by addition of 200 µM isopropyl-beta-D-thiogalactopyranoside for 3 h at 37° C. The cells were centrifuged and the pellet was lysed, sonicated and centrifuged again in lysis buffer (100 mM NaCl, 20 mM tris-HCl, 1% triton X-100, 2 mM EDTA) with freshly prepared 1 mM PMSF and 10 mM DTT at pH 7.4. The supernatant was incubated with glutathione-agarose beads (Sigma) for 2 h at 4° C. and the beads were washed three times with lysis buffer adjusted to 0.5 M NaCl. Protein lysates from HEK293 cells and rat brain were incubated with GST-S5a-containing agarose beads overnight at 4° C. and washed with lysis buffer adjusted to 300 mM NaCl four times. Then the agarose beads were incubated with 2×SDS sample loading buffer with β-mercaptoethanol at 100° C. for 10 min and samples were subjected to western blotting. For some proteins, such as the Trk neurotrophin receptor and dystrophin, the protein was immunoprecipitated and the immunoprecipitate was blotted with an anti-ubiquitin antibody. Agarose beads and protein A or protein G beads were used as a control for nonspecific pulldown and immunoprecipitation.

Ubiquitin antibody (P4D1), c-Myc antibody (9E10) and Trk antibody (C-14) were from Santa Cruz, calsenilin antibody (75-005) and SH3GRB2L antibody (75-049) were from UC Davis/NINDS/NIMH NeuroMab facility, dystrophin antibody (3B7) and annexin antibody (EH7a) were from Developmental Studies Hybridoma Bank.

Bioinformatic Analysis.

Protein biological processes were analysed and clustered by PANTHER (Thomas et al. *Genome Res* 13, 2129-2141 (2003)) after converting Swiss-Prot accession numbers of identified ubiquitinated proteins into RefSeq protein accession numbers by the Database for Annotation, Visualization and Integrated Discovery (DAVID) (Dennis et al. *Genome Biol* 4, P3 (2003)) online gene ID conversion function. In total, 582 biological processes were found in the database and the category was further grouped into eight classes. Protein subcellular localization of ubiquitinated proteins was extracted from the database provides by PENCE Proteome Analyst (Lu et al., *Bioinformatics* 20, 547-556 (2004)). Note that some proteins have multiple subcellular localizations.

The density plot for the diglycine-modified lysines was calculated as follows: A subset of protein sequence, 10 amino acids on either side of modified lysines, was extracted from the whole protein sequence. The frequency of each of the 20 individual amino acids at each position from −10 to +10 was calculated for diglycine-modified lysines and this value was normalized to the frequency of the same amino acid at the same position using all lysines in the Swiss-Prot database to obtain a relative ratio. If the ratio in one position (say −1) for a specific amino acid (say Pro) is larger than 1, there is a commensurately higher likelihood for Pro at the −1 position to be adjacent to a ubiquitinated lysine. The highest relative ratio detected was 2.1 and the range of the colormap was set from 0 to 2.5. The density plot was prepared by MATLAB.

To access the structural features of ubiquitinated lysine residues for mammalian proteins, we searched crystal structures for all the ubiquitinated proteins in protein database bank (PDB). In total, 24 PDB structures contained lysines that we found are susceptible to ubiquitination (25 modified lysines and 1066 totally lysines). In cases where multiple PDB structures for a single protein are reported, the structure with best quality was used. The secondary structure types for lysines were determined using the program DSSP (Kabsch et al., *Biopolymers* 22, 2577-2637 (1983)). H and G were considered to be helix, E and B to be strand, S, T and others for loop. The fraction of each secondary structure type of modified lysines was compared to that of all the lysine residues in 24 PDB structures. The secondary structures for peptides with two diglycine modified lysines were predicted by PSI-Pred (Jones, *J Mol Biol* 292, 195-202 (1999)) since most of them do not have crystal structures. The disordered region was predicted by DisEMBL (Linding et al. *Structure* 11, 1453-1459 (2003)) for all identified ubiquitinated proteins and the information for modified lysines and all lysines was extracted. The relative solvent accessible area (SAA) for the modified and all lysines in 24 crystal structures was calculated using NACCESS (Hubbard et al. *J Mol Biol* 220, 507-530 (1991)) with a probe of 1.4 Å, which corresponds to the size of a water molecule.

Example 2: Identifying Ubiquitinated Proteins and Ubiquitination Sites

This Example illustrates novel methods for identifying ubiquitinated proteins and ubiquitination sites using an antibody that selectively binds to the diglycine remnant in peptides generated from tryptic digestion of biological samples. Using this immunoaffinity approach coupled to nano LC-MS/MS, more than 300 ubiquitinated proteins and nearly 400 ubiquitination sites were identified. Of these ubiquitinated proteins, 224 have not previously been known to be ubiquitinated. These experiments illustrate that the immunoaffinity profiling methods described herein have broad utility in characterizing the occurrence and extent of ubiquitination in diverse tissues and disease states.

Figure 1B:
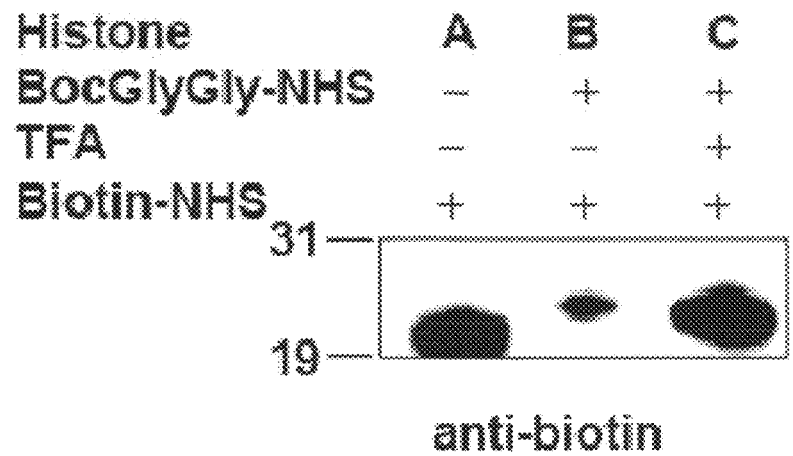

To generate an antibody that recognizes peptides containing the ubiquitin remnant, a protein antigen was prepared that contained one or more diglycine adducts the terminal amine of the side chain of lysines naturally present in the protein. The scheme of this antigen synthesis is shown in FIG. 1A. First, the lysine-rich type III-S histone was reacted with Boc-Gly-Gly-NHS, a reagent that specifically reacts with amines to form an amide-linked Boc-Gly-Gly adduct on amines. Reaction with Boc-Gly-Gly-NHS resulted in modification of nearly all amines in histone which, as detected by the marked inability of the modified protein to become biotinylated by the lysine-modifying reagent biotin-NHS, which was assessed using anti-biotin western blot analysis (FIG. 1B, lane B). The modified protein was treated with trifluoroacetic acid (TFA) to remove the Boc protecting group, which resulted in the adduct being trimmed to the desired Gly-Gly modification on lysine residues (FIG. 1A). Quantitative conversion of the Boc-Gly-Gly adduct, which does not contain an amine, to Gly-Gly, which contains an amine, was confirmed by the ability of the TFA-treated protein to be readily biotinylated by biotin-NHS (FIG. 1B, lane C).

The diglycine-modified histone was injected into rabbits to generate immune serum. The rabbits were bled and antisera were collected at four, eight, and ten weeks after immunization. The titer of the antibody was shown in Table 1.

Figure 1C:
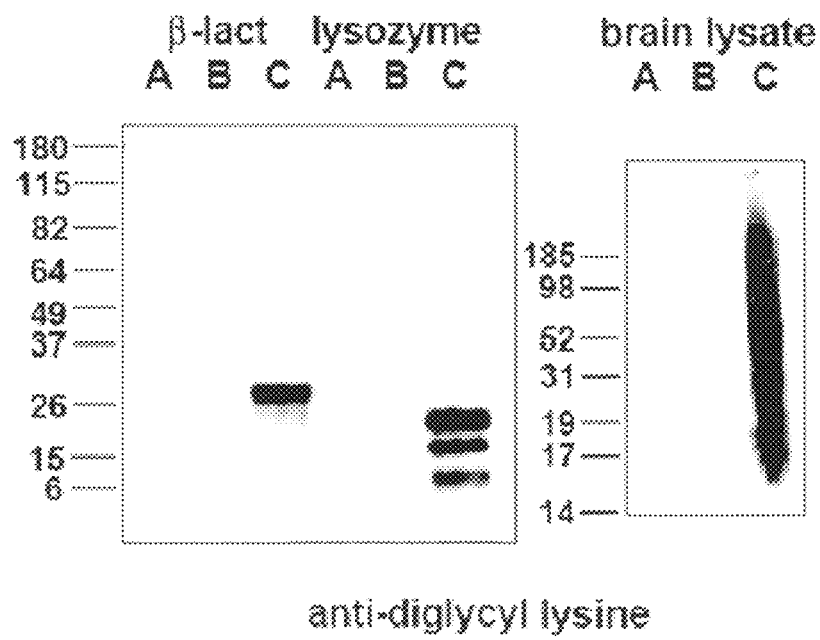

Gly-Gly-modified lysines). A western blot of three samples against the diglycl-lysine antibody, FIG. 1C, showed that the antibody has high specificity, which can selectively recognize diglycine modified lysines. The rat brain lysate result shown in FIG. 1C also indicated that the antibody affinity does not depend on backbone amino acid sequences since it can recognize various proteins in the tissue.

Figure 9A:
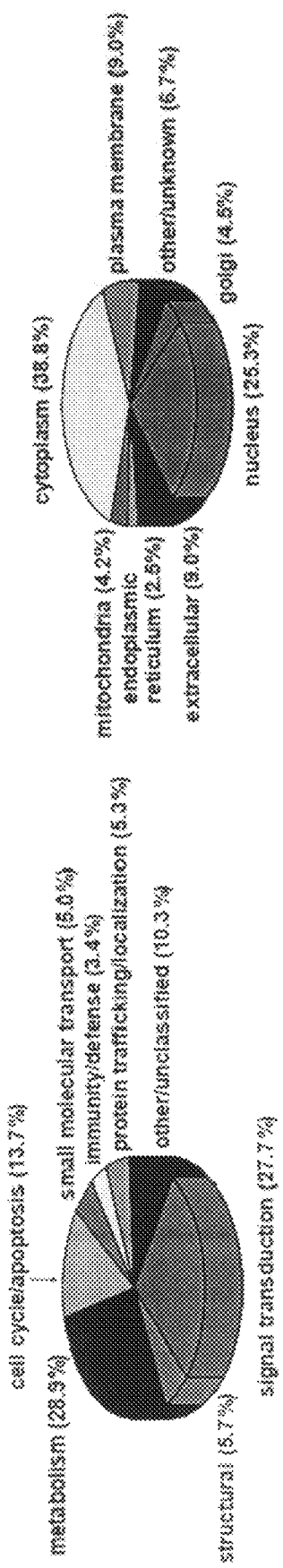
FIG. 9A-C illustrates the specificity of the anti-Gly-Gly-Lysine antibodies described herein. This figure shows a Western blot analysis of the specificity of anti-GG monoclonal antibody (clone 42) for Gly-Gly modified lysines from beta-lactoglobulin (FIG. 9A), bovine serum albumin (BSA, FIG. 9B) and rat brain lysate (RBL, FIG. 9C). The antibody specifically recognizes proteins with Gly-Gly modified lysines and does not interact with unmodified and Boc-Gly-Gly modified proteins. Lane 1 for each of FIG. 9A-C: intact proteins; lane 2 for each of FIG. 9A-C: Boc-Gly-Gly-modified proteins; lane 3 for each of FIG. 9A-C: Gly-Gly-modified proteins.
Figures 9A, 9B, 9C:
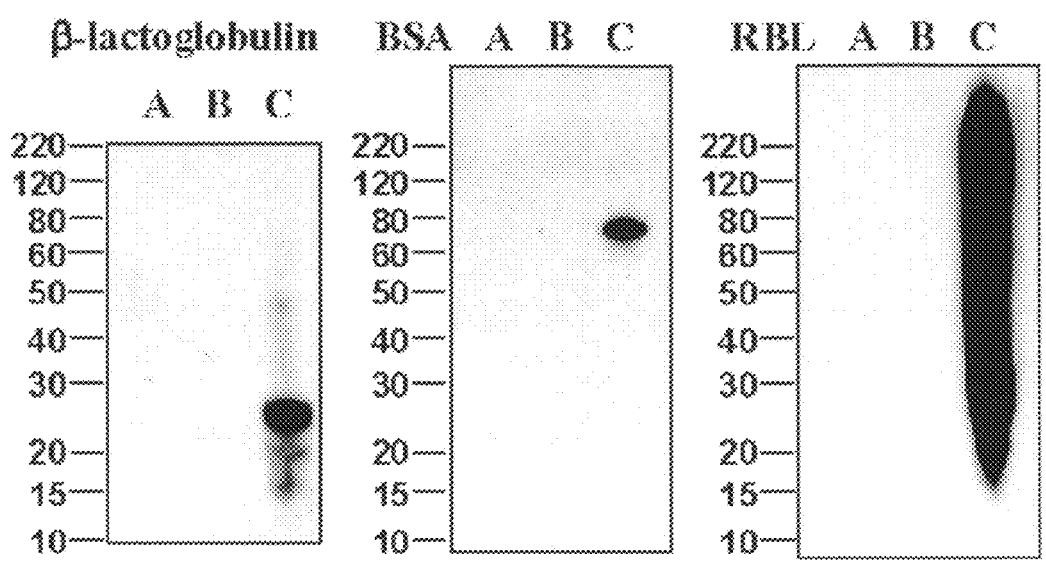
Figure 10A:
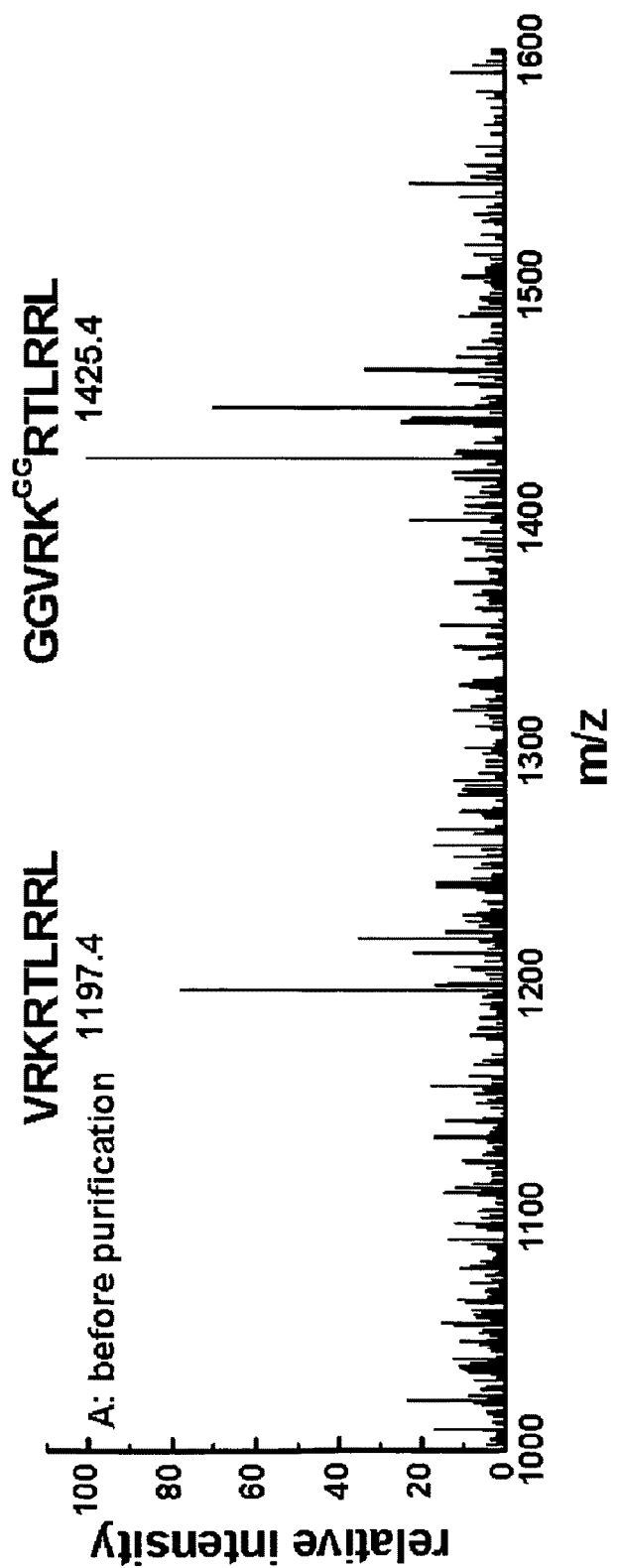
FIGS. 10A and 10B shows enrichment of a diglycine modified peptide (GlyGly modified PKC substrate 2) with the anti-GG monoclonal antibody (clone 49) from a 1:1 mixture of modified and unmodified peptides.
Figure 10B:
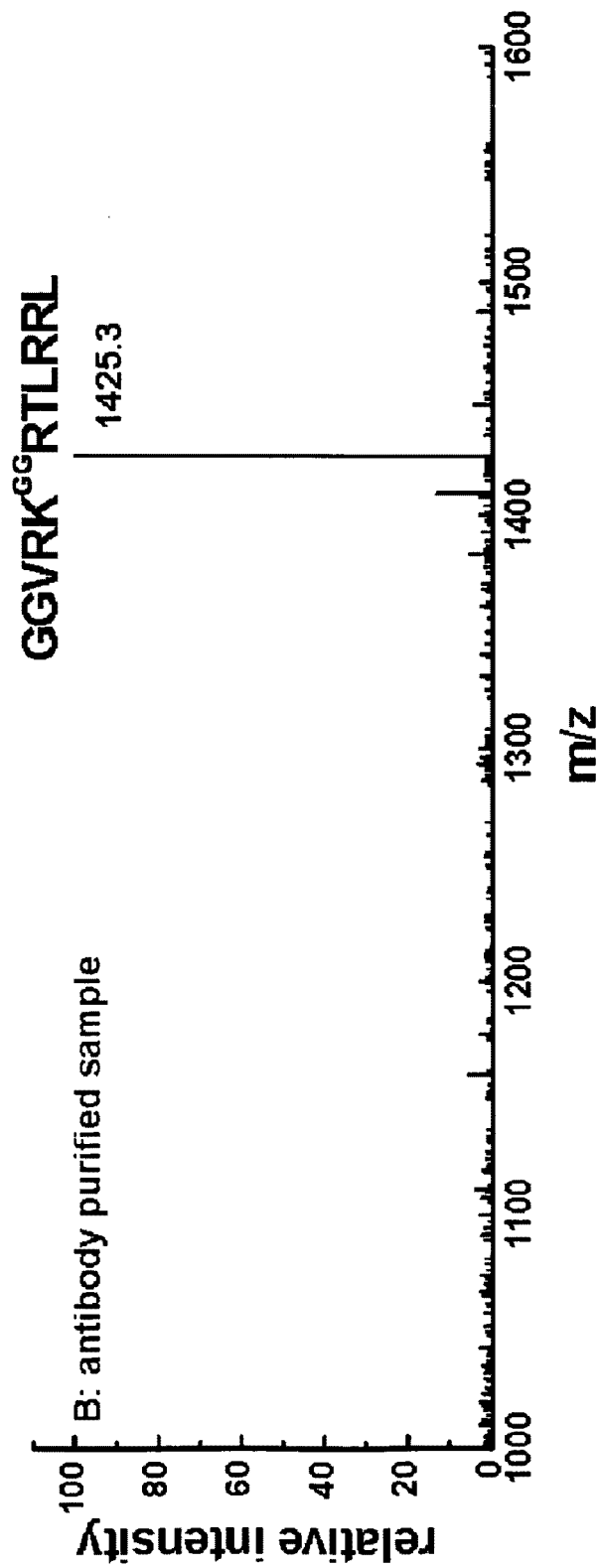
Figure 11A:
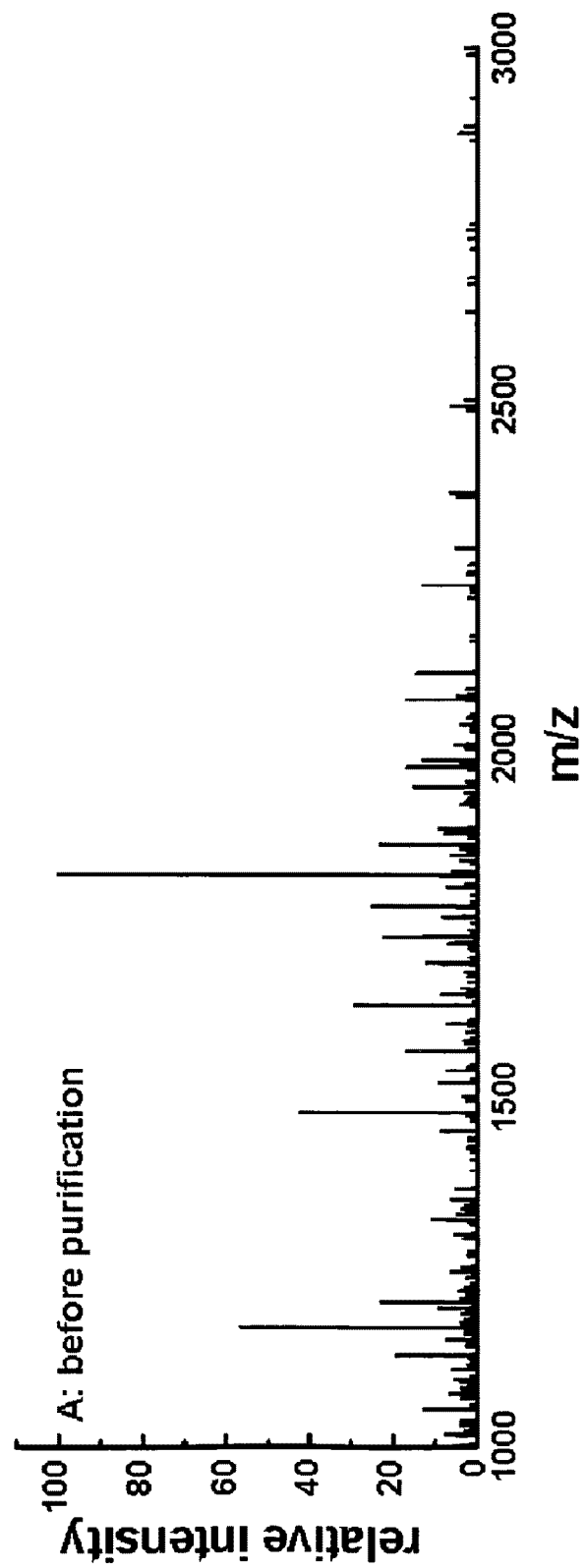
FIGS. 11A, 11B and 11C show isolation of a double diglycine modified peptide with monoclonal anti-GG antibody (clone 49) from a bovine serum albumin (BSA) digest.
Figure 11B:
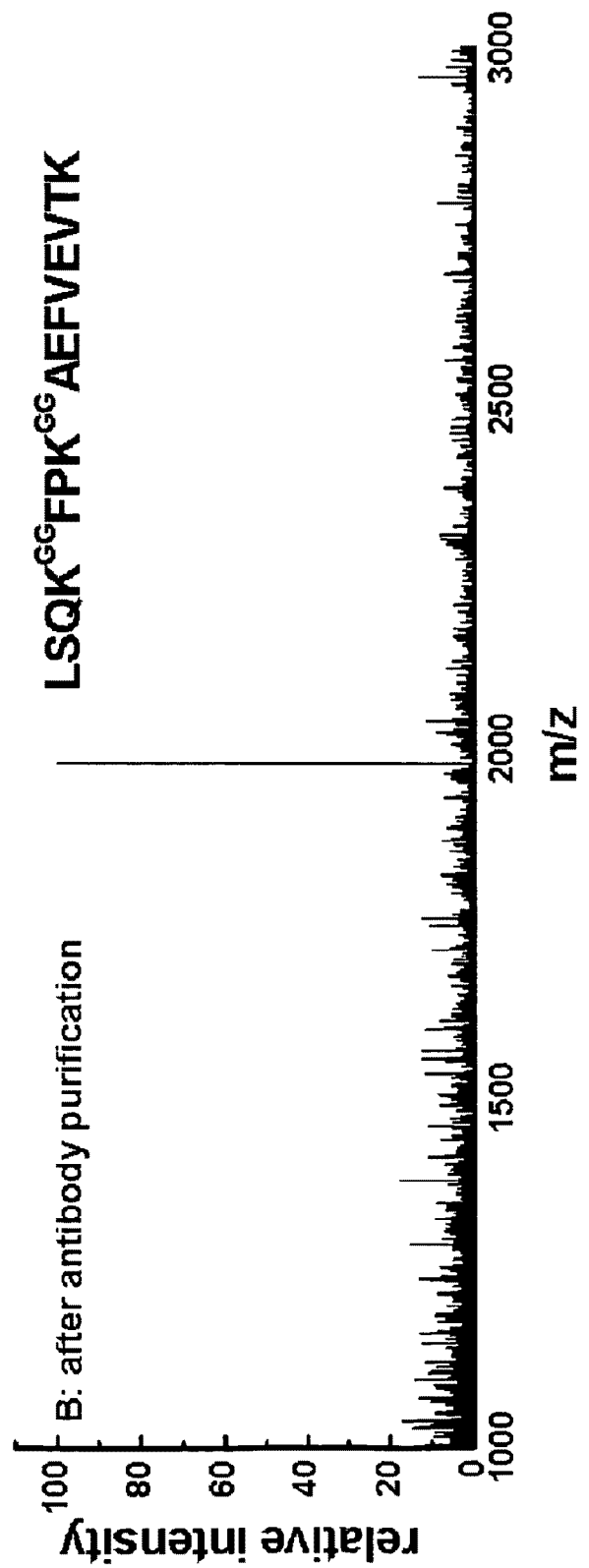
Figure 11C:
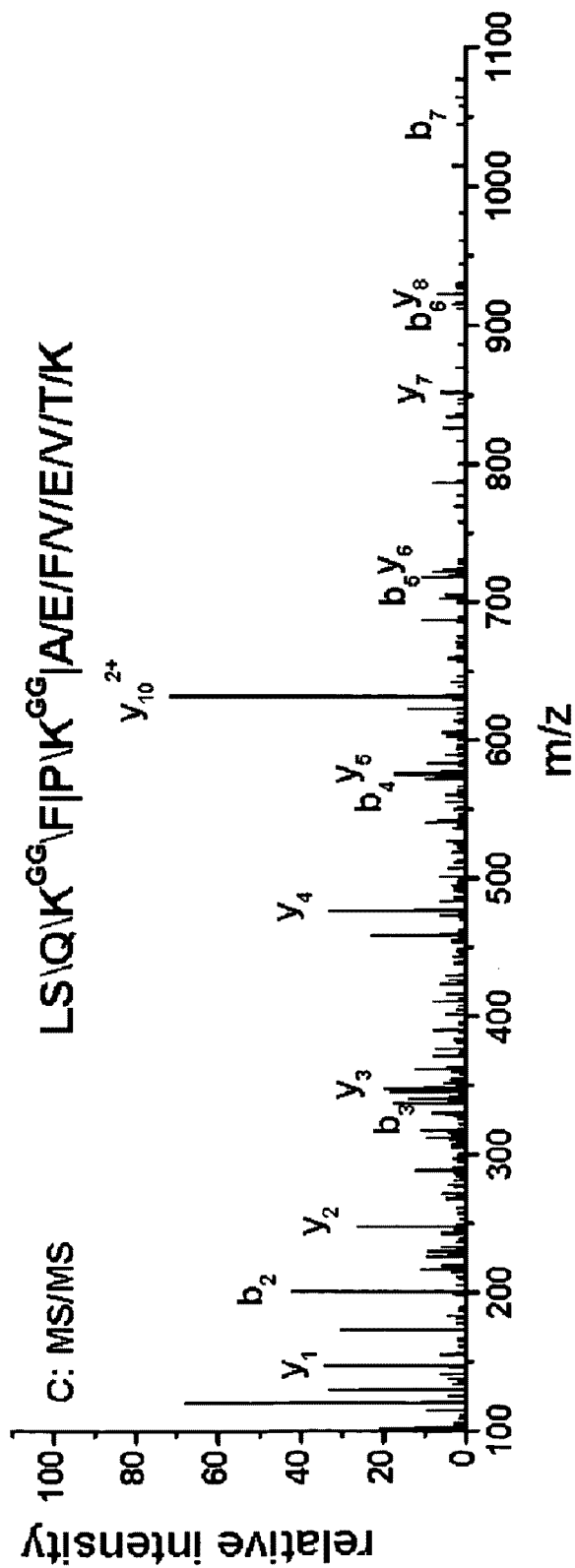

In addition, this antigen was used to immunize mice to develop B-cells producing antibody to the diglycine residue. B cells with this property were then hybridized to mouse myeloma cells to make hybridomas producing monoclonal antibodies in methods well known in the art. Hybridoma clones 41, 42, 45, 49 and 50 were developed which produced effective anti-diglycine monoclonals as shown in FIGS. 9-11. FIG. 9 shows that the antibody from clone 42 specifically recognizes proteins with Gly-Gly modified lysines and does not interact with unmodified and Boc-Gly-Gly modified proteins. FIG. 10 demonstrates that the anti-GG monoclonal antibody from clone 49 simplifies analysis of ubiquitination sites in a simple peptide mixture and FIG. 11 shows that this anti-GG monoclonal antibody simplifies analysis of ubiquitination sites in a complex peptide mixture.

Figure 2A:
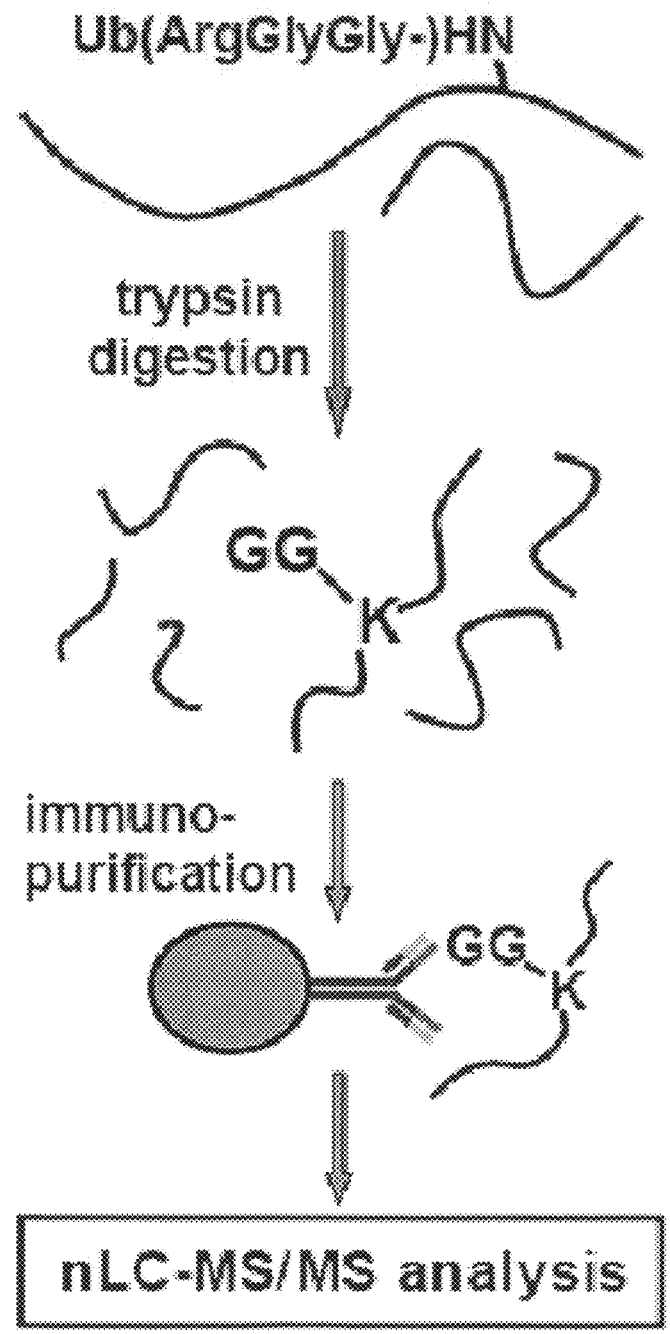

Next the anti-diglycl-lysine antibody was used to immunoprecipitate diglycine-modified peptides from a peptide mixture. A flow chart for sample preparation, immunoprecipitation, and MS/MS analysis is shown in (FIG. 2A). To test the ability of the antibody to recover diglycine-modified peptides, diglycine-modified proteins and immunoprecipitated diglycine-modified tryptic peptides were reacted with

TABLE 1

Titers of antibody collected at different times (weeks) and dilutions.

| | Dilution | | | | | | | | | |
|---|---|---|---|---|---|---|---|---|---|---|
| | 50 | 100 | 200 | 400 | 800 | 1600 | 3200 | 6400 | 12800 | 25600 |
| 0 wks | 0.0603 | 0.3471 | 0.2211 | 0.1371 | 0.1074 | 0.0957 | 0.0675 | 0.0662 | 0.0618 | 0.0927 |
| 4 wks | 0.6067 | 0.4718 | 0.3828 | 0.2218 | 0.1358 | 0.0995 | 0.0863 | 0.0665 | 0.0687 | 0.0594 |
| 8 wks | 1.6441 | 1.0971 | 0.5834 | 0.2892 | 0.1986 | 0.1321 | 0.0913 | 0.0708 | 0.0705 | 0.0612 |
| 10 wks | 2.5281 | 1.9679 | 1.0901 | 0.7851 | 0.4781 | 0.4533 | 0.1524 | 0.1097 | 0.0794 | 0.0682 |

Antibodies purified from immune serum exhibited pronounced specificity for peptides containing the diglycine modification on ϵ-amine of lysines. The antibodies failed to interact with unmodified lysozyme, which contains two separate internal Gly-Gly sequences, and lactoglobulin (FIG. 1C, left panel, lane A), or the corresponding proteins modified with Boc-Gly-Gly (FIG. 1C, left panel, lane B), but showed strong reactivity with proteins that contained the Gly-Gly modification (FIG. 1C, left panel, lane C). These results indicate that the antibody recognizes diglycine-modified amines. Similarly, the antibody exhibited negligible reactivity with rat brain lysate (FIG. 1C, right panel, lane A), and with rat brain lysate modified with Boc-Gly-Gly (FIG. 1C, right panel, lane B). However, the antibody exhibited significant reactivity with Gly-Gly-modified proteins from rat brain lysate (FIG. 1C, right panel, lane C). The absence of reactivity of the antibody with unmodified rat brain lysate demonstrates the high degree of specificity of the antibody for proteins that contain the ubiquitin remnant.

Figure 2B:
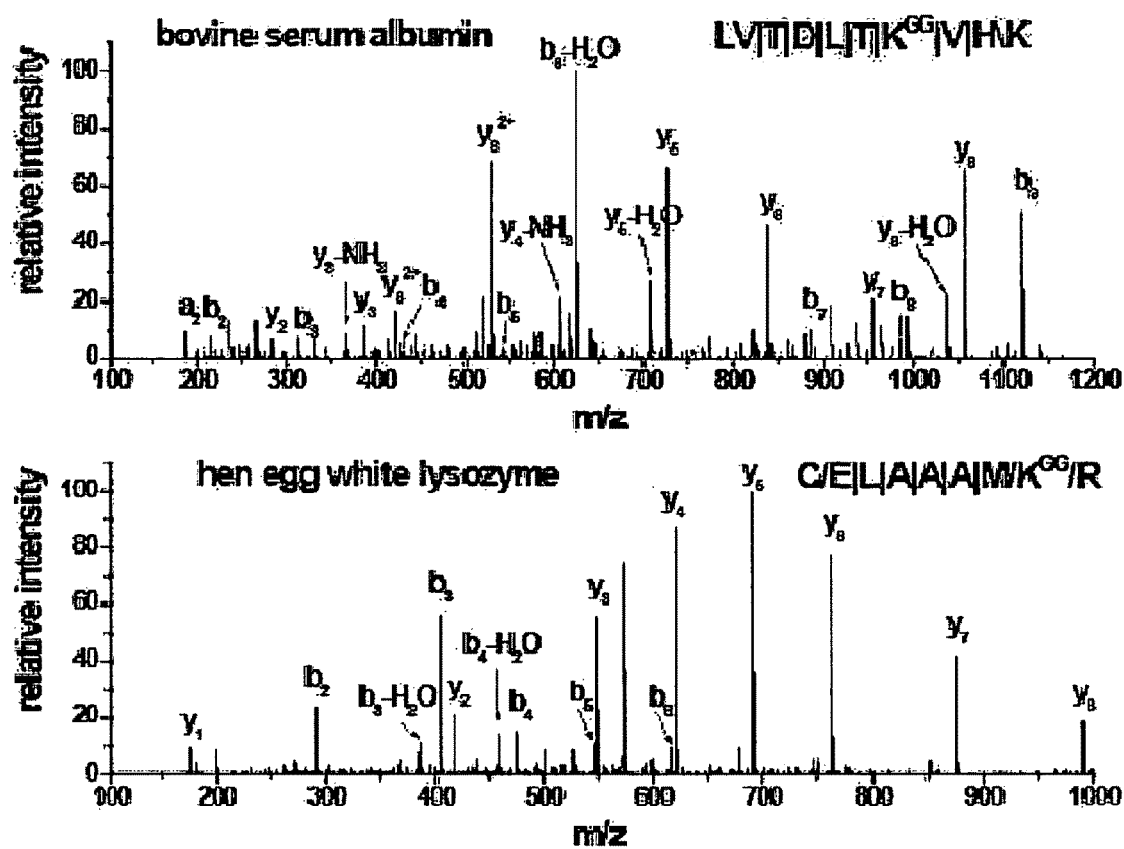

The crude antibody was purified by Melon gel IgG purification kit (Pierce) according to the manufacturer's protocol and evaluated using histone and rat brain lysate with or without modified lysines (sample A: with intact lysines; B: with Boc-Gly-Gly-modified lysines; C: with the anti-diglycyl-lysine antibody. BSA and lysozyme were partially modified with Boc-Gly-Gly-NHS as above, treated with TFA to liberate the Boc moiety, and then trypsinized. While immunoprecipitation with preimmune serum failed to immunoprecipitate peptides, immunoprecipitation with the immune serum recovered peptides from both diglycine-modified BSA and diglycine-modified lysozyme (FIG. 2B). Thus, the antibody is capable of enriching peptides containing diglycine-modified lysines.

The diversity of lysine ubiquitination was then assessed in tissue culture cells and animal tissues. Lysates were prepared from human embryonic kidney cells (HEK293), mouse endothelioma cells (sEnd.1), and rat brain and liver. To increase the types of ubiquitinated proteins analysed, crude lysates, as well as subcellular fractions, including nuclear, mitochondrial, and in some cases, synaptosomal fractions were prepared for analysis (see Example 1). Lysates were digested with trypsin and diglycine-modified peptides were immunopurified and subjected to LC-MS/MS followed by database searching and spectral validation (for examples see FIG. 2C). A full list of ubiquitinated peptides with ubiquitination sites, fragmentation map, score, charge states, corresponding Swiss-Prot accession number, protein name, whether the protein has been previously found to be ubiquitinated, and tissue of origin is provided in FIG. 22.

The majority of ubiquitin remnant-containing peptides have three charges, in part because the Gly-Gly adduct has its own N-terminal amine. Diglycine-modified lysines were detected both within the peptide sequence as well as at the N- and C-termini of peptides (FIG. 1). The presence of C-terminal diglycine-modified lysines indicates that trypsin can cleave at the carboxyl side of this lysine adduct, consistent with a recent report (Denis et al. *Proteomics* 7, 868-874 (2007). Most peptides contained a single diglycine-modified lysine, although 51 peptides did contain two diglycine-modified lysines.

Figures 2C, 2D:
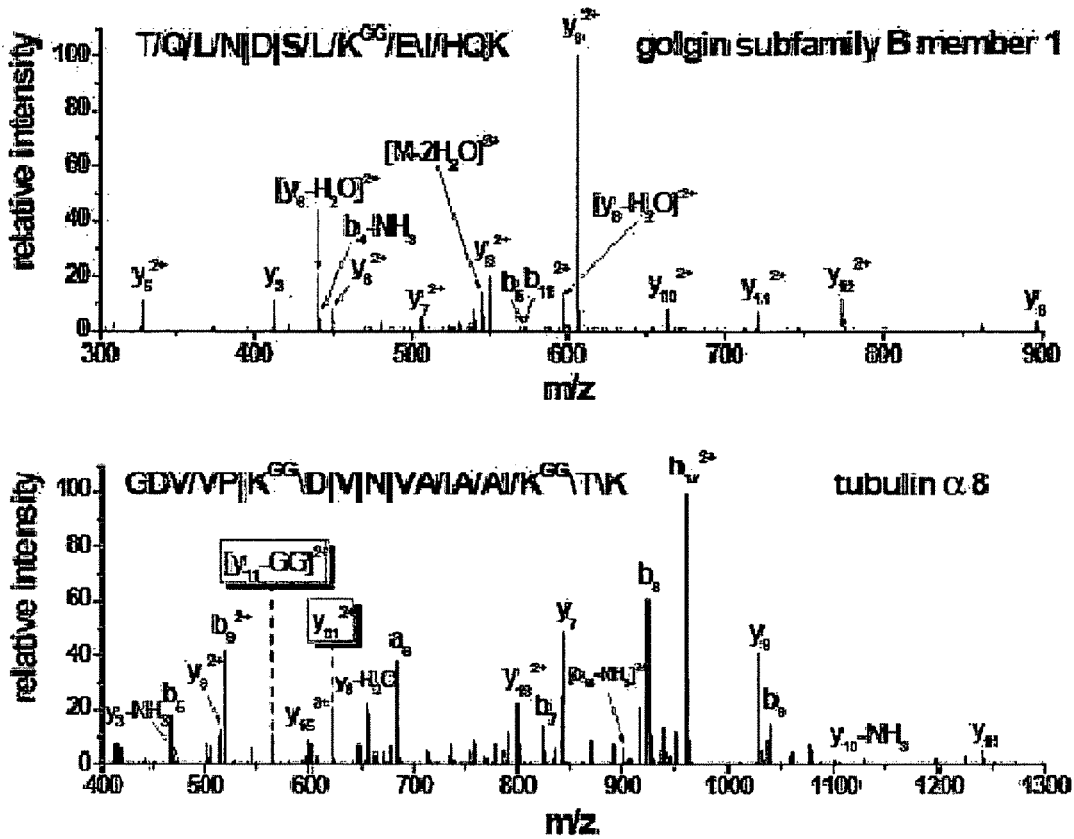

The presence of diglycine-modified lysines was detected in the MS/MS spectra by the presence of fragmentation ions separated by the m/z corresponding to diglycine-modified lysine. However, in some MS/MS spectra, ions consistent with the loss of Gly-Gly or Gly fragments were detected, and in some cases, both the peptide ions with and without this loss were detected, thus providing further confirmation for the presence of a diglycine adduct in these peptides. For example, the loss of a Gly-Gly fragment in a diglycine-containing tubulin peptide ion is indicated by a pair of MS/MS fragments (FIG. 2C). Only 32.3% of peptides derived from tissue lysates, and 22% of diglycine-modified peptides from synthetically Gly-Gly-modified lysozyme and BSA exhibited loss of Gly-Gly or Gly. Because this loss is not universal for ubiquitinated peptides, a finding which has been observed previously (Warren et al., *Rapid Commun Mass Spectrom* 19, 429-437 (2005)), this feature cannot be regarded as a fingerprint for diglycine-modified peptides.

The ubiquitinated proteins and peptides identified in human and mouse tissue culture cells, as well as rat tissues, are summarized in FIG. 2D. In total, over 300 ubiquitinated proteins and peptides were identified through our experiments, of which 224 (68%) have not previously been known to be ubiquitinated. Among the identified proteins, 268 proteins have one ubiquitination site, 61 have two, and two proteins have three or more ubiquitination sites. Although the other ubiquitin-like proteins that appear to be conjugated to large numbers of proteins, such as SUMO and ISG15, have an amino acid sequence that would not result in a diglycine adduct on lysines after trypsin digestion (Pedrioli et al. *Nat Methods* 3, 533-539 (2006); Denison et al., *Curr Opin Chem Biol* 9, 69-75 (2005)) it is important to validate that proteins found to contain a diglycine modification are indeed ubiquitinated under physiological conditions. Therefore, a subset of the identified proteins was selected and assessed to confirm that the proteins were ubiquitinated as determined by MS/MS spectra by another technique—immunoprecipitation or pull-down procedures.

In pull-down experiments, the GST-S5a was used to enrich for polyubiquitinated proteins. GST-S5a is a polyubiquitin-binding protein derived from the proteasome (Wang et al. *J Mol Biol* 348, 727-739 (2005)). The anti-Gly-Gly-Lys antibodies were used for immunoprecipitation experiments to precipitate proteins containing these epitopes. The ubiquitin adducts were then detected on a western blot using an anti-ubiquitin antibody.

In both these experiments, high molecular weight species were readily detected that were specifically associated with GST-S5a pull-down or immunoprecipitates, however the control samples did not exhibit bands indicative of such ubiquitinated proteins (FIG. 2E).

1e;2qThe ubiquitination targets include disease-related proteins, such as huntingtin, dystrophin, apolipoprotein B-100, superoxide dismutase, tuberin, and Rho-associated protein kinase (some spectra are shown in FIG. 5. The different proteins identified by ubiquitin remnant immunoaffinity profiling have roles in a wide range of biological processes, of which the largest number are involved in signal transduction and metabolism (FIG. 3A, left panel). Additionally, proteins were found that have roles in cell cycle/apoptosis, the immune system, protein trafficking/localization, and small molecule transport, consistent with previously reported roles for ubiquitination (Kirkpatrick et al., *Nat Cell Biol* 7, 750-757 (2005); Bonifacino & Weissman, *Annu Rev Cell Dev Biol* 14, 19-57 (1998); Rechsteiner, *Annu Rev Cell Biol* 3, 1-30 (1987); Nandi et al., *J Biosci* 31, 137-155 (2006); Mukhopadhyay & Riezman, *Science* 315, 201-205 (2007); Sun & Chen, *Curr Opin Cell Biol* 16, 119-126 (2004); Pickart, *Mol Cell* 8, 499-504 (2001)). Interestingly, some proteins identified are involved in processes that have not previously been linked to ubiquitination. For example several proteins linked to protein translation, including 40S ribosomal subunits S23, S5, and the 60S subunit L27a, were identified. This suggests that the stability or function of the ribosome is regulated by ubiquitination. Several mitochondrially-localized metabolic enzymes, including 3-hydroxyisobutyrate dehydrogenase, pyruvate dehydrogenase complex E2 subunit, succinyl-CoA ligase, isocitrate dehydrogenase, and ornithine aminotransferase were found to be ubiquitinated, suggesting a role for ubiquitination and the cognate E3 ubiquitin ligases in regulating mitochondrial metabolic function. Some of the proteins found to be ubiquitinated extend recent findings regarding the role of ubiquitination in certain cellular processes. For example, while histone H2 ubiquitination has been described (Wang et al. *Nature* 431, 873-878 (2004); Nickel & Davie, *Biochemistry* 28, 964-968 (1989)), the inventors find that histone H3 and H1 isoforms are also ubiquitinated, as well as histone acetyltransferases, supporting the idea that ubiquitin contributes to epigenetic gene regulation through multiple pathways. Several cellular effects mediated by molecular motors are affected by ubiquitination (Gordon & Roof, *Proc Natl Acad Sci USA* 98, 12515-12520 (2001)) indeed, the results identify specific kinesin and myosin isoforms and subunits that may mediate these effects. These studies also identify numerous transcription factors and kinases that are targets for ubiquitination, supporting the well-characterized role for ubiquitination in regulating signal transduction in cells.

The subcellular distribution of the detected proteins is likely to reflect, in part, the subcellular fractions that were used for MS/MS analysis. Subcellular localization analysis of the identified proteins using PENCE Proteome Analyst (Lu et al., *Bioinformatics* 20, 547-556 (2004)) indicates that most ubiquitinated proteins are cytosolic and nuclear proteins (FIG. 3A, right panel), which is consistent with the general observation that ubiquitin is primarily in intracellular protein (Bonifacino & Weissman, *Annu Rev Cell Dev Biol* 14, 19-57 (1998)). However, nine of the identified ubiquitinated proteins are located in endoplasmic reticulum, including apolipoprotein B-100. In some cases secreted proteins have been found to be ubiquitinated (Lu et al., *Endocrinology* 147, 5611-5623 (2006); Meerovitch et al., *J Biol Chem* 272, 6706-6713 (1997)) while in other cases, such as with apolipoprotein B-100, proteins can be retrogradely exported from the endoplasmic reticulum to the cytosol, where they are ubiquitinated and degraded (Liao et al., *J Cell Biochem* 89, 1019-1029 (2003)) and may reflect a mechanism to degrade proteins that misfold while in the ER (Galan et al., *FASEB J* 12, 315-323 (1998); Plemper & Wolf, *Mol Biol Rep* 26, 125-130 (1999).

Figure 3B:
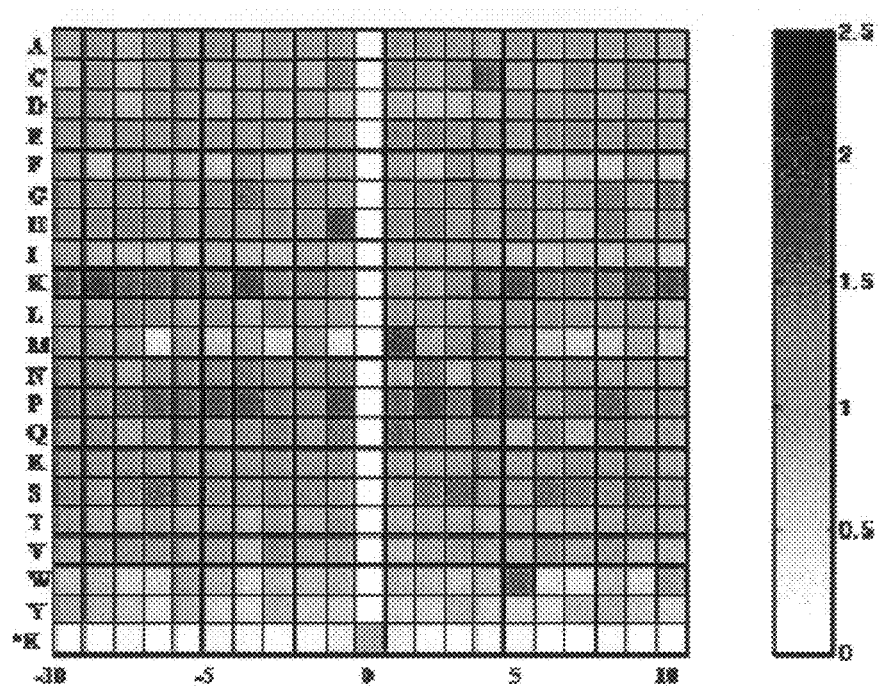
Figure 3C:
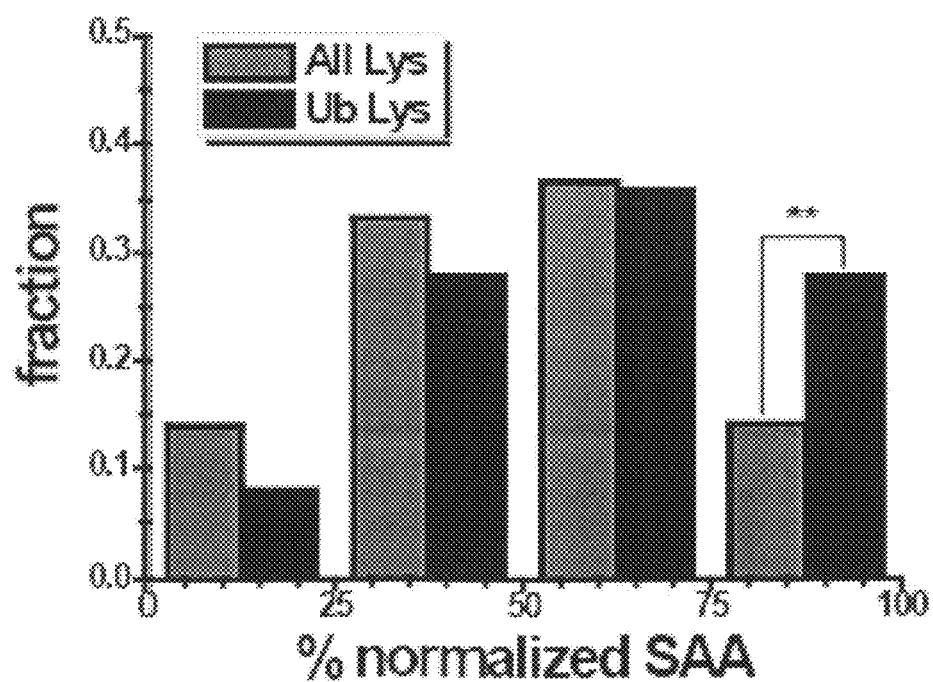
Figure 6A:
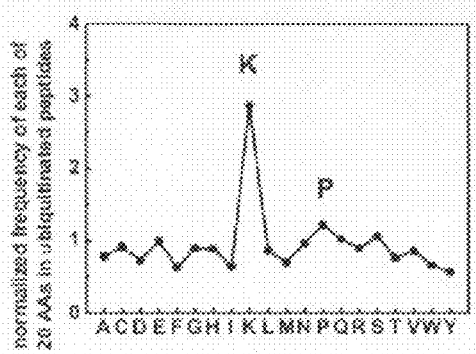
FIG. 6A-C illustrates the frequency of each of the 20 amino acids in the sequences near ubiquitinated lysines in protein sequences obtained from the Swiss-Prot database.
Figure 6C:
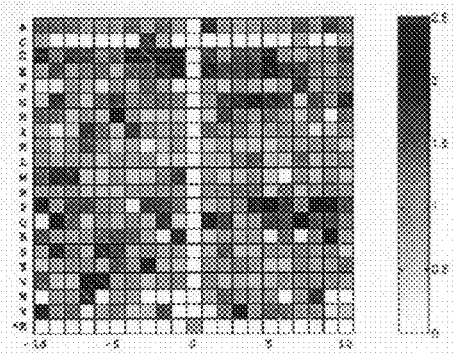
Figure 6B:
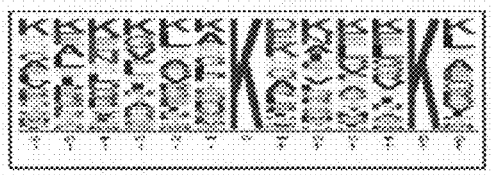
Figure 6B:
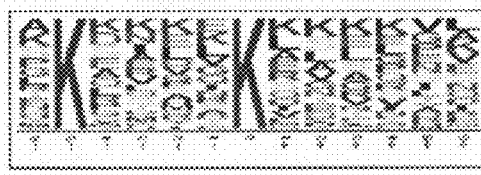
Figure 6B:
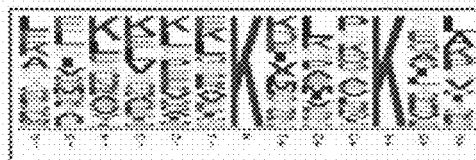
Figure 6B:
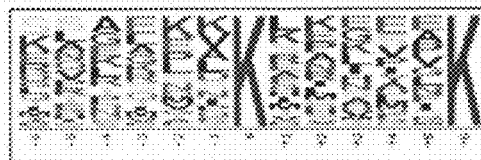
Figure 6B:
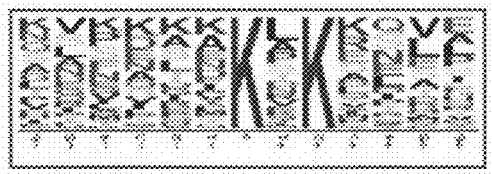
Figure 6B:
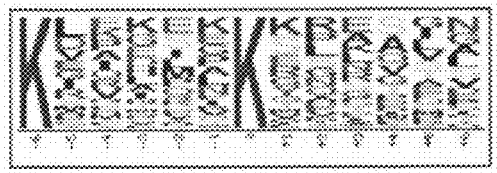
Figure 6B:
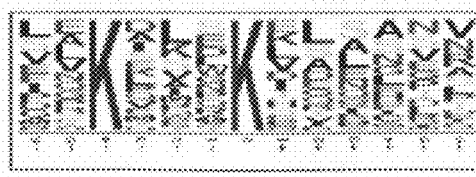
Figure 6B:
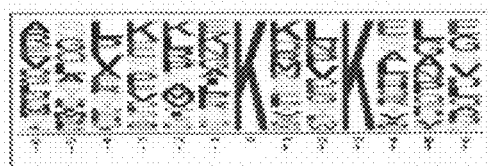

Next, the large number of ubiquitinated proteins was used to gain insight into how lysine ubiquitination might be regulated at the level of primary and secondary structure. Interestingly, we noticed that ubiquitin remnant-modified lysines tended to be localized in lysine-rich regions of proteins. Examination of the amino acid sequences surrounding the modified lysine revealed that 9.6% of the residues within a six amino acid span on either side are lysines, which is almost three times the expected abundance of lysine residues (3.3%) within a six amino acid span on either side of all lysines based on an analysis of all the proteins in the Swiss-Prot database (FIG. 6A). Consensus ubiquitination site analysis using Motif-x (Schwartz & Gygi, *Nat Biotechnol* 23, 1391-1398 (2005)) indicated that adjacent lysines were a common feature of possible motifs (FIG. 6B). The presence of multiple lysines may facilitate ubiquitination by providing multiple alternate adjacent ubiquitin acceptor sites at a specific area in a protein. To compare all 20 amino acids for their propensity to be adjacent to ubiquitinated lysines, a density map was prepared indicating the frequency of each amino acid, at any of the ten proximal positions on either side of the ubiquitinated lysines, compared to the frequency of that amino acid next to lysines in general, as assessed by surveying the Swiss-Prot database. This analysis indicates that other lysines are present near the ubiquitinated lysine residues. However, Cys, His, Met, and Pro, were also found to be slightly enriched at certain positions, although not to the same extent as lysine residues (FIG. 3B). In comparison, the inventors have found that for the recently identified ubiquitinated proteins in yeast, Asp, Glu, His and Pro are highly enriched (>2.3 times the expected value) at some positions (FIG. 6C).

Figure 7A:
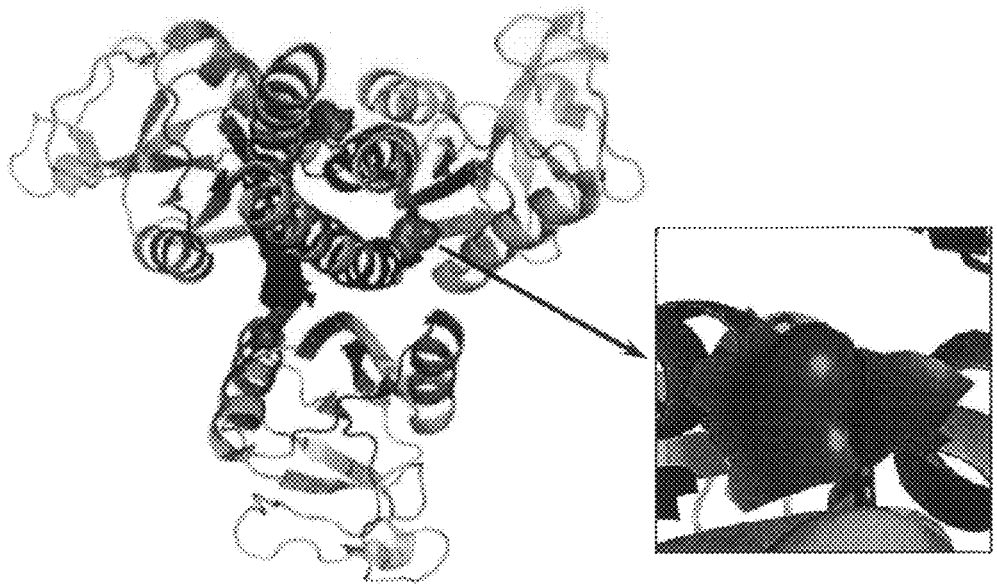
FIG. 7A-B provides examples of solvent exposed and buried ubiquitinated lysines.
Figure 7B:
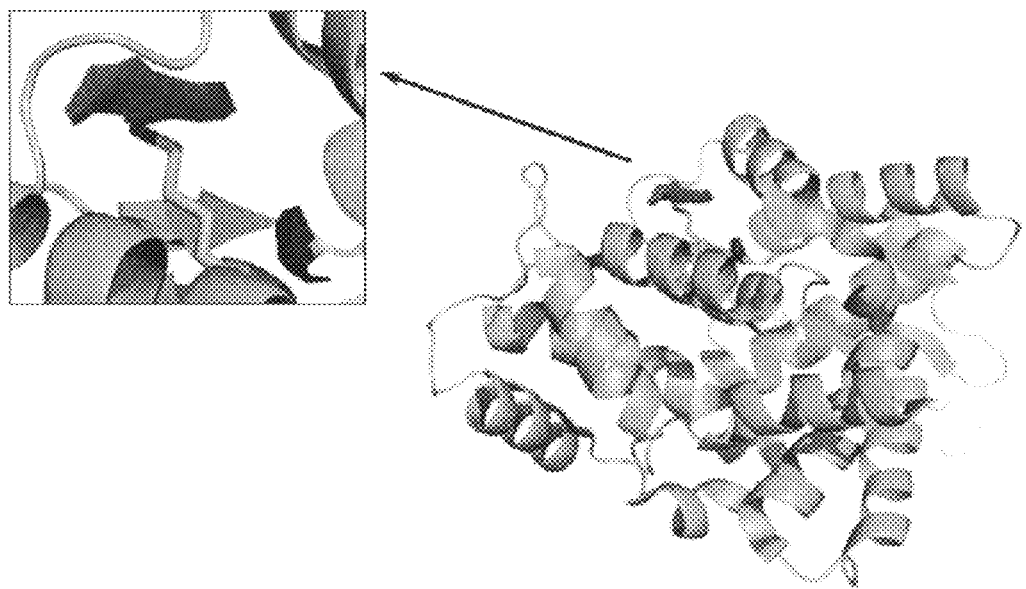

The inventors found that ubiquitinated lysines tend to appear on protein surfaces in preferred structural contexts. For 24 of the proteins identified in this study, structural information was present in Protein Data Bank (PDB), allowing the exposure of lysine residues to solvent to be measured. Measurements of the solvent accessible area of lysine residues in these proteins indicate that ubiquitinated lysines tend to be more solvent exposed than other lysines (FIG. 6C). If lysines with more than 25% surface exposed are considered solvent exposed residues, 92% (23/25) of the ubiquitinated lysines are exposed, which is higher than that of all lysines (85%). This is in agreement with a ubiquitination site survey for yeast proteins (Catic et al., *Bioinformatics* 20, 3302-3307 (2004)). Interestingly, in some cases, the ubiquitinated lysine is fully buried (for example, see FIG. 7). In these proteins, ubiquitination may be regulated by stimuli that induce the exposure of the lysine to the surface.

Figure 3D:
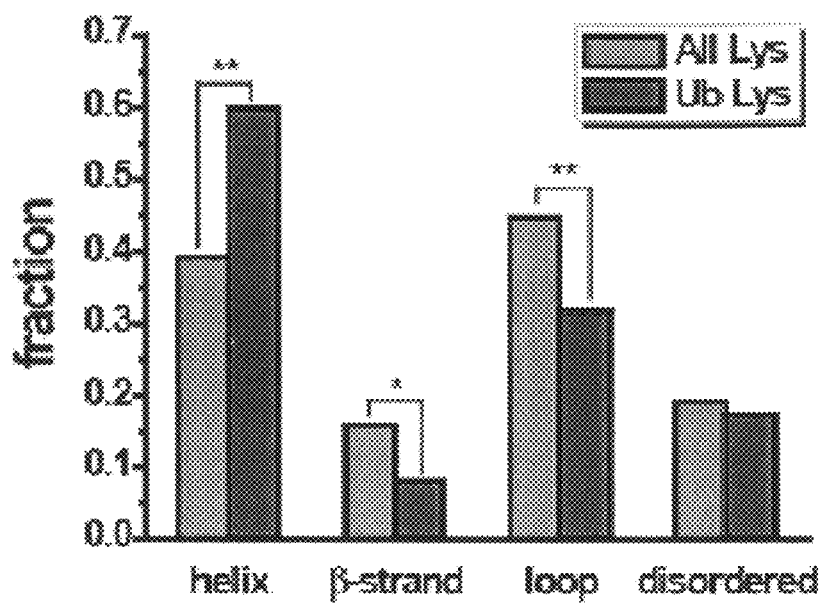
Figure 4:
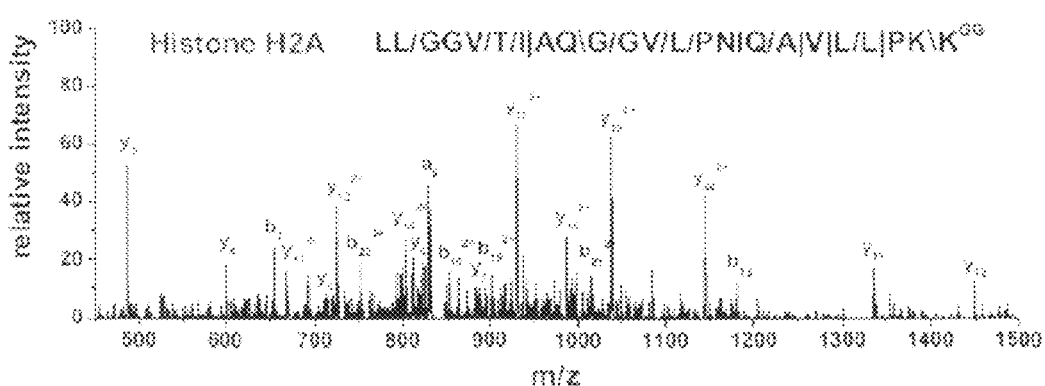
FIG. 4 shows a MS/MS spectrum of a ubiquitinated peptide from Histone H2A, which has a diglycine-modified lysine at C-terminus of the peptide (Lys 120). The results illustrate that Lys 120 in Histone H2A is ubiquitinated. See also, Wang et al., *J Mol Biol* 348, 727-739 (2005); Nickel & Davie, *Biochemistry* 28, 964-968 (1989). Note that in the Swiss-prot database, the histone H2A sequence has a preceding methionine but this methionine was not included in the sequence used in Wang et al. (2005) and therefore the ubiquitinated lysine in that paper is numbered as 119. The presence of C-terminal lysines containing the diglycine modification in some peptides such as the one from Histone H2A, indicates that trypsin can cleave peptides after this modification, albeit less efficiently than after lysines or arginines, presumably because the presence of a positive charge on the amino group of Gly-Gly allows this modified residue to interact with trypsin in a manner similar to the epsilon-amine of lysine.
Figure 5A:
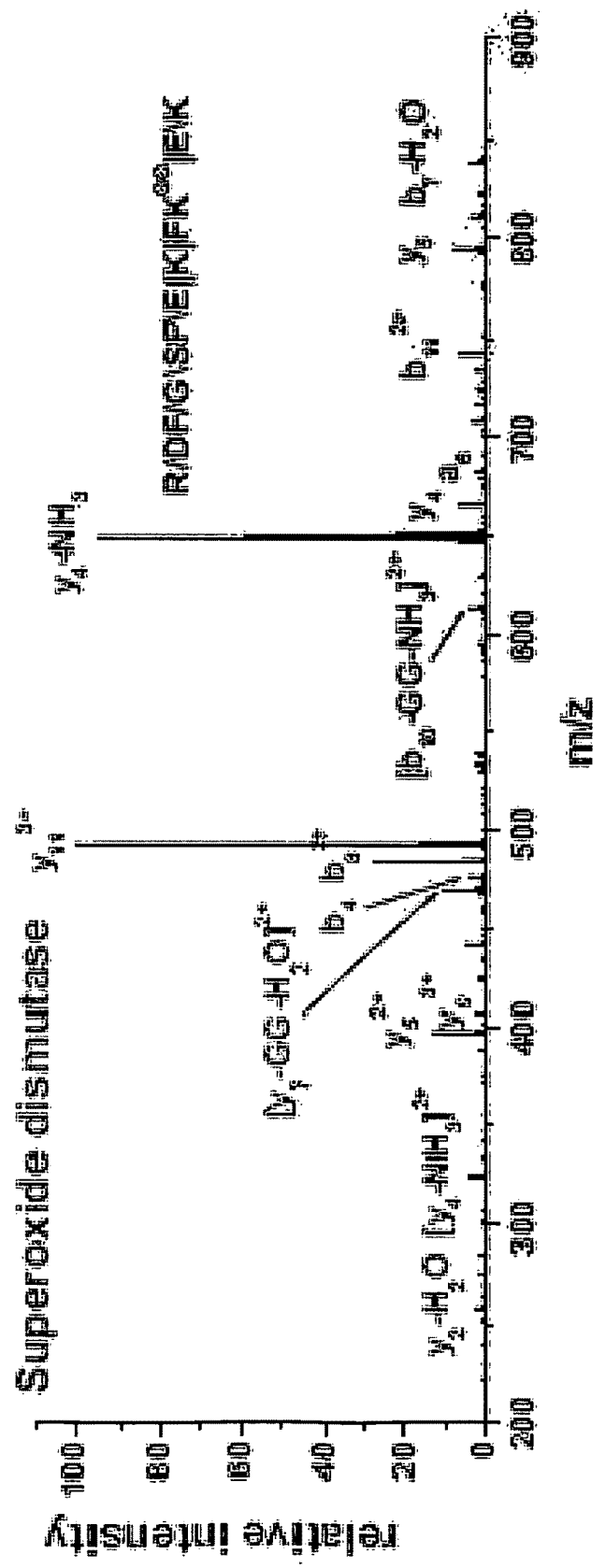
FIG. 5A-D shows representative MS/MS spectra of ubiquitinated peptides from disease-related proteins identified using the methods and antibodies described herein.
Figure 5B:
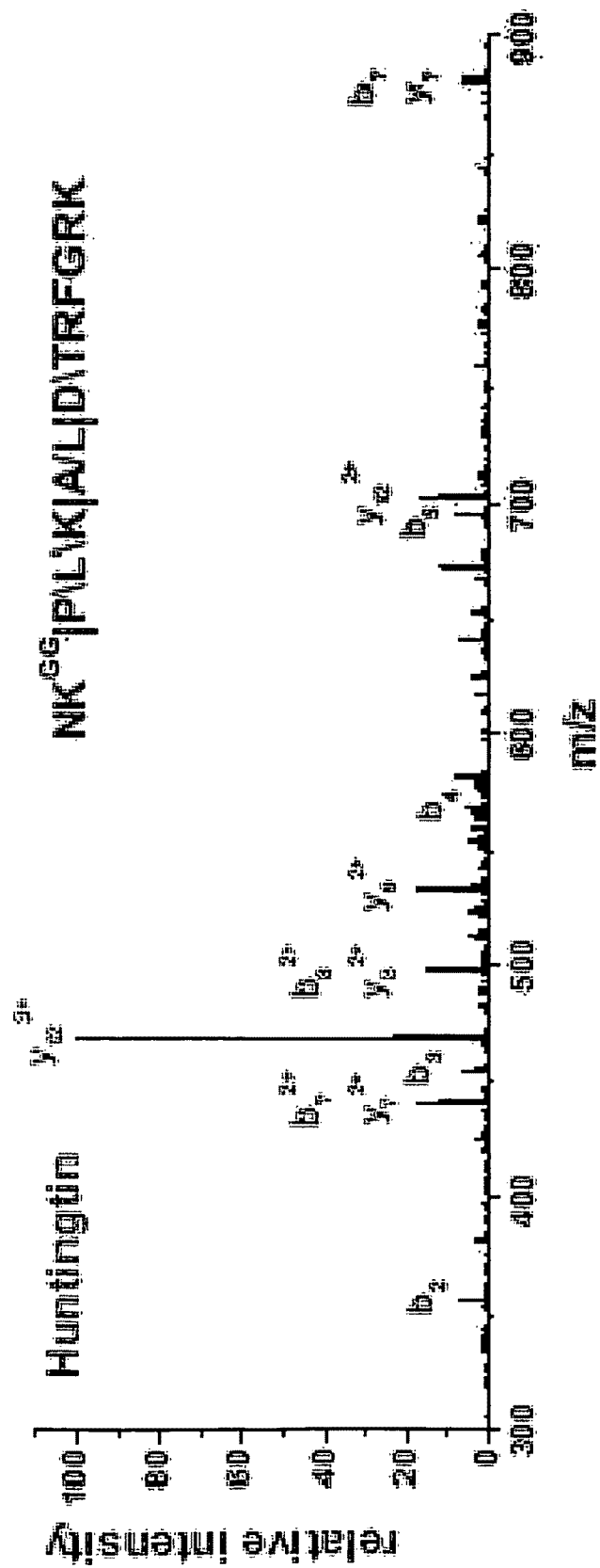
Figure 5C:
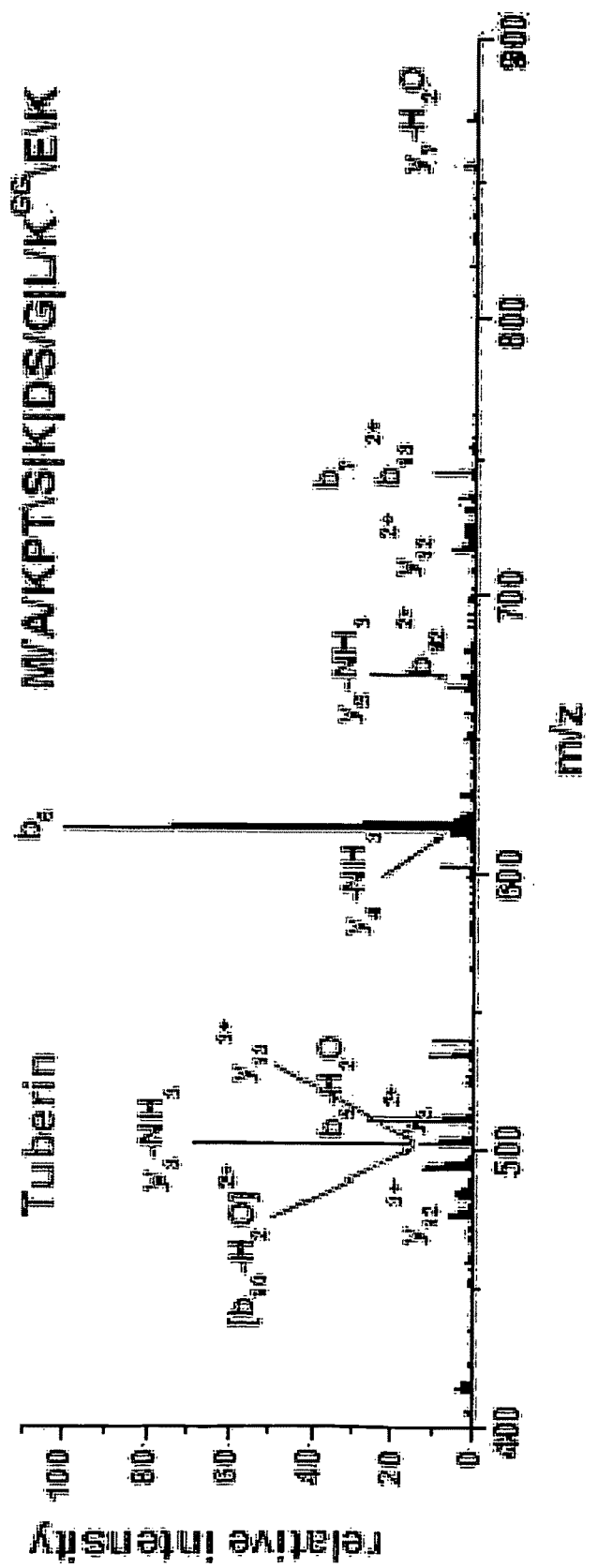
Figure 5D:
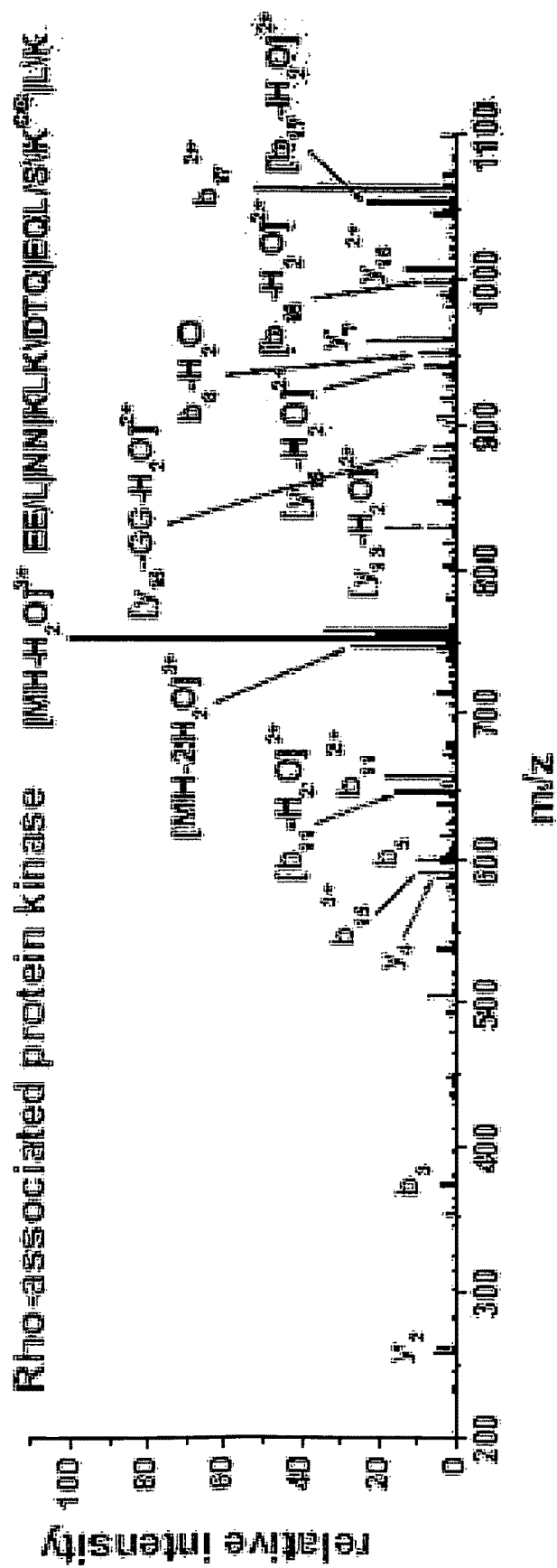
Figure 8A:
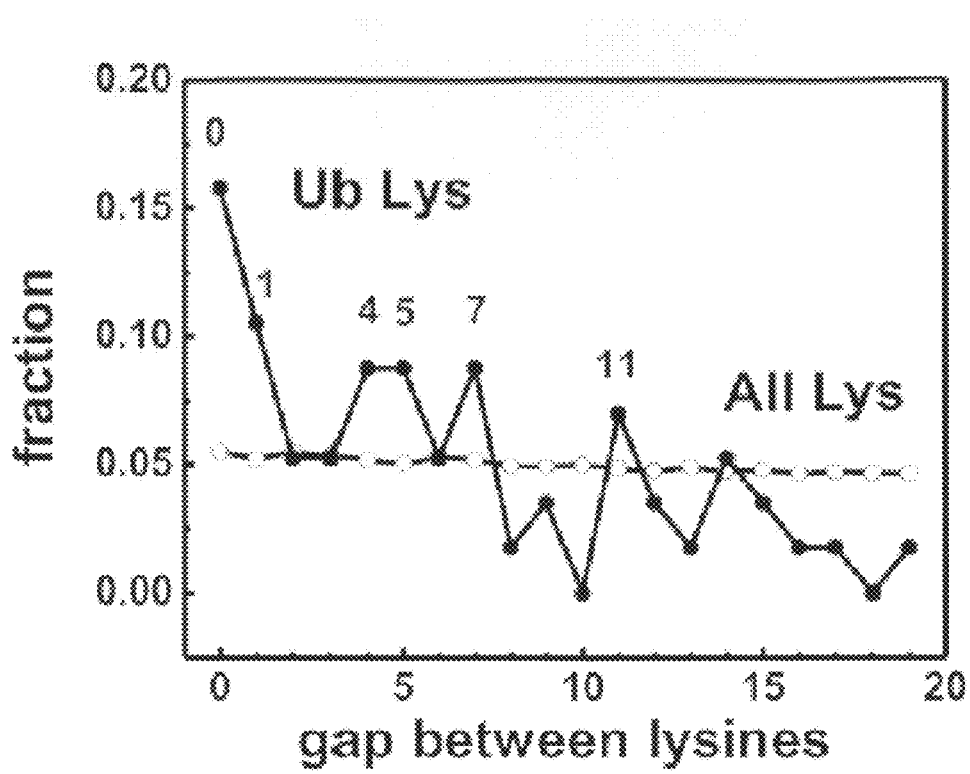
FIG. 8A shows the fraction of peptides with two ubiquitination sites as a function of the number of amino acids between the ubiquitination sites. This result indicates that when two lysines are ubiquitinated, they tend to be separated by 0, 1, 4, 5, 7 or 11 amino acids.
Figure 8B:
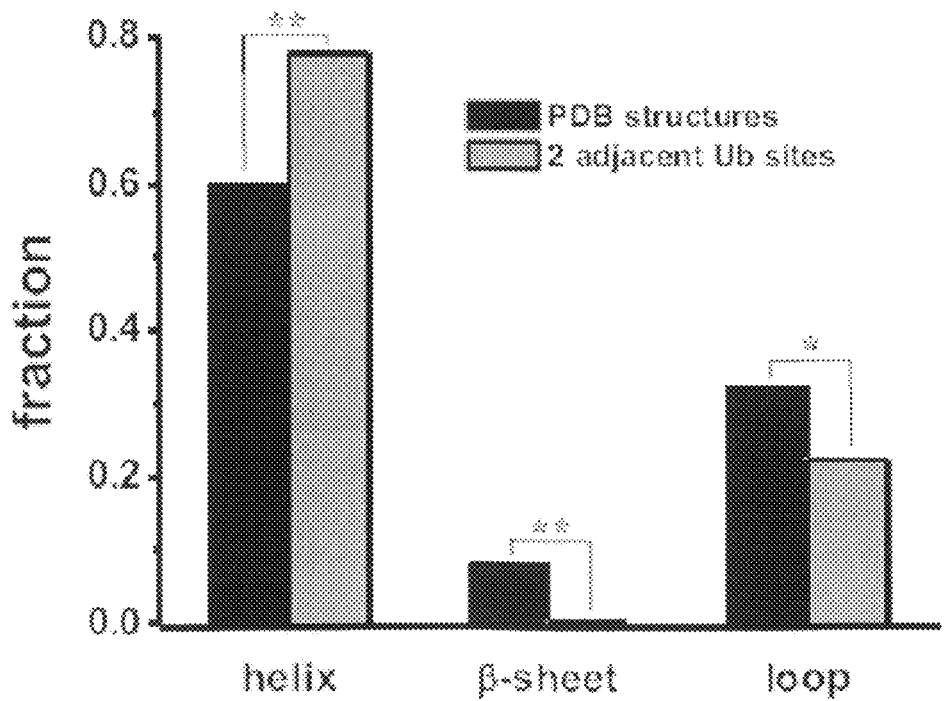
FIG. 8B shows the distribution of secondary structures, predicted by PSI-Pred (Jones, *J Mol Biol* 292, 195-202 (1999)) for peptides with two ubiquitination sites. **p-value<0.01:*p-value<0.05.

Secondary structure analysis for all lysines and ubiquitinated lysines indicates that ubiquitinated lysines prefer helical structures compared to all lysines, although ubiquitination sites can also be found in other structural contexts (FIG. 3D). This result is slightly different from a previous analysis of ubiquitinated yeast proteins, in which ubiquitination was found preferentially in both loops and helices (Catic et al., *Bioinformatics* 20, 3302-3307 (2004)). In some cases, peptides contained two ubiquitination sites. Structural prediction algorithms indicate that these lysines are likely to be in helical structures, with a higher likelihood observed for those pairs of ubiquitinated lysines that are closer together (FIG. 8). Additional crystal structures of proteins that are susceptible to ubiquitination are needed to more fully assess the structural contexts of ubiquitinated lysines.

Ubiquitination is a critical effector pathway of numerous signaling pathways and misregulation of ubiquitination has been implicated in cancer, neurodegenerative diseases, and other diseases (Jiang & Beaudet, *Curr Opin Pediatr* 16, 419-426 (2004)). The recent development of small molecule antagonists of specific E3 enzymes suggests that pharmacological manipulation of ubiquitination may be a major therapeutic strategy in various disorders (Nalepa et al. *Nat Rev Drug Discov* 5, 596-613 (2006)). The approaches described here demonstrate a simple and robust strategy to identify endogenously-ubiquitinated proteins in cells and tissues. Although different tissues and subcellular fractions were probed, the approaches described here will have utility in profiling changes in ubiquitination elicited by various signaling molecules, drugs, and in disease states. Additionally, although the above studies do not implicate specific consensus sequences in ubiquitination, specific sequence requirements may be detected when evaluating the proteins regulated by specific E1, E2, and E3 enzymes. Furthermore, identification of the proteins whose ubiquitination is dependent on specific E1, E2, or E3 enzymes may help to identify which of these ubiquitin ligases might serve as useful drug targets.

Example 3: Anti Diglycyl-Lysine Antibodies can be Used to Identify Ubiquitinated Ubiquitin, and the Specific Ubiquitin-Ubiquitin Linkages Ubiquitin is often present as polyubiquitin chains, with multiple ubiquitins attached in a chain or other branched configuration on proteins. The C-terminus of ubiquitin is conjugated to other ubiquitins via one of its seven lysine residues. The antibodies described here can be used to detect the presence or abundance of specific ubiquitin chains, due to the detection of ubiquitin-specific peptides.

Figure 12:
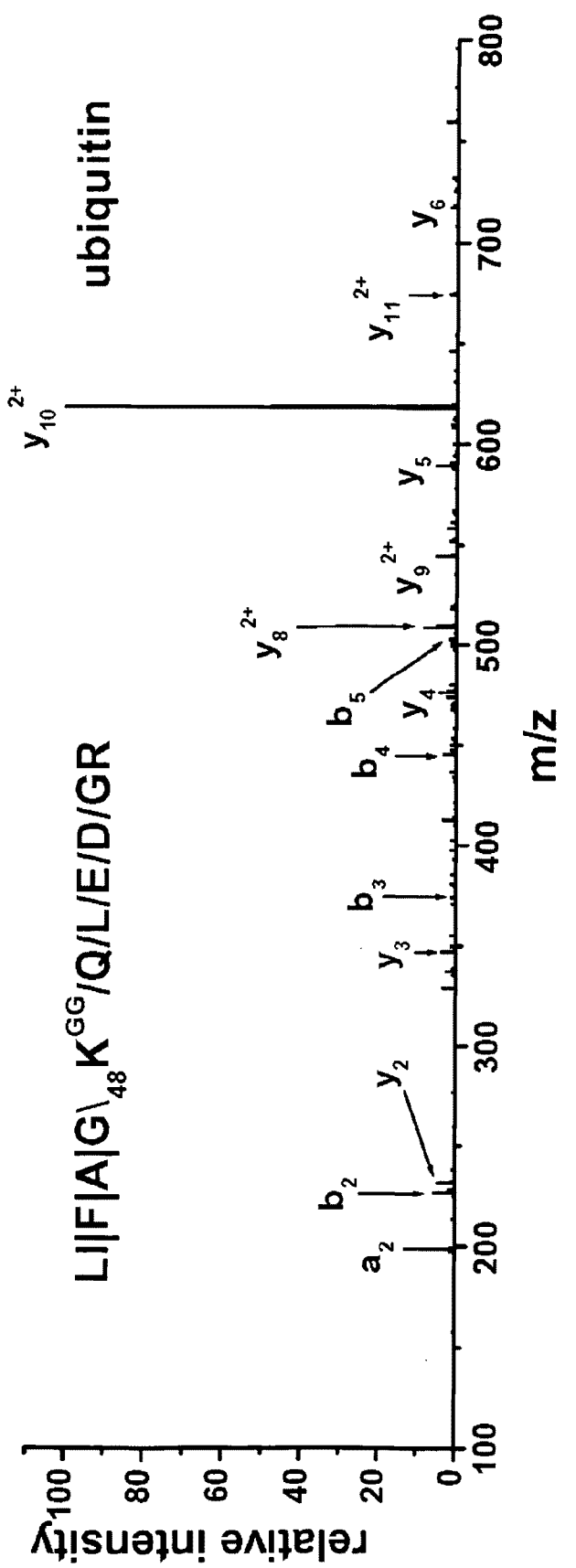
FIG. 12 shows a MS/MS spectrum of a peptide fragment from ubiquitin, which contains a ubiquitin remnant (the diglycine epitope) on K48. This peptide can be detected with either the polyclonal or monoclonal anti-diglycyl-lysine antibodies. In this case, the antibody was immobilized to protein A or protein G beads to facilitate isolation of the ubiquitin peptide containing the diglycine epitope. These results illustrate that ubiquitin can conjugate to other ubiquitin molecules.

FIG. 12 shows a MS/MS spectrum of a fragment from ubiquitin, containing a ubiquitin remnant diglycine on K48. This peptide can be detected with either the polyclonal or monoclonal anti-diglycyl-lysine antibodies. In this case, the antibody was immobilized to protein A or protein G beads. Cellular proteins were extracted from HEK293 cells, digested by trypsin, and immunoprecipitated by GlyGly-antibody and detected on ion-trap or Q-TOF LC-MS/MS.

The detection of different ubiquitinated lysines on ubiquitin itself can provide a way for quantification of different ubiquitin chains, which may change under various physiological conditions, such as ER stress.

Example 4: Purification of Peptides from the Membrane Protein TrkB Using Anti-Diglycyl-Lysine Antibodies This Example illustrates that the anti-diglycyl-lysine antibodies can be used to study ubiquitination in (1) membrane proteins; and (2) heterologously expressed proteins.

The TrkB cDNA was expressed in mouse N2a cells, and the TrkB protein was purified by immunoprecipitation with TrkB-specific antibodies. TrkB protein was then digested with trypsin and reimmunoprecipitated with anti-diglycyl-lysine antibodies.

Figure 13:
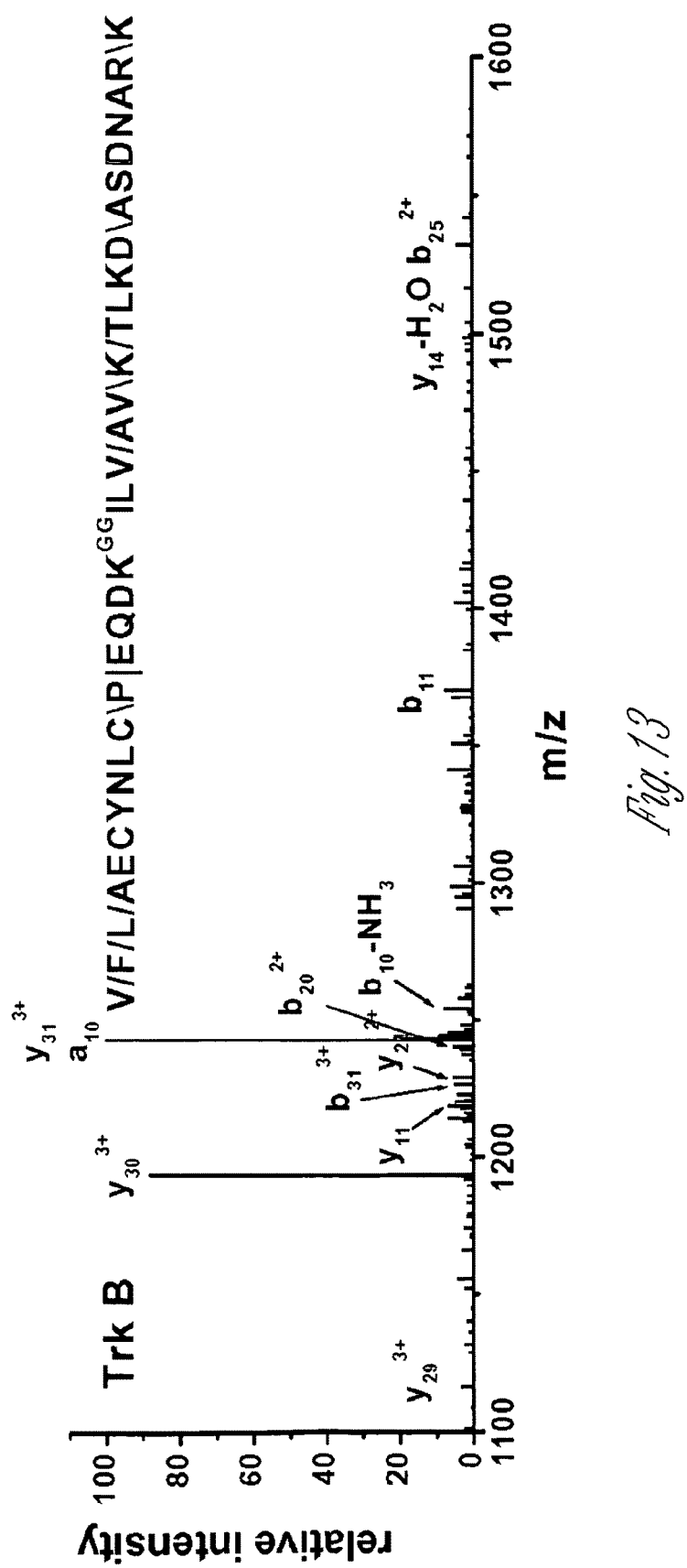
FIG. 13 shows a MS/MS spectrum of a peptide fragment from ubiquitinated TrkB that was digested with trypsin. These results illustrate that membrane-bound ubiquitinated proteins can be detected using the methods and antibodies described herein.

As shown in FIG. 13, LC-MS/MS analysis revealed that the TrkB protein had a peptide with a ubiquitination site.

Example 5: Anti-Diglycyl-Lysine Antibodies are Highly Specific for the Diglycyl-Lysine Epitope This Example illustrates the specificity of the anti-diglycyl-lysine antibodies
Anti-Diglycyl-Lysine Antibodies Recognize GlyGly Modifications on the Epsilon-, but not Alpha-Amine.

Figure 14A:
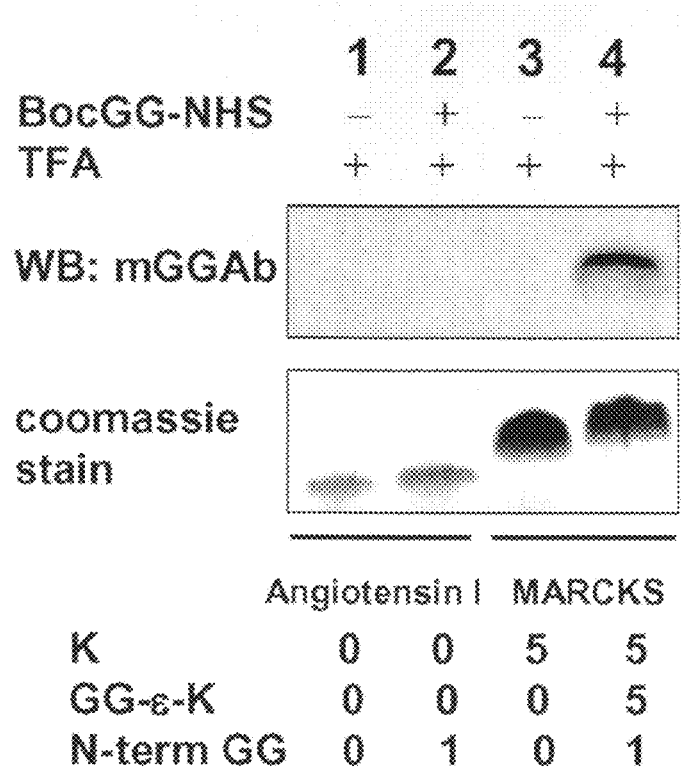
FIGS. 14A and 14B illustrate that monoclonal anti-diglycyl antibodies (mGGAb) can distinguish between diglycyl adducts on the epsilon amine of lysine vs. the alpha-amine of proteins.

Experiments were conducted to determine whether monoclonal anti-diglycyl antibodies (mGGAb) can distinguish between diglycyl adducts on the epsilon amine of lysine vs. the alpha-amine of proteins. Angiotensin I, which contains zero lysines (indicated as "K" in FIG. 14) was synthesized with the diglycyl modification selectively on the alpha amine by reaction with Boc-diglycine-NHS. As a control, another aliquot of angiotensin I was treated with vehicle. The small tables below the western blots shown in FIGS. 14A and 14B, list the number of diglycyl moieties incorporated on the epsilon amine of lysines, and the number of diglycyl moieties incorporated on alpha-amines. Because angiotensin I does not contain any epsilon amines, there is only a single diglycine modification on the alpha-amine. This is readily detected by Coomassie staining (FIG. 14A), where the modified protein exhibits a small upward mobility shift. As illustrated in FIG. 14A, this peptide exhibits no reactivity with the anti-diglycyl-lysine monoclonal antibodies ("mGGAb") was used to probe the Western blot.

In contrast, the MARCKS peptide, which contains five lysines, is reactive with the mGGAb after the MARCKS peptide was treated with Boc-diglycine-NHS (FIG. 14A). Thus, results indicate that the diglycine epitope was introduced onto the five epsilon amines and the one alpha-amine of the MARCKS peptide (FIG. 14A).

Figure 14B:
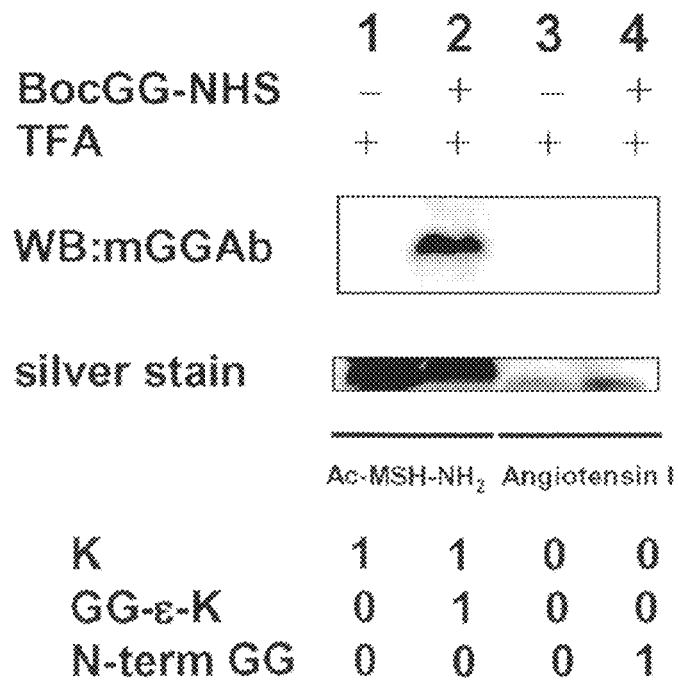

The specificity of the anti-diglycyl antibodies (mGGAb) towards diglycyl-modified epsilon amines but not alpha-amines is tested in more detail using a peptide, Ac-MSH-NH$_2$, which contains no alpha-amine (the alpha-amine is acetylated), and just one lysine. As shown for the MARCKS peptide in FIG. 14A, the conjugation of the diglycine to the Ac-MSH-NH$_2$ peptide is readily detected when (FIG. 14B). This is in contrast to Angiotensin I, where no diglycine epitopes are detected. The immunoreactivity of mGGAb for the Ac-MSH-NH$_2$ peptide therefore reflects binding of mGGAb to internal diglycyl-lysine, because the alpha-amine of the Ac-MSH-NH$_2$ peptide is acetylated.

Figure 15A:
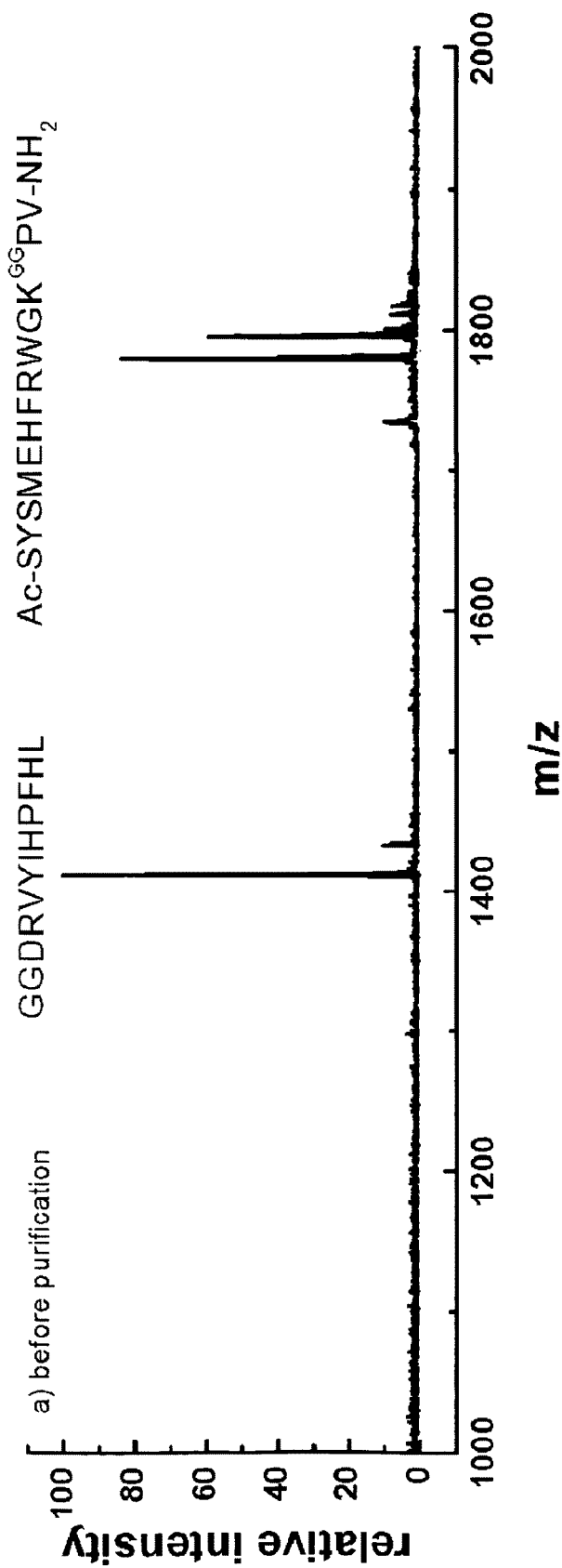
FIG. 15A-C illustrates that the polyclonal anti-diglycyl-lysine antibodies described herein immunoprecipitate peptides with GlyGly-modified lysines but not peptides with N-terminal GlyGly.
Figure 15B:
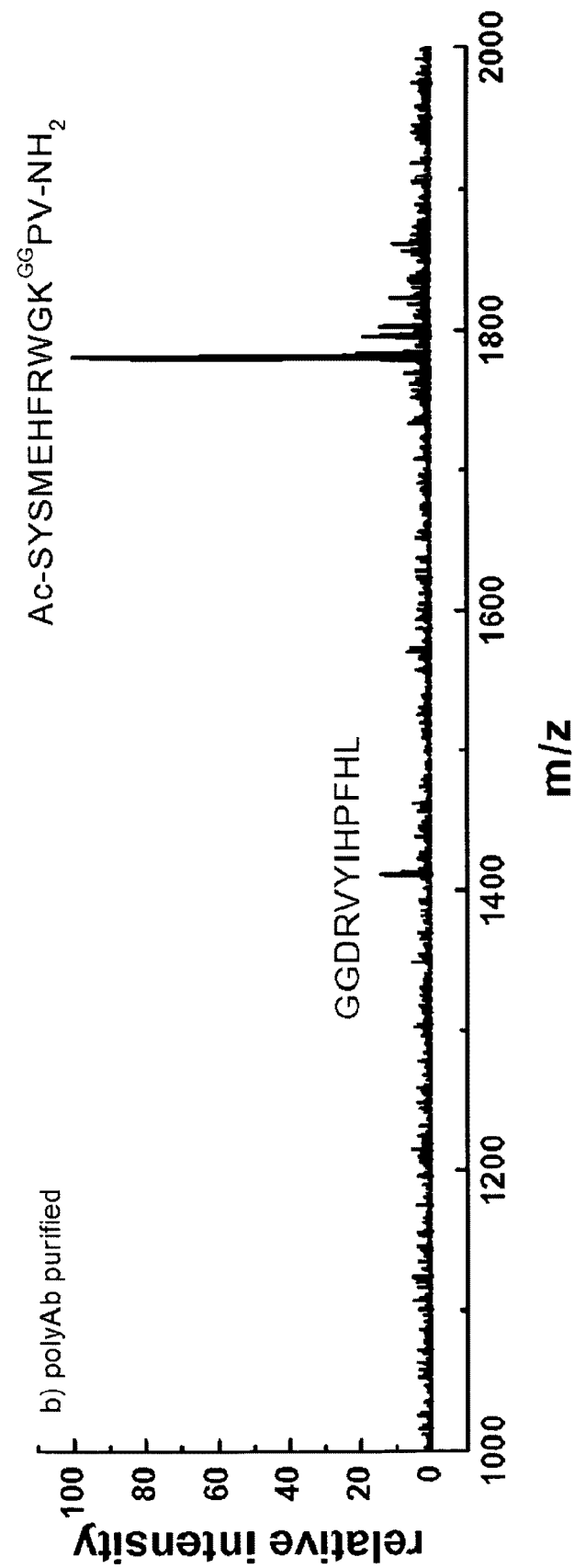
Figure 15C:
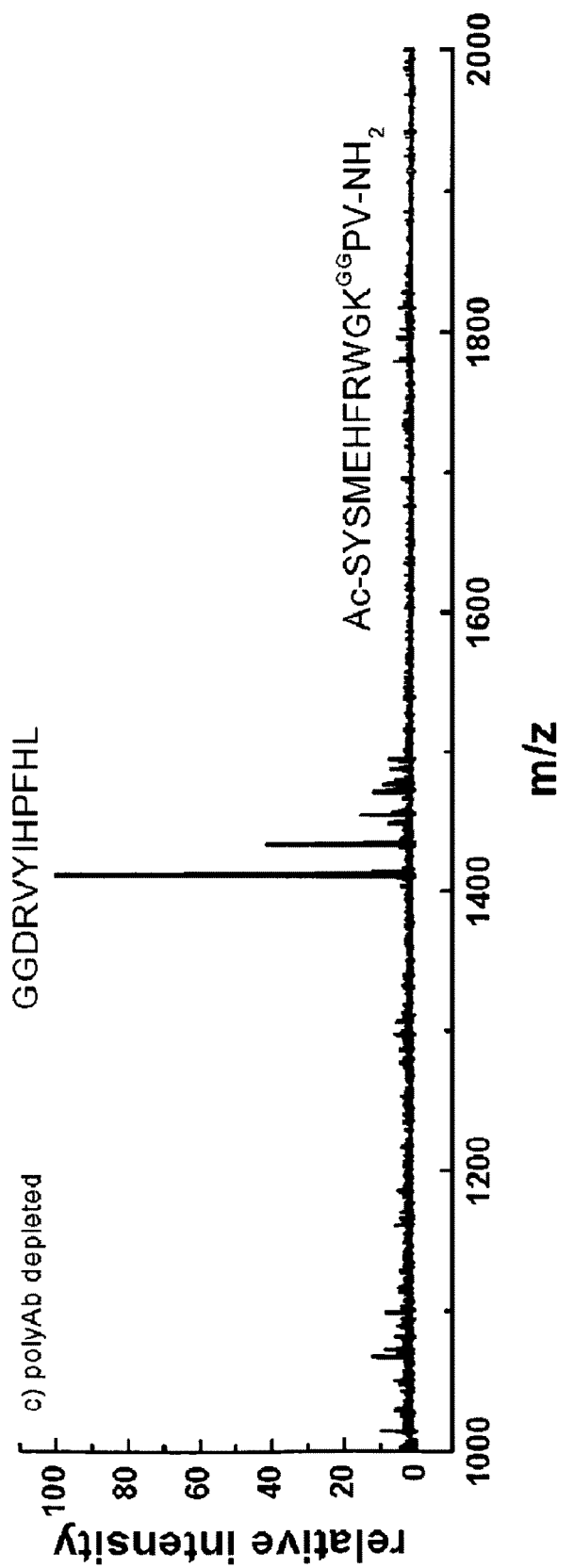

The Polyclonal Anti-Diglycyl-Lysine Antibody Immunoprecipitates Peptides with GlyGly-Modified Lysines but not Peptides with N-Terminal GlyGly Peptides with GlyGly modifications on the ε-amine of lysines were isolated by the anti-diglycyl-lysine antibody. Anti-diglycyl-lysine antibody bound to beads was incubated with a 1:1 mixture of GlyGly-modified Angiotensin I (one N-terminal GlyGly modification) and GlyGly-modified acetylated MSH peptide (one GlyGly-modified lysine). The beads were washed with 2XPBS, eluted with 0.1% TFA to remove the Boc moiety. MALDI-TOF-MS was used to detect the unpurified peptides in the original mixture (FIG. 15A), as well as the peptides that bound to immobilized anti-diglycyl-lysine antibodies (FIG. 15B), and the peptides in the "flow through," i.e., the liquid solution after incubation with immobilized antibody (FIG. 15C). The sequences of the peptides in the peaks are indicated in the spectra. These data illustrate that the anti-diglycyl-lysine antibodies can be used to selectively recover a peptide containing a diglycyl-modified lysine (FIG. 15B), while the flow through contains the peptide with the diglycyl modification on the alpha-amine. Hence, the anti-diglycyl-lysine antibodies can facilitate specific purification of peptides that have GlyGly-modified lysines.

A Monoclonal Anti-Diglycyl-Lysine Antibody Preparation can Detect at Least 170 Femtomoles of GlyGly-Lysine-Modified Peptides.

A "dot blot" was used to test the sensitivity of the monoclonal anti-diglycyl-lysine antibody. Insulin (Molecular Weight ~5800 Da) contains only one lysine in its heavy chain, which is readily conjugated to the Gly-Gly moiety using procedures and reagents as described herein. The fact that GlyGly-modified insulin contains just one GlyGly-modified lysine residue provides a convenient way to spot known amounts of diglycyl-modified protein on PVDF membranes. Dot blots were spotted with serially diluted amounts of GlyGly-modified insulin so that the amount of insulin (in ng) and the corresponding molar quantity (in pmol) was as listed above and below, respectively, the dot blots shown in FIGS. 16A and 16B. The affinity of the monoclonal antibody was assessed by probing these dot blot with monoclonal antibody 49 using a 1:2 dilution of ascites and 1:1000 dilution of secondary antibody and visualized by ECL Plus™ Western Blotting Detection System (GE Healthcare).

Figure 16A:
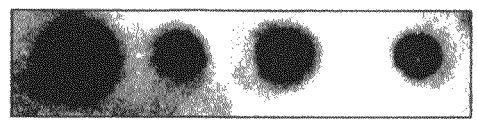
FIG. 16A-B illustrate that one of the monoclonal anti-diglycyl-lysine antibody preparations described herein can detect GlyGly-Lysine-modified peptides in amounts at least as low as 170 femtomoles.
Figure 16B:

As shown in FIG. 16A-B, this anti-diglycyl-lysine monoclonal antibody can detect at least 1 ng (170 fmol) of GlyGly-lysine-conjugated insulin in the presence of 1 mg/mL BSA.

Affinity Purified Monoclonal Anti-Diglycyl-Lysine Antibody can Detect GlyGly-Modified Proteins.

Figure 17A:
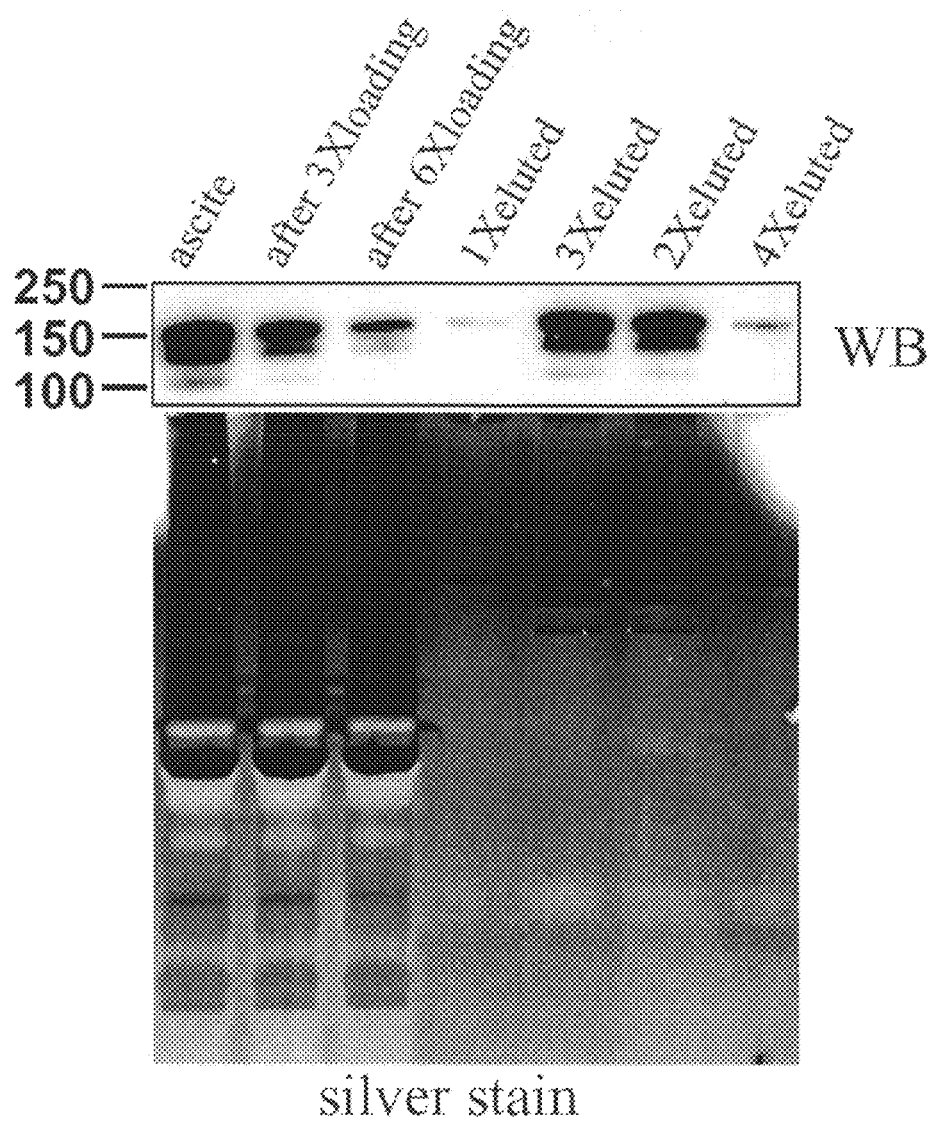
FIG. 17A-B show that affinity purified monoclonal anti-diglycyl-lysine antibodies can detect GlyGly-modified proteins. The tissue culture media in which the hybridoma cell line expressing anti-diglycyl-antibody #49 was growing (ascites) was used as a source of monoclonal antibody and the antibody was purified using diglycine-modified BSA immobilized on Affi-gel.
Figure 17B:
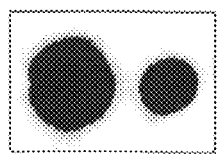
Figure 18:
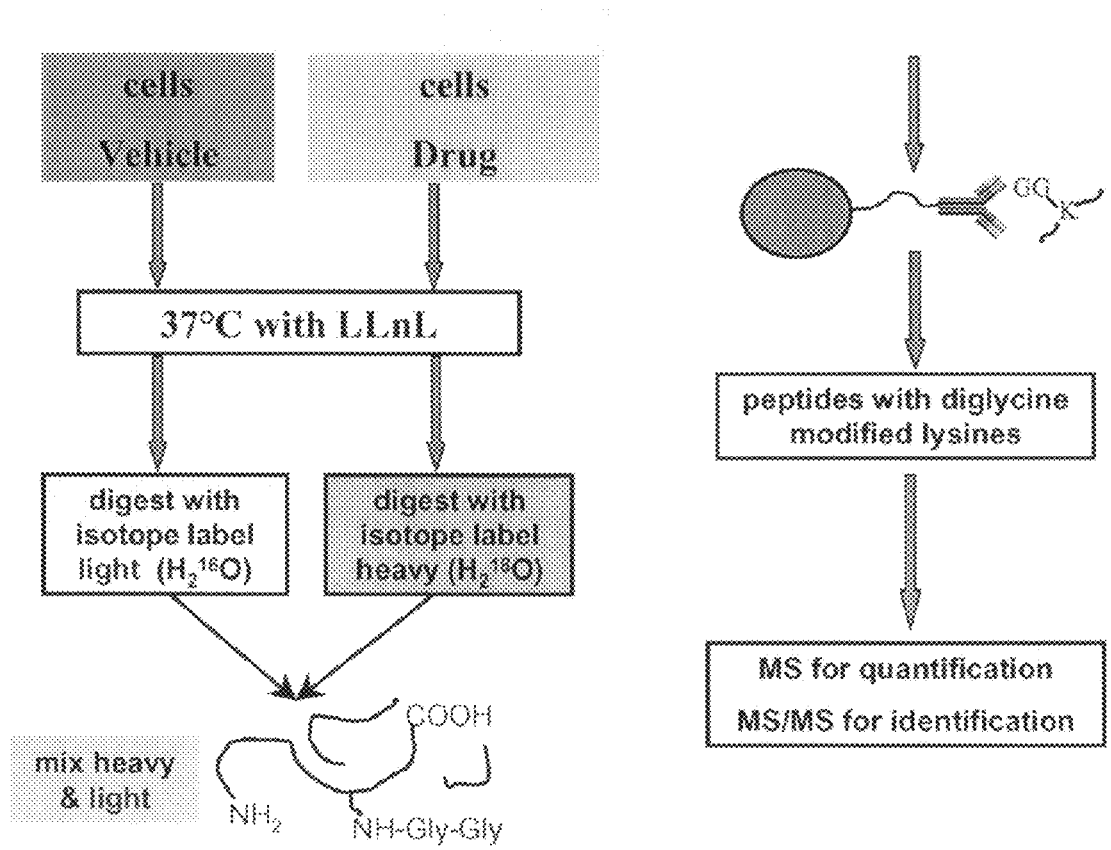
FIG. 18 is a schematic diagram illustrating one procedure to quantify ubiquitinated proteins in cells or tissues treated with a drug or other agent, that involves quantitative mass spectrometry. Cells are treated either by vehicle or drug for a period of time in the presence of proteasome inhibitor, such as LLnL. The cells are lysed and then digested with trypsin. The lysate from vehicle-treated cells (vehicle) is digested with protease in the presence of light water ($H_2^{16}O$), while the lysate from drug-treated cells is digested with protease in the presence of heavy water ($H_2^{18}O$). Therefore the carboxyl termini of cleaved (e.g., tryptic) peptides are labeled differently in the samples from drug treated ($^{18}O$) and non-treated ($^{16}O$) cells. The digested samples are combined with and immunopurified by the anti-diglycyl-lysine antibody, then the enriched ubiquitinated peptides are analyzed by tandem mass spectrometry (MS/MS). The sequences determined by MS/MS (e.g., by mass spectrometry software) are used to search protein databases to determine from which protein(s) the peptide(s) originated. The relative quantity of diglycyl-lysine tagged peptides can be determined by extracted ion chromatography (EIC) for the peptides of interest, by observation of the intensity ratios of the light form ($^{16}O$) and heavy form ($^{18}O$) of the peptides from, so that the effect of drug on alternation of ubiquitination levels can be investigated. This approach can also be used for quantification of protein ubiquitination between normal tissue and patient tissue for disease diagnostics when the proteasome inhibitor step is skipped. Here protein labeling can also been achieved by SILAC (stable isotope labeling by amino acid in cell culture) for cells.

This experiment evaluates whether the monoclonal anti-diglycyl-lysine antibody can be purified and still detect diglycine-modified proteins. In this experiment, the tissue culture media in which the hybridoma cell line expressing anti-diglycyl-antibody #49 was growing (ascites) was used as a source of monoclonal antibody. The antibody was purified using diglycine-modified BSA immobilized on Affi-gel. In the first three lanes in the gel shown in FIG. 17A, the silver stain shows the flow-through from Affi-gel after the media was incubated with the immobilized diglycine-modified BSA. A blot to detect antibody was also performed and shown above. This blot shows that the antibody is depleted from the media by incubation with the immobilized diglycine-modified BSA. Acid elution (last four lanes of FIG. 17A), results in the elution of specific antibody bands, which can be seen in both the silver stain and Western blot at the top of FIG. 17A. FIG. 17B shows a dot blot of diglycine-modified lactoglobulin. The purified antibody readily recognizes 0.01 μg of this protein. Thus, the purified antibody has a high purity and can recognize GlyGly-modified proteins at least at the nanogram level.

Example 6: Quantifying Ubiquitination Changes after Drug Treatment

The Example illustrates how protein ubiquitination changes in cells exposed to an inhibitor of nitric oxide synthase, NAME (N-nitro-L-arginine methyl ester).

sEnd.1 cells typically express large quantities of nitric oxide, which can be inhibited by applying the drug NAME. To identify proteins that are ubiquitinated by endogenous nitric oxide, sEnd.1 cells were treated either by vehicle (DMSO) or 1 mM NAME (dissolved in DMSO) for a period of 1-6 hours in the presence of proteasome inhibitor, LLnL (50 μM) and protein synthesis inhibitor, cycloheximide (CHX, 50 μg/mL). The proteasome inhibitor allows ubiquitinated proteins to accumulate without being rapidly digested so that there will be sufficient ubiquitinated proteins to readily be immunopurified. The protein synthesis inhibitor was used to prevent new proteins from being synthesized, which would complicate the analysis.

The cells were lysed followed by trypsin digestion overnight, where the vehicle-treated lysate was digested in the presence of light water ($H_2^{16}O$) and the lysate from NAME treated cells was digested in the presence of heavy water ($H_2^{18}O$). Therefore, the carboxyl termini of tryptic peptides were labeled differently for sample from NAME-treated ($^{18}O$) and non-treated cells ($^{16}O$).

The digested ($^{16}O$ and $^{18}O$ labeled) samples were mixed with, and immunopurified by, the anti-diglycyl-lysine antibody. The isolated diglycyl-lysine-containing (ubiquitinated) peptides were analyzed by tandem mass spectrometry. The MS/MS spectra were searched against Swiss-Prot database by Spectrum Mill to identify the type of protein that the various peptides were derived from and the relative quantity of diglycyl-lysine-containing (ubiquitinated) peptides was determined from the extracted ion chromatography (EIC) of the ubiquitinated peptides.

Each peptide was therefore detected on the mass spectrometer as a pair. One member of the pair is derived from the sample prepared with light water, the other from the sample that was labeled with heavy water. The intensity ratio of the light form ($^{16}O$) and heavy form ($^{18}O$) of the peptides from the spectrum or chromatogram can be used for quantification of the ubiquitinated peptides in two samples. Therefore a L:H (light to heavy) ratio can be obtained. If ubiquitination is not affected by the drug treatment, then the ratio is going to be 1:1. If the sample that was treated with NAME causes an increase in the abundance of a ubiquitinated peptide, the L/H ratio will drop because the amount of the "heavy" peptide will be greater than the amount of "light" peptide (H>L).

Figure 19:
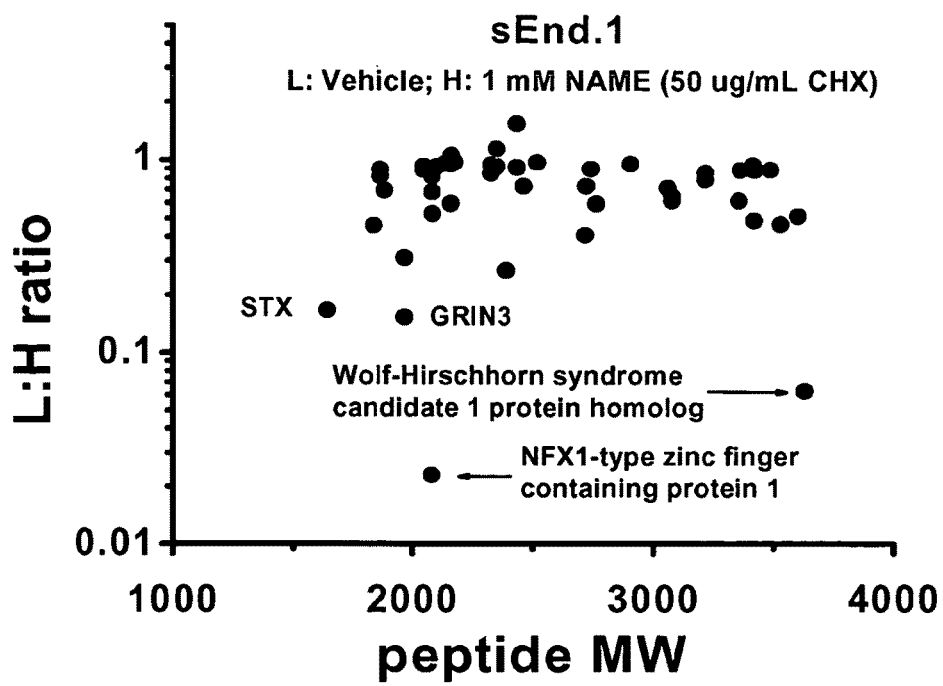
FIG. 19 is a graph of the ratio of ubiquitination of a peptide from control (L) cells relative to the ubiquitination of the same peptide from cells exposed to inhibitor of nitric oxide synthase, NAME (N-nitro-L-arginine methyl ester) (H), illustrating how protein ubiquitination changes in murine endothelioma (sEnd.1) cells exposed to NAME (N-nitro-L-arginine methyl ester).

In this experiment, the ubiquitination level for most proteins did not change so that the ratio of L:H was close to 1. However, the ubiquitination level of several proteins, STX (Sialyltransferase X), GRIN3 (G protein-regulated inducer of neurite outgrowth 3), Whsc1 (Wolf-Hirschhorn syndrome candidate 1 protein homolog), Znfx1 (NFX1-type zinc finger containing protein 1), was significantly increased upon NAME treatment (FIG. 19). These proteins may have a role in nitric oxide signaling that is modulated by ubiquitination upon inhibition of nitric oxide synthase.

Example 7: Quantifying Ubiquitination Changes after Drug Treatment

The Example illustrates how protein ubiquitination changes in mouse N2a neuroblastoma cells exposed to a nitric oxide producer, GSNO(S-nitrosoglutathione).

In this experiment, a cell line where nitric oxide is not expressed at readily detectable levels, mouse N2a neuroblastoma cells, was used to ascertain whether a nitric oxide generating drug would increase or decrease ubiquitination. This would identify ubiquitination events that are operably linked to this drug. Because certain NO donors have been shown to affect ubiquitination pathways, this is a demonstration of how a drug of interest can be tested to see whether it affects protein ubiquitination.

N2a cells were treated either with vehicle (DMSO) or with 100 µM GSNO (dissolved in DMSO) for a period of 1-6 hours in the presence of proteasome inhibitor, LLnL (50 µM) and protein synthesis inhibitor, cycloheximide (CHX, 50 µg/mL). The GSNO releases nitric oxide to the cells.

After this treatment, the cells were lysed and the proteins in the lysate were digested with trypsin overnight. In particular, the lysate from vehicle-treated cells was digested with light water ($H_2^{16}O$), while the lysate from GSNO-treated cells was digested with heavy water ($H_2^{18}O$). Therefore, the carboxyl termini of tryptic peptides from drug treated ($^{18}O$) and non-treated cells ($^{16}O$) were labeled differently. The digested samples ($^{16}O$ and $^{18}O$ labeled) were mixed with, and immunopurified by, the anti-diglycyl-lysine antibody. The isolated ubiquitinated peptides were analyzed by tandem mass spectrometry and the MS/MS spectra were searched against Swiss-Prot database by Spectrum Mill to identify the proteins from the peptides were derived. To quantify the ubiquitinated peptides, extracted ion chromatography (EIC) was used, where the intensity ratio of the light form ($^{16}O$) and heavy form ($^{18}O$) of the peptides was used to ascertain the relative amounts of the ubiquitinated peptides in two samples. The larger the ratio of L:H, the less the protein is ubiquitinated in the GSNO treated samples, and vice visa.

Figure 20:
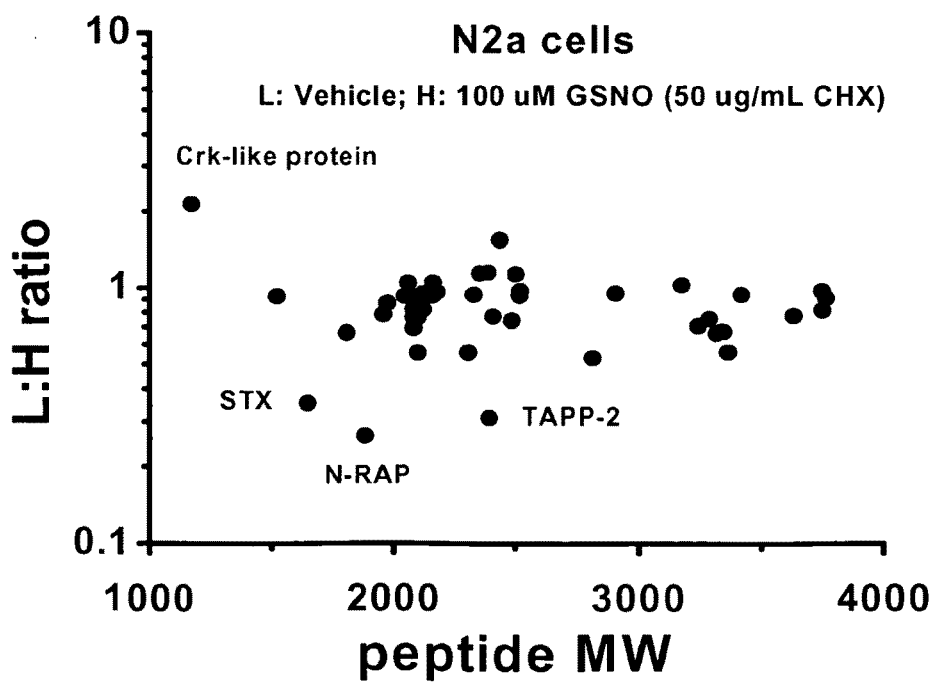
FIG. 20 is a graph of the ratio of ubiquitination of a peptide from control (L) cells relative to the ubiquitination of the same peptide from cells exposed to a nitric oxide producer, GSNO(S-nitrosoglutathione)(H), illustrating how protein ubiquitination changes in mouse N2a neuroblastoma cells exposed to GSNO (S-nitrosoglutathione).

In this experiment, the ubiquitination level for most proteins did not change very much so that the L:H ratios for these proteins was close to 1. However, the ubiquitination of several proteins, STX (Sialyltransferase X), N-RAP (Nebulin-related-anchoring protein), and TAPP-2 (Tandem PH domain-containing protein 2), was significantly increased upon GSNO treatment (FIG. 20). While, the ubiquitination level of Crk-like protein is significantly reduced upon the treatment. These proteins are possible nitric oxide effectors upon stimulation of nitric oxide.

Example 8: Different Types of Proteins are Ubiquitinated in Different Types of Cells This Example illustrates that different types of proteins are ubiquitinated in different types of cells.

FIG. 21A-D shows in what types of biological processes various ubiquitinated proteins are involved, in different cell lines (send.1, N2a, HEK293) and rat tissue. The biological processes were analyzed by PANTHER and were categorized into eight groups: signal transduction, structure, metabolism, cell cycle/apoptosis, small molecular transport, immunity and defense, protein rafficking/localization, and others/unclassified. For each cell line and tissue, ubiquitinated proteins are mainly involved in signal transduction, metabolism, and cell cycle/apoptosis.

However, there are some differences between the different cell lines. For example, in mouse N2a neuroblastoma cell (a cancer cell line), about 40% of ubiquitinated proteins are involved in signal transduction, which is more than twice the number of signal transduction proteins in mouse subcutaneous haemangioma endothelial cell line, sEnd.1 (a noncancerous line). Only 3.7 percent of ubiquitinated proteins are related to cell structure in the N2a cancer cells compared to 5.7 percent in sEnd.1 cells. In sEnd.1 cell, 12% of ubiquitinated proteins are related to small molecular transport, which is much higher (2.5 to 7 times) than that in other cell lines tested.

Therefore, the ubiquitination profile can distinguish different cell types, indicating that specific proteins or specific ubiquitination events, or combinations thereof, can also be used as markers to distinguish between these different cell types, states, or populations.

REFERENCES

1. Hershko, A. & Ciechanover, A. The ubiquitin system. *Annu Rev Biochem* 67, 425-479 (1998).

2. Hicke, L. Gettin' down with ubiquitin: turning off cell-surface receptors, transporters and channels. *Trends Cell Biol* 9, 107-112 (1999).
3. Conaway, R. C., Brower, C. S. & Conaway, J. W. Emerging roles of ubiquitin in transcription regulation. *Science* 296, 1254-1258 (2002).
4. Ulrich, H. D. Degradation or maintenance: actions of the ubiquitin system on eukaryotic chromatin. *Eukaryot Cell* 1, 1-10 (2002).
5. Kirkpatrick, D. S., Denison, C. & Gygi, S. P. Weighing in on ubiquitin: the expanding role of mass-spectrometry-based proteomics. *Nat Cell Biol* 7, 750-757 (2005).
6. Bonifacino, J. S. & Weissman, A. M. Ubiquitin and the control of protein fate in the secretory and endocytic pathways. *Annu Rev Cell Dev Biol* 14, 19-57 (1998).
7. Rechsteiner, M. Ubiquitin-mediated pathways for intracellular proteolysis. *Annu Rev Cell Biol* 3, 1-30 (1987).
8. Nandi, D., Tahiliani, P., Kumar, A. & Chandu, D. The ubiquitin-proteasome system. *J Biosci* 31, 137-155 (2006).
9. Mukhopadhyay, D. & Riezman, H. Proteasome-independent functions of ubiquitin in endocytosis and signaling. *Science* 315, 201-205 (2007).
10. Sun, L. & Chen, Z. J. The novel functions of ubiquitination in signaling. *Curr Opin Cell Biol* 16, 119-126 (2004).
11. Pickart, C. M. Ubiquitin enters the new millennium. *Mol Cell* 8, 499-504 (2001).
12. Pickart, C. M. Mechanisms underlying ubiquitination. *Annu Rev Biochem* 70, 503-533 (2001).
13. Xu, P. & Peng, J. Dissecting the ubiquitin pathway by mass spectrometry. *Biochim Biophys Acta* 1764, 1940-1947 (2006).
14. Banerjee, A., Kocarek, T. A. & Novak, R. F. Identification of a ubiquitination-Target/Substrate-interaction domain of cytochrome P-450 (CYP) 2E1. *Drug Metab Dispos* 28, 118-124 (2000).
15. Treier, M., Staszewski, L. M. & Bohmann, D. Ubiquitin-dependent c-Jun degradation in vivo is mediated by the delta domain. *Cell* 78, 787-798 (1994).
16. Baboshina, O. V. & Haas, A. L. Novel multiubiquitin chain linkages catalyzed by the conjugating enzymes E2EPF and RAD6 are recognized by 26 S proteasome subunit 5. *J Biol Chem* 271, 2823-2831 (1996).
17. Gregori, L., Poosch, M. S., Cousins, G. & Chau, V. A uniform isopeptide-linked multiubiquitin chain is sufficient to target substrate for degradation in ubiquitin-mediated proteolysis. *J Biol Chem* 265, 8354-8357 (1990).
18. Vasilescu, J., Smith, J. C., Ethier, M. & Figeys, D. Proteomic analysis of ubiquitinated proteins from human MCF-7 breast cancer cells by immunoaffinity purification and mass spectrometry. *J Proteome Res* 4, 2192-2200 (2005).
19. Vasilescu, J. et al. The proteomic reactor facilitates the analysis of affinity-purified proteins by mass spectrometry: application for identifying ubiquitinated proteins in human cells. *J Proteome Res* 6, 298-305 (2007).
20. Peng, J. et al. A proteomics approach to understanding protein ubiquitination. *Nat Biotechnol* 21, 921-926 (2003).
21. Peng, J. & Cheng, D. Proteomic analysis of ubiquitin conjugates in yeast. *Methods Enzymol* 399, 367-381 (2005).
22. Jeon, H. B. et al. A proteomics approach to identify the ubiquitinated proteins in mouse heart. *Biochem Biophys Res Commun* 357, 731-736 (2007).
23. Kirkpatrick, D. S., Weldon, S. F., Tsaprailis, G., Liebler, D. C. & Gandolfi, A. J. Proteomic identification of ubiquitinated proteins from human cells expressing His-tagged ubiquitin. *Proteomics* 5, 2104-2111 (2005).
24. Matsumoto, M. et al. Large-scale analysis of the human ubiquitin-related proteome. *Proteomics* 5, 4145-4151 (2005).
25. Denis, N. J., Vasilescu, J., Lambert, J. P., Smith, J. C. & Figeys, D. Tryptic digestion of ubiquitin standards reveals an improved strategy for identifying ubiquitinated proteins by mass spectrometry. *Proteomics* 7, 868-874 (2007).
26. Chemorudskiy, A. L. et al. UbiProt: a database of ubiquitylated proteins. *BMC Bioinformatics* 8, 126 (2007).
27. McLachlin, D. T. & Chait, B. T. Analysis of phosphorylated proteins and peptides by mass spectrometry. *Curr Opin Chem Biol* 5, 591-602 (2001).
28. Ferguson, P. L. & Smith, R. D. Proteome analysis by mass spectrometry. *Annu Rev Biophys Biomol Struct* 32, 399-424 (2003).
29. Warren, M. R., Parker, C. E., Mocanu, V., Klapper, D. & Borchers, C. H. Electrospray ionization tandem mass spectrometry of model peptides reveals diagnostic fragment ions for protein ubiquitination. *Rapid Commun Mass Spectrom* 19, 429-437 (2005).
30. Pedrioli, P. G. et al. Automated identification of SUMOylation sites using mass spectrometry and SUMmOn pattern recognition software. *Nat Methods* 3, 533-539 (2006).
31. Denison, C., Kirkpatrick, D. S. & Gygi, S. P. Proteomic insights into ubiquitin and ubiquitin-like proteins. *Curr Opin Chem Biol* 9, 69-75 (2005).
32. Wang, Q., Young, P. & Walters, K. J. Structure of S5a bound to monoubiquitin provides a model for polyubiquitin recognition. *J Mol Biol* 348, 727-739 (2005).
33. Wang, H. et al. Role of histone H2A ubiquitination in Polycomb silencing. *Nature* 431, 873-878 (2004).
34. Nickel, B. E. & Davie, J. R. Structure of polyubiquitinated histone H2A. *Biochemistry* 28, 964-968 (1989).
35. Gordon, D. M. & Roof, D. M. Degradation of the kinesin Kip1p at anaphase onset is mediated by the anaphase-promoting complex and Cdc20p. *Proc Natl Acad Sci US A* 98, 12515-12520 (2001).
36. Lu, Z. et al. Predicting subcellular localization of proteins using machine-learned classifiers. *Bioinformatics* 20, 547-556 (2004).
37. Lu, C. et al. Insulin-like peptide 6: characterization of secretory status and posttranslational modifications. *Endocrinology* 147, 5611-5623 (2006).
38. Meerovitch, K., Wing, S. & Goltzman, D. Preproparathyroid hormone-related protein, a secreted peptide, is a substrate for the ubiquitin proteolytic system. *J Biol Chem* 272, 6706-6713 (1997).
39. Liao, W., Chang, B. H., Mancini, M. & Chan, L. Ubiquitin-dependent and -independent proteasomal degradation of apoB associated with endoplasmic reticulum and Golgi apparatus, respectively, in HepG2 cells. *J Cell Biochem* 89, 1019-1029 (2003).
40. Galan, J. M., Cantegrit, B., Garnier, C., Namy, O. & Haguenauer-Tsapis, R. 'ER degradation' of a mutant yeast plasma membrane protein by the ubiquitin-proteasome pathway. *Faseb J* 12, 315-323 (1998).
41. Plemper, R. K. & Wolf, D. H. Endoplasmic reticulum degradation. Reverse protein transport and its end in the proteasome. *Mol Biol Rep* 26, 125-130 (1999).

42. Schwartz, D. & Gygi, S. P. An iterative statistical approach to the identification of protein phosphorylation motifs from large-scale data sets. *Nat Biotechnol* 23, 1391-1398 (2005).
43. Ahmad, S. & Gromiha, M. M. NETASA: neural network based prediction of solvent accessibility. *Bioinformatics* 18, 819-824 (2002).
44. Catic, A., Collins, C., Church, G. M. & Ploegh, H. L. Preferred in vivo ubiquitination sites. *Bioinformatics* 20, 3302-3307 (2004).
45. Jiang, Y. H. & Beaudet, A. L. Human disorders of ubiquitination and proteasomal degradation. *Curr Opin Pediatr* 16, 419-426 (2004).
46. Nalepa, G., Rolfe, M. & Harper, J. W. Drug discovery in the ubiquitin-proteasome system. *Nat Rev Drug Discov* 5, 596-613 (2006).
47. Hao, G., Derakhshan, B., Shi, L., Campagne, F. & Gross, S. S. SNOSID, a proteomic method for identification of cysteine S-nitrosylation sites in complex protein mixtures. *Proc Natl Acad Sci USA* 103, 1012-1017 (2006).
48. Benore-Parsons, M., Seidah, N. G. & Wennogle, L. P. Substrate phosphorylation can inhibit proteolysis by trypsin-like enzymes. *Arch Biochem Biophys* 272, 274-280 (1989).
49. Schlosser, A., Pipkorn, R., Bossemeyer, D. & Lehmann, W. D. Analysis of protein phosphorylation by a combination of elastase digestion and neutral loss tandem mass spectrometry. *Anal Chem* 73, 170-176 (2001).
50. Molina, H., Horn, D. M., Tang, N., Mathivanan, S. & Pandey, A. Global proteomic profiling of phosphopeptides using electron transfer dissociation tandem mass spectrometry. *Proc Natl Acad Sci USA* 104, 2199-2204 (2007).
51. Thomas, P. D. et al. PANTHER: a library of protein families and subfamilies indexed by function. *Genome Res* 13, 2129-2141 (2003).
52. Dennis, G., Jr. et al. DAVID: Database for Annotation, Visualization, and Integrated Discovery. *Genome Biol* 4, P3 (2003).
53. Kabsch, W. & Sander, C. Dictionary of protein secondary structure: pattern recognition of hydrogen-bonded and geometrical features. *Biopolymers* 22, 2577-2637 (1983).
54. Jones, D. T. Protein secondary structure prediction based on position-specific scoring matrices. *J Mol Biol* 292, 195-202 (1999).
55. Linding, R. et al. Protein disorder prediction: implications for structural proteomics. *Structure* 11, 1453-1459 (2003).
56. Hubbard, S. J., Campbell, S. F. & Thornton, J. M. Molecular recognition. Conformational analysis of limited proteolytic sites and serine proteinase protein inhibitors. *J Mol Biol* 220, 507-530 (1991).
57. Schneider, T. D. & Stephens, R. M. Sequence Logos—a New Way to Display Consensus Sequences. *Nucleic Acids Research* 18, 6097-6100 (1990).
58. Crooks, G. E., Hon, G., Chandonia, J. M. & Brenner, S. E. WebLogo: A sequence logo generator. *Genome Research* 14, 1188-1190 (2004).
59. Hou, D., C. Cenciarelli, et al. (1994). "Activation-dependent ubiquitination of a T cell antigen receptor subunit on multiple intracellular lysines." *J Biol Chem* 269(19): 14244-7.
60. Layfield, R., D. Tooth, et al. (2001). "Purification of poly-ubiquitinated proteins by S5a-affinity chromatography." *Proteomics* 1(6): 773-7.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of detecting a site of a diglycine (Gly-Gly) epitope linked to the epsilon amino group of a lysine in a protein present in a sample, wherein the method comprises
   (i) cleaving protein(s) in the sample with a protease which cleaves at the C-terminus of Arg to form a mixture of cleavage peptides, wherein at least one cleavage peptide in the mixture comprises a lysine which is linked through its epsilon amino group to the C-terminus of a Gly-Gly dipeptide;
   (ii) contacting the mixture of cleavage peptides with an antibody, wherein said antibody specifically binds to a Gly-Gly dipeptide linked to the epsilon amino group of a lysine, and said contacting is performed under conditions that allow said antibody to specifically bind to said at least one cleavage peptide; and
   (iii) isolating said at least one cleavage peptide bound to said antibody from the mixture of cleavage peptides, thereby detecting a site of a diglycine (Gly-Gly) epitope linked to an epsilon amino group of a lysine in a protein present in said sample.

2. The method of claim 1, wherein the diglycine (Gly-Gly) epitope linked to the epsilon amino group of a lysine comprises the following structure:

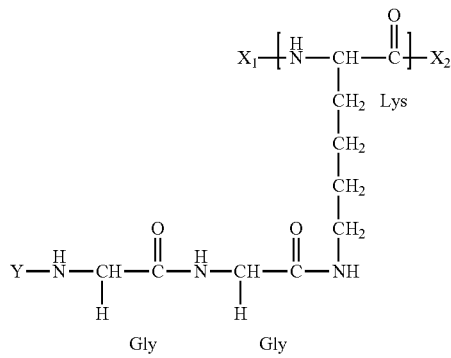

wherein: $X_1$ is hydrogen or a first peptide sequence;
$X_2$ is hydroxy or a second peptide sequence; and
Y is a peptide having Arg at its C-terminus, wherein the Y peptide is not a full-length protein.

3. The method of claim 2, wherein Y is Leu-Arg or STLHLVLRLR (SEQ ID NO:344).

4. The method of claim 1, wherein the protease cleaves ubiquitin and also cleaves protein(s) in the sample.

5. The method of claim 1, wherein the amino acid sequence of said peptide is determined.

6. The method of claim 1, wherein the protease is trypsin or Arg-C.

7. The method of claim 5, wherein sequencing of said peptide is performed by a method comprising mass spectrometry.

8. The method of claim 1, further comprising identifying the diglycine modified lysine site in the cleavage peptide.

9. The method of claim 1, further comprising identifying the protein from which the cleavage peptide was derived.

10. The method of claim 9, further comprising isolating the protein from which the cleavage peptide was derived.

11. The method of claim 1, wherein step (i) is performed in the presence of $H_2^{18}O$.

12. The method of claim 11, wherein the amount or proportion of cleavage peptides labeled with $^{18}O$ is determined.

13. The method of claim 1, wherein the sample is a protein sample, body fluid, tissue sample, cell lysate, fractionated cellular material, cellular extract, cell culture supernatant, or cultured cells.

14. The method of claim 13, wherein the body fluid is saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatite fluid, tissue extract, or glandular secretion.

15. The method of claim 1, wherein the sample is obtained from a mammal fed a diet containing an isotopically-labeled amino acid.

16. The method of claim 1, wherein the sample is obtained from culture media containing an isotopically-labeled amino acid.

17. The method of claim 1, wherein the sample comprises a selected cell or tissue type and the method further comprises identifying substantially all proteins that contain the epitope in the cell or tissue type to yield a profile of proteins from the cell or tissue type that contain the epitope.

18. The method of claim 17, further comprising comparing the profile of proteins from the cell or tissue type that contain the epitope with a profile of proteins that contain the epitope in the cell or tissue type after treatment or exposure of the selected cells or tissues to a drug or test agent.

19. The method of claim 17, further comprising comparing the profile of proteins from the cell or tissue type that contain the epitope with a profile of proteins that contain the epitope from cells with a mutation in, or an amplification of, a gene encoding a ubiquitin ligase, a ubiquitin conjugating enzyme or a ubiquitin activating enzyme.

20. The method of claim 19, wherein the mutation substantially eliminates expression or function of an E3 ubiquitin ligase, an E2 ubiquitin conjugating enzyme or an E1 ubiquitin activating enzymes.

21. The method of claim 1, wherein the diglycine (Gly-Gly) epitope site is a ubiquitinated site.

* * * * *

UNITED STATES PATENT AND TRADEMARK OFFICE
CERTIFICATE OF CORRECTION

PATENT NO. : 9,868,781 B2
APPLICATION NO. : 12/455496
DATED : January 16, 2018
INVENTOR(S) : Guoqiang Xu et al.

Page 1 of 1

It is certified that error appears in the above-identified patent and that said Letters Patent is hereby corrected as shown below:

In the Specification

Column 1, second paragraph should read:
This invention was made with government support under Grant Number AI068639 and CA062948 awarded by the National Institutes of Health. The government has certain rights in this invention.

Signed and Sealed this
Third Day of April, 2018

Andrei Iancu
*Director of the United States Patent and Trademark Office*